US011242407B2

(12) United States Patent
Tavazoie et al.

(10) Patent No.: US 11,242,407 B2
(45) Date of Patent: Feb. 8, 2022

(54) HIGH-AFFINITY ANTI-MERTK ANTIBODIES AND USES THEREOF

(71) Applicant: Rgenix, Inc., New York, NY (US)

(72) Inventors: Masoud Tavazoie, New York, NY (US); Isabel Kurth, New York, NY (US); Shugaku Takeda, Queens Village, NY (US); Celia Andreu-Agullo, New York, NY (US); Ivo Lorenz, Brooklyn, NY (US)

(73) Assignee: Inspirna, Inc., New York, NY (US)

(*) Notice: Subject to any disclaimer, the term of this patent is extended or adjusted under 35 U.S.C. 154(b) by 159 days.

(21) Appl. No.: 16/801,078

(22) Filed: Feb. 25, 2020

(65) Prior Publication Data

US 2020/0291135 A1    Sep. 17, 2020

Related U.S. Application Data

(60) Provisional application No. 62/810,841, filed on Feb. 26, 2019.

(51) Int. Cl.
| | |
|---|---|
| *C07K 16/40* | (2006.01) |
| *A61K 47/65* | (2017.01) |
| *A61K 47/68* | (2017.01) |
| *A61P 35/00* | (2006.01) |
| *A61K 39/395* | (2006.01) |

(52) U.S. Cl.
CPC .......... *C07K 16/40* (2013.01); *A61K 39/3955* (2013.01); *A61K 47/65* (2017.08); *A61K 47/6801* (2017.08); *A61P 35/00* (2018.01); *C07K 2317/24* (2013.01); *C07K 2317/31* (2013.01); *C07K 2317/54* (2013.01); *C07K 2317/55* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,122,464 A | 6/1992 | Wilson et al. | |
| 5,225,539 A | 7/1993 | Winter | |
| 5,530,101 A | 6/1996 | Queen et al. | |
| 5,565,332 A | 10/1996 | Hoogenboom et al. | |
| 5,585,089 A | 12/1996 | Queen et al. | |
| 5,766,886 A | 6/1998 | Studnicka et al. | |
| 5,837,242 A | 11/1998 | Holliger et al. | |
| 5,869,620 A | 2/1999 | Whitlow et al. | |
| 5,989,830 A | 11/1999 | Davis et al. | |
| 6,005,079 A | 12/1999 | Casterman et al. | |
| 6,132,992 A | 10/2000 | Ledbetter et al. | |
| 6,407,213 B1 | 6/2002 | Carter et al. | |
| 7,183,076 B2 | 2/2007 | Arathoon et al. | |
| 7,659,241 B2 | 2/2010 | Senter et al. | |
| 7,829,531 B2 | 11/2010 | Senter et al. | |
| 7,851,437 B2 | 12/2010 | Senter et al. | |
| 7,951,917 B1 | 5/2011 | Arathoon et al. | |
| 8,227,577 B2 | 7/2012 | Klein et al. | |
| 8,541,178 B2 | 9/2013 | Kaur et al. | |
| 8,586,713 B2 | 11/2013 | Davis et al. | |
| 10,221,248 B2 | 3/2019 | Tavazoie et al. | |
| 2005/0042664 A1 | 2/2005 | Wu et al. | |
| 2005/0048549 A1 | 3/2005 | Cao et al. | |
| 2018/0002444 A1* | 1/2018 | Tavazoie | A61K 31/513 |
| 2019/0241676 A1 | 8/2019 | Tavazoie et al. | |

FOREIGN PATENT DOCUMENTS

| | | |
|---|---|---|
| EP | 239400 | 9/1987 |
| EP | 519596 | 12/1992 |
| EP | 592106 | 4/1994 |
| WO | WO 86/05807 | 10/1986 |
| WO | WO 89/01036 | 2/1989 |
| WO | WO 93/17105 | 9/1993 |
| WO | WO 94/04678 | 3/1994 |

(Continued)

OTHER PUBLICATIONS

U.S. Appl. No. 16/626,456, filed Jun. 26, 2018, Tavazoie et al..
Ausubel et al., eds, 1989, Current Protocols in Molecular Biology, vol. I, Green Publishing Associates, Inc. and John Wiley & Sons, Inc., New York:6.3.1-6.3.6 and 2.10.3.
Baca et al., 1997, "Antibody Humanization Using Monovalent Phage Display", J Biol Chem, 272(16):10678-10684.
Beck et al., 2017, "Strategies and challenges for the next generation of antibody-drug conjugates", Nat Rev Drug Discov, 16(5):315-337.
Caldas et al., 2000, "Design and synthesis of germline-based hemi-humanized single-chain Fv against the CD18 surface antigen", Protein Eng, 13(5):353-360.

(Continued)

*Primary Examiner* — Nelson B Moseley, II
(74) *Attorney, Agent, or Firm* — Jones Day

(57) ABSTRACT

The present disclosure provides antibodies (e.g., humanized antibodies) that specifically bind to Mer Tyrosine Kinase (MERTK; e.g., human MERTK) and compositions comprising such antibodies. The present disclosure also provides antibody-drug conjugates comprising (i) an anti-MERTK antibody or antigen-binding fragment thereof described herein that specifically binds to MERTK (e.g., human MERTK), and (ii) cytotoxic agents conjugated directly to the antibodies or conjugated to the antibodies via linkers, and compositions comprising such antibody-drug conjugates. The present disclosure also provides methods for treating cancer, comprising administering to a human subject in need thereof (a) an anti-MERTK antibody that specifically binds to MERTK (e.g., human MERTK) or an antigen-binding fragment thereof described herein, or (b) an antibody-drug conjugate that comprises (i) an anti-MERTK antibody or antigen-binding fragment thereof that specifically binds to MERTK (e.g., human MERTK), and (ii) a cytotoxic agent conjugated directly to the antibody or conjugated to the antibody via a linker.

Figure 3A:
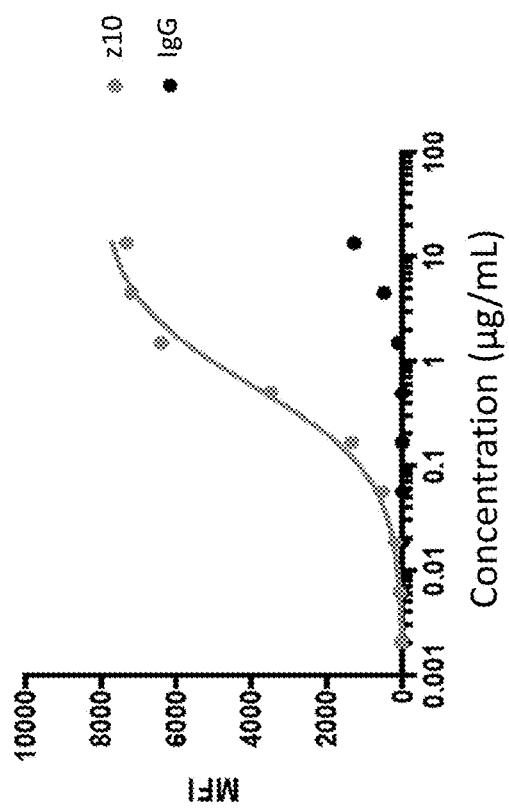

37 Claims, 25 Drawing Sheets
Specification includes a Sequence Listing.

(56) References Cited

FOREIGN PATENT DOCUMENTS

| WO | WO 94/25591 | 11/1994 |
|---|---|---|
| WO | WO 91/09967 | 7/1997 |
| WO | WO 01/44301 | 6/2001 |
| WO | WO 2016/106221 | 6/2016 |
| WO | WO 2019/005756 | 1/2019 |

OTHER PUBLICATIONS

Cannarile et al., "Colony-stimulating factor 1 receptor (CSF1R) inhibitors in cancer therapy," J Immunother Cancer. Jul. 18, 2017;5(1):53.
Cardillo et al., 2011, "Humanized Anti-Trop-2 IgG-SN-38 Conjugate for Effective Treatment of Diverse Epithelial Cancers: Preclinical Studies in Human Cancer Xenograft Models and Monkeys", Clin Cancer Res, 17(10):3157-3169.
Clackson et al., 1991, "Making antibody fragments using phage display libraries", Nature, 352(6336):624-628.
Cockett et al., 1990, "High Level Expression of Tissue Inhibitor of Metalloproteinases in Chinese Hamster Ovary Cells Using Glutamine Synthetase Gene Amplification", Biotechnology, 8(7):662-667.
Cook et al., 2013, "MerTK inhibition in tumor leukocytes decreases tumor growth and metastasis", J Clin Invest, 123(8):3231-3242.
Couto et al., 1995, "Anti-BA46 Monoclonal Antibody Mc3: Humanization Using a Novel Positional Consensus and in Vivo and in Vitro Characterization", Cancer Res, 55(8):1717-1722.
Couto et al., 1995, "Designing Human Consensus Antibodies with Minimal Positional Templates", Cancer Res, 55(23 Suppl):5973s-5977s.
Crittenden et al., 2016, "Mertk on tumor macrophages is a therapeutic target to prevent tumor recurrence following radiation therapy", Oncotarget, 7(48):78653-78666.
Cummings et al., 2013, "Molecular Pathways: MERTK Signaling in Cancer", Clin Cancer Res, 19(19):5275-5280.
Foecking and Hofstetter, 1986, "Powerful and versatile enhancer-promoter unit for mammalian expression vectors", Gene, 45(1):101-105.
Goldenberg et al., 2018, "The emergence of trophoblast cell-surface antigen 2 (TROP-2) as a novel cancer target", Oncotarget, 9(48):28989-29006.
Jackson, 2016, "Processes for Constructing Homogeneous Antibody Drug Conjugates", Org Process Res Dev, 20(5):852-866.
Kim and Hong, 2007, "Guided selection of human antibody light chains against TAG-72 using a phage display chain shuffling approach", J Microbiol, 45(6):572-577.
Kutmeier et al., 1994, "Assembly of humanized antibody genes from synthetic oligonucleotides using a single-round PCR", BioTechniques, 17(2):242-246.
Linger et al., 2013, "Mer or Axl Receptor Tyrosine Kinase Inhibition Promotes Apoptosis, Blocks Growth, and Enhances Chemosensitivity of Human Non-Small Cell Lung Cancer", Oncogene, 32(29):3420-3431.
Liu et al., 2013, "UNC1062, a new and potent Mer inhibitor", Eur J Med Chem, 65:83-93.
Mccombs and Owen, 2015, "Antibody Drug Conjugates: Design and Selection of Linker, Payload and Conjugation Chemistry", AAPS J, 17(2):339-351.
Minn et al., 2005, "Genes That Mediate Breast Cancer Metastasis to Lung", Nature, 436(7050):518-524.
Morea et al., 2000, "Antibody modeling: Implications for engineering and design", Methods, 20(3):267-279.
Muyldermans, 2001, "Single Domain Camel Antibodies: Current Status", J Biotechnol, 74(4):277-302.
Nuttall et al., 2000, "Immunoglobulin VH domains and beyond: design and selection of single-domain binding and targeting reagents", Curr Pharm Biotehnol, 1(3):253-263.
Padlan, 1991, "A Possible Procedure for Reducing the Immunogenicity of Antibody Variable Domains While Preserving Their Ligand-Binding Properties", Mol Immunol, 28(4/5):489-498.
Pedersen et al., 1994, "Comparison of Surface Accessible Residues in Human and Murine Immunoglobulin Fv Domains. Implication for Humanization of Murine Antibodies", J Mol Biol, 235(3):959-973.
Peters and Brown, 2015, "Antibody-drug conjugates as novel anti-cancer chemotherapeutics", Biosci Rep, 35(4):art:e00225.
Png et al., 2012, "A microRNA regulon that mediates endothelial recruitment and metastasis by cancer cells", Nature, 481(7380):190-194.
Rader et al., 1998, "A phage display approach for rapid antibody humanization: Designed combinatorial V gene libraries", Proc Natl Acad Sci USA, 95(15):8910-8915.
Reichmann and Muyldermans, 1999, "Single Domain Antibodies: Comparison of Camel VH and Camelised Human VH Domains", J Immunol, 231:25-38.
Roguska et al., 1994, "Humanization of murine monoclonal antibodies through variable domain resurfacing", Proc Natl Acad Sci USA, 91(3):969-973.
Roguska et al., 1996, "A comparison of two murine monoclonal antibodies humanized by CDR-grafting and variable domain resurfacing", Protein Eng, 9(10):895-904.
Sandhu, 1994, "A rapid procedure for the humanization of monoclonal antibodies", Gene, 150(2):409-410.
Sather et al., 2007, "A soluble form of the Mer receptor tyrosine kinase inhibits macrophage clearance of apoptotic cells and platelet aggregation", Blood, 109(3):1026-1033.
Studnicka et al., 1994, "Human-engineered monoclonal antibodies retain full specific binding activity by preserving non-CDR complementarity-modulating residues.", Prot Engineering, 7(6):805-814.
Tan et al., 2002, " "Superhumanized" Antibodies: Reduction of Immunogenic Potential by Complementarity-Determining Region Grafting with Human Germline Sequences: Application to an Anti-CD28", J Immunol, 169:1119-1125.
Verma et al., 2011, "Targeting Axl and Mer Kinases in Cancer," Mol Cancer Ther, 10(10):1763-1773.
Zizzo et al., 2012, "Efficient Clearance of Early Apoptotic Cells by Human Macrophages Requires M2c Polarization and MerTK Induction", J Immunology, 189(7):3508-3520.

* cited by examiner

| Ligand | Analyte | kd (1/s) |
| --- | --- | --- |
| rhMer/Fc Chimera | W3725-z1-IgG1K/(S24+S32) | 8.83E-06 |
| | W3725-z2-IgG1K/(S25+S32) | 2.53E-06 |
| | W3725-z3-IgG1K/(S26+S32) | 5.07E-06 |
| | W3725-z4-IgG1K/(S27+S32) | 1.21E-05 |
| | W3725-z5-IgG1K/(S28+S32) | 5.83E-06 |
| | W3725-z6-IgG1K/(S29+S32) | 7.98E-06 |
| | W3725-z7-IgG1K/(S30+S32) | 1.09E-05 |
| | W3725-z8-IgG1K/(S31+S32) | 6.97E-06 |
| | W3725-z9-IgG1K/(S24+S33) | 2.63E-06 |
| | W3725-z10-IgG1K/(S25+S33) | 1.29E-06 |
| | W3725-z11-IgG1K/(S26+S33) | <1.00E-06 |
| | W3725-z12-IgG1K/(S27+S33) | 5.81E-06 |
| | W3725-z13-IgG1K/(S28+S33) | <1.00E-06 |
| | W3725-z14-IgG1K/(S29+S33) | 1.32E-06 |
| | W3725-z15-IgG1K/(S30+S33) | 2.92E-06 |
| | W3725-z16-IgG1K/(S31+S33) | <1.00E-06 |
| | W3725-xAb-IgG1K/(S34+S35) | 7.00E-06 |
| | W3725-HyAb1-IgG1K/(S31+S35) | 3.84E-06 |
| | W3725-HyAb2-IgG1K/(S34+S33) | <1.00E-06 |

Fig. 1

| Protein Name | PI | Concentration (mg/ml) | Volume (ml) | Amount (mg) | Buffer | Purity by SEC-HPLC | Yield (mg/L) | Dialysis Recovery |
|---|---|---|---|---|---|---|---|---|
| W3725-z10-IgG1K/(S25+S33) | 8.40 | 1.7 | 3.1 | 5.3 | PBS | 99.33 % | 266.5 | 80.1% |
| W3725-z11-IgG1K/(S26+S33) | 8.40 | 2.3 | 2 | 4.6 | PBS | 99.75 % | 228.5 | 73.5% |
| W3725-z13-IgG1K/(S28+S33) | 8.40 | 1.6 | 3.4 | 5.5 | PBS | 98.93 % | 275.0 | 77.4% |
| W3725-xAb-IgG1K/(S34+S35) | 8.47 | 1.1 | 2 | 2.2 | PBS | 97.49 % | 111.5 | 68.1% |

Fig. 2

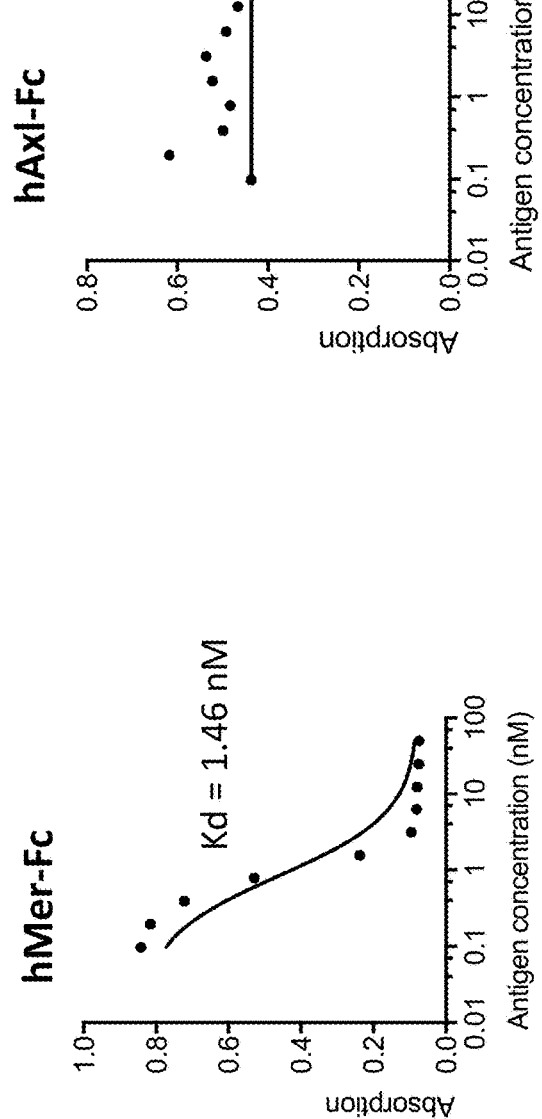
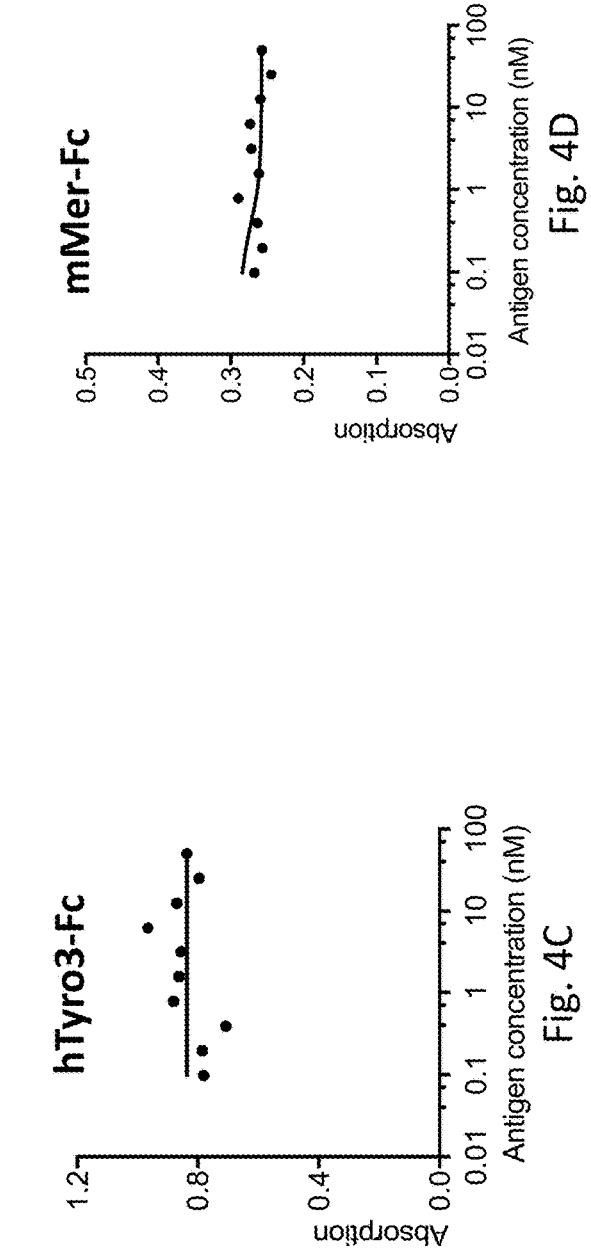
Fig. 4A
Fig. 4B
Fig. 4C
Fig. 4D

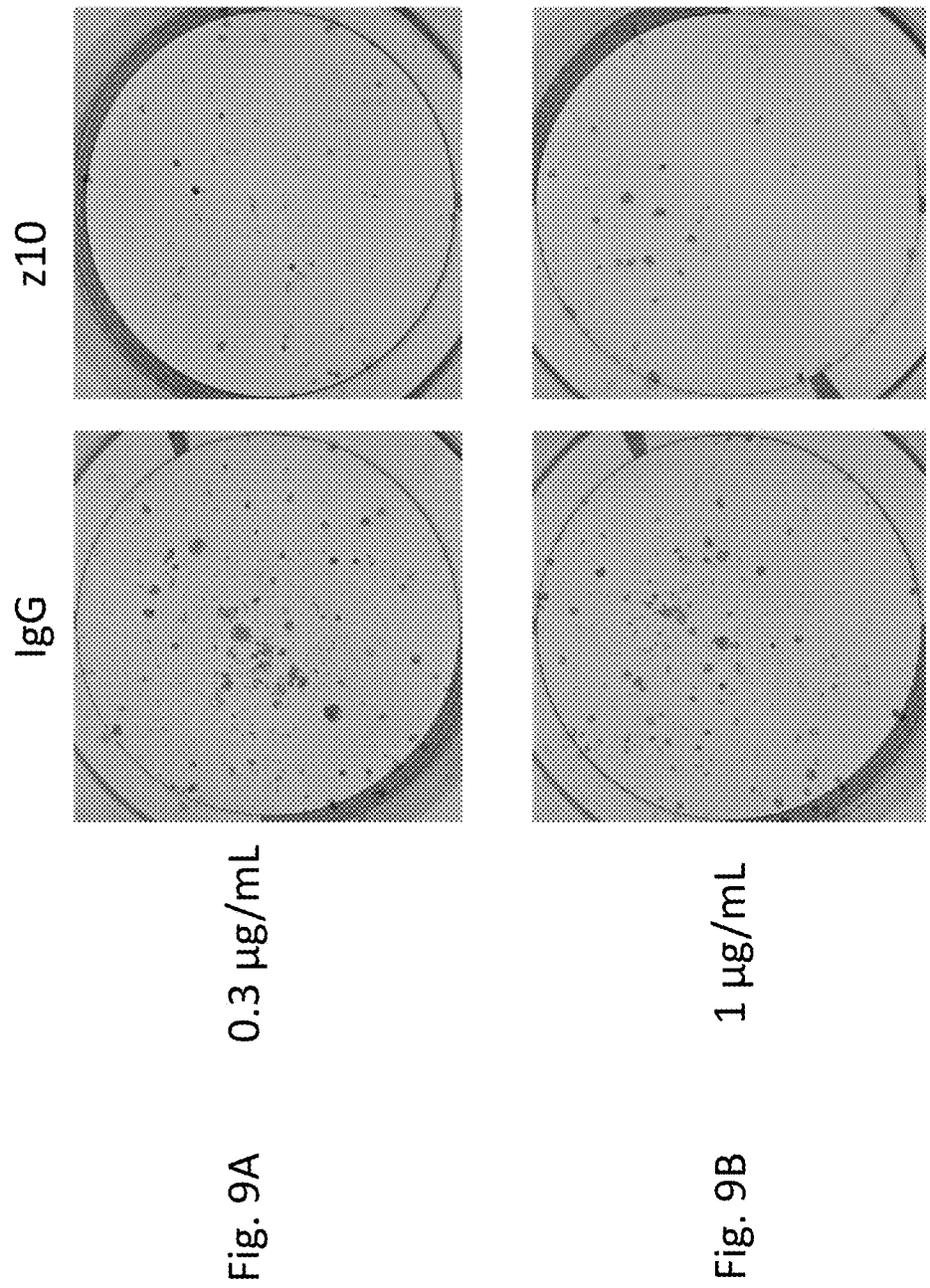
Fig. 9A  0.3 μg/mL
Fig. 9B  1 μg/mL

Competitive ELISA

| Antibody | Antigen | Kd |
|---|---|---|
| z10 | Mer-Fc | 0.17 nM |
| z10-MMAE | Mer-Fc | 0.081 nM |
| z10-SN38 | Mer-Fc | 0.021 nM |

Figure 15

SEQUENCE LISTING

```
<160> NUMBER OF SEQ ID NOS: 132

<210> SEQ ID NO 1
<211> LENGTH: 5
<212> TYPE: PRT
<213> ORGANISM: Artificial Sequence
<220> FEATURE:
```

<223> OTHER INFORMATION: Antibody z10/z11/z13/xAb VH CDR1 (Kabat)

<400> SEQUENCE: 1

Asn Tyr Gly Met Asn
1               5

<210> SEQ ID NO 2
<211> LENGTH: 7
<212> TYPE: PRT
<213> ORGANISM: Artificial Sequence
<220> FEATURE:
<223> OTHER INFORMATION: Antibody z10/z11/z13/xAb VH CDR1 (Chothia)

<400> SEQUENCE: 2

Gly Tyr Thr Phe Thr Asn Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: Antibody z10/z11/z13/xAb VH CDR1
      (AbM/Exemplary)

<400> SEQUENCE: 3

Gly Tyr Thr Phe Thr Asn Tyr Gly Met Asn
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Antibody z10/z11/z13/xAb VH CDR1 (Contact)

<400> SEQUENCE: 4

Thr Asn Tyr Gly Met Asn
1               5

<210> SEQ ID NO 5
<211> LENGTH: 8
<212> TYPE: PRT
<213> ORGANISM: Artificial Sequence
<220> FEATURE:
<223> OTHER INFORMATION: Antibody z10/z11/z13/xAb VH CDR1 (IMGT)

<400> SEQUENCE: 5

Gly Tyr Thr Phe Thr Asn Tyr Gly
1               5

<210> SEQ ID NO 6
<211> LENGTH: 17
<212> TYPE: PRT
<213> ORGANISM: Artificial Sequence
<220> FEATURE:
<223> OTHER INFORMATION: Antibody z10/z11/z13/xAb VH CDR2
      (Kabat/Exemplary)

<400> SEQUENCE: 6

Trp Ile Asn Thr Tyr Thr Gly Glu Pro Thr Tyr Ala Asp Asp Phe Lys
1               5                   10                  15

Gly

<210> SEQ ID NO 7
<211> LENGTH: 4

```
<212> TYPE: PRT
<213> ORGANISM: Artificial Sequence
<220> FEATURE:
<223> OTHER INFORMATION: Antibody z10/z11/z13/xAb VH CDR2 (Chothia)

<400> SEQUENCE: 7

Thr Tyr Thr Gly
1

<210> SEQ ID NO 8
<211> LENGTH: 10
<212> TYPE: PRT
<213> ORGANISM: Artificial Sequence
<220> FEATURE:
<223> OTHER INFORMATION: Antibody z10/z11/z13/xAb VH CDR2 (AbM)

<400> SEQUENCE: 8

Trp Ile Asn Thr Tyr Thr Gly Glu Pro Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Antibody z10/z11/z13/xAb VH CDR2 (Contact)

<400> SEQUENCE: 9

Trp Met Gly Trp Ile Asn Thr Tyr Thr Gly Glu Pro Thr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Antibody z10/z11/z13/xAb VH CDR2 (IMGT)

<400> SEQUENCE: 10

Ile Asn Thr Tyr Thr Gly Glu Pro
1               5

<210> SEQ ID NO 11
<211> LENGTH: 11
<212> TYPE: PRT
<213> ORGANISM: Artificial Sequence
<220> FEATURE:
<223> OTHER INFORMATION: Antibody z10/z11/z13/xAb VH CDR3 (Kabat/AbM/
      Exemplary)

<400> SEQUENCE: 11

Lys Ser Thr Val Val Ser Arg Tyr Phe Asp Val
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Antibody z10/z11/z13/xAb VH CDR3 (Chothia)

<400> SEQUENCE: 12

Ser Thr Val Val Ser Arg Tyr Phe Asp
1               5

<210> SEQ ID NO 13
<211> LENGTH: 12
```

```
<212> TYPE: PRT
<213> ORGANISM: Artificial Sequence
<220> FEATURE:
<223> OTHER INFORMATION: Antibody z10/z11/z13/xAb VH CDR3 (Contact)

<400> SEQUENCE: 13

Ala Arg Lys Ser Thr Val Val Ser Arg Tyr Phe Asp
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Antibody z10/z11/z13/xAb VH CDR3 (IMGT)

<400> SEQUENCE: 14

Ala Arg Lys Ser Thr Val Val Ser Arg Tyr Phe Asp Val
1               5                   10

<210> SEQ ID NO 15
<211> LENGTH: 30
<212> TYPE: PRT
<213> ORGANISM: Artificial Sequence
<220> FEATURE:
<223> OTHER INFORMATION: Antibody z10/Z11/z13 VH Framework Region VH FR1
      (Kabat)

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 16
<211> LENGTH: 14
<212> TYPE: PRT
<213> ORGANISM: Artificial Sequence
<220> FEATURE:
<223> OTHER INFORMATION: Antibody z10/z11/z13 VH Framework Region VH FR2
      (Kabat)

<400> SEQUENCE: 16

Trp Val Arg Gln Ala Pro Gly Gln Gly Leu Glu Trp Met Gly
1               5                   10

<210> SEQ ID NO 17
<211> LENGTH: 32
<212> TYPE: PRT
<213> ORGANISM: Artificial Sequence
<220> FEATURE:
<223> OTHER INFORMATION: Antibody z10 VH Framework Region VH FR3
      (Kabat/Exemplary)

<400> SEQUENCE: 17

Arg Val Thr Phe Thr Thr Asp Thr Ser Thr Ser Thr Ala Tyr Met Glu
1               5                   10                  15

Leu Arg Ser Leu Arg Ser Asp Asp Met Ala Val Tyr Tyr Cys Ala Arg
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Antibody z10/z11/z13 VH Framework Region VH FR4
      (Kabat)
```

```
<400> SEQUENCE: 18

Trp Gly Gln Gly Thr Thr Val Thr Val Ser Ser
1               5                  10

<210> SEQ ID NO 19
<211> LENGTH: 25
<212> TYPE: PRT
<213> ORGANISM: Artificial Sequence
<220> FEATURE:
<223> OTHER INFORMATION: Antibody z10/z11/z13 VH Framework Region VH FR1
      (Chothia)

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 20
<211> LENGTH: 20
<212> TYPE: PRT
<213> ORGANISM: Artificial Sequence
<220> FEATURE:
<223> OTHER INFORMATION: Antibody z10/z11/z13 VH Framework Region VH FR2
      (Chothia)

<400> SEQUENCE: 20

Gly Met Asn Trp Val Arg Gln Ala Pro Gly Gln Gly Leu Glu Trp Met
1               5                   10                  15

Gly Trp Ile Asn
            20

<210> SEQ ID NO 21
<211> LENGTH: 43
<212> TYPE: PRT
<213> ORGANISM: Artificial Sequence
<220> FEATURE:
<223> OTHER INFORMATION: Antibody z10 VH Framework Region VH FR3
      (Chothia)

<400> SEQUENCE: 21

Glu Pro Thr Tyr Ala Asp Asp Phe Lys Gly Arg Val Thr Phe Thr Thr
1               5                   10                  15

Asp Thr Ser Thr Ser Thr Ala Tyr Met Glu Leu Arg Ser Leu Arg Ser
            20                  25                  30

Asp Asp Met Ala Val Tyr Tyr Cys Ala Arg Lys
        35                  40

<210> SEQ ID NO 22
<211> LENGTH: 12
<212> TYPE: PRT
<213> ORGANISM: Artificial Sequence
<220> FEATURE:
<223> OTHER INFORMATION: Antibody z10/z11/z13 VH Framework Region VH FR4
      (Chothia)

<400> SEQUENCE: 22

Val Trp Gly Gln Gly Thr Thr Val Thr Val Ser Ser
1               5                   10

<210> SEQ ID NO 23
<211> LENGTH: 25
<212> TYPE: PRT
<213> ORGANISM: Artificial Sequence
```

```
<220> FEATURE:
<223> OTHER INFORMATION: Antibody z10/z11/z13 VH Framework Region VH FR1
      (AbM)

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 24
<211> LENGTH: 14
<212> TYPE: PRT
<213> ORGANISM: Artificial Sequence
<220> FEATURE:
<223> OTHER INFORMATION: Antibody z10/z11/z13 VH Framework Region VH FR2
      (AbM)

<400> SEQUENCE: 24

Trp Val Arg Gln Ala Pro Gly Gln Gly Leu Glu Trp Met Gly
1               5                   10

<210> SEQ ID NO 25
<211> LENGTH: 39
<212> TYPE: PRT
<213> ORGANISM: Artificial Sequence
<220> FEATURE:
<223> OTHER INFORMATION: Antibody z10 VH Framework Region VH FR3 (AbM)

<400> SEQUENCE: 25

Tyr Ala Asp Asp Phe Lys Gly Arg Val Thr Phe Thr Thr Asp Thr Ser
1               5                   10                  15

Thr Ser Thr Ala Tyr Met Glu Leu Arg Ser Leu Arg Ser Asp Asp Met
            20                  25                  30

Ala Val Tyr Tyr Cys Ala Arg
        35

<210> SEQ ID NO 26
<211> LENGTH: 11
<212> TYPE: PRT
<213> ORGANISM: Artificial Sequence
<220> FEATURE:
<223> OTHER INFORMATION: Antibody z10/z11/z13 VH Framework Region VH FR4
      (AbM)

<400> SEQUENCE: 26

Trp Gly Gln Gly Thr Thr Val Thr Val Ser Ser
1               5                   10

<210> SEQ ID NO 27
<211> LENGTH: 29
<212> TYPE: PRT
<213> ORGANISM: Artificial Sequence
<220> FEATURE:
<223> OTHER INFORMATION: Antibody z10/z11/z13 VH Framework Region VH FR1
      (Contact)

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe
            20                  25

<210> SEQ ID NO 28
<211> LENGTH: 11
```

```
<212> TYPE: PRT
<213> ORGANISM: Artificial Sequence
<220> FEATURE:
<223> OTHER INFORMATION: Antibody z10/z11/z13 VH Framework Region VH FR2
      (Contact)

<400> SEQUENCE: 28

Trp Val Arg Gln Ala Pro Gly Gln Gly Leu Glu
1               5                   10

<210> SEQ ID NO 29
<211> LENGTH: 37
<212> TYPE: PRT
<213> ORGANISM: Artificial Sequence
<220> FEATURE:
<223> OTHER INFORMATION: Antibody z10 VH Framework Region VH FR3
      (Contact)

<400> SEQUENCE: 29

Tyr Ala Asp Asp Phe Lys Gly Arg Val Thr Phe Thr Thr Asp Thr Ser
1               5                   10                  15

Thr Ser Thr Ala Tyr Met Glu Leu Arg Ser Leu Arg Ser Asp Asp Met
            20                  25                  30

Ala Val Tyr Tyr Cys
        35

<210> SEQ ID NO 30
<211> LENGTH: 12
<212> TYPE: PRT
<213> ORGANISM: Artificial Sequence
<220> FEATURE:
<223> OTHER INFORMATION: Antibody z10/z11/z13 VH Framework Region VH FR4
      (Contact)

<400> SEQUENCE: 30

Val Trp Gly Gln Gly Thr Thr Val Thr Val Ser Ser
1               5                   10

<210> SEQ ID NO 31
<211> LENGTH: 25
<212> TYPE: PRT
<213> ORGANISM: Artificial Sequence
<220> FEATURE:
<223> OTHER INFORMATION: Antibody z10/z11/z13 VH Framework Region VH FR1
      (IMGT)

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 32
<211> LENGTH: 17
<212> TYPE: PRT
<213> ORGANISM: Artificial Sequence
<220> FEATURE:
<223> OTHER INFORMATION: Antibody z10/z11/z13 VH Framework Region VH FR2
      (IMGT)

<400> SEQUENCE: 32

Met Asn Trp Val Arg Gln Ala Pro Gly Gln Gly Leu Glu Trp Met Gly
1               5                   10                  15

Trp
```

```
<210> SEQ ID NO 33
<211> LENGTH: 38
<212> TYPE: PRT
<213> ORGANISM: Artificial Sequence
<220> FEATURE:
<223> OTHER INFORMATION: Antibody z10 VH Framework Region VH FR3 (IMGT)

<400> SEQUENCE: 33

Thr Tyr Ala Asp Asp Phe Lys Gly Arg Val Thr Phe Thr Thr Asp Thr
1               5                   10                  15

Ser Thr Ser Thr Ala Tyr Met Glu Leu Arg Ser Leu Arg Ser Asp Asp
            20                  25                  30

Met Ala Val Tyr Tyr Cys
        35

<210> SEQ ID NO 34
<211> LENGTH: 11
<212> TYPE: PRT
<213> ORGANISM: Artificial Sequence
<220> FEATURE:
<223> OTHER INFORMATION: Antibody z10/z11/z13 VH Framework Region VH FR4
      (IMGT)

<400> SEQUENCE: 34

Trp Gly Gln Gly Thr Thr Val Thr Val Ser Ser
1               5                   10

<210> SEQ ID NO 35
<211> LENGTH: 25
<212> TYPE: PRT
<213> ORGANISM: Artificial Sequence
<220> FEATURE:
<223> OTHER INFORMATION: Antibody z10/z11/z13 VH Framework Region VH FR1
      (Exemplary)

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 36
<211> LENGTH: 14
<212> TYPE: PRT
<213> ORGANISM: Artificial Sequence
<220> FEATURE:
<223> OTHER INFORMATION: Antibody z10/z11/z13 VH Framework Region VH FR2
      (Exemplary)

<400> SEQUENCE: 36

Trp Val Arg Gln Ala Pro Gly Gln Gly Leu Glu Trp Met Gly
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Antibody z10/z11/z13 VH Framework Region VH FR4
      (Exemplary)

<400> SEQUENCE: 37

Trp Gly Gln Gly Thr Thr Val Thr Val Ser Ser
1               5                   10

<210> SEQ ID NO 38
```

```
<211> LENGTH: 32
<212> TYPE: PRT
<213> ORGANISM: Artificial Sequence
<220> FEATURE:
<223> OTHER INFORMATION: Antibody z11 VH Framework Region VH FR3 (Kabat/
      Exemplary)

<400> SEQUENCE: 38

Arg Val Thr Met Thr Leu Asp Thr Ser Thr Ser Thr Ala Tyr Met Glu
1               5                   10                  15

Leu Arg Ser Leu Arg Ser Asp Asp Met Ala Val Tyr Tyr Cys Ala Arg
            20                  25                  30

<210> SEQ ID NO 39
<211> LENGTH: 43
<212> TYPE: PRT
<213> ORGANISM: Artificial Sequence
<220> FEATURE:
<223> OTHER INFORMATION: Antibody z11 VH Framework Region VH FR3
      (Chothia)

<400> SEQUENCE: 39

Glu Pro Thr Tyr Ala Asp Asp Phe Lys Gly Arg Val Thr Met Thr Leu
1               5                   10                  15

Asp Thr Ser Thr Ser Thr Ala Tyr Met Glu Leu Arg Ser Leu Arg Ser
            20                  25                  30

Asp Asp Met Ala Val Tyr Tyr Cys Ala Arg Lys
        35                  40

<210> SEQ ID NO 40
<211> LENGTH: 39
<212> TYPE: PRT
<213> ORGANISM: Artificial Sequence
<220> FEATURE:
<223> OTHER INFORMATION: Antibody z11 VH Framework Region VH FR3 (AbM)

<400> SEQUENCE: 40

Tyr Ala Asp Asp Phe Lys Gly Arg Val Thr Met Thr Leu Asp Thr Ser
1               5                   10                  15

Thr Ser Thr Ala Tyr Met Glu Leu Arg Ser Leu Arg Ser Asp Asp Met
            20                  25                  30

Ala Val Tyr Tyr Cys Ala Arg
        35

<210> SEQ ID NO 41
<211> LENGTH: 37
<212> TYPE: PRT
<213> ORGANISM: Artificial Sequence
<220> FEATURE:
<223> OTHER INFORMATION: Antibody z11 VH Framework Region VH FR3
      (Contact)

<400> SEQUENCE: 41

Tyr Ala Asp Asp Phe Lys Gly Arg Val Thr Met Thr Leu Asp Thr Ser
1               5                   10                  15

Thr Ser Thr Ala Tyr Met Glu Leu Arg Ser Leu Arg Ser Asp Asp Met
            20                  25                  30

Ala Val Tyr Tyr Cys
        35

<210> SEQ ID NO 42
<211> LENGTH: 38
<212> TYPE: PRT
<213> ORGANISM: Artificial Sequence
```

```
<220> FEATURE:
<223> OTHER INFORMATION: Antibody z11 VH Framework Region VH FR3 (IMGT)

<400> SEQUENCE: 42

Thr Tyr Ala Asp Asp Phe Lys Gly Arg Val Thr Met Thr Leu Asp Thr
1               5                   10                  15

Ser Thr Ser Thr Ala Tyr Met Glu Leu Arg Ser Leu Arg Ser Asp Asp
            20                  25                  30

Met Ala Val Tyr Tyr Cys
        35

<210> SEQ ID NO 43
<211> LENGTH: 32
<212> TYPE: PRT
<213> ORGANISM: Artificial Sequence
<220> FEATURE:
<223> OTHER INFORMATION: Antibody z13 VH Framework Region VH FR3 (Kabat/
      Exemplary)

<400> SEQUENCE: 43

Arg Val Thr Phe Thr Leu Asp Thr Ser Thr Ser Thr Ala Tyr Met Glu
1               5                   10                  15

Leu Arg Ser Leu Arg Ser Asp Asp Met Ala Val Tyr Tyr Cys Ala Arg
            20                  25                  30

<210> SEQ ID NO 44
<211> LENGTH: 43
<212> TYPE: PRT
<213> ORGANISM: Artificial Sequence
<220> FEATURE:
<223> OTHER INFORMATION: Antibody z13 VH Framework Region VH FR3
      (Chothia)

<400> SEQUENCE: 44

Glu Pro Thr Tyr Ala Asp Asp Phe Lys Gly Arg Val Thr Phe Thr Leu
1               5                   10                  15

Asp Thr Ser Thr Ser Thr Ala Tyr Met Glu Leu Arg Ser Leu Arg Ser
            20                  25                  30

Asp Asp Met Ala Val Tyr Tyr Cys Ala Arg Lys
        35                  40

<210> SEQ ID NO 45
<211> LENGTH: 39
<212> TYPE: PRT
<213> ORGANISM: Artificial Sequence
<220> FEATURE:
<223> OTHER INFORMATION: Antibody z13 VH Framework Region VH FR3 (AbM)

<400> SEQUENCE: 45

Tyr Ala Asp Asp Phe Lys Gly Arg Val Thr Phe Thr Leu Asp Thr Ser
1               5                   10                  15

Thr Ser Thr Ala Tyr Met Glu Leu Arg Ser Leu Arg Ser Asp Asp Met
            20                  25                  30

Ala Val Tyr Tyr Cys Ala Arg
        35

<210> SEQ ID NO 46
<211> LENGTH: 37
<212> TYPE: PRT
<213> ORGANISM: Artificial Sequence
<220> FEATURE:
<223> OTHER INFORMATION: Antibody z13 VH Framework Region VH FR3
      (Contact)
```

```
-continued

<400> SEQUENCE: 46

Tyr Ala Asp Asp Phe Lys Gly Arg Val Thr Phe Thr Leu Asp Thr Ser
1               5                   10                  15

Thr Ser Thr Ala Tyr Met Glu Leu Arg Ser Leu Arg Ser Asp Asp Met
            20                  25                  30

Ala Val Tyr Tyr Cys
        35

<210> SEQ ID NO 47
<211> LENGTH: 38
<212> TYPE: PRT
<213> ORGANISM: Artificial Sequence
<220> FEATURE:
<223> OTHER INFORMATION: Antibody z13 VH Framework Region VH FR3 (IMGT)

<400> SEQUENCE: 47

Thr Tyr Ala Asp Asp Phe Lys Gly Arg Val Thr Phe Thr Leu Asp Thr
1               5                   10                  15

Ser Thr Ser Thr Ala Tyr Met Glu Leu Arg Ser Leu Arg Ser Asp Asp
            20                  25                  30

Met Ala Val Tyr Tyr Cys
        35

<210> SEQ ID NO 48
<211> LENGTH: 32
<212> TYPE: PRT
<213> ORGANISM: Artificial Sequence
<220> FEATURE:
<223> OTHER INFORMATION: Antibody VH FR3 Consensus sequence (Kabat)
<220> FEATURE:
<221> NAME/KEY: misc_feature
<222> LOCATION: (4)..(4)
<223> OTHER INFORMATION: Xaa = Phe or Met
<220> FEATURE:
<221> NAME/KEY: misc_feature
<222> LOCATION: (6)..(6)
<223> OTHER INFORMATION: Xaa = Thr or Leu

<400> SEQUENCE: 48

Arg Val Thr Xaa Thr Xaa Asp Thr Ser Thr Ser Thr Ala Tyr Met Glu
1               5                   10                  15

Leu Arg Ser Leu Arg Ser Asp Asp Met Ala Val Tyr Tyr Cys Ala Arg
            20                  25                  30

<210> SEQ ID NO 49
<211> LENGTH: 43
<212> TYPE: PRT
<213> ORGANISM: Artificial Sequence
<220> FEATURE:
<223> OTHER INFORMATION: Antibody VH FR3 Consensus sequence (Chothia)
<220> FEATURE:
<221> NAME/KEY: misc_feature
<222> LOCATION: (14)..(14)
<223> OTHER INFORMATION: Xaa = Phe or Met
<220> FEATURE:
<221> NAME/KEY: misc_feature
<222> LOCATION: (16)..(16)
<223> OTHER INFORMATION: Xaa = Thr or Leu

<400> SEQUENCE: 49

Glu Pro Thr Tyr Ala Asp Asp Phe Lys Gly Arg Val Thr Xaa Thr Xaa
1               5                   10                  15

Asp Thr Ser Thr Ser Thr Ala Tyr Met Glu Leu Arg Ser Leu Arg Ser
            20                  25                  30

Asp Asp Met Ala Val Tyr Tyr Cys Ala Arg Lys
```

<210> SEQ ID NO 50
<211> LENGTH: 39
<212> TYPE: PRT
<213> ORGANISM: Artificial Sequence
<220> FEATURE:
<223> OTHER INFORMATION: Antibody VH FR3 Consensus sequence (AbM)
<220> FEATURE:
<221> NAME/KEY: misc_feature
<222> LOCATION: (11)..(11)
<223> OTHER INFORMATION: Xaa = Phe or Met
<220> FEATURE:
<221> NAME/KEY: misc_feature
<222> LOCATION: (13)..(13)
<223> OTHER INFORMATION: Xaa = Thr or Leu

<400> SEQUENCE: 50

Tyr Ala Asp Asp Phe Lys Gly Arg Val Thr Xaa Thr Xaa Asp Thr Ser
1               5                   10                  15

Thr Ser Thr Ala Tyr Met Glu Leu Arg Ser Leu Arg Ser Asp Asp Met
            20                  25                  30

Ala Val Tyr Tyr Cys Ala Arg
        35

<210> SEQ ID NO 51
<211> LENGTH: 37
<212> TYPE: PRT
<213> ORGANISM: Artificial Sequence
<220> FEATURE:
<223> OTHER INFORMATION: Antibody VH FR3 Consensus sequence (Contact)
<220> FEATURE:
<221> NAME/KEY: misc_feature
<222> LOCATION: (11)..(11)
<223> OTHER INFORMATION: Xaa = Phe or Met
<220> FEATURE:
<221> NAME/KEY: misc_feature
<222> LOCATION: (13)..(13)
<223> OTHER INFORMATION: Xaa = Thr or Leu

<400> SEQUENCE: 51

Tyr Ala Asp Asp Phe Lys Gly Arg Val Thr Xaa Thr Xaa Asp Thr Ser
1               5                   10                  15

Thr Ser Thr Ala Tyr Met Glu Leu Arg Ser Leu Arg Ser Asp Asp Met
            20                  25                  30

Ala Val Tyr Tyr Cys
        35

<210> SEQ ID NO 52
<211> LENGTH: 38
<212> TYPE: PRT
<213> ORGANISM: Artificial Sequence
<220> FEATURE:
<223> OTHER INFORMATION: Antibody VH FR3 Consensus sequence (IMGT)
<220> FEATURE:
<221> NAME/KEY: misc_feature
<222> LOCATION: (12)..(12)
<223> OTHER INFORMATION: Xaa = Phe or Met
<220> FEATURE:
<221> NAME/KEY: misc_feature
<222> LOCATION: (14)..(14)
<223> OTHER INFORMATION: Xaa = Thr or Leu

<400> SEQUENCE: 52

Thr Tyr Ala Asp Asp Phe Lys Gly Arg Val Thr Xaa Thr Xaa Asp Thr
1               5                   10                  15

Ser Thr Ser Thr Ala Tyr Met Glu Leu Arg Ser Leu Arg Ser Asp Asp
            20                  25                  30

```
Met Ala Val Tyr Tyr Cys
        35

<210> SEQ ID NO 53
<211> LENGTH: 32
<212> TYPE: PRT
<213> ORGANISM: Artificial Sequence
<220> FEATURE:
<223> OTHER INFORMATION: Antibody VH FR3 Consensus sequence (Exemplary)
<220> FEATURE:
<221> NAME/KEY: misc_feature
<222> LOCATION: (4)..(4)
<223> OTHER INFORMATION: Xaa = Phe or Met
<220> FEATURE:
<221> NAME/KEY: misc_feature
<222> LOCATION: (6)..(6)
<223> OTHER INFORMATION: Xaa = Thr or Leu

<400> SEQUENCE: 53

Arg Val Thr Xaa Thr Xaa Asp Thr Ser Thr Ser Thr Ala Tyr Met Glu
1               5                   10                  15

Leu Arg Ser Leu Arg Ser Asp Asp Met Ala Val Tyr Tyr Cys Ala Arg
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Antibody xAb VH Framework Region VH FR1 (Kabat)

<400> SEQUENCE: 54

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30

<210> SEQ ID NO 55
<211> LENGTH: 14
<212> TYPE: PRT
<213> ORGANISM: Artificial Sequence
<220> FEATURE:
<223> OTHER INFORMATION: Antibody xAb VH Framework Region VH FR2 (Kabat/
      AbM/Exemplary)

<400> SEQUENCE: 55

Trp Val Lys Gln Ala Pro Gly Lys Gly Leu Lys Trp Met Gly
1               5                   10

<210> SEQ ID NO 56
<211> LENGTH: 32
<212> TYPE: PRT
<213> ORGANISM: Artificial Sequence
<220> FEATURE:
<223> OTHER INFORMATION: Antibody xAb VH Framework Region VH FR3 (Kabat/
      Exemplary)

<400> SEQUENCE: 56

Arg Phe Val Phe Ser Leu Glu Thr Ser Ala Ser Thr Ala Tyr Leu Gln
1               5                   10                  15

Ile Asn Asn Leu Lys Asn Glu Asp Met Ala Thr Tyr Phe Cys Ala Arg
            20                  25                  30

<210> SEQ ID NO 57
<211> LENGTH: 11
<212> TYPE: PRT
```

```
<213> ORGANISM: Artificial Sequence
<220> FEATURE:
<223> OTHER INFORMATION: Antibody xAb VH Framework Region VH FR4
      (Kabat/AbM/IMGT/Exemplary)

<400> SEQUENCE: 57

Trp Gly Ala Gly Thr Thr Val Thr Val Ser Ser
1               5                   10

<210> SEQ ID NO 58
<211> LENGTH: 25
<212> TYPE: PRT
<213> ORGANISM: Artificial Sequence
<220> FEATURE:
<223> OTHER INFORMATION: Antibody xAb VH Framework Region VH FR1
      (Chothia/AbM/IMGT/Exemplary)

<400> SEQUENCE: 58

Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

<210> SEQ ID NO 59
<211> LENGTH: 20
<212> TYPE: PRT
<213> ORGANISM: Artificial Sequence
<220> FEATURE:
<223> OTHER INFORMATION: Antibody xAb VH Framework Region VH FR2
      (Chothia)

<400> SEQUENCE: 59

Gly Met Asn Trp Val Lys Gln Ala Pro Gly Lys Gly Leu Lys Trp Met
1               5                   10                  15

Gly Trp Ile Asn
            20

<210> SEQ ID NO 60
<211> LENGTH: 43
<212> TYPE: PRT
<213> ORGANISM: Artificial Sequence
<220> FEATURE:
<223> OTHER INFORMATION: Antibody xAb VH Framework Region VH FR3
      (Chothia)

<400> SEQUENCE: 60

Glu Pro Thr Tyr Ala Asp Asp Phe Lys Gly Arg Phe Val Phe Ser Leu
1               5                   10                  15

Glu Thr Ser Ala Ser Thr Ala Tyr Leu Gln Ile Asn Asn Leu Lys Asn
            20                  25                  30

Glu Asp Met Ala Thr Tyr Phe Cys Ala Arg Lys
        35                  40

<210> SEQ ID NO 61
<211> LENGTH: 12
<212> TYPE: PRT
<213> ORGANISM: Artificial Sequence
<220> FEATURE:
<223> OTHER INFORMATION: Antibody xAb VH Framework Region VH FR4
      (Chothia/Contact)

<400> SEQUENCE: 61

Val Trp Gly Ala Gly Thr Thr Val Thr Val Ser Ser
1               5                   10
```

```
<210> SEQ ID NO 62
<211> LENGTH: 39
<212> TYPE: PRT
<213> ORGANISM: Artificial Sequence
<220> FEATURE:
<223> OTHER INFORMATION: Antibody xAb VH Framework Region VH FR3 (AbM)

<400> SEQUENCE: 62

Tyr Ala Asp Asp Phe Lys Gly Arg Phe Val Phe Ser Leu Glu Thr Ser
1               5                   10                  15

Ala Ser Thr Ala Tyr Leu Gln Ile Asn Asn Leu Lys Asn Glu Asp Met
            20                  25                  30

Ala Thr Tyr Phe Cys Ala Arg
        35

<210> SEQ ID NO 63
<211> LENGTH: 29
<212> TYPE: PRT
<213> ORGANISM: Artificial Sequence
<220> FEATURE:
<223> OTHER INFORMATION: Antibody xAb VH Framework Region VH FR1
      (Contact)

<400> SEQUENCE: 63

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe
            20                  25

<210> SEQ ID NO 64
<211> LENGTH: 11
<212> TYPE: PRT
<213> ORGANISM: Artificial Sequence
<220> FEATURE:
<223> OTHER INFORMATION: Antibody xAb VH Framework Region VH FR2
      (Contact)

<400> SEQUENCE: 64

Trp Val Lys Gln Ala Pro Gly Lys Gly Leu Lys
1               5                   10

<210> SEQ ID NO 65
<211> LENGTH: 37
<212> TYPE: PRT
<213> ORGANISM: Artificial Sequence
<220> FEATURE:
<223> OTHER INFORMATION: Antibody xAb VH Framework Region VH FR3
      (Contact)

<400> SEQUENCE: 65

Tyr Ala Asp Asp Phe Lys Gly Arg Phe Val Phe Ser Leu Glu Thr Ser
1               5                   10                  15

Ala Ser Thr Ala Tyr Leu Gln Ile Asn Asn Leu Lys Asn Glu Asp Met
            20                  25                  30

Ala Thr Tyr Phe Cys
        35

<210> SEQ ID NO 66
<211> LENGTH: 17
<212> TYPE: PRT
<213> ORGANISM: Artificial Sequence
<220> FEATURE:
<223> OTHER INFORMATION: Antibody xAb VH Framework Region VH FR2 (IMGT)

<400> SEQUENCE: 66
```

```
Met Asn Trp Val Lys Gln Ala Pro Gly Lys Gly Leu Lys Trp Met Gly
1               5                   10                  15

Trp

<210> SEQ ID NO 67
<211> LENGTH: 38
<212> TYPE: PRT
<213> ORGANISM: Artificial Sequence
<220> FEATURE:
<223> OTHER INFORMATION: Antibody xAb VH Framework Region VH FR3 (IMGT)

<400> SEQUENCE: 67

Thr Tyr Ala Asp Asp Phe Lys Gly Arg Phe Val Phe Ser Leu Glu Thr
1               5                   10                  15

Ser Ala Ser Thr Ala Tyr Leu Gln Ile Asn Asn Leu Lys Asn Glu Asp
                20                  25                  30

Met Ala Thr Tyr Phe Cys
                35

<210> SEQ ID NO 68
<211> LENGTH: 11
<212> TYPE: PRT
<213> ORGANISM: Artificial Sequence
<220> FEATURE:
<223> OTHER INFORMATION: Antibody z10/z11/z13/xAb VL CDR1 (Kabat/AbM/
      Exemplary)

<400> SEQUENCE: 68

Lys Ala Ser Gln Asp Val Gly Asp Ala Val Thr
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Antibody z10/z11/z13/xAb VL CDR2 (Kabat/AbM/
      Exemplary)

<400> SEQUENCE: 69

Trp Ala Ser Thr Arg His Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Antibody z10/z11/z13/xAb VL CDR3 (Kabat/AbM/
      IMGT/Exemplary)

<400> SEQUENCE: 70

Gln Gln Tyr Arg Ser Tyr Pro Leu Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Antibody z10/z11/z13/xAb VL CDR1 (Chothia)

<400> SEQUENCE: 71

Ser Gln Asp Val Gly Asp Ala
1               5
```

```
<210> SEQ ID NO 72
<211> LENGTH: 3
<212> TYPE: PRT
<213> ORGANISM: Artificial Sequence
<220> FEATURE:
<223> OTHER INFORMATION: Antibody z10/z11/z13/xAb VL CDR2 (Chothia/IMGT)

<400> SEQUENCE: 72

Trp Ala Ser
1

<210> SEQ ID NO 73
<211> LENGTH: 6
<212> TYPE: PRT
<213> ORGANISM: Artificial Sequence
<220> FEATURE:
<223> OTHER INFORMATION: Antibody z10/z11/z13/xAb VL CDR3 (Chothia)

<400> SEQUENCE: 73

Tyr Arg Ser Tyr Pro Leu
1               5

<210> SEQ ID NO 74
<211> LENGTH: 7
<212> TYPE: PRT
<213> ORGANISM: Artificial Sequence
<220> FEATURE:
<223> OTHER INFORMATION: Antibody z10/z11/z13 VL CDR1 (Contact)

<400> SEQUENCE: 74

Gly Asp Ala Val Thr Trp Tyr
1               5

<210> SEQ ID NO 75
<211> LENGTH: 10
<212> TYPE: PRT
<213> ORGANISM: Artificial Sequence
<220> FEATURE:
<223> OTHER INFORMATION: Antibody z10/z11/z13/xAb VL CDR2 (Contact)

<400> SEQUENCE: 75

Leu Leu Ile Tyr Trp Ala Ser Thr Arg His
1               5                   10

<210> SEQ ID NO 76
<211> LENGTH: 8
<212> TYPE: PRT
<213> ORGANISM: Artificial Sequence
<220> FEATURE:
<223> OTHER INFORMATION: Antibody z10/z11/z13/xAb VL CDR3 (Contact)

<400> SEQUENCE: 76

Gln Gln Tyr Arg Ser Tyr Pro Leu
1               5

<210> SEQ ID NO 77
<211> LENGTH: 6
<212> TYPE: PRT
<213> ORGANISM: Artificial Sequence
<220> FEATURE:
<223> OTHER INFORMATION: Antibody z10/z11/z13/xAb VL CDR1 (IMGT)

<400> SEQUENCE: 77

Gln Asp Val Gly Asp Ala
1               5
```

```
<210> SEQ ID NO 78
<211> LENGTH: 7
<212> TYPE: PRT
<213> ORGANISM: Artificial Sequence
<220> FEATURE:
<223> OTHER INFORMATION: Antibody xAb VL CDR1 (Contact)

<400> SEQUENCE: 78

Gly Asp Ala Val Thr Trp Cys
1               5

<210> SEQ ID NO 79
<211> LENGTH: 23
<212> TYPE: PRT
<213> ORGANISM: Artificial Sequence
<220> FEATURE:
<223> OTHER INFORMATION: Antibody z10/z11/z13 VL Framework Region VL FR1
      (Kabat/AbM/Exemplary)

<400> SEQUENCE: 79

Asp Ile Gln Met Thr Gln Ser Pro Ser Phe Leu Ser Ala Ser Val Gly
1               5                   10                  15

Asp Arg Val Thr Ile Thr Cys
            20

<210> SEQ ID NO 80
<211> LENGTH: 15
<212> TYPE: PRT
<213> ORGANISM: Artificial Sequence
<220> FEATURE:
<223> OTHER INFORMATION: Antibody z10/z11/z13 VL Framework Region VL FR2
      (Kabat/AbM/Exemplary)

<400> SEQUENCE: 80

Trp Tyr Gln Gln Lys Pro Gly Lys Ala Pro Lys Leu Leu Ile Tyr
1               5                   10                  15

<210> SEQ ID NO 81
<211> LENGTH: 32
<212> TYPE: PRT
<213> ORGANISM: Artificial Sequence
<220> FEATURE:
<223> OTHER INFORMATION: Antibody z10/z11/z13 VL Framework Region VL FR3
      (Kabat/AbM/Exemplary)

<400> SEQUENCE: 81

Gly Val Pro Asp Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 82
<211> LENGTH: 10
<212> TYPE: PRT
<213> ORGANISM: Artificial Sequence
<220> FEATURE:
<223> OTHER INFORMATION: Antibody z10/z11/z13 VL Framework Region VL FR4
      (Kabat/AbM/IMGT/Exemplary)

<400> SEQUENCE: 82

Phe Gly Gln Gly Thr Lys Leu Glu Ile Lys
1               5                   10

<210> SEQ ID NO 83
<211> LENGTH: 25
<212> TYPE: PRT
<213> ORGANISM: Artificial Sequence
```

-continued

```
<220> FEATURE:
<223> OTHER INFORMATION: Antibody z10/z11/z13 VL Framework Region VL FR1
      (Chothia)

<400> SEQUENCE: 83

Asp Ile Gln Met Thr Gln Ser Pro Ser Phe Leu Ser Ala Ser Val Gly
1               5                   10                  15

Asp Arg Val Thr Ile Thr Cys Lys Ala
            20                  25

<210> SEQ ID NO 84
<211> LENGTH: 17
<212> TYPE: PRT
<213> ORGANISM: Artificial Sequence
<220> FEATURE:
<223> OTHER INFORMATION: Antibody z10/z11/z13 VL Framework Region VL FR2
      (Chothia/IMGT)

<400> SEQUENCE: 84

Val Thr Trp Tyr Gln Gln Lys Pro Gly Lys Ala Pro Lys Leu Leu Ile
1               5                   10                  15

Tyr

<210> SEQ ID NO 85
<211> LENGTH: 38
<212> TYPE: PRT
<213> ORGANISM: Artificial Sequence
<220> FEATURE:
<223> OTHER INFORMATION: Antibody z10/z11/z13 VL Framework Region VL FR3
      (Chothia)

<400> SEQUENCE: 85

Thr Arg His Thr Gly Val Pro Asp Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys Gln Gln
            35

<210> SEQ ID NO 86
<211> LENGTH: 11
<212> TYPE: PRT
<213> ORGANISM: Artificial Sequence
<220> FEATURE:
<223> OTHER INFORMATION: Antibody z10/z11/z13 VL Framework Region VL FR4
      (Chothia/Contact)

<400> SEQUENCE: 86

Thr Phe Gly Gln Gly Thr Lys Leu Glu Ile Lys
1               5                   10

<210> SEQ ID NO 87
<211> LENGTH: 29
<212> TYPE: PRT
<213> ORGANISM: Artificial Sequence
<220> FEATURE:
<223> OTHER INFORMATION: Antibody z10/z11/z13 VL Framework Region VL FR1
      (Contact)

<400> SEQUENCE: 87

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val
            20                  25
```

<210> SEQ ID NO 88
<211> LENGTH: 9
<212> TYPE: PRT
<213> ORGANISM: Artificial Sequence
<220> FEATURE:
<223> OTHER INFORMATION: Antibody z10/z11/z13 VL Framework Region VL FR2
      (Contact)

<400> SEQUENCE: 88

Gln Gln Lys Pro Gly Lys Ala Pro Lys
1               5

<210> SEQ ID NO 89
<211> LENGTH: 33
<212> TYPE: PRT
<213> ORGANISM: Artificial Sequence
<220> FEATURE:
<223> OTHER INFORMATION: Antibody z10/z11/z13 VL Framework Region VL FR3
      (Contact)

<400> SEQUENCE: 89

Thr Gly Val Pro Asp Arg Phe Ser Gly Ser Gly Ser Gly Thr Asp Phe
1               5                   10                  15

Thr Leu Thr Ile Ser Ser Leu Gln Pro Glu Asp Phe Ala Thr Tyr Tyr
            20                  25                  30

Cys

<210> SEQ ID NO 90
<211> LENGTH: 26
<212> TYPE: PRT
<213> ORGANISM: Artificial Sequence
<220> FEATURE:
<223> OTHER INFORMATION: Antibody z10/z11/z13 VL Framework Region VL FR1
      (IMGT)

<400> SEQUENCE: 90

Asp Ile Gln Met Thr Gln Ser Pro Ser Phe Leu Ser Ala Ser Val Gly
1               5                   10                  15

Asp Arg Val Thr Ile Thr Cys Lys Ala Ser
            20                  25

<210> SEQ ID NO 91
<211> LENGTH: 36
<212> TYPE: PRT
<213> ORGANISM: Artificial Sequence
<220> FEATURE:
<223> OTHER INFORMATION: Antibody z10/z11/z13 VL Framework Region VL FR3
      (IMGT)

<400> SEQUENCE: 91

Thr Arg His Thr Gly Val Pro Asp Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
            35

<210> SEQ ID NO 92
<211> LENGTH: 23
<212> TYPE: PRT
<213> ORGANISM: Artificial Sequence
<220> FEATURE:
<223> OTHER INFORMATION: Antibody xAb VL Framework Region VL FR1 (Kabat/
      AbM/Exemplary)

```
<400> SEQUENCE: 92

Asp Ile Val Leu Thr Gln Ser His Lys Phe Met Ser Thr Ser Val Gly
1               5                   10                  15

Asp Arg Val Ser Ile Thr Cys
            20

<210> SEQ ID NO 93
<211> LENGTH: 15
<212> TYPE: PRT
<213> ORGANISM: Artificial Sequence
<220> FEATURE:
<223> OTHER INFORMATION: Antibody xAb VL Framework Region VL FR2 (Kabat/
      AbM/Exemplary)

<400> SEQUENCE: 93

Trp Cys Gln Gln Lys Pro Gly Gln Pro Pro Lys Leu Leu Ile Tyr
1               5                   10                  15

<210> SEQ ID NO 94
<211> LENGTH: 32
<212> TYPE: PRT
<213> ORGANISM: Artificial Sequence
<220> FEATURE:
<223> OTHER INFORMATION: Antibody xAb VL Framework Region VL FR3 (Kabat/
      AbM/Exemplary)

<400> SEQUENCE: 94

Gly Val Pro Asp Arg Phe Thr Gly Ser Gly Ser Gly Thr Asp Phe Thr
1               5                   10                  15

Leu Thr Ile Asn Asn Val Gln Ser Glu Asp Leu Ala Asp Tyr Phe Cys
            20                  25                  30

<210> SEQ ID NO 95
<211> LENGTH: 10
<212> TYPE: PRT
<213> ORGANISM: Artificial Sequence
<220> FEATURE:
<223> OTHER INFORMATION: Antibody xAb VL Framework Region VL FR4 (Kabat/
      AbM/IMGT/Exemplary)

<400> SEQUENCE: 95

Phe Gly Ala Gly Thr Lys Leu Glu Leu Lys
1               5                   10

<210> SEQ ID NO 96
<211> LENGTH: 25
<212> TYPE: PRT
<213> ORGANISM: Artificial Sequence
<220> FEATURE:
<223> OTHER INFORMATION: Antibody xAb VL Framework Region VL FR1
      (Chothia)

<400> SEQUENCE: 96

Asp Ile Val Leu Thr Gln Ser His Lys Phe Met Ser Thr Ser Val Gly
1               5                   10                  15

Asp Arg Val Ser Ile Thr Cys Lys Ala
            20                  25

<210> SEQ ID NO 97
<211> LENGTH: 17
<212> TYPE: PRT
<213> ORGANISM: Artificial Sequence
<220> FEATURE:
<223> OTHER INFORMATION: Antibody xAb VL Framework Region VL FR2
      (Chothia/IMGT)
```

<400> SEQUENCE: 97

Val Thr Trp Cys Gln Gln Lys Pro Gly Gln Pro Pro Lys Leu Leu Ile
1               5                   10                  15

Tyr

<210> SEQ ID NO 98
<211> LENGTH: 38
<212> TYPE: PRT
<213> ORGANISM: Artificial Sequence
<220> FEATURE:
<223> OTHER INFORMATION: Antibody xAb VL Framework Region VL FR3
      (Chothia)

<400> SEQUENCE: 98

Thr Arg His Thr Gly Val Pro Asp Arg Phe Thr Gly Ser Gly Ser Gly
1               5                   10                  15

Thr Asp Phe Thr Leu Thr Ile Asn Asn Val Gln Ser Glu Asp Leu Ala
            20                  25                  30

Asp Tyr Phe Cys Gln Gln
            35

<210> SEQ ID NO 99
<211> LENGTH: 11
<212> TYPE: PRT
<213> ORGANISM: Artificial Sequence
<220> FEATURE:
<223> OTHER INFORMATION: Antibody xAb VL Framework Region VL FR4
      (Chothia/Contact)

<400> SEQUENCE: 99

Thr Phe Gly Ala Gly Thr Lys Leu Glu Leu Lys
1               5                   10

<210> SEQ ID NO 100
<211> LENGTH: 29
<212> TYPE: PRT
<213> ORGANISM: Artificial Sequence
<220> FEATURE:
<223> OTHER INFORMATION: Antibody xAb VL Framework Region VL FR1
      (Contact)

<400> SEQUENCE: 100

Asp Ile Val Leu Thr Gln Ser His Lys Phe Met Ser Thr Ser Val Gly
1               5                   10                  15

Asp Arg Val Ser Ile Thr Cys Lys Ala Ser Gln Asp Val
            20                  25

<210> SEQ ID NO 101
<211> LENGTH: 9
<212> TYPE: PRT
<213> ORGANISM: Artificial Sequence
<220> FEATURE:
<223> OTHER INFORMATION: Antibody xAb VL Framework Region VL FR2
      (Contact)

<400> SEQUENCE: 101

Gln Gln Lys Pro Gly Gln Pro Pro Lys
1               5

<210> SEQ ID NO 102
<211> LENGTH: 33
<212> TYPE: PRT
<213> ORGANISM: Artificial Sequence
<220> FEATURE:
<223> OTHER INFORMATION: Antibody xAb VL Framework Region VL FR3

(Contact)

<400> SEQUENCE: 102

Thr Gly Val Pro Asp Arg Phe Thr Gly Ser Gly Ser Gly Thr Asp Phe
1               5                   10                  15

Thr Leu Thr Ile Asn Asn Val Gln Ser Glu Asp Leu Ala Asp Tyr Phe
            20                  25                  30

Cys

<210> SEQ ID NO 103
<211> LENGTH: 26
<212> TYPE: PRT
<213> ORGANISM: Artificial Sequence
<220> FEATURE:
<223> OTHER INFORMATION: Antibody xAb VL Framework Region VL FR1 (IMGT)

<400> SEQUENCE: 103

Asp Ile Val Leu Thr Gln Ser His Lys Phe Met Ser Thr Ser Val Gly
1               5                   10                  15

Asp Arg Val Ser Ile Thr Cys Lys Ala Ser
            20                  25

<210> SEQ ID NO 104
<211> LENGTH: 36
<212> TYPE: PRT
<213> ORGANISM: Artificial Sequence
<220> FEATURE:
<223> OTHER INFORMATION: Antibody xAb VL Framework Region VL FR3 (IMGT)

<400> SEQUENCE: 104

Thr Arg His Thr Gly Val Pro Asp Arg Phe Thr Gly Ser Gly Ser Gly
1               5                   10                  15

Thr Asp Phe Thr Leu Thr Ile Asn Asn Val Gln Ser Glu Asp Leu Ala
            20                  25                  30

Asp Tyr Phe Cys
        35

<210> SEQ ID NO 105
<211> LENGTH: 120
<212> TYPE: PRT
<213> ORGANISM: Artificial Sequence
<220> FEATURE:
<223> OTHER INFORMATION: Antibody z10 Heavy Chain Variable Region (VH)

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Tyr Ala Asp Asp Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Met Ala Val Tyr Tyr Cys
                85                  90                  95

Ala Arg Lys Ser Thr Val Val Ser Arg Tyr Phe Asp Val Trp Gly Gln
            100                 105                 110

Gly Thr Thr Val Thr Val Ser Ser

-continued

```
                115                 120

<210> SEQ ID NO 106
<211> LENGTH: 107
<212> TYPE: PRT
<213> ORGANISM: Artificial Sequence
<220> FEATURE:
<223> OTHER INFORMATION: Antibody z10/z11/z13 light Chain Variable
      Region (VL)

<400> SEQUENCE: 106

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Gly Asp Ala
            20                  25                  30

Val Thr Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Ser Tyr Pro Leu
                85                  90                  95

Thr Phe Gly Gln Gly Thr Lys Leu Glu Ile Lys
            100                 105

<210> SEQ ID NO 107
<211> LENGTH: 120
<212> TYPE: PRT
<213> ORGANISM: Artificial Sequence
<220> FEATURE:
<223> OTHER INFORMATION: Antibody z11 Heavy Chain Variable Region (VH)

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Leu Asp Thr Ser Thr Ser Thr Ala Tyr
65                  70                  75                  80

Met Glu Leu Arg Ser Leu Arg Ser Asp Asp Met Ala Val Tyr Tyr Cys
                85                  90                  95

Ala Arg Lys Ser Thr Val Val Ser Arg Tyr Phe Asp Val Trp Gly Gln
            100                 105                 110

Gly Thr Thr Val Thr Val Ser Ser
        115                 120

<210> SEQ ID NO 108
<211> LENGTH: 120
<212> TYPE: PRT
<213> ORGANISM: Artificial Sequence
<220> FEATURE:
<223> OTHER INFORMATION: Antibody z13 Heavy Chain Variable Region (VH)

<400> SEQUENCE: 108

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Phe Thr Leu Asp Thr Ser Thr Ser Thr Ala Tyr
65                  70                  75                  80

Met Glu Leu Arg Ser Leu Arg Ser Asp Asp Met Ala Val Tyr Tyr Cys
            85                  90                  95

Ala Arg Lys Ser Thr Val Val Ser Arg Tyr Phe Asp Val Trp Gly Gln
            100                 105                 110

Gly Thr Thr Val Thr Val Ser Ser
            115                 120

<210> SEQ ID NO 109
<211> LENGTH: 120
<212> TYPE: PRT
<213> ORGANISM: Artificial Sequence
<220> FEATURE:
<223> OTHER INFORMATION: Antibody Heavy Chain Variable Region Consensus
      sequence
<220> FEATURE:
<221> NAME/KEY: misc_feature
<222> LOCATION: (70)..(70)
<223> OTHER INFORMATION: Xaa = Phe or Met
<220> FEATURE:
<221> NAME/KEY: misc_feature
<222> LOCATION: (72)..(72)
<223> OTHER INFORMATION: Xaa =  Thr or Leu

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Xaa Thr Xaa Asp Thr Ser Thr Ser Thr Ala Tyr
65                  70                  75                  80

Met Glu Leu Arg Ser Leu Arg Ser Asp Asp Met Ala Val Tyr Tyr Cys
            85                  90                  95

Ala Arg Lys Ser Thr Val Val Ser Arg Tyr Phe Asp Val Trp Gly Gln
            100                 105                 110

Gly Thr Thr Val Thr Val Ser Ser
            115                 120

<210> SEQ ID NO 110
<211> LENGTH: 120
<212> TYPE: PRT
<213> ORGANISM: Artificial Sequence
<220> FEATURE:
<223> OTHER INFORMATION: Antibody xAb Heavy Chain Variable Region (VH)

<400> SEQUENCE: 110

Gln Ile Gln Leu Val Gln Ser Gly Pro Glu Leu Lys Lys Pro Gly Glu
1               5                   10                  15
```

```
Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
            85                  90                  95

Ala Arg Lys Ser Thr Val Val Ser Arg Tyr Phe Asp Val Trp Gly Ala
            100                 105                 110

Gly Thr Thr Val Thr Val Ser Ser
            115                 120

<210> SEQ ID NO 111
<211> LENGTH: 107
<212> TYPE: PRT
<213> ORGANISM: Artificial Sequence
<220> FEATURE:
<223> OTHER INFORMATION: Antibody xAb Light Chain Variable Region (VL)

<400> SEQUENCE: 111

Asp Ile Val Leu Thr Gln Ser His Lys Phe Met Ser Thr Ser Val Gly
1               5                   10                  15

Asp Arg Val Ser Ile Thr Cys Lys Ala Ser Gln Asp Val Gly Asp Ala
            20                  25                  30

Val Thr Trp Cys Gln Gln Lys Pro Gly Gln Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Arg Ser Tyr Pro Leu
            85                  90                  95

Thr Phe Gly Ala Gly Thr Lys Leu Glu Leu Lys
            100                 105

<210> SEQ ID NO 112
<211> LENGTH: 450
<212> TYPE: PRT
<213> ORGANISM: Artificial Sequence
<220> FEATURE:
<223> OTHER INFORMATION: Antibody z10 Heavy Chain

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Met Ala Val Tyr Tyr Cys
            85                  90                  95
```

```
Ala Arg Lys Ser Thr Val Val Ser Arg Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 113
<211> LENGTH: 214
<212> TYPE: PRT
<213> ORGANISM: Artificial Sequence
<220> FEATURE:
<223> OTHER INFORMATION: Antibody z10/z11/z13 Light Chain

<400> SEQUENCE: 113
```

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Gly Asp Ala
            20                  25                  30

Val Thr Trp Tyr Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Arg Ser Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 114
<211> LENGTH: 450
<212> TYPE: PRT
<213> ORGANISM: Artificial Sequence
<220> FEATURE:
<223> OTHER INFORMATION: Antibody z11 Heavy Chain

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Leu Asp Thr Ser Thr Ser Thr Ala Tyr
65              70                  75                  80

Met Glu Leu Arg Ser Leu Arg Ser Asp Asp Met Ala Val Tyr Tyr Cys
                85                  90                  95

Ala Arg Lys Ser Thr Val Val Ser Arg Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 115
<211> LENGTH: 450
<212> TYPE: PRT
<213> ORGANISM: Artificial Sequence
<220> FEATURE:
<223> OTHER INFORMATION: Antibody z13 Heavy Chain

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

```
Gly Trp Ile Asn Thr Tyr Thr Gly Glu Pro Thr Tyr Ala Asp Asp Phe
     50                  55                  60

Lys Gly Arg Val Thr Phe Thr Leu Asp Thr Ser Thr Ser Thr Ala Tyr
 65                  70                  75                  80

Met Glu Leu Arg Ser Leu Arg Ser Asp Asp Met Ala Val Tyr Tyr Cys
                 85                  90                  95

Ala Arg Lys Ser Thr Val Val Ser Arg Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

```
<210> SEQ ID NO 116
<211> LENGTH: 450
<212> TYPE: PRT
<213> ORGANISM: Artificial Sequence
<220> FEATURE:
<223> OTHER INFORMATION: Antibody Heavy Chain Consensus Sequences
<220> FEATURE:
<221> NAME/KEY: misc_feature
<222> LOCATION: (70)..(70)
<223> OTHER INFORMATION: Xaa = Phe or Met
<220> FEATURE:
<221> NAME/KEY: misc_feature
<222> LOCATION: (72)..(72)
<223> OTHER INFORMATION: Xaa = Thr or Leu

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Xaa Thr Xaa Asp Thr Ser Thr Ser Thr Ala Tyr
65                  70                  75                  80

Met Glu Leu Arg Ser Leu Arg Ser Asp Asp Met Ala Val Tyr Tyr Cys
                85                  90                  95

Ala Arg Lys Ser Thr Val Val Ser Arg Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                     325                 330                 335
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 117
<211> LENGTH: 450
<212> TYPE: PRT
<213> ORGANISM: Artificial Sequence
<220> FEATURE:
<223> OTHER INFORMATION: Antibody xAb Heavy Chain

<400> SEQUENCE: 117

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Lys Ser Thr Val Val Ser Arg Tyr Phe Asp Val Trp Gly Ala
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
```

```
                  225                 230                 235                 240
Pro Ser Val Phe Leu Phe Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 118
<211> LENGTH: 214
<212> TYPE: PRT
<213> ORGANISM: Artificial Sequence
<220> FEATURE:
<223> OTHER INFORMATION: Antibody xAb Light Chain

<400> SEQUENCE: 118

Asp Ile Val Leu Thr Gln Ser His Lys Phe Met Ser Thr Ser Val Gly
1               5                   10                  15

Asp Arg Val Ser Ile Thr Cys Lys Ala Ser Gln Asp Val Gly Asp Ala
            20                  25                  30

Val Thr Trp Cys Gln Gln Lys Pro Gly Gln Pro Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Arg Ser Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                130             135             140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

```
<210> SEQ ID NO 119
<211> LENGTH: 360
<212> TYPE: DNA
<213> ORGANISM: Artificial Sequence
<220> FEATURE:
<223> OTHER INFORMATION: Antibody z10 Variable Region VH DNA Sequences

<400> SEQUENCE: 119
caggtgcagc tggtgcagag cggcgctgag gtgaagaagc ccggcgctag cgtgaaggtg    60
agctgcaagg ccagcggcta caccttcacc aactacggca tgaactgggt gaggcaggct   120
cctggacagg gcctggagtg gatgggctgg atcaacacat acaccggcga gcccacctac   180
gccgacgact tcaagggcag ggtgaccttt accaccgaca ccagcaccag caccgcctac   240
atggagctga ggagcctgag aagcgacgac atggccgtgt actactgcgc cagaaagagc   300
accgtggtgt ccaggtactt cgacgtgtgg ggccagggca ccacagtgac cgtgagcagc   360

<210> SEQ ID NO 120
<211> LENGTH: 321
<212> TYPE: DNA
<213> ORGANISM: Artificial Sequence
<220> FEATURE:
<223> OTHER INFORMATION: Antibody z10/z11/z13 Variable Region VL DNA
      Sequences

<400> SEQUENCE: 120
gacatccaga tgacccagag ccccagcttc ctgtccgcta gcgtgggcga cagggtgacc    60
atcacctgca aggccagcca ggacgtgggc gatgccgtga cctggtatca gcagaagccc   120
ggcaaggccc ccaagctgct gatctactgg gccagcacaa ggcacacagg cgtgcccgac   180
agattcagcg gcagcggaag cggcaccgac ttcaccctga ccatcagcag cctgcagccc   240
gaggacttcg ccacctacta ctgccagcag tacaggagct accccctgac cttcggccag   300
ggcaccaagc tggaaatcaa g                                             321

<210> SEQ ID NO 121
<211> LENGTH: 360
<212> TYPE: DNA
<213> ORGANISM: Artificial Sequence
<220> FEATURE:
<223> OTHER INFORMATION: Antibody z11 Variable Region VH DNA Sequences

<400> SEQUENCE: 121
caggtgcagc tggtgcagag cggagccgag gtgaagaagc ctggcgccag cgtgaaggtg    60
agctgcaagg ccagcggcta caccttcacc aactacggca tgaactgggt gaggcaggct   120
cctggccagg gactggagtg gatgggctgg atcaacacct acaccggcga gcccacctac   180
gccgacgact tcaagggcag ggtgaccatg accctggaca ccagcaccag caccgcctac   240
```

```
atggagctga ggagcctgag gagcgacgac atggccgtgt actactgcgc caggaagagc    300
accgtggtgt ccaggtactt cgacgtgtgg ggacagggca ccaccgtgac cgtgagcagc    360
```

<210> SEQ ID NO 122
<211> LENGTH: 360
<212> TYPE: DNA
<213> ORGANISM: Artificial Sequence
<220> FEATURE:
<223> OTHER INFORMATION: Antibody z13 Variable Region VH DNA Sequences

<400> SEQUENCE: 122

```
caggtgcagc tggtgcagag cggagccgaa gtgaagaagc ccggcgccag cgtgaaggtg    60
agctgcaagg ccagcggcta caccttcacc aactacggca tgaactgggt gagacaggcc   120
cctggacagg gactggagtg gatgggctgg atcaacacct acaccggcga gcccacctac   180
gccgacgact tcaagggcag ggtgaccttc accctggaca ccagcaccag caccgcctac   240
atggagctga ggagcctgag gagcgacgac atggccgtgt actattgcgc caggaagagc   300
accgtggtga gcaggtactt cgacgtgtgg ggccagggaa ccaccgtgac cgtgagcagc   360
```

<210> SEQ ID NO 123
<211> LENGTH: 360
<212> TYPE: DNA
<213> ORGANISM: Artificial Sequence
<220> FEATURE:
<223> OTHER INFORMATION: Antibody xAb Variable Region VH DNA Sequences

<400> SEQUENCE: 123

```
cagatccagt tggtgcagtc tggacctgag ctgaagaagc ctggagagac agtcaagatc    60
tcctgcaagg cttctggata taccttcaca aactatggaa tgaactgggt gaagcaggct   120
ccaggaaagg gtttaaagtg gatgggctgg ataaacacct acactggaga gccaacatat   180
gctgatgact tcaagggacg gtttgtcttc tctttggaaa cctctgccag cactgcctac   240
ttgcagatca acaacctcaa aaatgaggac atggccacat atttctgtgc aagaaaaagt   300
acggtagtaa gtaggtactt cgatgtctgg ggcgcaggga ccacggtcac cgtctcctca   360
```

<210> SEQ ID NO 124
<211> LENGTH: 321
<212> TYPE: DNA
<213> ORGANISM: Artificial Sequence
<220> FEATURE:
<223> OTHER INFORMATION: Antibody xAb Variable Region VL DNA Sequences

<400> SEQUENCE: 124

```
gacattgtgc tgacccagtc tcacaaattc atgtccacat cagtaggaga cagggtcagc    60
atcacctgca aggccagtca ggatgtgggt gatgctgtaa cctggtgtca acagaaacca   120
ggtcaacctc ctaaactact gatttactgg gcatccaccc ggcacactgg agtccctgat   180
cgcttcacag gcagtgggtc tgggacagat ttcactctca ccattaacaa tgtgcagtct   240
gaggacttgg cagattattt ctgtcagcaa tatcgcagct atcctctcac gttcggtgct   300
gggaccaagc tggagctgaa a                                              321
```

<210> SEQ ID NO 125
<211> LENGTH: 1353
<212> TYPE: DNA
<213> ORGANISM: Artificial Sequence
<220> FEATURE:
<223> OTHER INFORMATION: Antibody z10 Heavy Chain DNA Sequences

<400> SEQUENCE: 125

```
caggtgcagc tggtgcagag cggcgctgag gtgaagaagc ccggcgctag cgtgaaggtg      60
agctgcaagg ccagcggcta caccttcacc aactacggca tgaactgggt gaggcaggct     120
cctggacagg gcctggagtg gatgggctgg atcaacacat acaccggcga gcccacctac     180
gccgacgact tcaagggcag ggtgaccttt accaccgaca ccagcaccag caccgcctac     240
atggagctga ggagcctgag aagcgacgac atggccgtgt actactgcgc cagaaagagc     300
accgtggtgt ccaggtactt cgacgtgtgg ggccagggca ccacagtgac cgtgagcagc     360
gcgtcgacca agggcccatc cgtcttcccc ctggcaccct cctccaagag cacctctggg     420
ggcacagcgg ccctgggctg cctggtcaag gactacttcc ccgaaccggt gacggtgtcc     480
tggaactcag gcgctctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtctacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagct taagcctgtc tccgggtaaa tga                                 1353
```

<210> SEQ ID NO 126
<211> LENGTH: 645
<212> TYPE: DNA
<213> ORGANISM: Artificial Sequence
<220> FEATURE:
<223> OTHER INFORMATION: Antibody z10/z11/z13 Light Chain DNA Sequences

<400> SEQUENCE: 126

```
gacatccaga tgacccagag ccccagcttc ctgtccgcta gcgtgggcga cagggtgacc      60
atcacctgca aggccagcca ggacgtgggc gatgccgtga cctggtatca gcagaagccc     120
ggcaaggccc ccaagctgct gatctactgg gccagcacaa ggcacacagg cgtgcccgac     180
agattcagcg gcagcggaag cggcaccgac ttcaccctga ccatcagcag cctgcagccc     240
gaggacttcg ccacctacta ctgccagcag tacaggagct accccctgac cttcggccag     300
ggcaccaagc tggaaatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttga                    645
```

<210> SEQ ID NO 127
<211> LENGTH: 1353
<212> TYPE: DNA
<213> ORGANISM: Artificial Sequence
<220> FEATURE:
<223> OTHER INFORMATION: Antibody z11 Heavy Chain DNA Sequences

<400> SEQUENCE: 127

```
caggtgcagc tggtgcagag cggagccgag gtgaagaagc tggcgccag cgtgaaggtg      60 agctgcaagg ccagcggcta caccttcacc aactacggca tgaactgggt gaggcaggct    120
cctggccagg gactggagtg gatgggctgg atcaacacct acaccggcga gcccacctac    180
gccgacgact tcaagggcag ggtgaccatg accctggaca ccagcaccag caccgcctac    240
atggagctga ggagcctgag gagcgacgac atggccgtgt actactgcgc caggaagagc    300
accgtggtgt ccaggtactt cgacgtgtgg ggacagggca ccaccgtgac cgtgagcagc    360
gcgtcgacca agggcccatc cgtcttcccc ctggcaccct cctccaagag cacctctggg    420
ggcacagcgg ccctgggctg cctggtcaag gactacttcc ccgaaccggt gacggtgtcc    480
tggaactcag gcgctctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggagga gcagtacaac    900 agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtctacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagct taagcctgtc tccgggtaaa tga                                 1353
```

<210> SEQ ID NO 128
<211> LENGTH: 1353
<212> TYPE: DNA
<213> ORGANISM: Artificial Sequence
<220> FEATURE:
<223> OTHER INFORMATION: Antibody z13 Heavy Chain DNA Sequences

<400> SEQUENCE: 128

```
caggtgcagc tggtgcagag cggagccgaa gtgaagaagc ccggcgccag cgtgaaggtg      60
agctgcaagg ccagcggcta caccttcacc aactacggca tgaactgggt gagacaggcc    120
cctggacagg gactggagtg gatgggctgg atcaacacct acaccggcga gcccacctac    180
gccgacgact tcaagggcag ggtgaccttc accctggaca ccagcaccag caccgcctac    240
atggagctga ggagcctgag gagcgacgac atggccgtgt actattgcgc caggaagagc    300
accgtggtga gcaggtactt cgacgtgtgg ggccagggaa ccaccgtgac cgtgagcagc    360
```

| | |
|---|---|
| gcgtcgacca agggcccatc cgtcttcccc ctggcaccct cctccaagag cacctctggg | 420 |
| ggcacagcgg ccctgggctg cctggtcaag gactacttcc ccgaaccggt gacggtgtcc | 480 |
| tggaactcag gcgctctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttgagccc | 660 |
| aaatcttgtg acaaaactca cacatgccca ccgtgcccag cacctgaact cctggggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtctacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagct taagcctgtc tccgggtaaa tga | 1353 |

<210> SEQ ID NO 129
<211> LENGTH: 1353
<212> TYPE: DNA
<213> ORGANISM: Artificial Sequence
<220> FEATURE:
<223> OTHER INFORMATION: Antibody xAb Heavy Chain DNA Sequences

<400> SEQUENCE: 129

| | |
|---|---|
| cagatccagt tggtgcagtc tggacctgag ctgaagaagc ctggagagac agtcaagatc | 60 |
| tcctgcaagg cttctggata taccttcaca aactatggaa tgaactgggt gaagcaggct | 120 |
| ccaggaaagg gtttaaagtg gatgggctgg ataaacacct acactggaga gccaacatat | 180 |
| gctgatgact tcaagggacg gtttgtcttc tctttggaaa cctctgccag cactgcctac | 240 |
| ttgcagatca caaacctcaa aaatgaggac atggccacat atttctgtgc aagaaaaagt | 300 |
| acggtagtaa gtaggtactt cgatgtctgg ggcgcaggga ccacggtcac cgtctcctca | 360 |
| gcgtcgacca agggcccatc cgtcttcccc ctggcaccct cctccaagag cacctctggg | 420 |
| ggcacagcgg ccctgggctg cctggtcaag gactacttcc ccgaaccggt gacggtgtcc | 480 |
| tggaactcag gcgctctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttgagccc | 660 |
| aaatcttgtg acaaaactca cacatgccca ccgtgcccag cacctgaact cctggggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtctacaccc tgcccccatc ccgggaggag | 1080 |

| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagct taagcctgtc tccgggtaaa tga | 1353 |

<210> SEQ ID NO 130
<211> LENGTH: 645
<212> TYPE: DNA
<213> ORGANISM: Artificial Sequence
<220> FEATURE:
<223> OTHER INFORMATION: Antibody xAb Light Chain DNA Sequences

<400> SEQUENCE: 130

| gacattgtgc tgacccagtc tcacaaattc atgtccacat cagtaggaga cagggtcagc | 60 |
| atcacctgca aggccagtca ggatgtgggt gatgctgtaa cctggtgtca acagaaacca | 120 |
| ggtcaacctc ctaaactact gatttactgg gcatccaccc ggcacactgg agtccctgat | 180 |
| cgcttcacag gcagtgggtc tgggacagat ttcactctca ccattaacaa tgtgcagtct | 240 |
| gaggacttgg cagattattt ctgtcagcaa tatcgcagct atcctctcac gttcggtgct | 300 |
| gggaccaagc tggagctgaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaacacaaa gtctacgcct gcgaagtcac ccatcagggc | 600 |
| ctgagctcgc ccgtcacaaa gagcttcaac aggggagagt gttga | 645 |

<210> SEQ ID NO 131
<211> LENGTH: 999
<212> TYPE: PRT
<213> ORGANISM: Homo sapiens
<220> FEATURE:
<223> OTHER INFORMATION: Full-Length Human MERTK (Swiss-Prot ID: Q12866.2)

<400> SEQUENCE: 131

Met Gly Pro Ala Pro Leu Pro Leu Leu Leu Gly Leu Phe Leu Pro Ala
1               5                   10                  15

Leu Trp Arg Arg Ala Ile Thr Glu Ala Arg Glu Glu Ala Lys Pro Tyr
            20                  25                  30

Pro Leu Phe Pro Gly Pro Phe Pro Gly Ser Leu Gln Thr Asp His Thr
        35                  40                  45

Pro Leu Leu Ser Leu Pro His Ala Ser Gly Tyr Gln Pro Ala Leu Met
    50                  55                  60

Phe Ser Pro Thr Gln Pro Gly Arg Pro His Thr Gly Asn Val Ala Ile
65                  70                  75                  80

Pro Gln Val Thr Ser Val Glu Ser Lys Pro Leu Pro Pro Leu Ala Phe
                85                  90                  95

Lys His Thr Val Gly His Ile Ile Leu Ser Glu His Lys Gly Val Lys
            100                 105                 110

Phe Asn Cys Ser Ile Ser Val Pro Asn Ile Tyr Gln Asp Thr Thr Ile
        115                 120                 125

Ser Trp Trp Lys Asp Gly Lys Glu Leu Leu Gly Ala His His Ala Ile

```
              130                 135                 140
Thr Gln Phe Tyr Pro Asp Asp Glu Val Thr Ala Ile Ile Ala Ser Phe
145                 150                 155                 160

Ser Ile Thr Ser Val Gln Arg Ser Asp Asn Gly Ser Tyr Ile Cys Lys
                165                 170                 175

Met Lys Ile Asn Asn Glu Glu Ile Val Ser Asp Pro Ile Tyr Ile Glu
            180                 185                 190

Val Gln Gly Leu Pro His Phe Thr Lys Gln Pro Glu Ser Met Asn Val
        195                 200                 205

Thr Arg Asn Thr Ala Phe Asn Leu Thr Cys Gln Ala Val Gly Pro Pro
    210                 215                 220

Glu Pro Val Asn Ile Phe Trp Val Gln Asn Ser Ser Arg Val Asn Glu
225                 230                 235                 240

Gln Pro Glu Lys Ser Pro Ser Val Leu Thr Val Pro Gly Leu Thr Glu
                245                 250                 255

Met Ala Val Phe Ser Cys Glu Ala His Asn Asp Lys Gly Leu Thr Val
            260                 265                 270

Ser Lys Gly Val Gln Ile Asn Ile Lys Ala Ile Pro Ser Pro Pro Thr
        275                 280                 285

Glu Val Ser Ile Arg Asn Ser Thr Ala His Ser Ile Leu Ile Ser Trp
    290                 295                 300

Val Pro Gly Phe Asp Gly Tyr Ser Pro Phe Arg Asn Cys Ser Ile Gln
305                 310                 315                 320

Val Lys Glu Ala Asp Pro Leu Ser Asn Gly Ser Val Met Ile Phe Asn
                325                 330                 335

Thr Ser Ala Leu Pro His Leu Tyr Gln Ile Lys Gln Leu Gln Ala Leu
            340                 345                 350

Ala Asn Tyr Ser Ile Gly Val Ser Cys Met Asn Glu Ile Gly Trp Ser
        355                 360                 365

Ala Val Ser Pro Trp Ile Leu Ala Ser Thr Thr Glu Gly Ala Pro Ser
    370                 375                 380

Val Ala Pro Leu Asn Val Thr Val Phe Leu Asn Glu Ser Ser Asp Asn
385                 390                 395                 400

Val Asp Ile Arg Trp Met Lys Pro Pro Thr Lys Gln Gln Asp Gly Glu
                405                 410                 415

Leu Val Gly Tyr Arg Ile Ser His Val Trp Gln Ser Ala Gly Ile Ser
            420                 425                 430

Lys Glu Leu Leu Glu Glu Val Gly Gln Asn Gly Ser Arg Ala Arg Ile
        435                 440                 445

Ser Val Gln Val His Asn Ala Thr Cys Thr Val Arg Ile Ala Ala Val
    450                 455                 460

Thr Arg Gly Gly Val Gly Pro Phe Ser Asp Pro Val Lys Ile Phe Ile
465                 470                 475                 480

Pro Ala His Gly Trp Val Asp Tyr Ala Pro Ser Ser Thr Pro Ala Pro
                485                 490                 495

Gly Asn Ala Asp Pro Val Leu Ile Ile Phe Gly Cys Phe Cys Gly Phe
            500                 505                 510

Ile Leu Ile Gly Leu Ile Leu Tyr Ile Ser Leu Ala Ile Arg Lys Arg
        515                 520                 525

Val Gln Glu Thr Lys Phe Gly Asn Ala Phe Thr Glu Glu Asp Ser Glu
    530                 535                 540

Leu Val Val Asn Tyr Ile Ala Lys Lys Ser Phe Cys Arg Arg Ala Ile
545                 550                 555                 560
```

```
Glu Leu Thr Leu His Ser Leu Gly Val Ser Glu Leu Gln Asn Lys
                565                 570                 575
Leu Glu Asp Val Val Ile Asp Arg Asn Leu Leu Ile Leu Gly Lys Ile
            580                 585                 590
Leu Gly Glu Gly Glu Phe Gly Ser Val Met Glu Gly Asn Leu Lys Gln
            595                 600                 605
Glu Asp Gly Thr Ser Leu Lys Val Ala Val Lys Thr Met Lys Leu Asp
610                 615                 620
Asn Ser Ser Gln Arg Glu Ile Glu Glu Phe Leu Ser Glu Ala Ala Cys
625                 630                 635                 640
Met Lys Asp Phe Ser His Pro Asn Val Ile Arg Leu Leu Gly Val Cys
                645                 650                 655
Ile Glu Met Ser Ser Gln Gly Ile Pro Lys Pro Met Val Ile Leu Pro
                660                 665                 670
Phe Met Lys Tyr Gly Asp Leu His Thr Tyr Leu Leu Tyr Ser Arg Leu
                675                 680                 685
Glu Thr Gly Pro Lys His Ile Pro Leu Gln Thr Leu Leu Lys Phe Met
            690                 695                 700
Val Asp Ile Ala Leu Gly Met Glu Tyr Leu Ser Asn Arg Asn Phe Leu
705                 710                 715                 720
His Arg Asp Leu Ala Ala Arg Asn Cys Met Leu Arg Asp Asp Met Thr
                725                 730                 735
Val Cys Val Ala Asp Phe Gly Leu Ser Lys Lys Ile Tyr Ser Gly Asp
                740                 745                 750
Tyr Tyr Arg Gln Gly Arg Ile Ala Lys Met Pro Val Lys Trp Ile Ala
            755                 760                 765
Ile Glu Ser Leu Ala Asp Arg Val Tyr Thr Ser Lys Ser Asp Val Trp
            770                 775                 780
Ala Phe Gly Val Thr Met Trp Glu Ile Ala Thr Arg Gly Met Thr Pro
785                 790                 795                 800
Tyr Pro Gly Val Gln Asn His Glu Met Tyr Asp Tyr Leu Leu His Gly
                805                 810                 815
His Arg Leu Lys Gln Pro Glu Asp Cys Leu Asp Glu Leu Tyr Glu Ile
                820                 825                 830
Met Tyr Ser Cys Trp Arg Thr Asp Pro Leu Asp Arg Pro Thr Phe Ser
                835                 840                 845
Val Leu Arg Leu Gln Leu Glu Lys Leu Leu Glu Ser Leu Pro Asp Val
850                 855                 860
Arg Asn Gln Ala Asp Val Ile Tyr Val Asn Thr Gln Leu Leu Glu Ser
865                 870                 875                 880
Ser Glu Gly Leu Ala Gln Gly Ser Thr Leu Ala Pro Leu Asp Leu Asn
                885                 890                 895
Ile Asp Pro Asp Ser Ile Ile Ala Ser Cys Thr Pro Arg Ala Ala Ile
                900                 905                 910
Ser Val Val Thr Ala Glu Val His Asp Ser Lys Pro His Glu Gly Arg
            915                 920                 925
Tyr Ile Leu Asn Gly Gly Ser Glu Glu Trp Glu Asp Leu Thr Ser Ala
            930                 935                 940
Pro Ser Ala Ala Val Thr Ala Glu Lys Asn Ser Val Leu Pro Gly Glu
945                 950                 955                 960
Arg Leu Val Arg Asn Gly Val Ser Trp Ser His Ser Ser Met Leu Pro
                965                 970                 975
```

-continued

Leu Gly Ser Ser Leu Pro Asp Glu Leu Phe Ala Asp Ser Ser
                980             985             990

Glu Gly Ser Glu Val Leu Met
        995

<210> SEQ ID NO 132
<211> LENGTH: 474
<212> TYPE: PRT
<213> ORGANISM: Artificial Sequence
<220> FEATURE:
<223> OTHER INFORMATION: Extracellular Doman of MERTK Used for
      Immunization

<400> SEQUENCE: 132

Arg Glu Glu Ala Lys Pro Tyr Pro Leu Phe Pro Gly Pro Phe Pro Gly
1               5                   10                  15

Ser Leu Gln Thr Asp His Thr Pro Leu Leu Ser Leu Pro His Ala Ser
            20                  25                  30

Gly Tyr Gln Pro Ala Leu Met Phe Ser Pro Thr Gln Pro Gly Arg Pro
        35                  40                  45

His Thr Gly Asn Val Ala Ile Pro Gln Val Thr Ser Val Glu Ser Lys
    50                  55                  60

Pro Leu Pro Pro Leu Ala Phe Lys His Thr Val Gly His Ile Ile Leu
65                  70                  75                  80

Ser Glu His Lys Gly Val Lys Phe Asn Cys Ser Ile Ser Val Pro Asn
                85                  90                  95

Ile Tyr Gln Asp Thr Thr Ile Ser Trp Trp Lys Asp Gly Lys Glu Leu
            100                 105                 110

Leu Gly Ala His His Ala Ile Thr Gln Phe Tyr Pro Asp Asp Glu Val
        115                 120                 125

Thr Ala Ile Ile Ala Ser Phe Ser Ile Thr Ser Val Gln Arg Ser Asp
    130                 135                 140

Asn Gly Ser Tyr Ile Cys Lys Met Lys Ile Asn Asn Glu Glu Ile Val
145                 150                 155                 160

Ser Asp Pro Ile Tyr Ile Glu Val Gln Gly Leu Pro His Phe Thr Lys
                165                 170                 175

Gln Pro Glu Ser Met Asn Val Thr Arg Asn Thr Ala Phe Asn Leu Thr
            180                 185                 190

Cys Gln Ala Val Gly Pro Pro Glu Pro Val Asn Ile Phe Trp Val Gln
        195                 200                 205

Asn Ser Ser Arg Val Asn Glu Gln Pro Glu Lys Ser Pro Ser Val Leu
    210                 215                 220

Thr Val Pro Gly Leu Thr Glu Met Ala Val Phe Ser Cys Glu Ala His
225                 230                 235                 240

Asn Asp Lys Gly Leu Thr Val Ser Lys Gly Val Gln Ile Asn Ile Lys
                245                 250                 255

Ala Ile Pro Ser Pro Pro Thr Glu Val Ser Ile Arg Asn Ser Thr Ala
            260                 265                 270

His Ser Ile Leu Ile Ser Trp Val Pro Gly Phe Asp Gly Tyr Ser Pro
        275                 280                 285

Phe Arg Asn Cys Ser Ile Gln Val Lys Glu Ala Asp Pro Leu Ser Asn
    290                 295                 300

Gly Ser Val Met Ile Phe Asn Thr Ser Ala Leu Pro His Leu Tyr Gln
305                 310                 315                 320

Ile Lys Gln Leu Gln Ala Leu Ala Asn Tyr Ser Ile Gly Val Ser Cys
                325                 330                 335

```
Met Asn Glu Ile Gly Trp Ser Ala Val Ser Pro Trp Ile Leu Ala Ser
            340                 345                 350
Thr Thr Glu Gly Ala Pro Ser Val Ala Pro Leu Asn Val Thr Val Phe
            355                 360                 365
Leu Asn Glu Ser Ser Asp Asn Val Asp Ile Arg Trp Met Lys Pro Pro
    370                 375                 380
Thr Lys Gln Gln Asp Gly Glu Leu Val Gly Tyr Arg Ile Ser His Val
385                 390                 395                 400
Trp Gln Ser Ala Gly Ile Ser Lys Glu Leu Leu Glu Glu Val Gly Gln
                405                 410                 415
Asn Gly Ser Arg Ala Arg Ile Ser Val Gln Val His Asn Ala Thr Cys
            420                 425                 430
Thr Val Arg Ile Ala Ala Val Thr Arg Gly Gly Val Gly Pro Phe Ser
            435                 440                 445
Asp Pro Val Lys Ile Phe Ile Pro Ala His Gly Trp Val Asp Tyr Ala
    450                 455                 460
Pro Ser Ser Thr Pro Ala Pro Gly Asn Ala
465                 470
```

HIGH-AFFINITY ANTI-MERTK ANTIBODIES AND USES THEREOF

This application claims the benefit of U.S. Provisional Application No. 62/810,841, filed Feb. 26, 2019, which is incorporated by reference herein in its entirety.

1. FIELD

This application incorporates by reference a Sequence Listing submitted with this application as a text file in ASCII format entitled "13256-008-999_SEQ_LISTING.txt" created on Feb. 19, 2020 and having a size of 94,274 bytes.

The present disclosure provides antibodies (e.g., humanized antibodies) that specifically bind to Mer Tyrosine Kinase (MERTK; e.g., human MERTK) and compositions comprising such antibodies. The present disclosure also provides antibody-drug conjugates comprising (i) an anti-MERTK antibody or antigen-binding fragment thereof described herein that specifically binds to MERTK (e.g., human MERTK), and (ii) cytotoxic agents conjugated directly to the antibodies or conjugated to the antibodies via linkers, and compositions comprising such antibody-drug conjugates. The present disclosure also provides methods for treating cancer, comprising administering to a human subject in need thereof (a) an anti-MERTK antibody that specifically binds to MERTK (e.g., human MERTK) or an antigen-binding fragment thereof described herein, or (b) an antibody-drug conjugate that comprises (i) an anti-MERTK antibody or antigen-binding fragment thereof that specifically binds to MERTK (e.g., human MERTK), and (ii) a cytotoxic agent conjugated directly to the antibody or conjugated to the antibody via a linker.

2. BACKGROUND

Mer Tyrosine Kinase (MERTK), also referred to as c-mer, MER, Proto-oncogene c-Mer, Receptor Tyrosine Kinase MerTK, Tyrosine-protein Kinase Mer, STK Kinase, RP38, or MGC133349, is a member of the TAM family of receptor tyrosine kinases, which also include AXL and TYRO3 kinases. MERTK transduces signals from the extracellular space via activation by binding of ligands, most notably Gas-6, a soluble protein. Gas-6 binding to MERTK induces autophosphorylation of MERTK on its intracellular domain, resulting in downstream signal activation (Cummings C T et al., (2013) Clin Cancer Res 19: 5275-5280; Verma A et al., (2011) Mol Cancer Ther 10: 1763-1773).

MERTK exists in both membrane bound and soluble forms. The extracellular domain can be cleaved to generate a soluble extracellular domain, which is hypothesized to act as a decoy receptor to negatively regulate MERTK receptor activation on cells by reducing the ability and/or availability of soluble Gas-6 ligand to bind membrane-bound MERTK (Sather S et al., (2007) Blood 109: 1026-1033). As a result MERTK has dual roles related to cancer progression, angiogenesis, and metastasis. On the one hand, Gas-6 activation of MERTK on endothelial cells results in inhibition of endothelial cell recruitment by cancer cells in a co-culture system. Endothelial recruitment is a key feature of cancer cells that allows for tumor angiogenesis, tumor growth, and metastasis. Downregulation of MERTK on metastatic breast cancer cells was also shown to inhibit endothelial recruitment (Png K J et al., (2012) Nature 481: 190-194). However, on the other hand, MERTK plays an opposite role in cancer cells, where its over-expression leads to increased metastasis, likely by releasing cleaved MERTK to generate soluble MERTK extracellular domain protein as a decoy receptor. Additionally, ligand-dependent MERTK activation on cancer cells stimulates oncogenic pathways, including the AKT pathway (Linger R M, Cohen R A, Cummings C T, Sather S, Migdall-Wilson J, Middleton D H, Lu X, Barón A E, Franklin W A, Merrick D T, Jedlicka P, DeRyckere D, Heasley L E, Graham D K. Mer or Axl receptor tyrosine kinase inhibition promotes apoptosis, blocks growth and enhances chemosensitivity of human non-small cell lung cancer (Oncogene. 2013 Jul. 18; 32(29):3420-31). Thus, tumor cells overexpress MERTK to promote oncogenic signaling. Also, tumors cells secrete a soluble form of the extracellular MERTK receptor that acts as a decoy receptor to reduce the ability (and/or availability) of soluble Gas-6 ligand to activate MERTK on endothelial cells, ultimately leading to endothelial recruitment, angiogenesis, and cancer progression (Png K J et al., (2012) Nature 481: 190-194).

MERTK is also involved in modulating macrophage homeostasis and the maintenance of anti-inflammatory conditions. On macrophages, MERTK mediates phagocytotic clearance of apoptotic cells and the release of IL-10 and acute inflammatory cytokines, whose expression are stimulated by Gas6-dependent binding to MERTK (Zizzo et al., (2012) J. Immunology October 1; 189(7):3508-20; Cook et al., *J Clin Invest.* 2013; 123(8):3231-3242).

Historically, there have been efforts to generate inhibitors, of MERTK for the treatment of cancer (e.g., compound UNC1062, a potent small molecule MERTK inhibitor developed as an anticancer compound), because MERTK was thought to solely function as an oncogene (Liu J et al., (2013) Eur J Med Chem 65: 83-93; Cummings C T et al., (2013) Clin Cancer Res 19: 5275-5280; Verma A et al., (2011) Mol Cancer Ther 10: 1763-1773). In recent years, antibody-drug conjugates (ADCs) have become one of the fastest growing classes of cancer therapeutics (Beck A et al., (2017) Nat Rev Drug Discov 16: 315-337; Peters C and Brown S, (2015) Biosci Rep 35: art:e00225).

Citation of a reference herein shall not be construed as an admission that such is prior art to the present disclosure.

3. SUMMARY

Disclosed herein are antibodies and antigen-binding fragments thereof that specifically bind to MERTK (e.g., human MERTK) with high affinity. In a specific embodiment of any of the antibodies or antigen-binding fragments thereof described herein, the antibody specifically recognizes the extracellular domain of MERTK (e.g., human MERTK), and the extracellular domain comprises the amino acid sequence of SEQ ID NO: 132

In a specific embodiment, an anti-MERTK antibody or an antigen-binding fragment thereof specifically binds to MERTK (e.g., human MERTK) and leads to internalization of MERTK from the cell surface. In a specific embodiment, an anti-MERTK antibody or antigen-binding fragment thereof blocks Gas-6 induced AKT phosphorylation. In another specific embodiment, an anti-MERTK antibody or an antigen-binding fragment thereof prevents MERTK activation. In another specific embodiment, an anti-MERTK antibody or antigen-binding fragment thereof described herein specifically recognizes the extracellular portion of human MERTK. In another specific embodiment, an anti-MERTK antibody or antigen-binding fragment thereof reduces colony formation by cancer cells. In a particular embodiment, an anti-MERTK antibody or antigen-binding fragment described herein is monoclonal. In another particular embodiment, an anti-MERTK antibody or antigen-binding fragment thereof described herein is an immunoglobulin comprising two identical light chains and two identical heavy chains. In a specific embodiment, an anti-MERTK antibody is a humanized antibody.

In a particular embodiment, an anti-MERTK antibody or an antigen-binding fragment thereof described herein, which specifically binds to MERTK (e.g., human MERTK), comprises a heavy chain variable region (VH) comprising the amino acid sequence of SEQ ID NO: 105.

In another particular embodiment, an anti-MERTK antibody or an antigen-binding fragment thereof described herein, which specifically binds to MERTK (e.g., human MERTK), comprises a heavy chain variable region (VH) comprising the amino acid sequence of SEQ ID NO: 107.

In another particular embodiment, an anti-MERTK antibody or an antigen-binding fragment thereof described herein, which specifically binds to MERTK (e.g., human MERTK), comprises a heavy chain variable region (VH) comprising the amino acid sequence of SEQ ID NO: 108.

In another particular embodiment, an anti-MERTK antibody or an antigen-binding fragment thereof, which specifically binds to MERTK (e.g., human MERTK) comprises a heavy chain variable region (VH) comprising the amino acid sequence of SEQ ID NO: 109.

In another particular embodiment, an anti-MERTK antibody or an antigen-binding fragment thereof described herein, which specifically binds to MERTK (e.g., human MERTK), comprises a heavy chain variable region (VH) comprising the amino acid sequence of SEQ ID NO: 110.

In another embodiment, an anti-MERTK antibody or an antigen-binding fragment thereof described herein, which specifically binds to MERTK (e.g., human MERTK), comprises a light chain variable region (VL) comprising the amino acid sequence of SEQ ID NO: 106. In another particular embodiment, an anti-MERTK antibody or an antigen-binding fragment thereof described herein, which specifically binds to MERTK (e.g., human MERTK), comprises a light chain variable region (VL) comprising the amino acid sequence of SEQ ID NO: 111.

In another embodiment, an anti-MERTK antibody or an antigen-binding fragment thereof, which specifically binds to MERTK (e.g., human MERTK), comprises (a) a VH comprising the amino acid sequence of SEQ ID NO: 105 and (b) a VL comprising the amino acid sequence of SEQ ID NO: 106. In another embodiment, an anti-MERTK antibody or an antigen-binding fragment thereof, which specifically binds to MERTK (e.g., human MERTK), comprises (a) a VH comprising the amino acid sequence of SEQ ID NO: 107 and (b) a VL comprising the amino acid sequence of SEQ ID NO: 106. In another embodiment, an anti-MERTK antibody or the antigen-binding fragment thereof, which specifically binds to MERTK (e.g., human MERTK), comprises (a) a VH comprising the amino acid sequence of SEQ ID NO: 108 and (b) a VL comprising the amino acid sequence of SEQ ID NO: 106. In another embodiment, an anti-MERTK antibody or an antigen-binding fragment thereof which specifically binds to MERTK (e.g. human MERTK), comprises (a) a VH comprising the amino acid sequence of SEQ ID NO: 109 and (b) a VL comprising the amino acid sequence of SEQ ID NO: 106. In another embodiment, an anti-MERTK antibody or antigen-binding fragment thereof, which specifically binds to MERTK (e.g., human MERTK), comprises (a) a VH comprising the amino acid sequence of SEQ ID NO: 110 and (b) a VL comprising the amino acid sequence of SEQ ID NO: 111.

In certain embodiments, an antibody provided herein, which specifically binds to MERTK (e.g., human MERTK), comprises heavy chain constant regions, or light chain constant regions, or both. In some embodiments, the heavy chain constant region is selected from the group of human immunoglobulins consisting of IgG$_1$, IgG$_2$, IgG$_3$, IgG$_4$, IgA$_1$, and IgA$_2$. In certain embodiments, the light chain constant region is selected from the group of human immunoglobulins consisting of IgGκ and IgGλ. In some embodiments, the antibody comprises a constant region having increased binding affinity to one or more human Fc gamma receptor(s).

In some embodiments, the antibody comprises a constant region having decreased binding affinity to one or more human Fc gamma receptor(s).

In a specific embodiment of the embodiment wherein the antibody is an immunoglobulin comprising two identical light chains and two identical heavy chains, each of the heavy chains comprises a variable region (VH), which comprises the amino acid sequence of SEQ ID: 105. In one further embodiment of such a specific embodiment, each of the light chains comprises a variable region (VL), which comprises the amino acid of SEQ ID NO: 106

In a specific embodiment of the embodiment wherein the antibody is an immunoglobulin comprising two identical light chains and two identical heavy chains, each of the heavy chains comprises a variable region (VH) which comprises the amino acid of SEQ ID NO: 107. In one further embodiment of such a specific embodiment, each of the light chains comprises a variable region (VL) comprising the amino acid sequence of SEQ ID NO: 106.

In a specific embodiment of the embodiment wherein the antibody is an immunoglobulin comprising two identical light chains and two identical heavy chains, each of the heavy chains comprises a variable region (VH) comprising the amino acid sequence of SEQ ID NO: 108. In one further embodiment of such a specific embodiment, each of the light chains comprises a variable region (VL), comprising the amino acid sequence of SEQ ID NO: 106

In a specific embodiment of the embodiment wherein the antibody is an immunoglobulin comprising two identical light chains and two identical heavy chains, each of the heavy chains comprises a variable region (VH) comprising the amino acid sequence of SEQ ID NO: 110. In one further embodiment of such a specific embodiment, each of the light chains comprises a variable region (VL) comprising the amino acid sequence of SEQ ID: 111.

In a specific embodiment of the embodiment wherein the antibody is an immunoglobulin comprising two identical light chains and two identical heavy chains, each of the heavy chains comprises a variable region (VH) comprising the amino acid sequence of SEQ ID NO: 109. In one further embodiment of such a specific embodiment, each of the light chains comprises a variable region (VL) comprising the amino acid sequence of SEQ ID: 106.

In a specific embodiment of the embodiment wherein the antibody is an immunoglobulin comprising two identical light chains and two identical heavy chains, the light chain comprises a variable region (VL), which comprises SEQ ID NO: 106.

In a specific embodiment of the embodiment wherein the antibody is an immunoglobulin comprising two identical light chains and two identical heavy chains, the light chain comprises a variable region (VL) which comprises SEQ ID NO: 111.

In a specific embodiment of the embodiment wherein the antibody is an immunoglobulin comprising two identical light chains and two identical heavy chains, the heavy chain comprises a variable region (VH), which comprises SEQ ID NO: 105.

In a specific embodiment of the embodiment wherein the antibody is an immunoglobulin comprising two identical light chains and two identical heavy chains, the heavy chain comprises a variable region (VH), which comprises SEQ ID NO: 107.

In a specific embodiment of the embodiment wherein the antibody is an immunoglobulin comprising two identical light chains and two identical heavy chains, the heavy chain comprises a variable region (VH), which comprises SEQ ID NO: 108.

In a specific embodiment of the embodiment wherein the antibody is an immunoglobulin comprising two identical light chains and two identical heavy chains, the heavy chain comprises a variable region (VH) which comprises SEQ ID NO: 109.

In a specific embodiment of the embodiment wherein the antibody is an immunoglobulin comprising two identical light chains and two identical heavy chains, the heavy chain comprises a variable region (VH), which comprises SEQ ID NO: 110.

In a specific embodiment of any of the antibodies or antigen-binding fragments thereof provided herein, wherein the antibody is an immunoglobulin comprising two identical light chains and two identical heavy chains, the antibody or antigen-binding fragment thereof comprises a human-derived constant region. In one further embodiment of such a specific embodiment, the heavy chain constant region has an isotype selected from the group consisting of gamma1, gamma2, gamma3, and gamma4.

In a specific embodiment of any of the antibodies or antigen-binding fragments thereof provided herein, the antibody binds MERTK (e.g., human MERTK) on cells with an EC50 in the range of about 1 nM to 15 nM (e.g., 6.5 nM to 8 nM.)

In a specific embodiment of any of the antibodies or antigen-binding fragments thereof provided herein, the antibody or antigen-binding fragment decreases the expression level of MERTK on cancer cells (e.g. the melanoma cell line SKMEL5). In another specific embodiment of any of the antibodies or antigen-binding fragments thereof provided herein, the antibody or antigen-binding fragment decreases the expression level of MERTK on human M2 macrophages. In another specific embodiment of any of the antibodies or antigen-binding fragments thereof provided herein, the antibody or antigen-binding fragment decreases the level of MERTK on in vitro differentiated human M2 macrophages.

In a specific embodiment of any of the antibodies or antigen-binding fragments thereof provided herein, the antibody or antigen-binding fragment thereof comprises a human-derived constant region. In one further embodiment of such a specific embodiment, the antibody or antigen-binding fragment thereof is a humanized immunoglobulin.

In a specific embodiment of any of the antibodies or antigen-binding fragments thereof provided herein, wherein the antibody is not a monoclonal antibody or an immunoglobulin comprising two identical light chains and two identical heavy chains, the antibody or antigen-binding fragment thereof is a bispecific antibody.

In another aspect, provided herein is an immunoglobulin that specifically binds to MERTK (e.g., human MERTK), comprising (i) a heavy chain variable region that comprises the amino acid sequence of SEQ ID NO: 105, and (ii) a light chain variable region that comprises the amino acid sequence of SEQ ID NO: 106.

In another aspect, provided herein is an immunoglobulin that specifically binds to MERTK (e.g., human MERTK), comprising (i) a heavy chain variable region that comprises the amino acid sequence of SEQ ID NO: 107, and (ii) a light chain variable region that comprises the amino acid sequence of SEQ ID NO: 106.

In another aspect provided herein is an immunoglobulin that specifically binds to MERTK (e.g., human MERTK) comprising (i) a heavy chain variable region that comprises the amino acid sequence of SEQ ID NO: 108, and (ii) a light chain variable region that comprises the amino acid of SEQ ID NO: 106.

In another aspect, provided herein is an immunoglobulin that specifically binds to MERTK (e.g., human MERTK) comprising (i) a heavy chain variable region that comprises the amino acid sequence of SEQ ID NO: 109, and (ii) a light chain variable region that comprises the amino acid sequence of SEQ ID NO: 106.

In another aspect, provided herein is a humanized immunoglobulin that specifically binds to MERTK (e.g., human MERTK), comprising:
(A) (i) a heavy chain variable region that comprises the amino acid sequence of SEQ ID NO: 105, and (ii) a light chain variable region that comprises the amino acid sequence of SEQ ID NO: 106; or
(B) (i) a heavy chain variable region that comprises the amino acid sequence of SEQ ID NO: 107, and (ii) a light chain variable region that comprises the amino acid sequence of SEQ ID NO: 106, or
(C) (i) a heavy chain variable region that comprises the amino acid sequence of SEQ ID NO: 108, and (ii) a light chain variable region that comprises the amino acid sequence of SEQ ID NO: 106, or
(D) (i) a heavy chain variable region that comprises the amino acid sequence of SEQ ID NO: 109, and (ii) a light chain variable region that comprises the amino acid sequence of SEQ ID NO: 106.

In some embodiments, the antibody provided herein is an IgG. In some embodiments, antigen-binding fragment provided herein is an Fab, F(ab')2 or scFv fragment.

In another aspect, provided herein is a chimeric antibody or antigen-binding fragment thereof which binds to MERTK (e.g., human MERTK). In some embodiments, the chimeric antibody comprises a heavy chain variable region (VH) comprising an amino acid of SEQ ID NO: 110. In some embodiments, the chimeric antibody comprises a variable light chain region (VL) comprising an amino acid of SEQ ID NO: 111. In a specific embodiment, the chimeric antibody comprises a VH of SEQ ID NO: 110 and a VL of SEQ ID NO: 111.

In another specific embodiment, the antibody comprises a heavy chain comprising the amino acid sequence of SEQ ID NO: 112, 114, 115, 116 or 117. In another specific embodiment, an anti-MERTK antibody or an antigen-binding fragment thereof, which specifically binds MERTK (e.g. human MERTK) comprises a light chain comprising the amino acid of SEQ ID NO: 113 or 118. In another specific embodiment, an anti-MERTK antibody comprises:
(A) a heavy chain comprising the amino acid of SEQ ID NO: 112 and a light chain comprising the amino acid sequence of SEQ ID NO: 113; or
(B) a heavy chain comprising the amino acid of SEQ ID NO: 114 and a light chain comprising the amino acid sequence of SEQ ID NO: 113; or
(C) a heavy chain comprising the amino acid of SEQ ID NO: 115 and a light chain comprising the amino acid sequence of SEQ ID NO: 113; or (D) a heavy chain comprising the amino acid of SEQ ID NO: 116 and a light chain comprising the amino acid sequence of SEQ ID NO: 113; or (E) a heavy chain comprising the amino acid of SEQ ID NO: 117 and a light chain comprising the amino acid sequence of SEQ ID NO: 113.

In certain embodiments, an anti-MERTK antibody is a bispecific antibody, which comprises two different antigen binding regions, wherein one binding region specifically binds to MERTK (e.g., human MERTK) and the other binding region binds to an antigen of interest (e.g., an immune cell receptor, a checkpoint receptor, or a tumor-associated antigen).

In specific embodiments, the binding region that binds to MERTK comprises the variable regions of the z10, z11 or z13 antibody described herein (e.g. those set forth in Tables 11, 12 and 13 infra). In some specific embodiments, the other binding region of the bispecific antibody binds to CD3. In other specific embodiments, the other binding region of the bispecific antibody binds to PD-L1. In other specific embodiments, the other binding region of the bispecific antibody binds to LRP1. In other specific embodiments, the other binding region of the bispecific antibody binds to LPR8. In other specific embodiments, the other binding region of the bispecific antibody binds to TGF-β. In other specific embodiments, the other binding region of the bispecific antibody binds to ICOS. In other specific embodiments, the other binding region of the bispecific antibody binds to CD40. In other specific embodiments, the other binding region of the bispecific antibody binds to NKGD2. In other specific embodiments, the other binding region of the bispecific antibody binds to TIGIT. In a particular embodiment, the binding region that binds to CD40 is an agonistic antibody. In another particular embodiment, the binding region that binds to ICOS is an agonistic antibody. In another particular embodiment, the binding region that binds to PD-L1 is a blocking antibody.

In another embodiment, provided herein is an anti-MERTK antibody or antigen-binding fragment thereof (e.g, a humanized or human antibody or antigen-binding fragment thereof) that binds to the same epitope of MERTK (e.g., human MERTK) as an anti-MERTK antibody described herein. In another embodiment, provided herein is an anti-MERTK antibody or antigen-binding fragment thereof (e.g, a humanized or human antibody or antigen-binding fragment thereof) that competes with an anti-MERTK antibody or an antigen-binding fragment thereof described herein, for binding to MERTK (e.g., human MERTK). In another specific embodiment, provided herein is a first anti-MERTK antibody or antigen-binding fragment thereof that competes with an anti-MERTK antibody or an antigen-binding fragment thereof described herein for binding to MERTK (e.g., human MERTK), wherein the competition is exhibited as reduced binding of the first anti-MERTK antibody or antigen-binding fragment thereof to MERTK (e.g., human MERTK) by more than 80% (e.g., 85%, 90%, 95%, or 98%, or between 80% to 85%, 80% to 90%, 85% to 90%, or 85% to 95%) in the presence of the anti-MERTK antibody or antigen-binding fragment thereof described herein. In a specific embodiment, the anti-MERTK antibody or antigen-binding fragment thereof that binds to the same epitope as MERTK (or competes with binding to an anti-MERTK antibody or antigen-binding fragment thereof) is not a murine antibody or antigen-binding fragment thereof.

In certain embodiments, an anti-MERTK antibody provided herein, which specifically binds to MERTK (e.g., human MERTK) with an $EC_{50}$ in the range of about 1 nM to 10 nM in an assay such as described herein. In some embodiments, an anti-MERTK antibody or antigen-binding fragment thereof, which specifically binds to human MERTK. In a specific embodiment, the antibody or antigen-binding fragment thereof provided herein does not bind or does not appreciably bind to human Axl, human Tyro3 or murine MERTK as assessed by an assay described therein or known to one of skill in the art. In some embodiments, an anti-MERTK antibody or an antigen-binding fragment thereof binds to human MERTK and cynomolgus monkey MERTK. In specific embodiments, an antibody provided herein is isolated. In specific embodiments, an antibody provided herein is a monoclonal antibody. In a specific embodiment, an anti-MERTK antibody or antigen-binding fragment thereof provided herein is bivalent and is capable of binding to two MERTK molecules (e.g. human MERTK molecules).

In another aspect, provided herein are polynucleotide sequences encoding an antibody or an antigen-binding fragment thereof. In a specific embodiment, provided herein is a polynucleotide sequence comprising a nucleic acid molecule that encodes a heavy chain variable region, wherein the nucleic acid molecule comprises the nucleic acid sequence of SEQ ID NO: 119, SEQ ID NO: 121, SEQ ID NO: 122, or SEQ ID NO: 123. In another specific embodiment, provided herein is a polynucleotide sequence comprising a nucleic acid molecule that encodes a light chain variable region, wherein the nucleic acid molecule comprises the nucleic acid sequence of SEQ ID NO: 120 or SEQ ID NO: 124. In specific embodiments, the nucleic acid molecule or polynucleotide sequence is isolated.

In another aspect, provided herein are vectors comprising a polynucleotide sequence encoding an antibody or an antigen-binding fragment described herein. In certain embodiments, a vector (e.g., an isolated vector) comprises a polynucleotide encoding a heavy chain variable region and/or a light chain variable region, or a heavy chain and/or a light chain of an anti-MERTK antibody described herein. In certain embodiments, a host cell comprises the polynucleotide or vector. Examples of host cells include *E. coli, Pseudomonas, Bacillus, Streptomyces*, yeast, 293F, CHO, YB/20, NS0, PER-C6, HEK-293, HEK-293T, NIH-3T3, HeLa, BHK, Hep G2, SP2/0, R1.1, B-W, L-M, COS 1, COS 7, BSC1, BSC40, BMT10 cells, plant cells, insect cells, and human cells in tissue culture. In a specific embodiment, provided herein is a method of producing an anti-MERTK antibody or antigen-binding fragment thereof that specifically binds to MERTK (e.g., human MERTK) comprising culturing a host cell so that the polynucleotide is expressed and the antibody is produced.

In another aspect, provided herein is an ex vivo cell containing one or more polynucleotides encoding of any of the antibodies or antigen-binding fragments thereof described herein, or the any of the immunoglobulins described herein. In a specific embodiment, an ex vivo cell contains one or more polynucleotides encoding an antibody selected from the group consisting of:

(a) a first immunoglobulin comprising (i) a heavy chain variable region that comprises the amino acid sequence of SEQ ID NO: 105, and (ii) a light chain variable region that comprises the amino acid sequence of SEQ ID NO: 106;

(b) a second immunoglobulin comprising (i) a heavy chain variable region that comprises the amino acid sequence of SEQ ID NO: 107, and (ii) a light chain variable region that comprises the amino acid sequence of SEQ ID NO: 106; and (c) a third immunoglobulin comprising (i) a heavy chain variable region that comprises the amino acid sequence of SEQ ID NO: 108, and (ii) a light chain variable region that comprises the amino acid sequence of SEQ ID NO: 106;

(d) a fourth immunoglobulin comprising (i) a heavy chain region that comprises the amino acid sequence of SEQ ID NO: 109 and (ii) a light chain variable region that comprises the amino acid sequence of SEQ ID NO: 106; and (e) a fifth immunoglobulin comprising (i) a heavy chain variable region that comprises the amino acid sequence of SEQ ID NO: 110, and (ii) a light chain variable region that comprises the amino acid sequence of SEQ ID NO: 111.

In another aspect, provided herein is an ex vivo cell containing a polynucleotide encoding any of the antibody heavy chains described herein.

In another aspect, provided herein is an ex vivo cell containing a polynucleotide encoding any of the antibody light chains described herein. In another aspect, provided herein is a method of producing an antibody or antigen-binding fragment thereof, comprising culturing an ex vivo cell containing one or more polynucleotides encoding any of the antibodies or antigen-binding fragments described herein, under conditions such that the one or more polynucleotides are expressed by the cell to produce the antibody or the antigen-binding fragment thereof encoded by the polynucleotides. In a specific embodiment a method of producing an antibody or antigen-binding fragment thereof comprises culturing an ex vivo cell containing one or more polynucleotides encoding an antibody selected from the group consisting of:

(a) a first immunoglobulin comprising (i) a heavy chain variable region that comprises the amino acid sequence of SEQ ID NO: 105, and (ii) a light chain variable region that comprises the amino acid sequence of SEQ ID NO: 106;

(b) a second immunoglobulin comprising (i) a heavy chain variable region that comprises the amino acid sequence of SEQ ID NO: 107, and (ii) a light chain variable region that comprises the amino acid sequence of SEQ ID NO: 106;

(c) a third immunoglobulin comprising (i) a heavy chain variable region that comprises the amino acid sequence of SEQ ID NO: 108, and (ii) a light chain variable region that comprises the amino acid sequence of SEQ ID NO: 106;

(d) a fourth immunoglobulin comprising (i) a heavy chain region that comprises the amino acid sequence of SEQ ID NO: 109 and (ii) a light chain variable region that comprises the amino acid sequence of SEQ ID NO: 106; and (e) a fifth immunoglobulin comprising (i) a heavy chain variable region that comprises the amino acid sequence of SEQ ID NO: 110, and (ii) a light chain variable region that comprises the amino acid sequence of SEQ ID NO: 111, under conditions such that the one or more polynucleotides are expressed by the cell to produce the antibody encoded by the polynucleotide.

In another aspect, provided herein is a method of producing an antibody heavy chain, comprising culturing an ex vivo cell containing a polynucleotide encoding any of the antibody heavy chains described herein under conditions such that the polynucleotide is expressed by the cell to produce the antibody heavy chain encoded by the polynucleotide.

In another aspect, provided herein is a method of producing an antibody light chain, comprising culturing an ex vivo cell containing a polynucleotide encoding any of the antibody light chains described herein under conditions such that the polynucleotide is expressed by the cell to produce the antibody light chain encoded by the polynucleotide.

In another aspect, provided herein are antibody-drug conjugates comprising: (a) an antibody moiety described herein that is an antibody or antigen-binding fragment thereof that specifically binds MERTK (e.g., human MERTK); (b) one or more drug moieties, each drug moiety being a cytotoxic agent; and (c) optionally a linker; wherein the cytotoxic agent is conjugated directly to the antibody moiety or is conjugated to the antibody moiety via the linker.

In a specific embodiment, the molar ratio of the antibody moiety to the drug moiety is between 1:1 and 1:12.

In a specific embodiment, the molar ratio of the antibody moiety to the drug moiety is between 1:1 and 1:8.

In another specific embodiment, the molar ratio of the antibody moiety to the drug moiety is between 1:3 and 1:5.

In another specific embodiment, the molar ratio of the antibody moiety to the drug moiety is between 1:9.

In a specific embodiment, the antibody-drug conjugate comprises the linker and the linker is a cleavable linker.

In another specific embodiment, the antibody-drug conjugate comprises the linker and the linker is a non-cleavable linker.

Figure 13A:
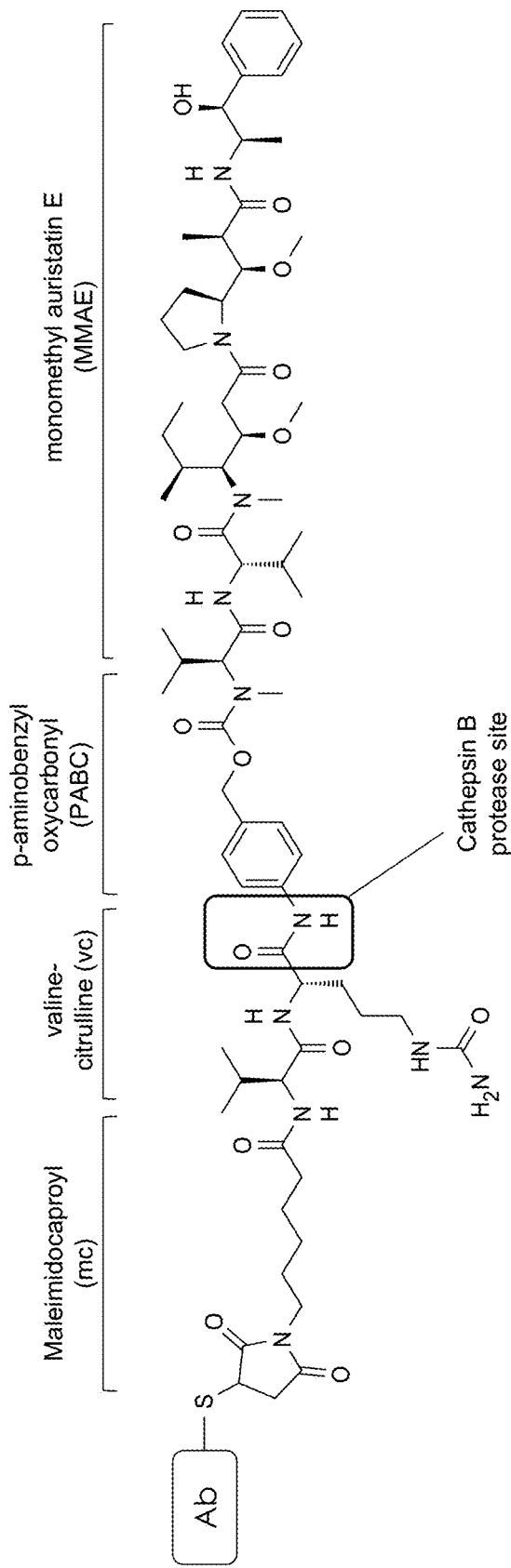

In another specific embodiment, the antibody-drug conjugate comprises the linker and the linker is maleimido-caproyl-valine-citrulline-p-aminobenzyloxycarbonyl (also known as "mc-vc-PABC") (for the structure of mc-vc-PABC; see FIG. 13A). In another specific embodiment, the antibody-drug conjugate comprises the linker and the linker is CL2 (for the structure of CL2, see FIG. 13B and Cardillo et al. 2011, Clin Cancer Res; 17(10); 3157-69. In another specific embodiment, the antibody-drug conjugate comprises the linker and the linker is CL2A (for the structure of CL2A, see FIG. 13B and Goldberg et al. 2018, Oncotarget; 9(48); 28989-29006, and Cardillo et al. 2011, Clin Cancer Res; 17(10); 3157-69).

In specific embodiments, the cytotoxic agent is a small molecule, a nucleotide, a peptide, or a non-antibody protein. In one further embodiment of such a specific embodiment, the cytotoxic agent is a small molecule.

In another specific embodiment, the cytotoxic agent is an auristatin, a maytansinoid, a pyrrolobenzodiazepine, an indolinobenzodiazepine, a calicheamicin, a camptothecin analogue, a duocarmycin, a tubulin inhibitor, a tubulysin or tubulysin analogue, amberstatin269, doxorubicin, an antibiotic, an anthracycline, a microtubule inhibitor, a spliceostatin, or a thailanstatin. In one further embodiment of such a specific embodiment, the cytotoxic agent is monomethyl auristatin E (MMAE) or monomethyl auristatin F (MMAF). In another further embodiment of such a specific embodiment, the cytotoxic agent is DM1 or DM4. In another further embodiment of such a specific embodiment, the cytotoxic agent is SN-38.

In another aspect, provided herein is a method of producing an antibody-drug conjugate described herein wherein the linker is not present, the method comprising: (a) conjugating the cytotoxic agent directly to the antibody moiety to produce the antibody-drug conjugate; and (b) purifying the antibody-drug conjugate.

In another aspect, provided herein is a method of producing an antibody-drug conjugate described herein wherein the antibody-drug conjugate comprises the linker, the method comprising the following steps in the order stated: (a) conjugating the linker directly to the antibody moiety to produce a linker-antibody moiety; (b) conjugating the linker of the linker-antibody moiety directly to the cytotoxic agent to produce the antibody-drug conjugate; and (c) purifying the antibody-drug conjugate.

In another aspect, provided herein is a method of producing an antibody-drug conjugate described herein, wherein the antibody-drug conjugate comprises the linker, the method comprising the following steps in the order stated: (a) conjugating the linker directly to the cytotoxic agent to produce a linker-cytotoxic agent moiety; (b) conjugating the linker of the linker-cytotoxic agent moiety directly to the antibody moiety to produce the antibody-drug conjugate; and (c) purifying the antibody-drug conjugate.

In another aspect, provided herein are pharmaceutical compositions comprising an anti-MERTK antibody or antigen-binding fragment thereof described herein, or an antibody-drug-conjugate described herein. In a specific embodiment, provided herein is a pharmaceutical composition comprising a therapeutically effective amount of any of the antibodies or antigen-binding fragments described herein or any of the antibody-drug conjugates described herein. In a specific embodiment, a pharmaceutical composition comprises:

(a) a first immunoglobulin comprising (i) a heavy chain variable region that comprises the amino acid sequence of SEQ ID NO: 105, and (ii) a light chain variable region that comprises the amino acid sequence of SEQ ID NO: 106;

(b) a second immunoglobulin comprising (i) a heavy chain variable region that comprises the amino acid sequence of SEQ ID NO: 107, and (ii) a light chain variable region that comprises the amino acid sequence of SEQ ID NO: 106;

(c) a third immunoglobulin comprising (i) a heavy chain variable region that comprises the amino acid sequence of SEQ ID NO: 108, and (ii) a light chain variable region that comprises the amino acid sequence of SEQ ID NO: 106, (d) a fourth immunoglobulin comprising (i) a heavy chain region that comprises the amino acid sequence of SEQ ID NO: 109 and (ii) a light chain variable region that comprises the amino acid sequence of SEQ ID NO: 106; or (e) a fifth immunoglobulin comprising (i) a heavy chain variable region that comprises the amino acid sequence of SEQ ID NO: 110, and (ii) a light chain variable region that comprises the amino acid sequence of SEQ ID NO: 111, and a pharmaceutically acceptable carrier.

In some embodiments, a pharmaceutical composition comprises a polynucleotide sequence comprising a nucleic acid sequence encoding an antibody or an antigen-binding fragment thereof.

In another aspect, provided herein are methods of treating cancer in a subject in need thereof, comprising administering to said subject an anti-MERTK antibody or an antigen-binding fragment thereof described herein, or an antibody-drug conjugate described herein. In a specific embodiment, provided herein is a method of treating cancer in a subject in need thereof, comprising administering to said subject any of the pharmaceutical compositions described herein.

In some embodiments, a tumor sample from the subject is assessed for overexpression of phosphorylated MERTK prior to treatment in accordance with the methods described herein. In certain embodiments, the subject is treated if the tumor sample overexpresses phosphorylated MERTK.

In a specific embodiment of the preceding aspect of a method of treating cancer, the cancer is a cancer of the head and neck, lung, breast, bone, ovary, stomach, pancreas, larynx, esophagus, testes, liver, parotid, biliary tract, colon, rectum, cervix, uterus, endometrium, kidney, bladder, prostate or thyroid. In a certain embodiment of such a specific embodiment, the cancer is breast cancer. In a further embodiment of such a certain embodiment, the cancer is triple-negative breast cancer.

In a specific embodiment of the preceding aspect of a method of treating cancer, the cancer is a sarcoma, squamous cell carcinoma, melanoma, glioma, glioblastoma, neuroblastoma, gastric cancer, colorectal cancer, non-small cell lung carcinoma or Kaposi's sarcomas. In a specific embodiment of the aspect of a method of treating cancer, the cancer is a leukemia or lymphoma. In a further specific embodiment, the cancer is acute myelogenous leukemia. In another further specific embodiment, the cancer is acute lymphocytic leukemia. In another further embodiment, the cancer is multiple myeloma.

In a specific embodiment, a cancer treated in accordance with the methods described herein overexpresses MERTK, is associated with constitutively active MERTK (e.g., human MERTK), or both. In another specific embodiment, cancerous cells of the cancer overexpress phosphorylated MERTK.

In a specific embodiment of the method of treating cancer, the method further comprises administering to the subject an additional therapeutic agent.

In a specific embodiment of the embodiment wherein the method further comprises administering to the subject an additional therapeutic agent, the additional therapeutic agent is for treating the cancer. The additional therapeutic agent may be administered in the same pharmaceutical composition or in a different pharmaceutical composition than the anti-MERTK antibody or an antigen-binding fragment thereof, or an antibody-drug conjugate.

In a specific embodiment of the embodiment wherein the additional therapeutic agent is for treating the cancer, the additional therapeutic agent is an agent used to treat breast cancer, an agent used to treat melanoma, an immunotherapy, or an angiogenesis inhibitor. In one further embodiment of such a specific embodiment, the additional therapeutic agent is an agent used to treat breast cancer that is selected from the group consisting of Tamoxifen, Raloxifene, Paclitaxel, Cyclophosphamide, Docetaxel, Vinblastine, Fluorouracil, Everolimus, Trastuzumab, Trastuzumab-Emtansine, Pertuzumab, and Lapatinib Ditosylate. In another further embodiment of such a specific embodiment, the additional therapeutic agent is an agent used to treat melanoma that is selected from the group consisting of a BRAF inhibitor, a MEK inhibitor, and Dacarbazine. In another further embodiment of such a specific embodiment, the additional therapeutic agent is an agent that blocks immune checkpoint signaling. In another further embodiment, the additional therapeutic agent is an anti-CTLA-4 antibody, an anti-PD-1 antibody, or an anti-PD-L1 antibody. In another further embodiment of such a specific embodiment, the additional therapeutic agent is an angiogenesis inhibitor that is selected from the group consisting of a VEGF inhibitor, a VEGFR2 inhibitor, Sunitinib, and Sorafenib.

In a specific embodiment of the method of treating cancer, the subject is a human. In a specific embodiment, provided herein is an antibody-drug conjugate comprising an antibody moiety comprising a heavy chain variable region (VH) and a light chain variable region (VL), wherein the VH comprises the amino acid sequence of sequence of SEQ ID NO: 105 and the VL comprises the amino acid sequence of SEQ ID NO: 106, wherein the antibody moiety is linked to MMAE via the mc-vc-PABC linker. In another specific embodiment, provided herein is an antibody-drug conjugate comprising an antibody moiety comprising a heavy chain variable region (VH) and a light chain variable region (VL), wherein the VH comprises the amino acid sequence of SEQ ID NO: 105 and the VL comprises the amino acid sequence of SEQ ID NO: 106, wherein the antibody moiety is linked to SN-38 via the CL2A linker.

In certain embodiments, the antibody-drug conjugate comprises an antibody moiety that is an immunoglobulin. In some embodiments, the antibody-drug conjugate comprises an antibody moiety wherein the antibody moiety is and immunoglobulin and the immunoglobulin comprises a human constant region.

4. BRIEF DESCRIPTIONS OF FIGURES

FIG. 1. Determination of off-rates ($K_d$) for humanized anti-MERTK antibodies and a chimeric anti-MERTK antibody using surface plasmon resonance (SPR) measurements.

FIG. 2. Protein purification summary for three humanized anti-MERTK antibodies (z10, z11, and z13) and a chimeric anti-MERTK antibody (xAb).

Figure 3B:
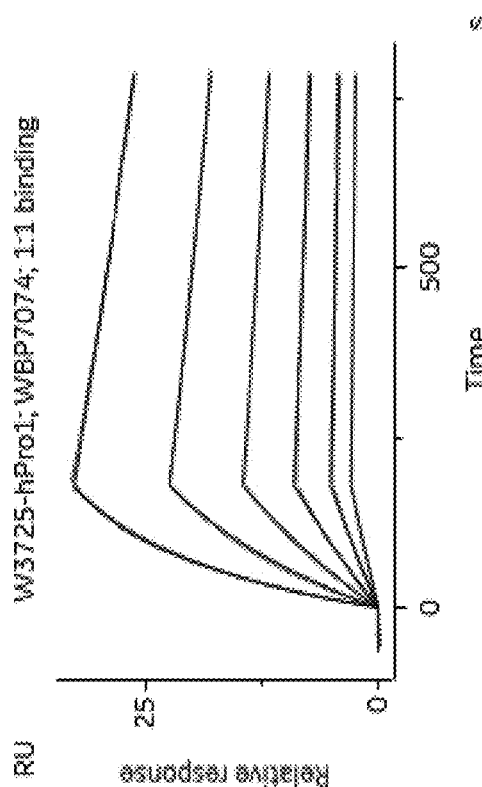

FIG. 3A-FIG. 3B. FIG. 3A. Flow cytometry analysis of the z10 antibody binding affinity for human MERTK expressed by melanoma cells. FIG. 3B. SPR measurements of the binding of the z10 antibody to human extracellular MERTK.

FIGS. 4A-4D. The z10 antibody specifically binds to human MERTK (FIG. 4A), as measured in an affinity binding assay using ELISA. However, the z10 antibody does not bind to the extracellular domain of human Axl (FIG. 4B), human Tyro 3 (FIG. 4C) or murine MERTK (FIG. 4D), as assessed in an affinity binding assay using ELISA. The extracellular domains of human MERTK, human Axl and murine MERTK were conjugated to an IgG Fc domain and used in the ELISA.

Figure 5A:
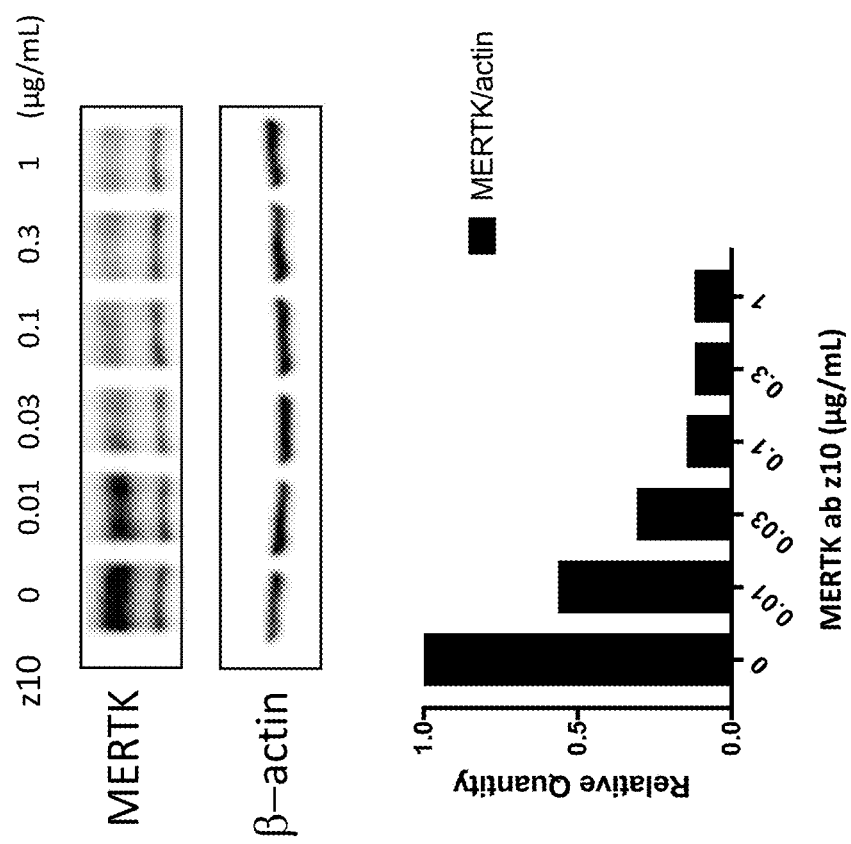
Figure 5B:
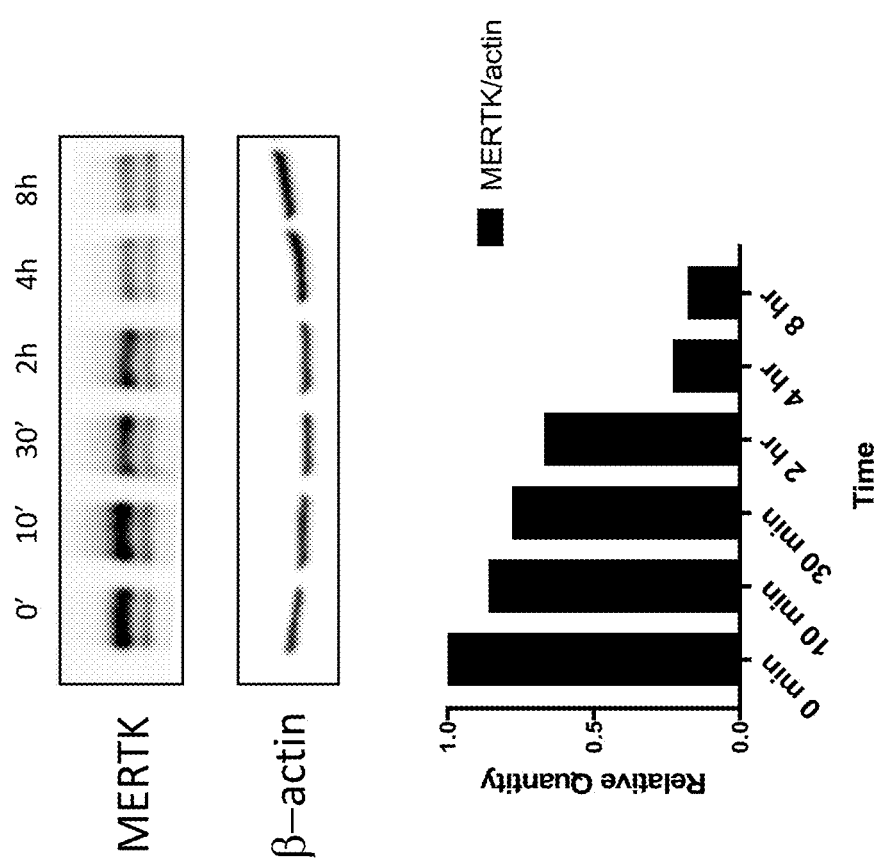

FIGS. 5A-5B. The z10 antibody induces human MERTK degradation on cancer cells (specifically SKMEL5 cells). SKMEL5 cells were incubated with z10 antibody at various concentrations for 24 hours (FIG. 5A) or with 0.3 µg/mL of the antibody for various time periods (FIG. 5B) before the level of human MERTK was assessed by Western Blot analysis.

Figure 6A:
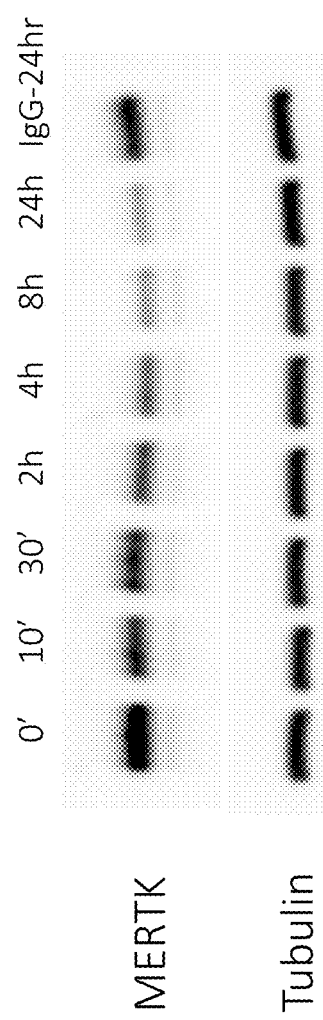
Figure 6B:
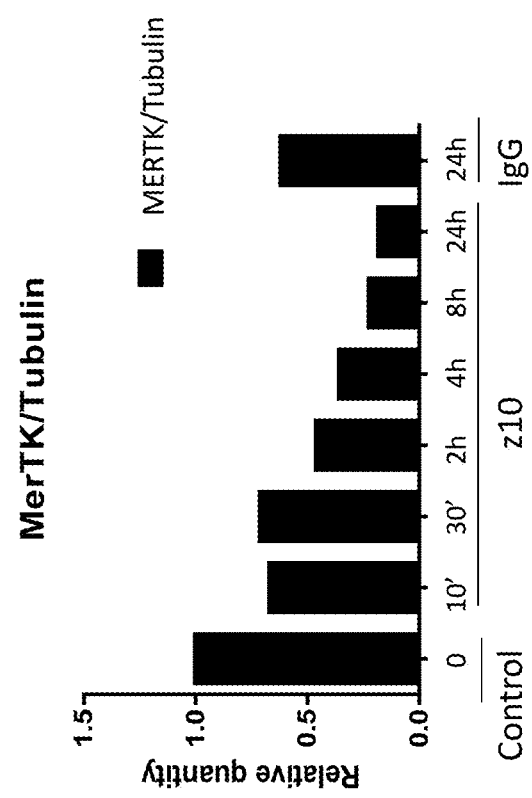

FIGS. 6A-6B. The z10 antibody degrades human MERTK on in vitro differentiated human M2 macrophages. In vitro M2 macrophages were treated with 0.3 µg/mL of the z10 antibody or control IgG, and the cells were incubated for various periods of time before the level of human MERTK was assessed by Western Blot analysis. FIG. 6A provides the Western Blot results and FIG. 6B provides the relative quantification of human MERTK to tubulin.

Figure 7A:
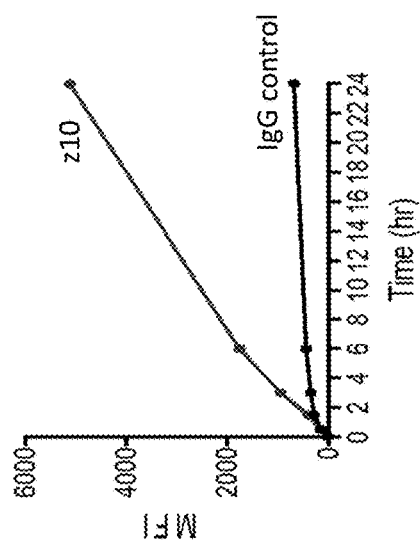
Figure 7B:
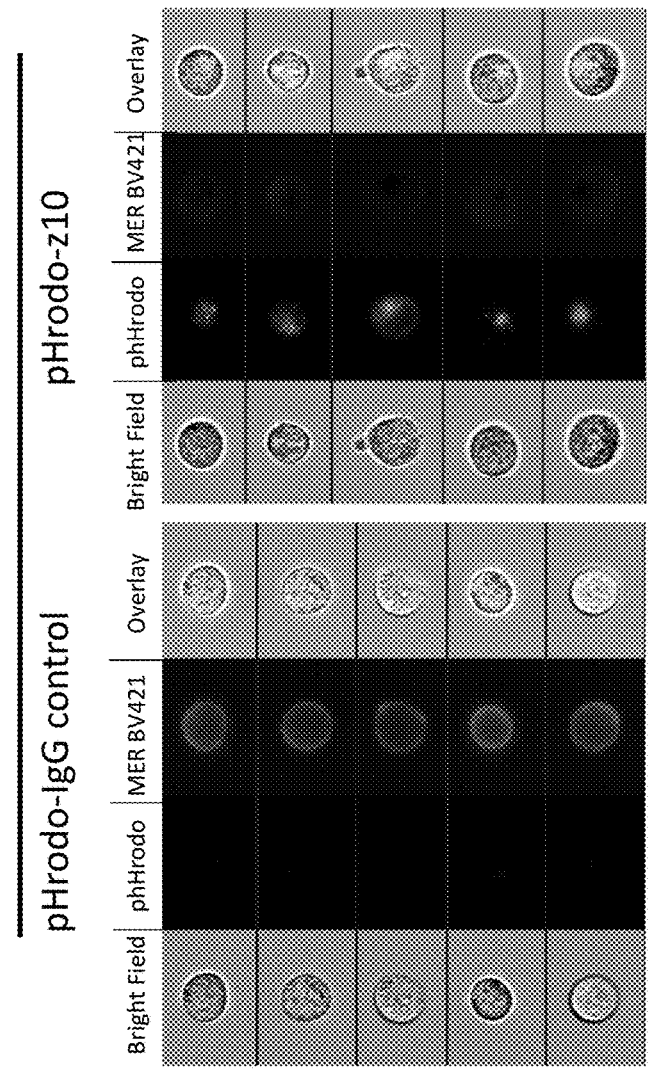

FIGS. 7A-7B. Human MERTK degradation is mediated via internalization of human MERTK of SKMEL5 cells. SKMEL5 cells were incubated with control IgG or the z10 antibody, both labeled with pHrodo, which is only measureable in low pH conditions e.g. upon uptake into lysosomes. Surface human MERTK was measured using a commercially available MERTK antibody. FIG. 7A shows the fluorescence over time and FIG. 7B are representative images.

Figure 8B:
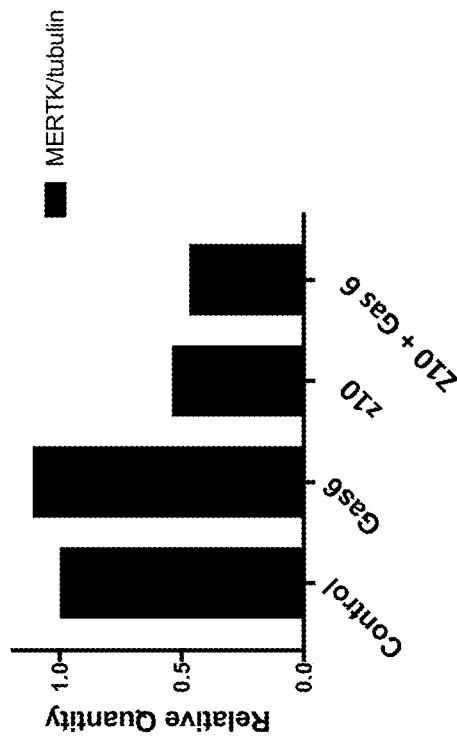
Figure 8C:
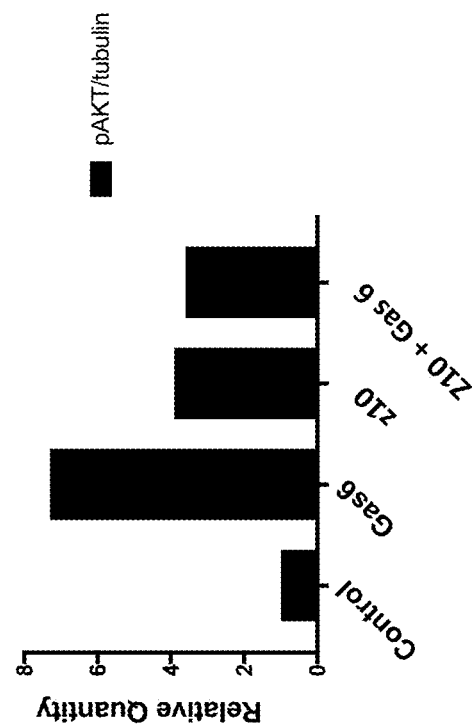
Figure 8A:
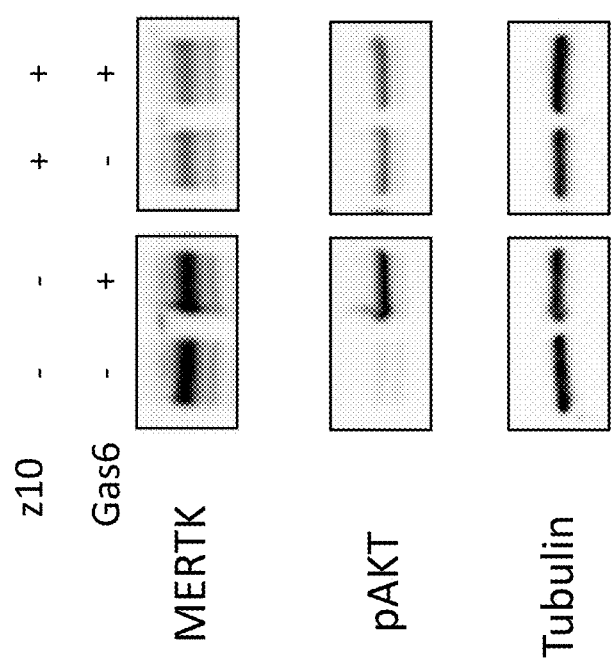

FIGS. 8A-8C. The z10 antibody blocks Gas6-induced phosphorylation of AKT in human cancer cells. SKMEL5 cells were incubated with 0.3 µl/mL of the z10 antibody or control IgG for 2 hours before being incubated with 200 nM of Gas6 for 10 minutes. FIG. 8A shows a Western Blot result, FIG. 8B shows the quantity of human MERTK relative to tubulin, and FIG. 8C shows the quantity of phosphorylated AKT to tubulin.

Figure 9C:
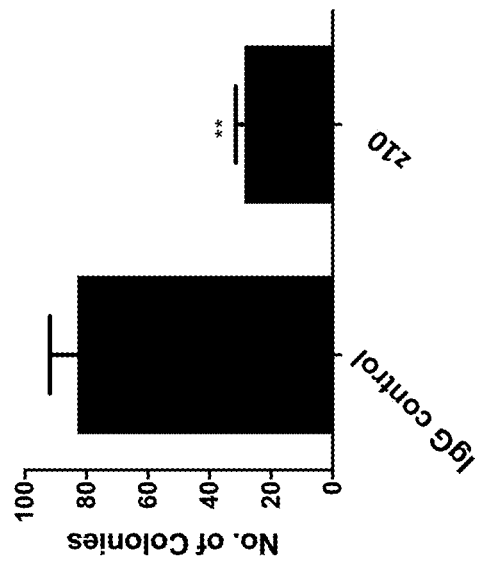
Figure 9D:
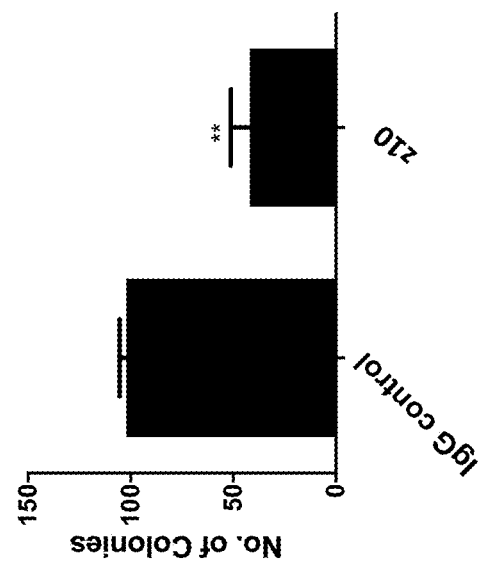

FIGS. 9A-9D. The z10 antibody inhibits colony formation of human cancer cells. The figure shows the reduction in the number of colonies observed after 500 SKMEL5 cells were cultured for 12 days in the presence of 0.3 µg/mL or 1 µg/mL of the z10 antibody relative to the number of colonies observed when 500 SKMEL5 cells were cultured for 12 days with control IgG. FIG. 9A shows colony formation of cancer cells after 12 days of incubation with 0.3 g/mL of the z10 antibody or control IgG antibody. FIG. 9B shows colony formation of cancer cells after 12 days of incubation with 1 g/mL of the z10 antibody or control IgG antibody. FIG. 9C shows numbers of colonies formed after 12 days of incubation with 0.3 µg/mL of the z10 antibody or control IgG antibody. FIG. 9D shows numbers of colonies formed after 12 days of incubation with 1 µg/mL of the z10 antibody or control IgG antibody.

Figure 10:
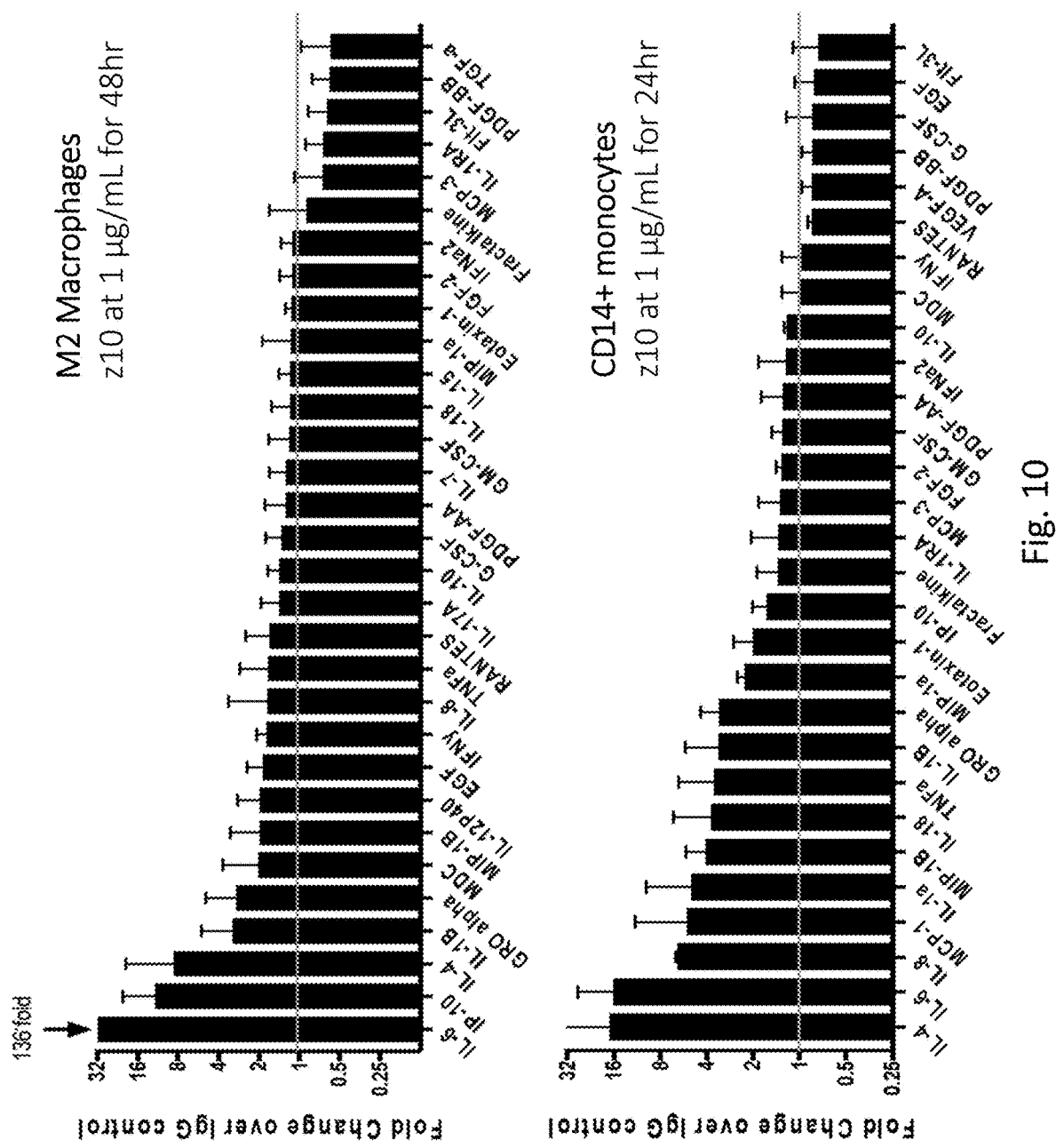

FIG. 10. The z10 antibody induces cytokine responses in M2 macrophages and CD14+ monocytes.

Figure 11A:
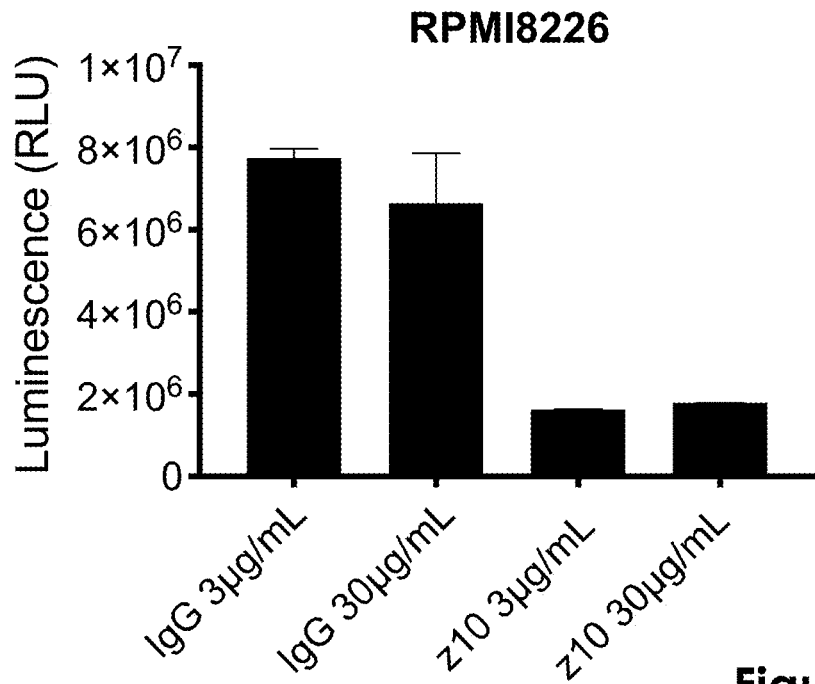
Figure 11B:
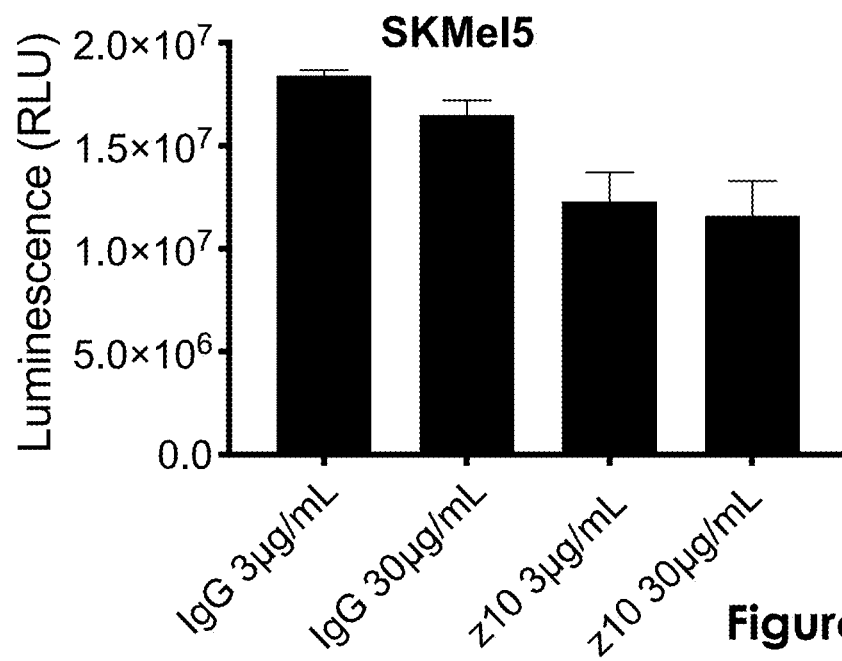

FIGS. 11A and 11B. z10 inhibits cancer cell survival in vitro. 1,000 RPMI8226 multiple myeloma cells (FIG. 11A) or 200 SKMEL5 melanoma cells (FIG. 11B) were cultured in the presence of either IgG control or z10. On day 6 (RPMI8226) or day 4 (SKMel5), viability was assessed using CellTiter-Glo 2.0 Cell Viability Assay.

Figure 12A:
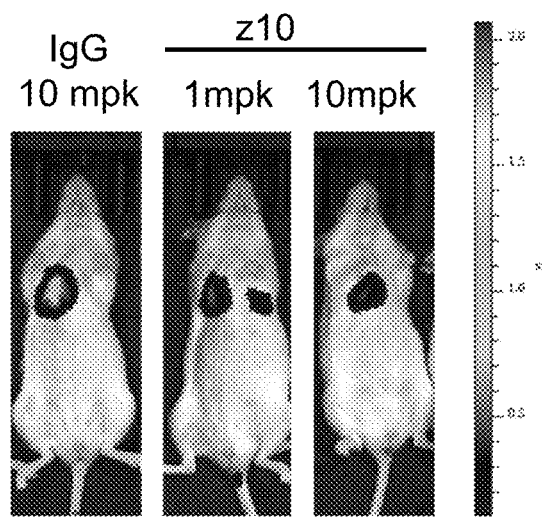
Figure 12B:
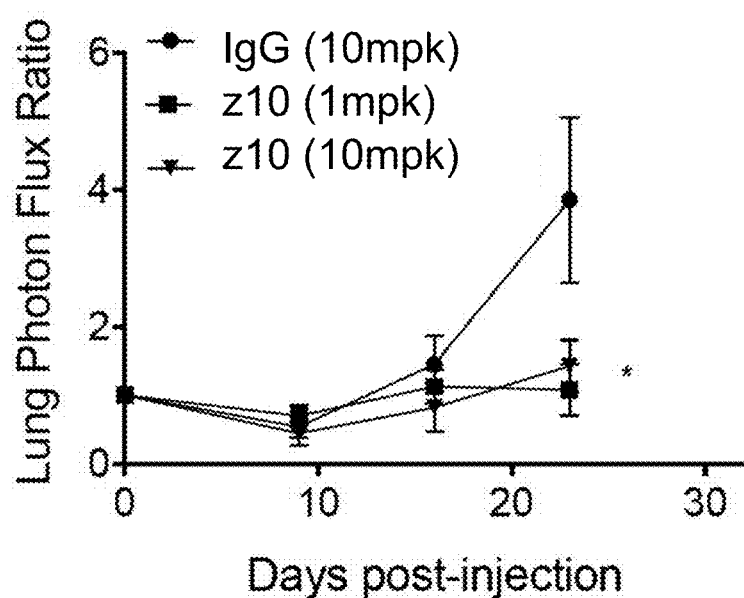

FIGS. 12A and 12B. MDA-MB-231-LM2: z10 Naked Antibody Anti-tumor efficacy. 50,000 MDA-MB-231-LM2 TNBC cells were injected into the tail vein of NSG mice. Treatment started on the day of tumor cell inoculation, twice per week i.p. for the duration of the study. FIG. 12A shows lung colonization of MDA-MB-231 LM2 triple negative breast cancer cells using IVIS imaging. FIG. 12B quantifies the lung colonization of MDA-MB-231 LM2 triple negative breast cancer cells. * designates a p-value of less than 0.05.

Figure 13B:
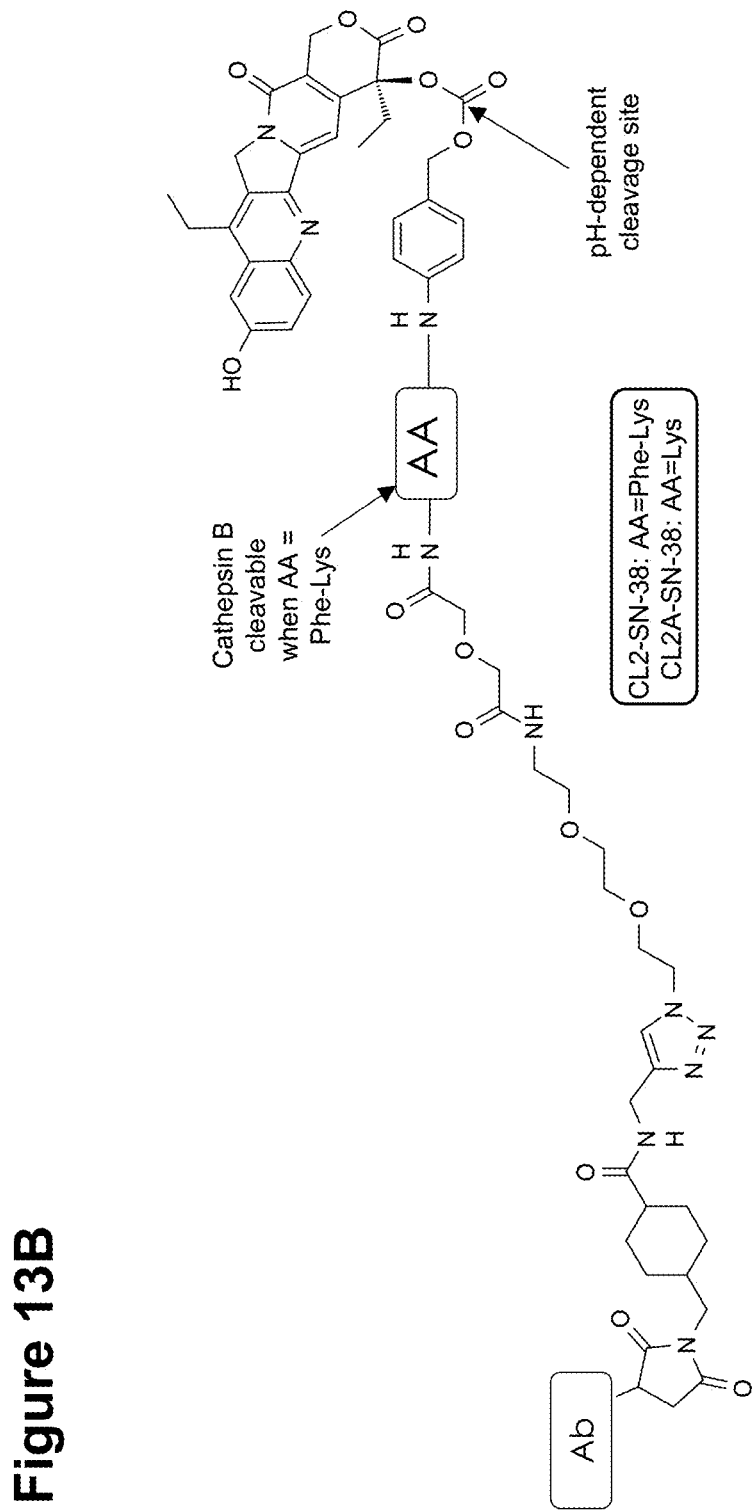

FIGS. 13A and 13B. FIG. 13A shows the structure of maleimidocaproyl-valine-citrulline-p-aminobenzyloxycarbonyl-monomethyl auristatin E (mc-vc-PABC-MMAE) conjugated to an antibody (Ab). FIG. 13B shows the structure of SN-38 conjugated to an antibody (Ab) via a CL2 or CL2A linker. "Ab" represents an antibody, which by way of example but not limitation can be z10 or a control IgG. The CL2 linker has a Cathepsin B cleavage site (see FIG. 13B when AA is phenylalanine-lysine), while the CL2A linker has no Cathepsin B cleavage site (see FIG. 13B when AA is lysine).

Figure 14A:
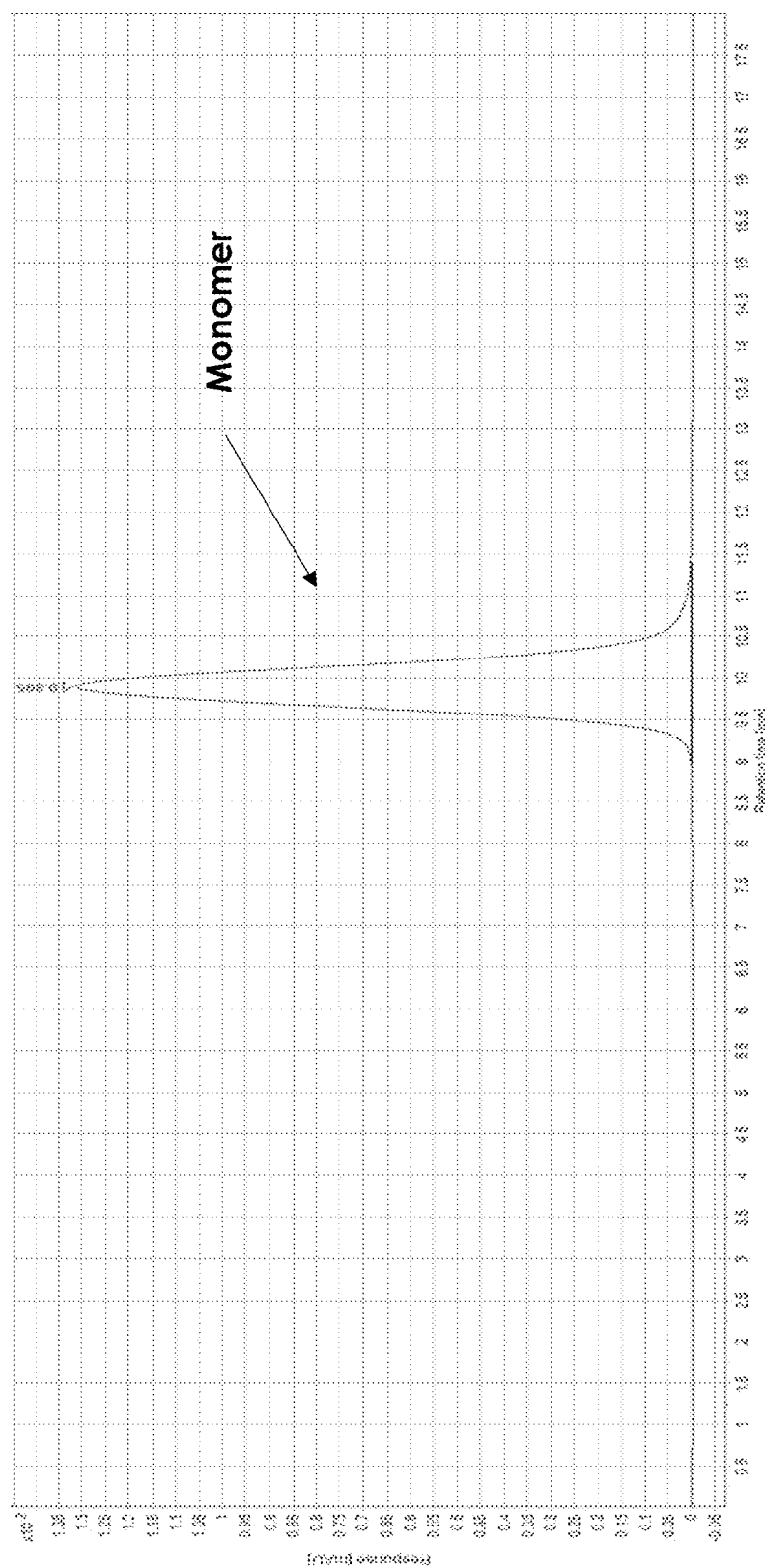
Figure 14B:
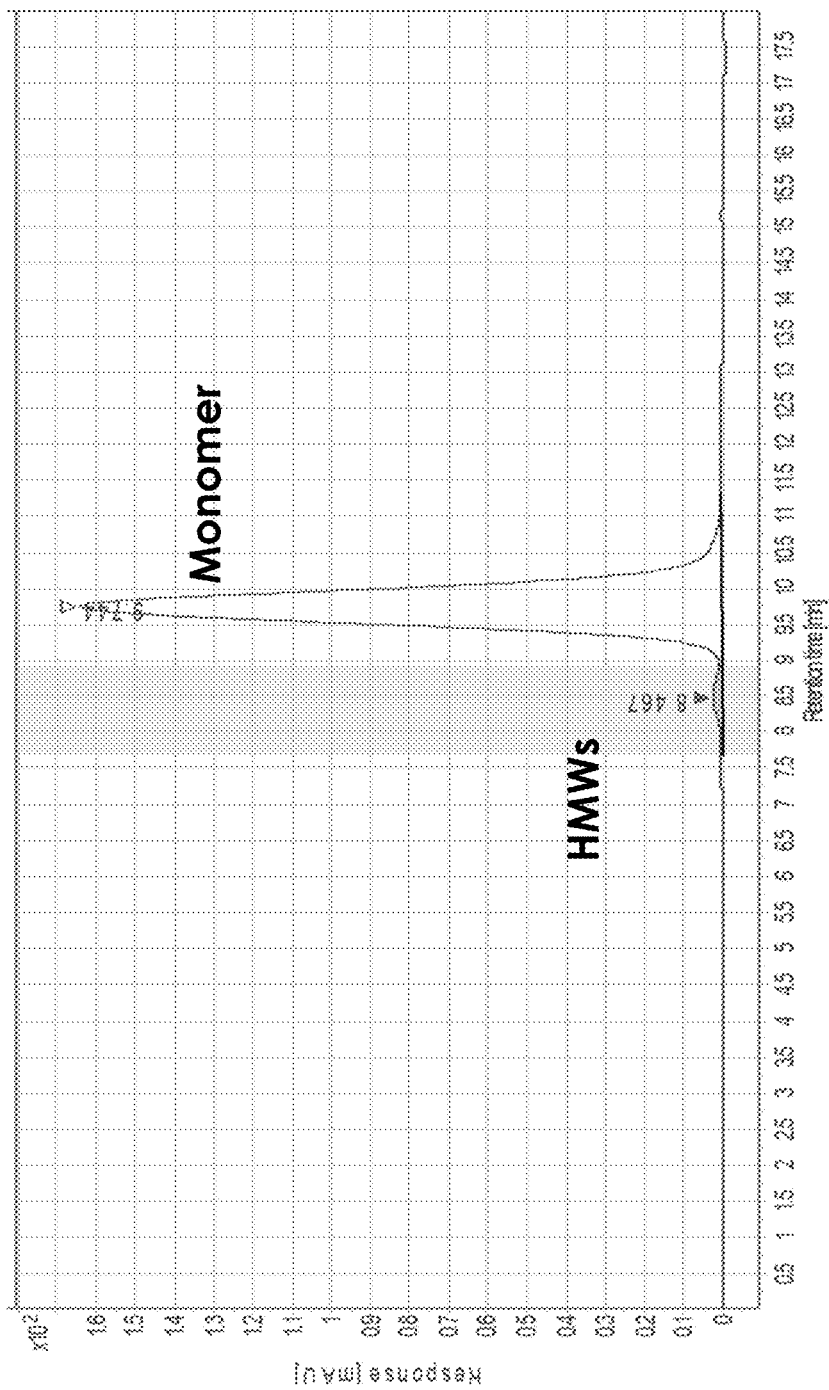

FIGS. 14A and 14B show the results of size-exclusion high pressure liquid chromatography, measuring the purity of z10 conjugated to MMAE via a mc-vc-PABC linker (z10-MMAE, see FIG. 13A where Ab is z10) (FIG. 14A) and z10 conjugated to SN-38 via a CL2A linker (z10-SN-38, see FIG. 13B where Ab is z10 and AA is lysine) (FIG. 14B).

FIG. 15: z10-ADCs bind to MERTK with a Kd similar to z10. FIG. 15 provides z10-ADC binding affinity data. hMER recombinant protein (Mer-Fc conjugate) (50 nM-0.05 nM) was equilibrated with 0.3 nM z10, z10-MMAE or z10-SN-38, respectively before addition to ELISA plates pre-coated with hMER recombinant protein. Antibody binding was detected using AP-conjugated anti-human IgG secondary antibody and developed using a GloMax microplate reader.

Figure 16A:
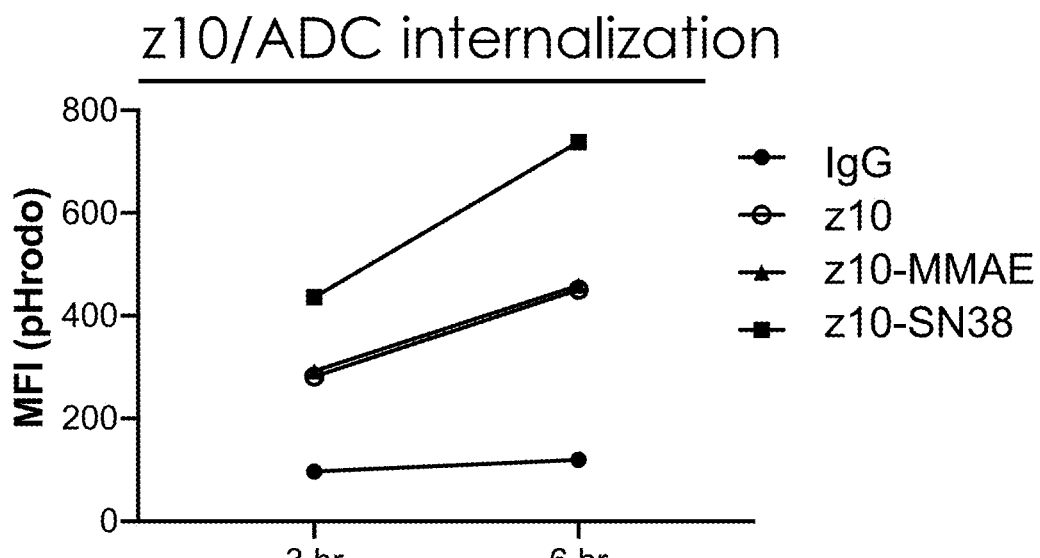
Figure 16B:
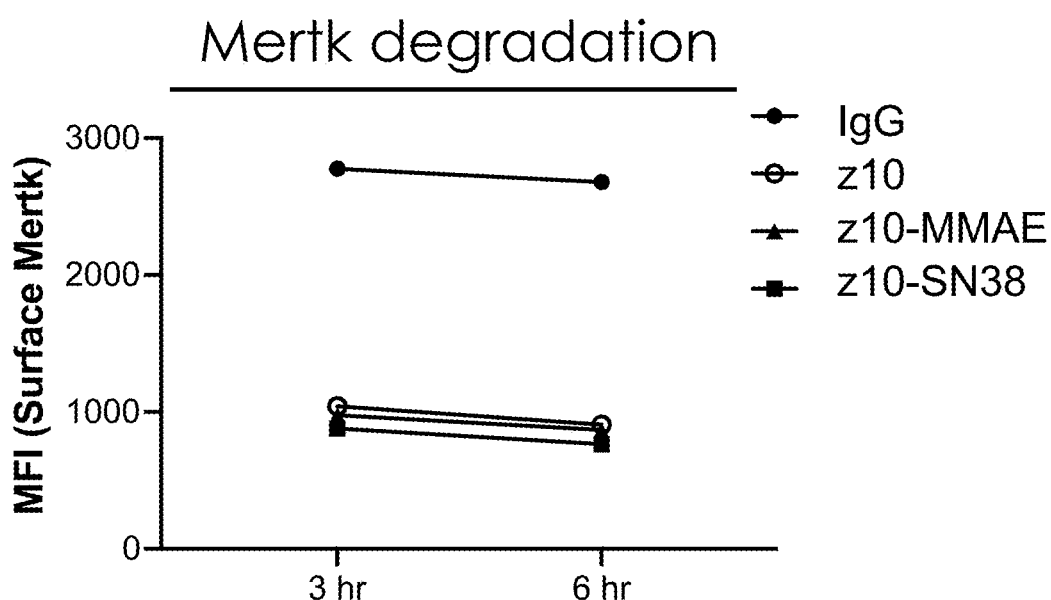

FIGS. 16A and 16B. FIGS. 16A and 16B show that following incubation with z10, z10-MMAE, or z10-SN-38, MERTK is internalized by SKMel5 cells (FIG. 16A) and MERTK is degraded (FIG. 16B). z10, z10-MMAE and z10-SN-38 degrade MERTK to a similar extent. SKMel5 cells were incubated with 6.7 nM of pHrodo-labeled z10, z10-MMAE or z10-SN-38. pHrodo signal is only measurable in low pH conditions e.g. upon uptake into lysosomes. Surface MERTK was stained with a BV421-conjugated MERTK antibody. Binding was measured by flow cytometry.

Figure 17A:
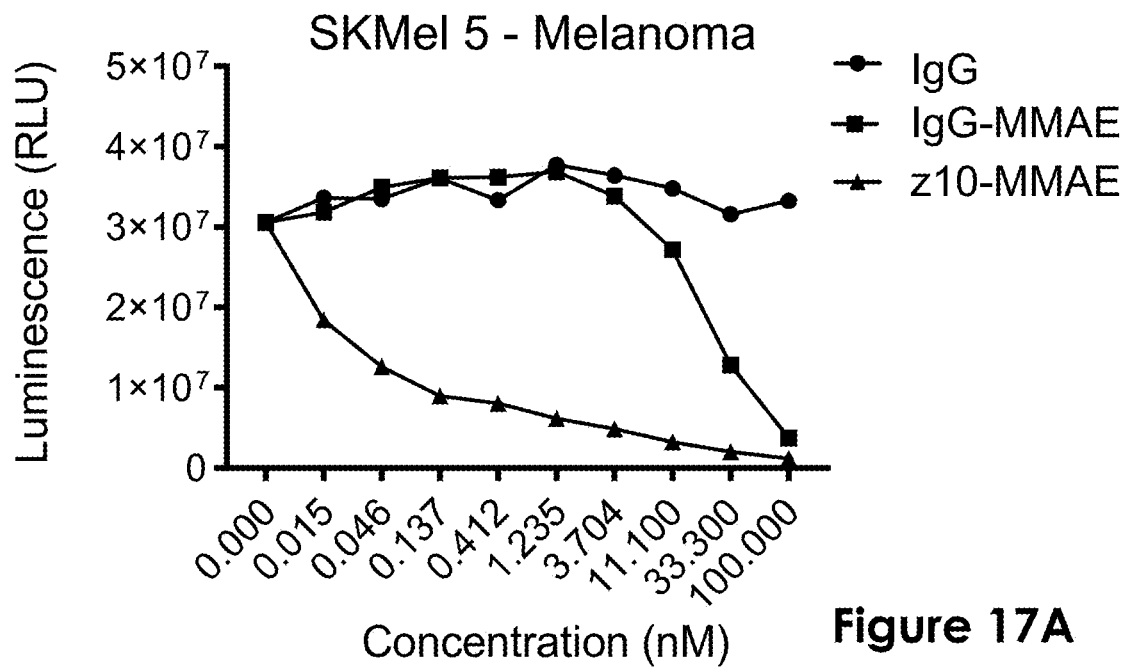
Figure 17B:
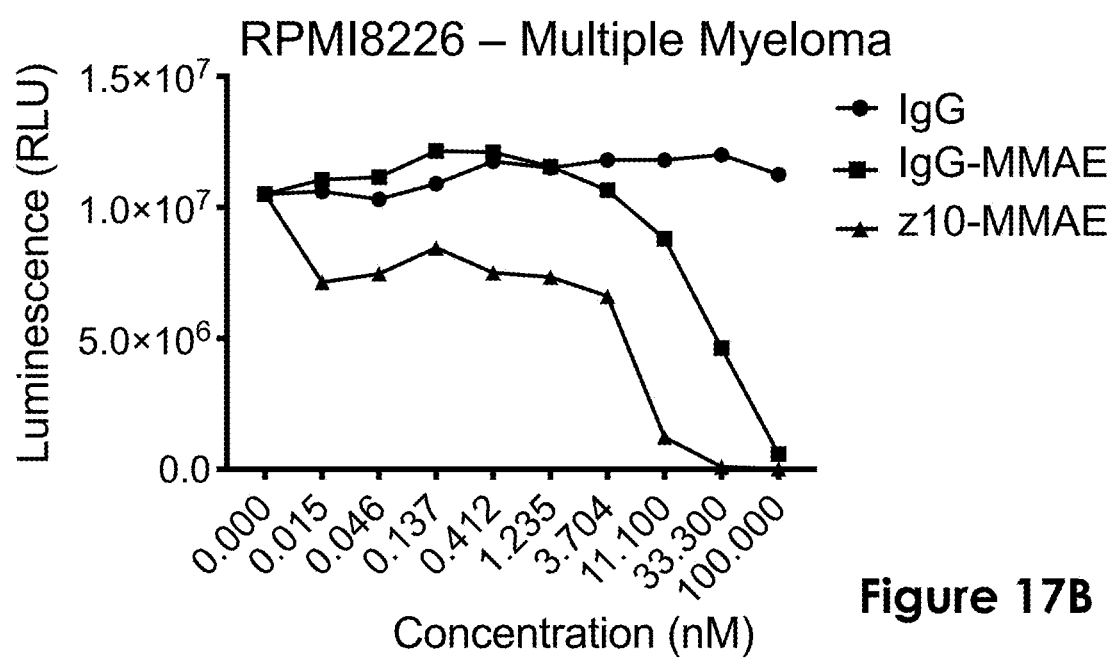
Figure 17C:
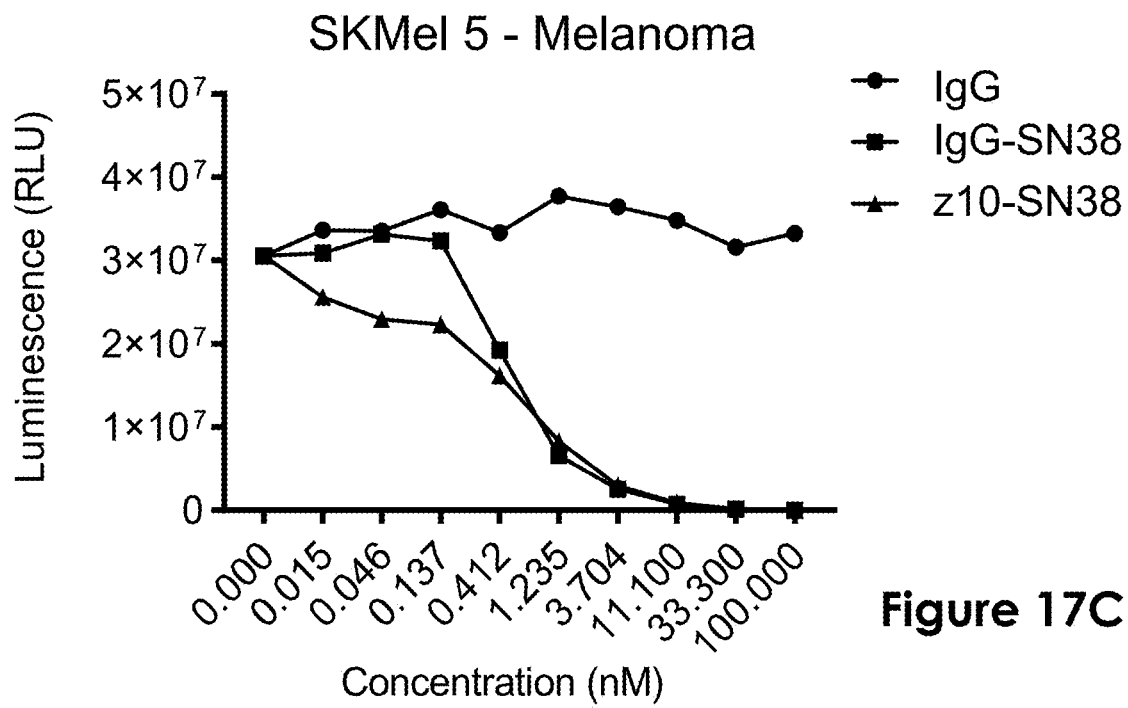
Figure 17D:
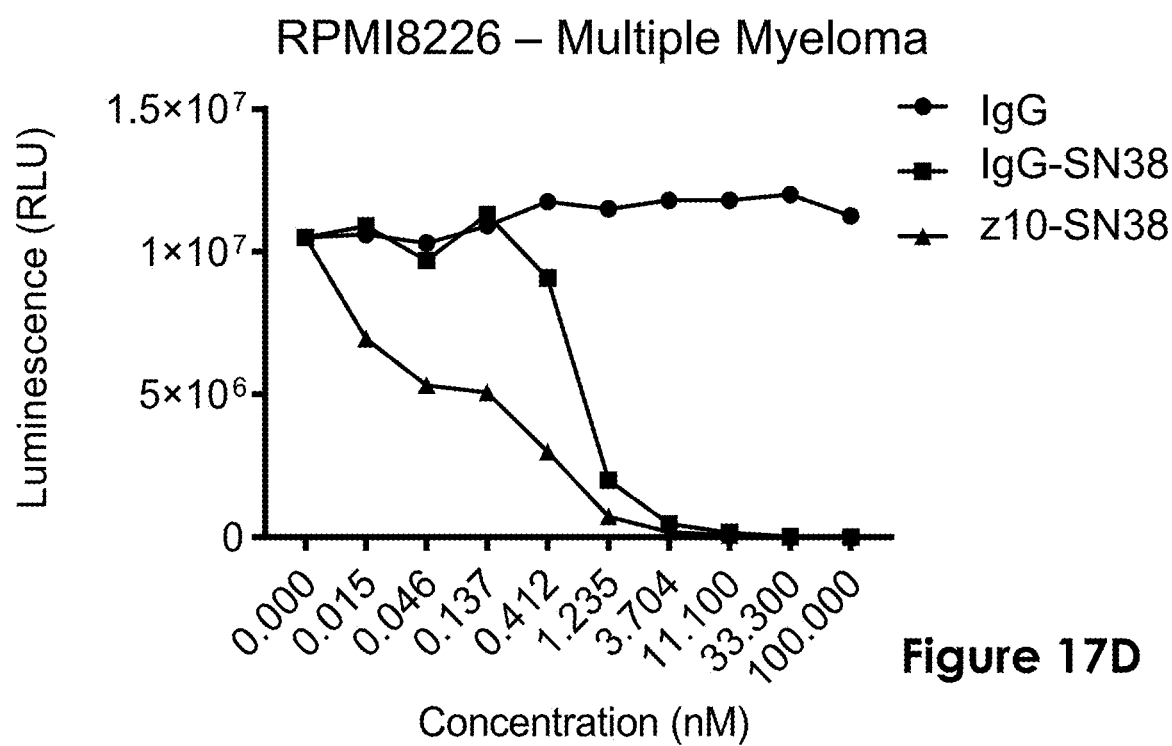
Figure 17E:
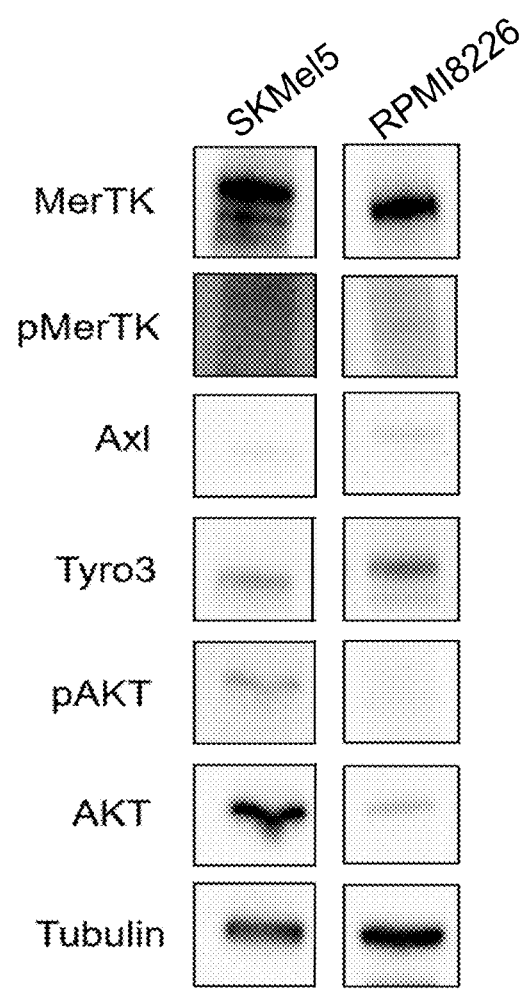

FIGS. 17A-17E. z10-MMAE and z10-SN-38 kill MERTK-expressing cancer cells. SKMel5 (FIG. 17A) or RPMI8226 (FIG. 17B) cells were incubated with IgG control, IgG control conjugated to MMAE via a mc-mv-PABC linker (IgG-MMAE, see FIG. 13A where Ab is IgG) or z10-MMAE for 7 days. Cell viability was measured using CellTiterGlo. -SKMel5 (FIG. 17C) or RPMI8226 (FIG. 17D) cells were incubated with IgG control, IgG control conjugated to SN-38 via a CL2A linker (IgG-SN-38, see FIG. 13B where Ab is IgG and AA is lysine), or z10-SN-38 at indicated concentrations for 7 days. Cell viability was measured using CellTiterGlo. FIG. 17E shows Western Blot analysis of whole cell lysates prepared from SKMel5 or RPMI8226 cells.

Figure 18A:
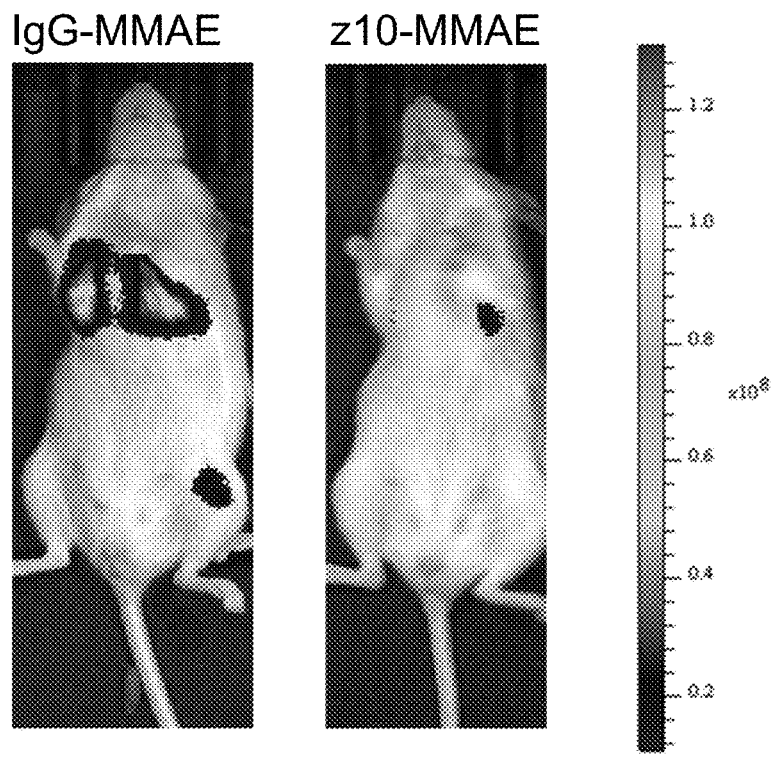
Figure 18B:
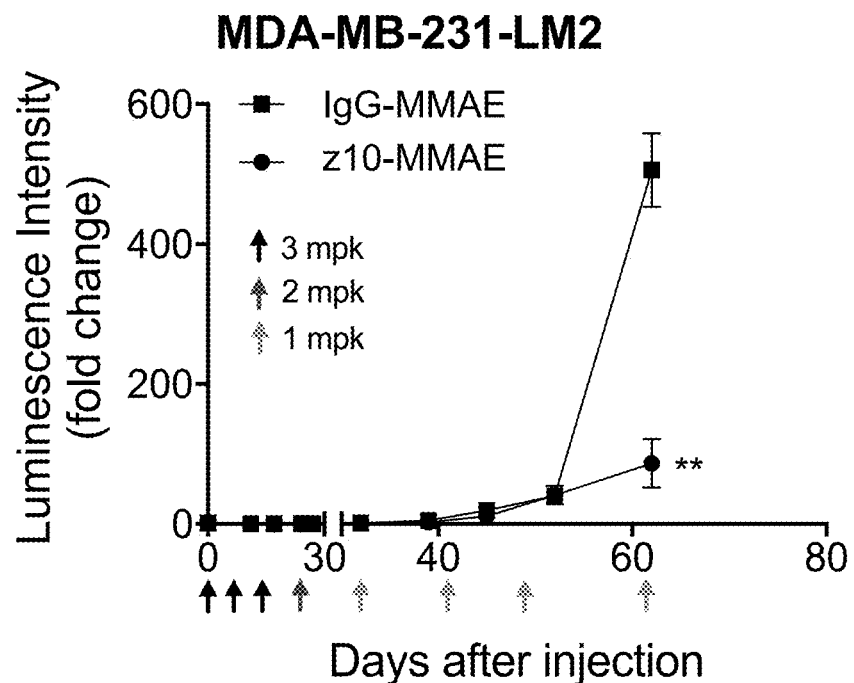

FIGS. 18A and 18B. z10-MMAE inhibits lung colonization of MDA-MB-231-LM2 TNBC cells. FIG. 18A shows lung colonization of MDA-MB-231-LM2 triple negative breast cancer cells using IVIS imaging. FIG. 18B quantifies the lung colonization of MDA-MB-231-LM2 triple negative breast cancer cells. 50,000 MDA-MB-231-LM2 TNBC cells were injected into the tail vein of NSG mice. Treatment started on the day of tumor cell inoculation and lung metastatic colonization was monitored by bioluminescence imaging. Arrows in FIG. 18B indicate days of dosing. ** indicates a p-value of less than 0.01.

Figure 19A:
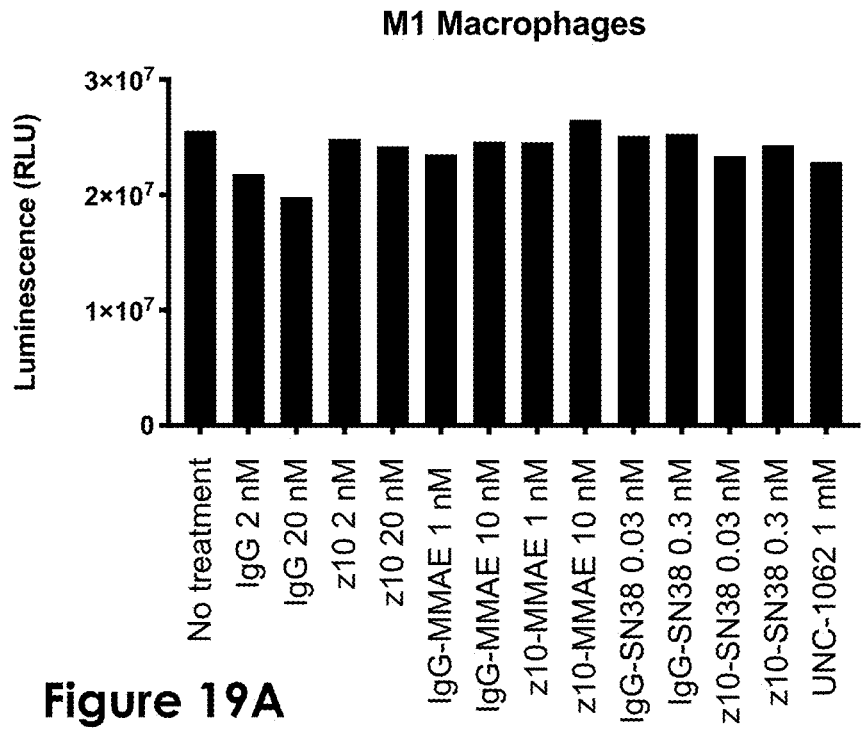
Figure 19B:
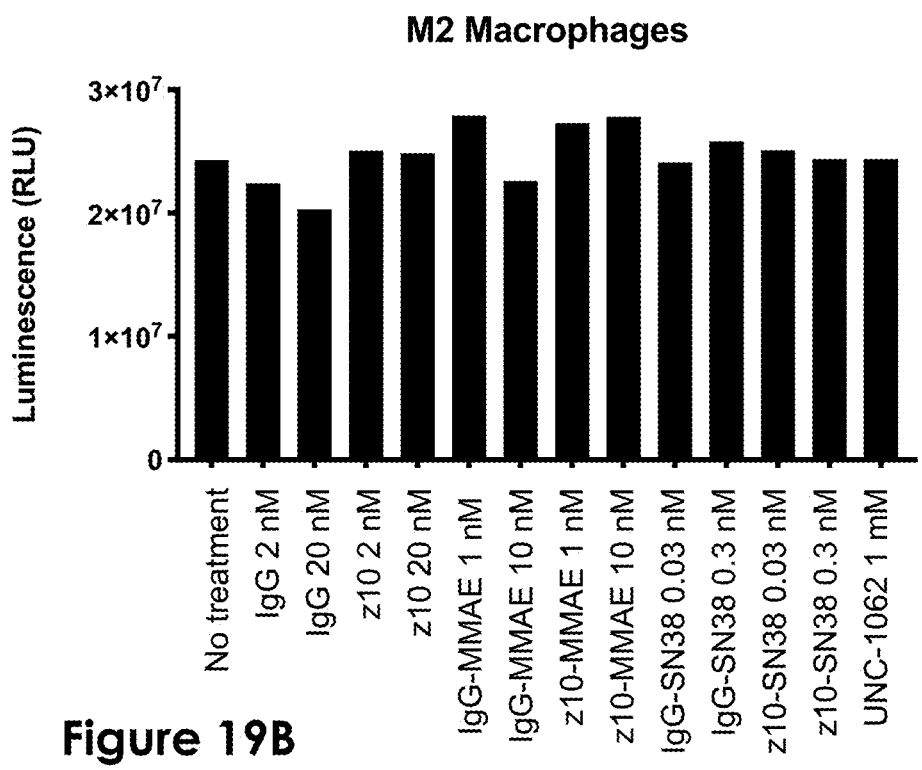

FIGS. 19A and 19B. z10/z10-ADCs do not affect viability of MERTK expressing M1 macrophages (FIG. 19A) or M2 macrophages (FIG. 19B). M2 macrophages were differentiated by culturing $8 \times 10^4$ monocytes in PBMC medium with M-CSF (50 ng/mL) for 8 days. M1 macrophages were differentiated by culturing $8 \times 10^4$ monocytes in PBMC medium with GM-CSF (20 ng/mL) for 5 days, then cultured with GM-CSF (20 ng/mL), IFNg (20 ng/mL), IL-6 (20 ng/mL), and LPS (10 pg/mL) for additional 3 days. M2 and M1 macrophages were treated with indicated antibodies or ADCs for 4 days in differentiating medium and viability was assessed using CellTiter-Glo 2.0 Cell Viability Assay.

5. DETAILED DESCRIPTION

Provided herein are anti-MERTK antibodies (e.g., monoclonal antibodies), and antigen-binding fragments thereof, that specifically bind to MERTK (e.g., human MERTK).

In certain embodiments, an anti-MERTK antibody (e.g., a humanized antibody) or antigen-binding fragment thereof, described herein specifically recognizes the extracellular domain of MERTK (e.g., human MERTK). In a particular embodiment, an anti-MERTK antibody (e.g., a humanized antibody) or antigen-binding fragment thereof described herein does not bind human Axl, human Tyro 3, or murine MERTK as detected by a technique known to one of skill in the art, or described herein. In a specific embodiment, an anti-MERTK antibody (e.g., a humanized antibody) or antigen-binding fragment thereof described herein does not bind to human Axl, human Tyro3, or murine MERTK as assessed with an affinity binding assay using ELISA such as described in Section 6.2, infra.

In a specific embodiment, an anti-MERTK antibody (e.g., a humanized antibody) or antigen-binding fragment thereof described herein specifically binds to human MERTK protein comprising the amino acid sequence of SEQ ID NO: 131. In another specific embodiment, an anti-MERTK antibody (e.g., a humanized antibody) or antigen-binding fragment thereof described herein specifically binds to the extracellular region of human MERTK, comprising the amino acid sequence of SEQ ID NO: 132. In another specific embodiment, an anti-MERTK antibody (e.g., a humanized antibody) or antigen-binding fragment thereof described herein specifically binds to SEQ ID NO: 132. In a specific embodiment, an anti-MERTK antibody (e.g., a humanized antibody) or antigen-binding fragment thereof is bivalent. In a specific embodiment, an anti-MERTK antibody (e.g., a humanized antibody) or antigen-binding fragment thereof described herein comprises two antigen-binding sites that bind to MERTK (e.g., human MERTK). In a particular embodiment, the two antigen-binding sites bind to the same epitope on MERTK (e.g., human MERTK). In a particular embodiment, the two-antigen binding sites comprise identical CDRs.

In certain embodiments, an anti-MERTK antibody (e.g., a humanized antibody) or antigen-binding fragment thereof binds to a recombinant MERTK-Fc chimeric (e.g., a recombinant human MERTK-Fc chimeric) with a $K_D$ of about 1 pM to 10 nM as determined using a technique known to one of skill in the art or described herein. In a specific embodiment, an anti-MERTK antibody (e.g., a humanized antibody) or an antigen-binding fragment thereof described herein binds to a recombinant MERTK-Fc chimeric (e.g., a recombinant human MERTK-Fc chimeric) with a $K_D$ of about 1 pM to about 6 pM as determined using surface plasmon resonance (SPR), such as described in Section 6, infra. In certain embodiments, an anti-MERTK antibody (e.g., a humanized antibody) or an antigen-binding fragment thereof described herein binds to MERTK (e.g, human MERTK) with an $EC_{50}$ of about 1 nM to 20 nM using an assay described herein or known to one of skill in the art. In a specific certain embodiment, an anti-MERTK antibody (e.g., a humanized antibody) or an antigen-binding fragment thereof as described herein binds to MERTK (e.g, human MERTK) in an assay described in Section 6, infra, with a $K_D$ of about 1 nM to 10 nM.

In certain embodiments, an anti-MERTK antibody (e.g., a humanized antibody) or an antibody fragment thereof as described herein binds to human MERTK expressing cells (e.g., human MERTK cancer cells or M2 macrophages) with an $EC_{50}$ of about 1 nM to 20 nM as assessed by flow cytometry such as described herein or known to one of skill in the art. In a specific embodiment, an anti-MERTK antibody (e.g., a humanized antibody) or an antigen-binding fragment thereof as described herein binds to human MERTK expressing cells (e.g., human MERTK cancer cells or M2 macrophages) with an $EC_{50}$ of 1 nm to 10 nM as assessed by flow cytometry such as described in Section 6.2, infra.

In certain embodiments, an anti-MERTK antibody (e.g., a humanized antibody) or antigen-binding fragment thereof described herein decreases the expression level of human MERTK on cancer cells as assessed by an assay described herein (e.g., in Section 6.2, infra) or an assay known to one of skill in the art. In a particular embodiment, an anti-MERTK antibody (e.g., a humanized antibody) or antigen-binding fragment thereof described herein decreases the expression level of human MERTK on the melanoma cell line SKMEL5 as assessed by an assay described herein (e.g., in Section 6.2, infra) or an assay known to one of skill in the art. In certain embodiments, an anti-MERTK antibody (e.g., a humanized antibody) or antigen-binding fragment thereof decreases the expression level of human MERTK on human M2 macrophages as assessed by an assay described herein (e.g., in Section 6.2, infra) or an assay known to one of skill in the art. In certain embodiments, an anti-MERTK antibody (e.g., a humanized antibody) or antigen-binding fragment thereof decreases the expression level of human MERTK by internalization of MERTK as assessed by an assay described herein (e.g., in Section 6.2, infra) or an assay known to one of skill in the art. In certain embodiments, an anti-MERTK antibody (e.g., a humanized antibody) or antigen-binding fragment thereof decreases the expression level of human MERTK by internalization into lysosomes as assessed by an assay described herein (e.g., in Section 6.2, infra) or an assay known to one of skill in the art.

In certain embodiments, an anti-MERTK antibody (e.g., a humanized antibody) or an antigen-binding fragment thereof described herein reduces Gas 6-induced AKT phosphorylation in human MERTK expressing cells (e.g., cancer cells) as assessed by an assay described herein (e.g., Section 6.2, infra) or an assay known to one of skill in the art. In a specific embodiment, an anti-MERTK antibody (e.g., a humanized antibody) or an antigen-binding fragment thereof described herein prevents Gas-6-induced AKT phosphorylation in human MERTK expressing cancer cells, such as e.g., melanoma SKMEL5 cells, as assessed by an assay described herein (e.g., Section 6.2, infra) or an assay known to one of skill in the art. In certain embodiments an anti-MERTK antibody (e.g., a humanized antibody) or an antigen-binding fragment thereof described herein reduces Gas-6-induced phosphorylation of human MERTK in human MERTK expressing cells as assessed by an assay known to one of skill in the art. In a specific embodiment, an anti-MERTK antibody (e.g., a humanized antibody) or an antigen-binding fragment thereof described herein blocks Gas-6-induced activation of MERTK in human MERTK expressing cancer cells (e.g., melanoma cells, such as, e.g., SKMEL5) as assessed by an assay known to one of skill in the art.

In certain embodiments, an anti-MERTK antibody (e.g., a humanized antibody) or antigen-binding fragment described herein, reduces the colony formation ability of cancer cells as assessed by an assay described herein (e.g., in Section 6.2, infra) or an assay known to one of skill in the art. In certain embodiments, an anti-MERTK antibody (e.g., a humanized antibody) or antigen-binding fragment thereof described herein inhibits colony formation of cancer cells (e.g. melanoma cells such as SKMEL5).

In certain embodiments, an anti-MERTK antibody (e.g., a humanized antibody) or antigen-binding fragment thereof described herein induces cytokine responses in M2 macrophages, CD14+ monocytes, or both, such as provided in FIG. 10, as assessed using an assay described herein or known to one of skill in the art.

In specific embodiments, an anti-MERTK antibody (e.g., a humanized antibody) or antigen-binding fragment thereof described herein is isolated.

Antibodies described herein may include monoclonal antibodies or polyclonal antibodies. In a specific embodiment, an antibody may be an immunoglobulin, a tetrameric antibody comprising two heavy chain and two light chain molecules, an antibody light chain monomer, an antibody heavy chain monomer, an antibody light chain dimer, an antibody heavy chain dimer, an antibody light chain-antibody heavy chain pair, a single domain antibody, monovalent antibodies, a single chain antibody, a single-chain Fv (scFv), a disulfide-linked Fv (scFv), and an anti-idiotypic (anti-Id) antibody (including, e.g., anti-anti-Id antibody).

In certain embodiments, an antibody described herein may be multispecific or bispecific. In certain embodiments, an antibody described herein is a bispecific monoclonal antibody. In certain embodiments, an antibody described herein is monovalent. In a specific embodiment, an antibody described herein is bivalent. In a particular embodiment, an antibody described herein binds to a human MERTK on cells. In some embodiments, an antibody described herein is monospecific. In certain embodiments, an antibody described herein is recombinantly produced. In some embodiments, an antibody described herein is a synthetic antibody. In a specific embodiment, an antibody described herein is a humanized antibody. In other embodiments, an antibody described herein may be a human antibody.

The antibodies described herein can be of any type (e.g., IgG, IgE, IgM, IgD, IgA or IgY), any class (e.g., $IgG_1$, $IgG_2$, $IgG_3$, $IgG_4$, $IgA_1$ or $IgA_2$), or any subclass (e.g., $IgG_{2a}$ or $IgG_{2b}$) of immunoglobulin molecules. In certain embodiments, the antibody described herein is an IgG antibody, or a class or subclass thereof. In a specific embodiment, an antibody (e.g., a humanized antibody) described herein is a monoclonal antibody. In a specific embodiment, an anti-MERTK antibody described herein is an IgG antibody.

As used herein, the terms "antigen-binding fragment", "antigen-binding region", and similar terms refer to a portion of an antibody molecule which comprises the amino acid residues that confer on the antibody molecule its specificity for the antigen (e.g., the complementarity determining regions (CDR)). The antigen-binding region can be derived from any animal species, such as rodents (e.g., mouse, rat or hamster) and humans. By way of example, antigen-binding fragments include Fab fragments, $F(ab')_2$ fragments, and antigen binding fragments of any of the antibodies described above. In a specific embodiment, an antigen-binding fragment of a humanized antibody comprises a variable heavy chain region, a variable light chain region or both of the z10, z11 or z13 antibody described herein.

As used herein, the terms "variable region" or "variable domain" are used interchangeably and are common in the art. The variable region typically refers to a portion of an antibody, generally, a portion of a light or heavy chain, which differs extensively in sequence among antibodies and is used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen.

CDRs are defined in various ways in the art, including the Kabat, Chothia, AbM, contact, IMGT, and Exemplary definitions. The Kabat definition is based on sequence variability and is the most commonly used definition to predict CDR regions (Kabat, Elvin A. et al., Sequences of Proteins of Immunological Interest. Bethesda: National Institutes of Health, 1983). The Chothia definition is based on the location of the structural loop regions (Chothia et al., (1987) J Mol Biol 196: 901-917). The AbM definition, a compromise between the Kabat and Chothia definitions, is an integral suite of programs for antibody structure modeling produced by the Oxford Molecular Group (bioinf.org.uk/abs) (Martin A C R et al., (1989) PNAS 86: 9268-9272). The contact definition is based on an analysis of the available complex crystal structures (bioinf.org.uk/abs) (see MacCallum R M et al., (1996) J Mol Biol 5: 732-745). The IMGT definition is from the IMGT ("IMGT®, the international ImMunoGeneTics information System® website imgt.org, founder and director: Marie-Paule Lefranc, Montpellier, France). The Exemplary definition is a combination of AbM and Kabat (Presta et al., (1997) Cancer Res 57: 4593-4599).

In a specific embodiment, a humanized antibody or an antigen-binding fragment thereof described herein comprises a variable heavy chain region, a variable light chain region, or both, wherein the variable heavy chain region, variable light chain region or both are the variable heavy chain region, the variable heavy chain region, or both, of the z10, z11 or z12 antibody, which are provided in Table 11, 12 and 13, respectively. In another specific embodiment, a humanized antibody or an antigen-binding fragment described herein comprises a variable heavy chain region, a variable light chain region, or both, wherein the variable heavy chain comprises the amino acid sequence of the variable heavy chain region in Table 14, and the variable light chain region comprises the amino acid sequence of the variable light chain region in Table 11, 12 or 13, infra. In specific embodiments, the humanized antibody is monoclonal. In some embodiments, the humanized antibody is an immunoglobulin, a tetrameric antibody comprising two heavy chain and two light chain molecules, an antibody light chain monomer, an antibody heavy chain monomer, an antibody light chain-antibody heavy chain dimer, an antibody light chain-antibody heavy chain pair, a single domain antibody, a single chain antibody, single chain Fv, a disulfide-linked Fv or an anti-idiotypic antibody. The humanized antibody may be of any type (e.g. IgG, IgE, IgM, IgD, IgA, or IgY), any class ($IgG_1$, $IgG_2$, $IgG_3$, $IgG_4$, IgA, or $IgA_2$), or any subclass (e.g. $IgG_{2a}$ or $IgG_{2b}$) of immunoglobulin molecules. In a specific embodiment, a humanized antibody described herein is an IgG, or a class or subclass thereof.

The application not only contemplates antibodies and antigen-binding fragments thereof that comprise the sequences disclosed herein (e.g., CDRs, framework regions, variable regions) but also antibodies and antigen-binding fragments thereof, that consist or consist essentially of the sequences disclosed herein. For example, an antibody may consist of the light and heavy chains sequences of the z10, z11 or z13 antibodies described herein.

In a specific embodiment, provided herein is a chimeric anti-MERTK antibody or a antigen-binding fragment thereof, which comprises a variable heavy chain region, a variable light chain region or both, wherein the variable light chain comprises the amino acid sequence of the variable light chain region in Table 15, infra, and the variable heavy chain comprises the amino acid sequence of the variable heavy chain region in Table 15, infra. In specific embodiments, the chimeric antibody is monoclonal. In some embodiments, the chimeric antibody is an immunoglobulin, a tetrameric antibody comprising two heavy chain and two light chain molecules, an antibody light chain monomer, an antibody heavy chain monomer, an antibody light chain dimer, and antibody heavy chain dimer, an antibody light chain-antibody heavy chain pair, a single domain antibody, a single chain antibody, single chain Fv, a disulfide-linked Fv or an anti-idiotypic antibody. The chimeric antibody can be of any type (e.g. IgG, IgE, IgM, IgD, IgA, or IgY), any class ($IgG_1$, $IgG_2$, $IgG_3$, $IgG_4$, IgA, or $IgA_2$), or any subclass (e.g. $IgG_{2a}$ or $IgG_{2b}$) of immunoglobulin molecules. In certain embodiments, a chimeric antibody described herein is an IgG antibody, or a class or subclass thereof.

In another aspect, provided herein are multispecific antibodies and heteroconjugate antibodies. In a specific embodiment, provided herein is a bispecific antibody which comprises two different antigen binding regions, wherein one of the binding regions binds MERTK (e.g., human MERTK), and comprises a variable heavy chain region, a variable light chain region or both, of an antibody described herein (e.g., the z10, z11, z13 or xAb antibody), and the other binding region binds to an antigen of interest. In some embodiments, a bispecific antibody comprises two different antigen binding regions, wherein one of the binding regions specifically binds MERTK (e.g., human MERTK) and the other binding region binds an antigen of interest, and wherein the binding region that specifically binds to MERTK (e.g., human MERTK) comprises a variable heavy chain region and a variable light chain region of the z10, z12 or z13 antibody described herein. In a specific embodiment, the antigen of interest is an immune cell receptor or a tumor-associated antigen. See section 5.1.3, infra, regarding bispecific antibodies.

Also provided herein are heteroconjugate antibodies. In a specific embodiment a heteroconjugate antibody comprises two monoclonal antibodies with specificities for two different antigens, wherein one of the monoclonal antibodies comprises a variable heavy chain region and a variable light chain region of an described herein (e.g., the z10, z11, z13 or xAb antibody).

Also provided are isolated nucleic acids (polynucleotides), such as complementary DNA (cDNA), encoding the anti-MERTK antibodies, and antigen-binding fragments thereof described herein. In certain embodiments, provided herein are polynucleotides comprising the nucleic acid sequence of the VH, the VL, or both of the z10, z11, z13 or xAb antibody set forth in Table 21, 22, 23 or 24. In some embodiments, provided herein are polynucleotides comprising the heavy chain, light chain, or both of the z10, z11, z13 or xAb antibody as set forth in Table 25, 26, 27 or 28.

Further provided are vectors (e.g., expression vectors) and cells (e.g., host cells) comprising nucleic acids (polynucleotides) encoding the anti-MERTK antibodies or antigen-binding fragments thereof described herein. Also provided are methods of making such antibodies.

In another aspect, provided herein are antibody-drug conjugates comprising: (a) an antibody moiety that is an anti-MERTK antibody or an antigen-binding fragment thereof described herein, which specifically binds to MERTK (e.g., human MERTK) described herein; (b) one or more drug moieties, each drug moiety being a cytotoxic agent; and (c) optionally a linker; wherein the cytotoxic agent is conjugated directly to the antibody moiety or is conjugated to the antibody moiety via the linker. The term "conjugated" as used in this disclosure shall mean covalently bound, which can be directly or via an intervening covalently bound structure.

In the case where the cytotoxic agent is a peptide or protein, or where the cytotoxic agent and the linker (if there is one) are peptides or proteins, nucleic acids encoding the antibody-drug conjugates are also provided. In other aspects, provided herein are methods of producing the antibody-drug conjugates that comprise (i) the anti-MERTK antibodies or antigen-binding fragments thereof, and (ii) cytotoxic agents conjugated directly to the anti-MERTK antibodies or antigen-binding fragments, or conjugated to the anti-MERTK antibodies or antigen-binding fragments via linkers.

In another aspect, provided herein are compositions (e.g. pharmaceutical compositions) comprising an anti-MERTK antibody or antigen-binding fragment thereof described herein. In a specific embodiment, a pharmaceutical composition comprises an anti-MERTK antibody or antigen-binding fragment thereof described herein, one or more pharmaceutically acceptable carriers, excipients, or both, and optionally one or more other therapeutic agents.

In another aspect, provided herein are compositions (e.g. pharmaceutical compositions) comprising an antibody-drug conjugate described herein. In a specific embodiment, a pharmaceutical composition comprises an antibody-drug conjugate described herein, one or more pharmaceutically acceptable carriers, excipients, or both, and optionally one or more other therapeutic agents.

In another aspect, provided herein are methods of treating cancer in a subject, comprising administering to the subject an effective amount of an anti-MERTK antibody or antigen-binding fragment thereof described herein or a composition thereof. In a specific embodiment, the anti-MERTK antibody or an antigen-binding fragment thereof is a humanized antibody or an antigen-binding fragment described herein. In other embodiments, the anti-MERTK antibody or an antigen-binding fragment thereof is a bispecific antibody or a heteroconjugate antibody described herein. In some embodiments, the anti-MERTK antibody or antigen-binding fragment thereof is a chimeric antibody or antigen-binding fragment thereof.

In another aspect, provided herein is a method of treating cancer in a subject comprising administering to the subject an effective amount of antibody-drug conjugate described herein. In a specific embodiment, provided herein is a method of treating cancer in a subject comprising administering to the subject an effective amount of an antibody-drug conjugate that comprises (i) an anti-MERTK antibody or antigen-binding fragment thereof, and (ii) cytotoxic agents conjugated directly to the anti-MERTK antibody or antigen-binding fragments thereof, or conjugated to the anti-MERTK antibody or antigen-binding fragments thereof via linkers.

5.1. Antibodies 5.1.1. Sequences and Variants

Provided in Tables 1 and 7 or 8, infra, are VH CDRs and VL CDRs, respectively, of an anti-MERTK antibody or an antigen-binding fragment thereof as defined using different systems. Tables 2, 3, 4, 5 and 6 infra, provide VH framework regions as defined using different systems which may be combined with the CDRs in Table 1. In a specific embodiment, the CDRs in Table 1 are combined with the consensus sequence VH framework region 3, using one numbering system, along the VH framework region 1, 2 and 4, using the same numbering system, which are provided in Tables 2, 3, 4 or 6. Tables 9 and 10, infra, provide VL framework regions as defined using different systems which may be combined with the CDRs in Table 7 or 8. Tables 11, 12, 13 and 15 provide the amino acid sequences of the VH and VL of particular antibodies. Table 14 provides the amino acid sequence of a VH that may be combined with the VL provided in Tables 11, 12, 13 or 15. Tables 16, 17, 18, and 20 provide the heavy chain and light chain amino acid sequences of particular antibodies. Table 19 provides a heavy chain amino acid sequence that may be combined with the light chain amino acid sequence in Table 16, 17 or 18. Tables 21, 22, 23 and 24 provide the nucleic acid sequences encoding the variable regions of particular antibodies. Tables 25, 26, 27 and 28 provide the nucleic acid sequences encoding the heavy chain and light chain of particular antibodies. Tables 29 and 30 provide exemplary human MERTK amino acid sequences to which an anti-MERTK antibody or an antigen-binding fragment thereof described herein may bind.

In specific embodiments, an anti-MERTK antibody or antigen-binding fragment thereof provided herein comprises the VH CDR1 of the antibody in Table 1 as defined by Kabat, Chothia, AbM, Contact, IMGT, or Exemplary. In some embodiments, an anti-MERTK antibody or antigen-binding fragment thereof provided herein comprises the VH CDR2 of the antibody in Tables 1 as defined by Kabat, Chothia, AbM, Contact, IMGT, or Exemplary. In some embodiments, an anti-MERTK antibody or antigen-binding fragment thereof provided herein comprises the VH CDR3 of the antibody in Table 1 as defined by Kabat, Chothia, AbM, Contact, IMGT, or Exemplary. In some embodiments, an anti-MERTK antibody or antigen-binding fragment thereof provided herein comprises one, two or all three of VH CDRs of an antibody in Table 1 as determined by one numbering system.

In specific embodiments, an anti-MERTK antibody or antigen-binding fragment thereof provided herein comprises the VL CDR1 of the antibody in Table 7 as defined by Kabat, Chothia, AbM, Contact, IMGT, or Exemplary. In some embodiments, an anti-MERTK antibody or antigen-binding fragment thereof provided herein comprises the VL CDR2 of the antibody in Table 7 as defined by Kabat, Chothia, AbM, Contact, IMGT, or Exemplary. In some embodiments, an anti-MERTK antibody or antigen-binding fragment thereof provided herein comprises the VL CDR3 of the antibody in Table 7 as defined by Kabat, Chothia, AbM, Contact, IMGT, or Exemplary. In some embodiments, an anti-MERTK antibody or antigen-binding fragment thereof provided herein comprises one, two or all three of VL CDRs of an antibody in Table 7 as determined by one numbering system.

TABLE 1

| Antibody z10/z11/z13/xAb VH CDR Amino Acid Sequences | | | |
|---|---|---|---|
| Definitions | VH CDR1 | VH CDR2 | VH CDR3 |
| Kabat | NYGMN (SEQ ID NO: 1) | WINTYTGEPTYADDFKG (SEQ ID NO: 6) | KSTVVSRYFDV (SEQ ID NO: 11) |
| Chothia | GYTFTNY (SEQ ID NO: 2) | TYTG (SEQ ID NO: 7) | STVVSRYFD (SEQ ID NO: 12) |
| AbM | GYTFTNYGMN (SEQ ID NO: 3) | WINTYTGEPT (SEQ ID NO: 8) | KSTVVSRYFDV (SEQ ID NO: 11) |
| Contact | TNYGMN (SEQ ID NO: 4) | WMGWINTYTGEPT (SEQ ID NO: 9) | ARKSTVVSRYFD (SEQ ID NO: 13) |

TABLE 1-continued

Antibody z10/z11/z13/xAb VH CDR Amino Acid Sequences

| Definitions | VH CDR1 | VH CDR2 | VH CDR3 |
|---|---|---|---|
| IMGT | GYTFTNYG (SEQ ID NO: 5) | INTYTGEP (SEQ ID NO: 10) | ARKSTVVSRYFDV (SEQ ID NO: 14) |
| Exemplary | GYTFTNYGMN (SEQ ID NO: 3) | WINTYTGEPTYADDFKG (SEQ ID NO: 6) | KSTVVSRYFDV (SEQ ID NO: 11) |

TABLE 2

Antibody z10 VH Framework Region Amino Acid Sequences

| Definitions | VH FR1 | VH FR2 | VH FR3 | VH FR4 |
|---|---|---|---|---|
| Kabat | QVQLVQSGAEVKKPGASVKVSCKASGYTFT (SEQ ID NO: 15) | WVRQAPGQGLEWMG (SEQ ID NO: 16) | RVTFTTDTSTSTAYMELRSLRSDDMAVYYCAR (SEQ ID NO: 17) | WGQGTTVTVSS (SEQ ID NO: 18) |
| Chothia | QVQLVQSGAEVKKPGASVKVSCKAS (SEQ ID NO: 19) | GMNWVRQAPGQGLEWMGWIN (SEQ ID NO: 20) | EPTYADDFKGRVTFTTDTSTSTAYMELRSLRSDDMAVYYCARK (SEQ ID NO: 21) | VWGQGTTVTVSS (SEQ ID NO: 22) |
| AbM | QVQLVQSGAEVKKPGASVKVSCKAS (SEQ ID NO: 23) | WVRQAPGQGLEWMG (SEQ ID NO: 24) | YADDFKGRVTFTTDTSTSTAYMELRSLRSDDMAVYYCAR (SEQ ID NO: 25) | WGQGTTVTVSS (SEQ ID NO: 26) |
| Contact | QVQLVQSGAEVKKPGASVKVSCKASGYTF (SEQ ID NO: 27) | WVRQAPGQGLE (SEQ ID NO: 28) | YADDFKGRVTFTTDTSTSTAYMELRSLRSDDMAVYYC (SEQ ID NO: 29) | VWGQGTTVTVSS (SEQ ID NO: 30) |
| IMGT | QVQLVQSGAEVKKPGASVKVSCKAS (SEQ ID NO: 31) | MNWVRQAPGQGLEWMGW (SEQ ID NO: 32) | TYADDFKGRVTFTTDTSTSTAYMELRSLRSDDMAVYYC (SEQ ID NO: 33) | WGQGTTVTVSS (SEQ ID NO: 34) |
| Exemplary | QVQLVQSGAEVKKPGASVKVSCKAS (SEQ ID NO: 35) | WVRQAPGQGLEWMG (SEQ ID NO: 36) | RVTFTTDTSTSTAYMELRSLRSDDMAVYYCAR (SEQ ID NO: 17) | WGQGTTVTVSS (SEQ ID NO: 37) |

TABLE 3

Antibody z11 VH Framework Region Amino Acid Sequences

| Definitions | VH FR1 | VH FR2 | VH FR3 | VH FR4 |
|---|---|---|---|---|
| Kabat | QVQLVQSGAEVKKPGASVKVSCKASGYTFT (SEQ ID NO: 15) | WVRQAPGQGLEWMG (SEQ ID NO: 16) | RVTMTLDTSTSTAYMELRSLRSDDMAVYYCAR (SEQ ID NO: 38) | WGQGTTVTVSS (SEQ ID NO: 18) |
| Chothia | QVQLVQSGAEVKKPGASVKVSCKAS (SEQ ID NO: 19) | GMNWVRQAPGQGLEWMGWIN (SEQ ID NO: 20) | EPTYADDFKGRVTMTLDTSTSTAYMELRSLRSDDMAVYYCARK (SEQ ID NO: 39) | VWGQGTTVTVSS (SEQ ID NO: 22) |
| AbM | QVQLVQSGAEVKKPGASVKVSCKAS (SEQ ID NO: 23) | WVRQAPGQGLEWMG (SEQ ID NO: 24) | YADDFKGRVTMTLDTSTSTAYMELRSLRSDDMAVYYCAR (SEQ ID NO: 40) | WGQGTTVTVSS (SEQ ID NO: 26) |

TABLE 3-continued

Antibody z11 VH Framework Region Amino Acid Sequences

| Definitions | VH FR1 | VH FR2 | VH FR3 | VH FR4 |
|---|---|---|---|---|
| Contact | QVQLVQSGAE VKKPGASVKV SCKASGYTF (SEQ ID NO: 27) | WVRQAPGQGL E (SEQ ID NO: 28) | YADDFKGRVT MTLDTSTSTAY MELRSLRSDD MAVYYC (SEQ ID NO: 41) | VWGQGTTVTVS S (SEQ ID NO: 30) |
| IMGT | QVQLVQSGAE VKKPGASVKV SCKAS (SEQ ID NO: 31) | MNWVRQAPG QGLEWMGW (SEQ ID NO: 32) | TYADDFKGRV TMTLDTSTSTA YMELRSLRSDD MAVYYC (SEQ ID NO: 42) | WGQGTTVTVSS (SEQ ID NO: 34) |
| Exemplary | QVQLVQSGAE VKKPGASVKV SCKAS (SEQ ID NO: 35) | WVRQAPGQGL EWMG (SEQ ID NO: 36) | RVTMTLDTSTS TAYMELRSLRS DDMAVYYCAR (SEQ ID NO: 38) | WGQGTTVTVSS (SEQ ID NO: 37) |

TABLE 4

Antibody z13 VH Framework Region Amino Acid Sequences

| Definitions | VH FR1 | VH FR2 | VH FR3 | VH FR4 |
|---|---|---|---|---|
| Kabat | QVQLVQSGAE VKKPGASVKV SCKASGYTFT (SEQ ID NO: 15) | WVRQAPGQGL EWMG (SEQ ID NO: 16) | RVTFTLDTSTS TAYMELRSLRS DDMAVYYCAR (SEQ ID NO: 43) | WGQGTTVTVSS (SEQ ID NO: 18) |
| Chothia | QVQLVQSGAE VKKPGASVKV SCKAS (SEQ ID NO: 19) | GMNWVRQAP GQGLEWMGWI N (SEQ ID NO: 20) | EPTYADDFKGR VTFTLDTSTST AYMELRSLRSD DMAVYYCARK (SEQ ID NO: 44) | VWGQGTTVTVS S (SEQ ID NO: 22) |
| AbM | QVQLVQSGAE VKKPGASVKV SCKAS (SEQ ID NO: 23) | WVRQAPGQGL EWMG (SEQ ID NO: 24) | YADDFKGRVT FTLDTSTSTAY MELRSLRSDD MAVYYCAR (SEQ ID NO: 45) | WGQGTTVTVSS (SEQ ID NO: 26) |
| Contact | QVQLVQSGAE VKKPGASVKV SCKASGYTF (SEQ ID NO: 27) | WVRQAPGQGL E (SEQ ID NO: 28) | YADDFKGRVT FTLDTSTSTAY MELRSLRSDD MAVYYC (SEQ ID NO: 46) | VWGQGTTVTVS S (SEQ ID NO: 30) |
| IMGT | QVQLVQSGAE VKKPGASVKV SCKAS (SEQ ID NO: 31) | MNWVRQAPG QGLEWMGW (SEQ ID NO: 32) | TYADDFKGRV TFTLDTSTSTA YMELRSLRSDD MAVYYC (SEQ ID NO: 47) | WGQGTTVTVSS (SEQ ID NO: 34) |
| Exemplary | QVQLVQSGAE VKKPGASVKV SCKAS (SEQ ID NO: 35) | WVRQAPGQGL EWMG (SEQ ID NO: 36) | RVTFTLDTSTS TAYMELRSLRS DDMAVYYCAR (SEQ ID NO: 43) | WGQGTTVTVSS (SEQ ID NO: 37) |

TABLE 5

Antibody VH FR3 Consensus Amino Acid Sequences
($X_1$ is F or M; $X_2$ is T or L)

| Definitions | VH FR3 |
|---|---|
| Kabat | RVTX$_1$TX$_2$DTSTSTAYMELRSLRSDDMAVYYCAR (SEQ ID NO: 48) |
| Chothia | EPTYADDFKGRVTX$_1$TX$_2$DTSTSTAYMELRSLRSDDMAVY YCARK (SEQ ID NO: 49) |
| AbM | YADDFKGRVTX$_1$TX$_2$DTSTSTAYMELRSLRSDDMAVYCA R (SEQ ID NO: 50) |
| Contact | YADDFKGRVTX$_1$TX$_2$DTSTSTAYMELRSLRSDDMAVYYC (SEQ ID NO: 51) |

TABLE 5-continued

Antibody VH FR3 Consensus Amino Acid Sequences
($X_1$ is F or M; $X_2$ is T or L)

| Definitions | VH FR3 |
|---|---|
| IMGT | TYADDFKGRVT$X_1$T$X_2$DTSTSTAYMELRSLRSDDMAVYYC (SEQ ID NO: 52) |
| Exemplary | RVT$X_1$T$X_2$DTSTSTAYMELRSLRSDDMAVYYCAR (SEQ ID NO: 53) |

TABLE 6

Antibody xAb VH Framework Region Amino Acid Sequences

| Definitions | VH FR1 | VH FR2 | VH FR3 | VH FR4 |
|---|---|---|---|---|
| Kabat | QIQLVQSGPEL KKPGETVKISC KASGYTFT (SEQ ID NO: 54) | WVKQAPGKGL KWMG (SEQ ID NO: 55) | RFVFSLETSAST AYLQINNLKNE DMATYFCAR (SEQ ID NO: 56) | WGAGTTVTVSS (SEQ ID NO: 57) |
| Chothia | QIQLVQSGPEL KKPGETVKISC KAS (SEQ ID NO: 58) | GMNWVKQAP GKGLKWMGWI N (SEQ ID NO: 59) | EPTYADDFKGR FVFSLETSAST AYLQINNLKNE DMATYFCARK (SEQ ID NO: 60) | VWGAGTTVTVS S (SEQ ID NO: 61) |
| AbM | QIQLVQSGPEL KKPGETVKISC KAS (SEQ ID NO: 58) | WVKQAPGKGL KWMG (SEQ ID NO: 55) | YADDFKGRFV FSLETSASTAY LQINNLKNED MATYFCAR (SEQ ID NO: 62) | WGAGTTVTVSS (SEQ ID NO: 57) |
| Contact | QIQLVQSGPEL KKPGETVKISC KASGYTF (SEQ ID NO: 63) | WVKQAPGKGL K (SEQ ID NO: 64) | YADDFKGRFV FSLETSASTAY LQINNLKNED MATYFC (SEQ ID NO: 65) | VWGAGTTVTVS S (SEQ ID NO: 61) |
| IMGT | QIQLVQSGPEL KKPGETVKISC KAS (SEQ ID NO: 58) | MNWVKQAPG KGLKWMGW (SEQ ID NO: 66) | TYADDFKGRF VFSLETSASTA YLQINNLKNED MATYFC (SEQ ID NO: 67) | WGAGTTVTVSS (SEQ ID NO: 57) |
| Exemplary | QIQLVQSGPEL KKPGETVKISC KAS (SEQ ID NO: 58) | WVKQAPGKGL KWMG (SEQ ID NO: 55) | RFVFSLETSAST AYLQINNLKNE DMATYFCAR (SEQ ID NO: 56) | WGAGTTVTVSS (SEQ ID NO: 57) |

TABLE 7

Antibody z10/z11/z13 VL CDR Amino Acid Sequences

| Definitions | VL CDR1 | VL CDR2 | VL CDR3 |
|---|---|---|---|
| Kabat | KASQDVGDAVT (SEQ ID NO: 68) | WASTRHT (SEQ ID NO: 69) | QQYRSYPLT (SEQ ID NO: 70) |
| Chothia | SQDVGDA (SEQ ID NO: 71) | WAS (SEQ ID NO: 72) | YRSYPL (SEQ ID NO: 73) |
| AbM | KASQDVGDAVT (SEQ ID NO: 68) | WASTRHT (SEQ ID NO: 69) | QQYRSYPLT (SEQ ID NO: 70) |
| Contact | GDAVTWY (SEQ ID NO: 74) | LLIYWASTRH (SEQ ID NO: 75) | QQYRSYPL (SEQ ID NO: 76) |
| IMGT | QDVGDA (SEQ ID NO: 77) | WAS (SEQ ID NO: 72) | QQYRSYPLT (SEQ ID NO: 70) |
| Exemplary | KASQDVGDAVT (SEQ ID NO: 68) | WASTRHT (SEQ ID NO: 69) | QQYRSYPLT (SEQ ID NO: 70) |

TABLE 8

Antibody xAb VL CDR Amino Acid Sequences

| Definitions | VL CDR1 | VL CDR2 | VL CDR3 |
|---|---|---|---|
| Kabat | KASQDVGDAVT (SEQ ID NO: 68) | WASTRHT (SEQ ID NO: 69) | QQYRSYPLT (SEQ ID NO: 70) |
| Chothia | SQDVGDA (SEQ ID NO: 71) | WAS (SEQ ID NO: 72) | YRSYPL (SEQ ID NO: 73) |
| AbM | KASQDVGDAVT (SEQ ID NO: 68) | WASTRHT (SEQ ID NO: 69) | QQYRSYPLT (SEQ ID NO: 70) |
| Contact | GDAVTWC (SEQ ID NO: 78) | LLIYWASTRH (SEQ ID NO: 75) | QQYRSYPL (SEQ ID NO: 76) |
| IMGT | QDVGDA (SEQ ID NO: 77) | WAS (SEQ ID NO: 72) | QQYRSYPLT (SEQ ID NO: 70) |
| Exemplary | KASQDVGDAVT (SEQ ID NO: 68) | WASTRHT (SEQ ID NO: 69) | QQYRSYPLT (SEQ ID NO: 70) |

TABLE 9

Antibody z10/z11/z13 VL Framework Region Amino Acid Sequences

| Definitions | VL FR1 | VL FR2 | VL FR3 | VL FR4 |
|---|---|---|---|---|
| Kabat | DIQMTQSPSFLSASVGDRVTITC (SEQ ID NO: 79) | WYQQKPGKAPKLLIY (SEQ ID NO: 80) | GVPDRFSGSGSGTDFTLTISSLQPEDFATYYC (SEQ ID NO: 81) | FGQGTKLEIK (SEQ ID NO: 82) |
| Chothia | DIQMTQSPSFLSASVGDRVTITCKA (SEQ ID NO: 83) | VTWYQQKPGKAPKLLIY (SEQ ID NO: 84) | TRHTGVPDRFSGSGSGTDFTLTISSLQPEDFATYYCQQ (SEQ ID NO: 85) | TFGQGTKLEIK (SEQ ID NO: 86) |
| AbM | DIQMTQSPSFLSASVGDRVTITC (SEQ ID NO: 79) | WYQQKPGKAPKLLIY (SEQ ID NO: 80) | GVPDRFSGSGSGTDFTLTISSLQPEDFATYYC (SEQ ID NO: 81) | FGQGTKLEIK (SEQ ID NO: 82) |
| Contact | DIQMTQSPSFLSASVGDRVTITCKASQDV (SEQ ID NO: 87) | QQKPGKAPK (SEQ ID NO: 88) | TGVPDRFSGSGSGTDFTLTISSLQPEDFATYYC (SEQ ID NO: 89) | TFGQGTKLEIK (SEQ ID NO: 86) |
| IMGT | DIQMTQSPSFLSASVGDRVTITCKAS (SEQ ID NO: 90) | VTWYQQKPGKAPKLLIY (SEQ ID NO: 84) | TRHTGVPDRFSGSGSGTDFTLTISSLQPEDFATYYC (SEQ ID NO: 91) | FGQGTKLEIK (SEQ ID NO: 82) |
| Exemplary | DIQMTQSPSFLSASVGDRVTITC (SEQ ID NO: 79) | WYQQKPGKAPKLLIY (SEQ ID NO: 80) | GVPDRFSGSGSGTDFTLTISSLQPEDFATYYC (SEQ ID NO: 81) | FGQGTKLEIK (SEQ ID NO: 82) |

TABLE 10

Antibody xAb VL Framework Region Amino Acid Sequences

| Definitions | VL FR1 | VL FR2 | VL FR3 | VL FR4 |
|---|---|---|---|---|
| Kabat | DIVLTQSHKFMSTSVGDRVSITC (SEQ ID NO: 92) | WCQQKPGQPPKLLIY (SEQ ID NO: 93) | GVPDRFTGSGSGTDFTLTINNVQSEDLADYFC (SEQ ID NO: 94) | FGAGTKLELK (SEQ ID NO: 95) |

TABLE 10-continued

Antibody xAb VL Framework Region Amino Acid Sequences

| Definitions | VL FR1 | VL FR2 | VL FR3 | VL FR4 |
|---|---|---|---|---|
| Chothia | DIVLTQSHKFM STSVGDRVSIT CKA (SEQ ID NO: 96) | VTWCQQKPGQ PPKLLIY (SEQ ID NO: 97) | TRHTGVPDRFT GSGSGTDFTLTI NNVQSEDLAD YFCQQ (SEQ ID NO: 98) | TFGAGTKLELK (SEQ ID NO: 99) |
| AbM | DIVLTQSHKFM STSVGDRVSIT C (SEQ ID NO: 92) | WCQQKPGQPP KLLIY (SEQ ID NO: 93) | GVPDRFTGSGS GTDFTLTINNV QSEDLADYFC (SEQ ID NO: 94) | FGAGTKLELK (SEQ ID NO: 95) |
| Contact | DIVLTQSHKFM STSVGDRVSIT CKASQDV (SEQ ID NO: 100) | QQKPGQPPK (SEQ ID NO: 101) | TGVPDRFTGSG SGTDFTLTINN VQSEDLADYFC (SEQ ID NO: 102) | TFGAGTKLELK (SEQ ID NO: 99) |
| IMGT | DIVLTQSHKFM STSVGDRVSIT CKAS (SEQ ID NO: 103) | VTWCQQKPGQ PPKLLIY (SEQ ID NO: 97) | TRHTGVPDRFT GSGSGTDFTLTI NNVQSEDLAD YFC (SEQ ID NO: 104) | FGAGTKLELK (SEQ ID NO: 95) |
| Exemplary | DIVLTQSHKFM STSVGDRVSIT C (SEQ ID NO: 92) | WCQQKPGQPP KLLIY (SEQ ID NO: 93) | GVPDRFTGSGS GTDFTLTINNV QSEDLADYFC (SEQ ID NO: 94) | FGAGTKLELK (SEQ ID NO: 95) |

TABLE 11

Antibody z10 Variable Region Amino Acid Sequences

| VH | QVQLVQSGAEVKKPGASVKVSCKASGYTFTNYGMNWVRQAPGQGLE WMGWINTYTGEPTYADDFKGRVTFTTDTSTSTAYMELRSLRSDDMA VYYCARKSTVVSRYFDVWGQGTTVTVSS (SEQ ID NO: 105) |
|---|---|
| VL | DIQMTQSPSFLSASVGDRVTITCKASQDVGDAVTWYQQKPGKAPKL LIYWASTRHTGVPDRFSGSGSGTDFTLTISSLQPEDFATYYCQQYR SYPLTFGQGTKLEIK (SEQ ID NO: 106) |

TABLE 12

Antibody z11 Variable Region Amino Acid Sequences

| VH | QVQLVQSGAEVKKPGASVKVSCKASGYTFTNYGMNWVRQAPGQGLE WMGWINTYTGEPTYADDFKGRVTMTLDTSTSTAYMELRSLRSDDMA VYYCARKSTVVSRYFDVWGQGTTVTVSS (SEQ ID NO: 107) |
|---|---|
| VL | DIQMTQSPSFLSASVGDRVTITCKASQDVGDAVTWYQQKPGKAPKL LIYWASTRHTGVPDRFSGSGSGTDFTLTISSLQPEDFATYYCQQYR SYPLTFGQGTKLEIK (SEQ ID NO: 106) |

TABLE 13

Antibody z13 Variable Region Amino Acid Sequences

| VH | QVQLVQSGAEVKKPGASVKVSCKASGYTFTNYGMNWVRQAPGQG LEWMGWINTYTGEPTYADDFKGRVTFTLDTSTSTAYMELRSLRS DDMAVYYCARKSTVVSRYFDVWGQGTTVTVSS (SEQ ID NO: 108) |
|---|---|

TABLE 13-continued

Antibody z13 Variable Region Amino Acid Sequences

| VL | DIQMTQSPSFLSASVGDRVTITCKASQDVGDAVTWYQQKPGKAP KLLIYWASTRHTGVPDRFSGSGSGTDFTLTISSLQPEDFATYYC QQYRSYPLTFGQGTKLEIK (SEQ ID NO: 106) |
|---|---|

TABLE 14

Antibody Heavy Chain Variable Region Consensus Amino Acid Sequence ($X_1$ is F or M; $X_2$ is T or L)

| VH | QVQLVQSGAEVKKPGASVKVSCKASGYTFTNYGMNWVRQAPGQGLE WMGWINTYTGEPTYADDFKGRVTX$_1$TX$_2$DTSTSTAYMELRSLRSDD MAVYYCARKSTVVSRYFDVWGQGTTVTVSS (SEQ ID NO: 109) |
|---|---|

TABLE 15

Antibody xAb Variable Region Amino Acid Sequences

| VH | QIQLVQSGPELKKPGETVKISCKASGYTFTNYGMNWVKQAPGKGLK WMGWINTYTGEPTYADDFKGRFVFSLETSASTAYLQINNLKNEDMA TYFCARKSTVVSRYFDVWGAGTTVTVSS (SEQ ID NO: 110) |
|---|---|
| VL | DIVLTQSHKFMSTSVGDRVSITCKASQDVGDAVTWCQQKPGQPPKL LIYWASTRHTGVPDRFTGSGSGTDFTLTINNVQSEDLADYFCQQYR SYPLTFGAGTKLELK (SEQ ID NO: 111) |

TABLE 16

Antibody z10 Heavy Chain and Light Chain Amino Acid Sequences

Heavy Chain
QVQLVQSGAEVKKPGASVKVSCKASGYTFTNYGMNWVRQAPGQ
GLEWMGWINTYTGEPTYADDFKGRVTFTTDTSTSTAYMELRSL
RSDDMAVYYCARKSTVVSRYFDVWGQGTTVTVSSASTKGPS
VFPLAPSSKSTSGGTAALGCLVKDYFPEPVTVSWNSGALTSGVHT
FPAVLQSSGLYSLSSVVTVPSSSLGTQTYICNVNHKPSNTKVD
KRVEPKSCDKTHTCPPCPAPELLGGPSVFLFPPKPKDTLMISR
TPEVTCVVVDVSHEDPEVKFNWYVDGVEVHNAKTKPREEQYNS
TYRVVSVLTVLHQDWLNGKEYKCKVSNKALPAPIEKTISKAKG
QPREPQVYTLPPSREEMTKNQVSLTCLVKGFYPSDIAVEWESN
GQPENNYKTTPPVLDSDGSFFLYSKLTVDKSRWQQGNVFSCSV
MHEALHNHYTQKSLSLSPGK
(SEQ ID NO: 112)

Light Chain
DIQMTQSPSFLSASVGDRVTITCKASQDVGDAVTWYQQKPGKA
PKLLIYWASTRHTGVPDRFSGSGSGTDFTLTISSLQPEDFATY
YCQQYRSYPLTFGQGTKLEIKRTVAAPSVFIFPPSDEQLKSGT
ASVVCLLNNFYPREAKVQWKVDNALQSGNSQESVTEQDSKDST
YSLSSTLTLSKADYEKHKVYACEVTHQGLSSPVTKSFNRGEC
(SEQ ID NO: 113)

TABLE 17

Antibody z11 Heavy Chain and Light Chain Amino Acid Sequences

Heavy Chain
QVQLVQSGAEVKKPGASVKVSCKASGYTFTNYGMNWVRQAPGQ
GLEWMGWINTYTGEPTYADDFKGRVTMTLDTSTSTAYMELRSL
RSDDMAVYYCARKSTVVSRYFDVWGQGTTVTVSSASTKGPSVF
PLAPSSKSTSGGTAALGCLVKDYFPEPVTVSWNSGALTSGVHT
FPAVLQSSGLYSLSSVVTVPSSSLGTQTYICNVNHKPSNTKVD
KRVEPKSCDKTHTCPPCPAPELLGGPSVFLFPPKPKDTLMISR
TPEVTCVVVDVSHEDPEVKFNWYVDGVEVHNAKTKPREEQYNS
TYRVVSVLTVLHQDWLNGKEYKCKVSNKALPAPIEKTISKAKG
QPREPQVYTLPPSREEMTKNQVSLTCLVKGFYPSDIAVEWESN
GQPENNYKTTPPVLDSDGSFFLYSKLTVDKSRWQQGNVFSCSV
MHEALHNHYTQKSLSLSPGK
(SEQ ID NO: 114)

Light Chain
DIQMTQSPSFLSASVGDRVTITCKASQDVGDAVTWYQQKPGKA
PKLLIYWASTRHTGVPDRFSGSGSGTDFTLTISSLQPEDFATY
YCQQYRSYPLTFGQGTKLEIKRTVAAPSVFIFPPSDEQLKSGT
ASVVCLLNNFYPREAKVQWKVDNALQSGNSQESVTEQDSKDST
YSLSSTLTLSKADYEKHKVYACEVTHQGLSSPVTKSFNRGEC
(SEQ ID NO: 113)

TABLE 18

Antibody z13 Heavy Chain and Light Chain Amino Acid Sequences

Heavy Chain
QVQLVQSGAEVKKPGASVKVSCKASGYTFTNYGMNWVRQAPGQ
GLEWMGWINTYTGEPTYADDFKGRVTFTLDTSTSTAYMELRSL
RSDDMAVYYCARKSTVVSRYFDVWGQGTTVTVSSASTKGPSVF
PLAPSSKSTSGGTAALGCLVKDYFPEPVTVSWNSGALTSGVHT
FPAVLQSSGLYSLSSVVTVPSSSLGTQTYICNVNHKPSNTKVD
KRVEPKSCDKTHTCPPCPAPELLGGPSVFLFPPKPKDTLMISR
TPEVTCVVVDVSHEDPEVKFNWYVDGVEVHNAKTKPREEQYNS
TYRVVSVLTVLHQDWLNGKEYKCKVSNKALPAPIEKTISKAKG
QPREPQVYTLPPSREEMTKNQVSLTCLVKGFYPSDIAVEWESN
GQPENNYKTTPPVLDSDGSFFLYSKLTVDKSRWQQGNVFSCSV
MHEALHNHYTQKSLSLSPGK
(SEQ ID NO: 115)

Light Chain
DIQMTQSPSFLSASVGDRVTITCKASQDVGDAVTWYQQKPGKA
PKLLIYWASTRHTGVPDRFSGSGSGTDFTLTISSLQPEDFATY
YCQQYRSYPLTFGQGTKLEIKRTVAAPSVFIFPPSDEQLKSGT
ASVVCLLNNFYPREAKVQWKVDNALQSGNSQESVTEQDSKDST
YSLSSTLTLSKADYEKHKVYACEVTHQGLSSPVTKSFNRGEC
(SEQ ID NO: 113)

TABLE 19

Antibody Heavy Chain Consensus Amino Acid Sequences ($X_1$ is F or M; $X_2$ is T or L)

Heavy Chain
QVQLVQSGAEVKKPGASVKVSCKASGYTFTNYGMNWVRQAPGQ
GLEWMGWINTYTGEPTYADDFKGRVTX$_1$TX$_2$DTSTSTAYMELR
SLRSDDMAVYYCARKSTVVSRYFDVWGQGTTVTVSSASTKGPS
VFPLAPSSKSTSGGTAALGCLVKDYFPEPVTVSWNSGALTSGV
HTFPAVLQSSGLYSLSSVVTVPSSSLGTQTYICNVNHKPSNTK
VDKRVEPKSCDKTHTCPPCPAPELLGGPSVFLFPPKPKDTLMI
SRTPEVTCVVVDVSHEDPEVKFNWYVDGVEVHNAKTKPREEQY
NSTYRVVSVLTVLHQDWLNGKEYKCKVSNKALPAPIEKTISKA
KGQPREPQVYTLPPSREEMTKNQVSLTCLVKGFYPSDIAVEWE
SNGQPENNYKTTPPVLDSDGSFFLYSKLTVDKSRWQQGNVFSC
SVMHEALHNHYTQKSLSLSPGK
(SEQ ID NO: 116)

TABLE 20

Antibody xAb Heavy Chain and Light Chain Amino Acid Sequences

Heavy Chain
QIQLVQSGPELKKPGETVKISCKASGYTFTNYGMNWVKQAPGK
GLKWMGWINTYTGEPTYADDFKGRFVFSLETSASTAYLQINNL
KNEDMATYFCARKSTVVSRYFDVWGAGTTVTVSSASTKGPSVF
PLAPSSKSTSGGTAALGCLVKDYFPEPVTVSWNSGALTSGVHT
FPAVLQSSGLYSLSSVVTVPSSSLGTQTYICNVNHKPSNTKVD
KRVEPKSCDKTHTCPPCPAPELLGGPSVFLFPPKPKDTLMISR
TPEVTCVVVDVSHEDPEVKFNWYVDGVEVHNAKTKPREEQYNS
TYRVVSVLTVLHQDWLNGKEYKCKVSNKALPAPIEKTISKAKG
QPREPQVYTLPPSREEMTKNQVSLTCLVKGFYPSDIAVEWESN
GQPENNYKTTPPVLDSDGSFFLYSKLTVDKSRWQQGNVFSCSV
MHEALHNHYTQKSLSLSPGK
(SEQ ID NO: 117)

Light Chain
DIVLTQSHKFMSTSVGDRVSITCKASQDVGDAVTWCQQKPGQP
PKLLIYWASTRHTGVPDRFTGSGSGTDFTLTINNVQSEDLADY
FCQQYRSYPLTFGAGTKLELKRTVAAPSVFIFPPSDEQLKSGT
ASVVCLLNNFYPREAKVQWKVDNALQSGNSQESVTEQDSKDST
YSLSSTLTLSKADYEKHKVYACEVTHQGLSSPVTKSFNRGEC
(SEQ ID NO: 118)

TABLE 21

Antibody z10 Variable Region DNA Sequences

VH
caggtgcagctggtgcagagcggcgctgaggtgaagaagcccggcg
ctagcgtgaaggtgagctgcaaggccagcggctacaccttcaccaa
ctacggcatgaactgggtgaggcaggctcctggacagggcctggag
tggatgggctggatcaacacatacaccggcgagcccacctacgcg
acgacttcaagggcagggtgaccttcaccaccgacaccagcaccag
caccgcctacatggagctgaggagcctgagaagcgacgacatggcc
gtgtactactgcgccagaaagagcaccgtggtgtccaggtacttcg
acgtgtggggccagggcaccacagtgaccgtgagcagc
(SEQ ID NO: 119)

VL
gacatccagatgacccagagccccagcttcctgtccgctagcgtgg
gcgacagggtgaccatcacctgcaaggccagccaggacgtgggcga
tgccgtgacctggtatcagcagaagcccggcaaggcccccaagctg
ctgatctactgggccagcacaaggcacaccggcgtgcccgacagat
tcagcggcagcggaagcggcaccgacttcaccctgaccatcagcag
cctgcagcccgaggacttcgccacctactactgccagcagtacagg
agctaccccctgaccttcggccagggcaccaagctggaaatcaag
(SEQ ID NO: 120)

TABLE 22

Antibody z11 Variable Region DNA Sequences

VH
caggtgcagctggtgcagagcggagccgaggtgaagaagcctggcg
ccagcgtgaaggtgagctgcaaggccagcggctacaccttcaccaa
ctacggcatgaactgggtgaggcaggctcctggccagggactggag
tggatgggctggatcaacacctacaccggcgagcccacctacgccg
acgacttcaagggcagggtgaccatgaccctggacaccagcaccag

TABLE 22-continued

Antibody z11 Variable Region DNA Sequences caccgcctacatggagctgaggagcctgaggagcgacgacatggcc
gtgtactactgcgcgcaggaagagcaccgtggtgtccaggtacttcg
acgtgtggggacagggcaccaccgtgaccgtgagcagc
(SEQ ID NO: 121)

VL gacatccagatgacccagagccccagcttcctgtccgctagcgtgg
gcgacagggtgaccatcacctgcaaggccagccaggacgtgggcga
tgccgtgacctggtatcagcagaagcccggcaaggcccccaagctg
ctgatctactgggccagcacaaggcacacaggcgtgcccgacagat
tcagcggcagcggaagcggcaccgacttcaccctgaccatcagcag
cctgcagcccgaggacttcgccacctactactgccagcagtacagg
agctaccccctgaccttcggccagggcaccaagctggaaatcaag
(SEQ ID NO: 120)

TABLE 23

Antibody z13 Variable Region DNA Sequences

VH caggtgcagctggtgcagagcggagccgaagtgaagaagcccggcg
ccagcgtgaaggtgagctgcaaggccagcggctacaccttcaccaa
ctacggcatgaactgggtgagacaggcccctggacagggactggag
tggatgggctggatcaacacctacaccggcgagcccacctacgccg
acgacttcaagggcagggtgaccttcacccttggacactgaccaccag
caccgcctacatggagctgaggagcctgaggagcgacgacatggcc
gtgtactattgcgcgcaggaagagcaccgtggtgagcaggtacttcg
acgtgtggggccagggaaccaccgtgaccgtgagcagc
(SEQ ID NO: 122)

VL gacatccagatgacccagagccccagcttcctgtccgctagcgtgg
gcgacagggtgaccatcacctgcaaggccagccaggacgtgggcga
tgccgtgacctggtatcagcagaagcccggcaaggcccccaagctg
ctgatctactgggccagcacaaggcacacaggcgtgcccgacagat
tcagcggcagcggaagcggcaccgacttcaccctgaccatcagcag
cctgcagcccgaggacttcgccacctactactgccagcagtacagg
agctaccccctgaccttcggccagggcaccaagctggaaatcaag
(SEQ ID NO: 120)

TABLE 24

Antibody xAb Variable Region DNA Sequences

VH cagatccagttggtgcagtctggacctgagctgaagaagcctggag
agacagtcaagatctcctgcaaggcttctggatataccttcacaaa
ctatggaatgaactgggtgaagcaggctccaggaaagggtttaaag
tggatgggctggataaacacctacactggagagccaacatatgctg
atgacttcaaggacggtttgtcttctctttggaaacctctgccag
cactgcctacttgcagatcaacaacctcaaaaatgaggacatggcc
acatatttctgtgcaagaaaaagtacgtagtaagtaggtacttcg
atgtctgggcgcagggaccacggtcaccgtctcctca
(SEQ ID NO: 123)

VL gacattgtgctgacccagtctcacaaattcatgtccacatcagtag
gagacagggtcagcatcacctgcaaggccagtcaggatgtgggtga
tgctgtaacctggtgtcaacagaaaccaggtcaacctcctaaacta
ctgatttactgggcatccacccggcacactggagtgcctgatcgt
tcacaggcagtgggtctgggacagatttcactcttcaccattaacaa
tgtgcagtctgaggacttggcagatatttctgtcagcaatatcgc
agctatcctctcacgttcggtgctgggaccaagctggagctgaaa
(SEQ ID NO: 124)

TABLE 25

Antibody z10 Heavy Chain and Light Chain DNA Sequences

Heavy caggtgcagctggtgcagagcggcgctgaggtgaagaagcccgg
Chain cgccagcgtgaaggtgagctgcaaggccagcggctacaccttc
caccaactacggcatgaactgggtgaggcaggctcctggacag
ggcctggagtggatgggctggatcaacacatacaccggcgagc
ccacctacgccgacgacttcaagggcagggtgaccttaccac
cgacaccagcaccagcaccgcctacatggagctgaggagcctg

TABLE 25-continued

Antibody z10 Heavy Chain and Light Chain DNA Sequences agaagcgacgacatggccgtgtactactgcgccagaaagagca
ccgtggtgtccaggtacttcgacgtgtggggccagggcaccac
agtgaccgtgagcagcgcgtcgaccaagggcccatccgtcttc
cccctggcaccctcctccaagagcacctctgggggcacagcgg
ccctgggctgcctggtcaaggactacttccccgaaccggtgac
ggtgtcctggaactcaggcgctctgaccagcggcgtgcacacc
ttccggctgtcctacagtcctcaggactctactccctcagca
gcgtggtgaccgtgccctccagcagcttgggcacccagaccta
catctgcaacgtgaatcacaagcccagcaacaccaaggtggac
aagagagttgagcccaaatcttgtgacaaaactcacacatgcc
caccgtgcccagcacctgaactcctggggggaccgtcagtctt
cctcttccccccaaaacccaaggacaccctcatgatctcccgg
acccctgaggtcacatgcgtggtggtggacgtgagccacgaaga
ccctgaggtcaagttcaactggtacgtggacggcgtggaggt
gcataatgccaagacaaagccgcgggaggagcagtacaacagc
acgtaccgtgtggtcagcgtcctcaccgtcctgcaccaggact
ggctgaatggcaaggagtacaagtgcaaggtctccaacaaagc
cctcccagcccccatcgagaaaaccatctccaaagccaaaggg
cagccccgagaaccacaggtctacaccctgcccccatcccggg
aggagatgaccaagaaccaggtcagcctgacctgcctggtcaa
aggcttctatcccagcgacatcgccgtggagtgggagagcaat
gggcagccggagaacaactacaagaccacgcctcccgtgctgg
actccgacggctccttcttcctctatagcaagctcaccgtgga
caagagcaggtggcagcaggggaacgtcttctcatgctccgtg
atgcatgaggctctgcacaaccactacacgcagaagagataag
cctgtctccgggtaaatga
(SEQ ID NO: 125)

Light gacatccagatgacccagagccccagcttcctgtccgctagcg
Chain tgggcgacagggtgaccatcacctgcaaggccagccaggacgt
gggcgatgccgtgacctggtatcagcagaagcccggcaaggcc
cccaagctgctgatctactgggccagcacaaggcacacaggcg
tgcccgacagattcagcggcagcggaagcggcaccgacttcac
cctgaccatcagcagcctgcagcccgaggacttcgccacctac
tactgccagcagtacaggagctaccccctgaccttcggccagg
gcaccaagctggaaatcaagcgtacggtggctgcaccatcgt
cttcatcttcccgccatctgatgagcagttgaaatctggaact
gcctctgttgtgtgcctgctgaataacttctatcccagagagg
ccaaagtacagtggaaggtggataacgccctccaatcgggtaa
ctcccaggagagtgtcacagagcaggacagcaaggacagcacc
tacagcctcagcagcaccctgacgctgagcaaagcagactacg
agaaacacaaagtctacgcctgcgaagtcacccatcagggcct
gagctcgcccgtcacaaagagcttcaacaggggagagtgttga
(SEQ ID NO: 126)

TABLE 26

Antibody z11 Heavy Chain and Light Chain DNA Sequences

Heavy caggtgcagctggtgcagagcggaccgaggtgaagaagcctg
Chain gcgccagcgtgaaggtgagctgcaaggccagcggctacacctt
caccaactacggcatgaactgggtgaggcaggctcctggccag
ggactggagtggatgggctggatcaacacctacaccggcgagc
ccacctacgccgacgacttcaagggcagggtgaccatgaccct
ggacaccagcaccagcaccgcctacatggagctgaggagcctg
aggagcgacgacatggccgtgtactactgcgcgcaggaagagca
ccgtggtgtccaggtacttcgacgtgtggggacagggcaccac
cgtgaccgtgagcagcgcgtcgaccaagggcccatccgtcttc
cccctggcaccctcctccaagagcacctctgggggcacagcgg
ccctgggctgcctggtcaaggactacttccccgaaccggtgac
ggtgtcctggaactcaggcgctctgaccagcggcgtgcacacc
ttccggctgtcctacagtcctcaggactctactccctcagca
gcgtggtgaccgtgccctccagcagcttgggcacccagaccta
catctgcaacgtgaatcacaagcccagcaacaccaaggtggac
aagagagttgagcccaaatcttgtgacaaaactcacacatgcc
caccgtgcccagcacctgaactcctggggggaccgtcagtctt
cctcttccccccaaaacccaaggacaccctcatgatctcccgg
acccctgaggtcacatgcgtggtggtggacgtgagccacgaaga
ccctgaggtcaagttcaactggtacgtggacggcgtggaggt
gcataatgccaagacaaagccgcgggaggagcagtacaacagc
acgtaccgtgtggtcagcgtcctcaccgtcctgcaccaggact
ggctgaatggcaaggagtacaagtgcaaggtctccaacaaagc
cctcccagcccccatcgagaaaaccatctccaaagccaaaggg

TABLE 26-continued

Antibody z11 Heavy Chain and Light Chain DNA Sequences cagccccgagaaccacaggtctacaccctgccccatcccggg
aggagatgaccaagaaccaggtcagcctgacctgcctggtcaa
aggcttctatcccagcgacatcgccgtggagtgggagagcaat
gggcagccggagaacaactacaagaccacgcctcccgtgctgg
actccgacggctccttcttcctctatagcaagctcaccgtgga
caagagcaggtggcagcaggggaacgtcttctcatgctccgtg
atgcatgaggctctgcacaaccactacacgcagaagagcttaa
gcctgtctccgggtaaatga
(SEQ ID NO: 127)

Light Chain
gacatccagatgacccagagccccagcttcctgtccgctagcg
tgggcgacagggtgaccatcacctgcaaggccagccaggacgt
gggcgatgccgtgacctggtatcagcagaagcccggcaaggcc
cccaagctgctgatctactgggccagcacaaggcacacaggcg
tgcccgacagattcagcggcagcggaagcggcaccgacttcac
cctgaccatcagcagcctgcagcccgaggacttcgccacctac
tactgccagcagtacaggagctaccccctgaccttcggccagg
gcaccaagctggaaatcaagcgtacggtggctgcaccatctgt
cttcatcttcccgccatctgatgagcagttgaaatctggaact
gcctctgttgtgtgcctgctgaataacttctatcccagagagg
ccaaagtacagtggaaggtggataacgccctccaatcgggtaa
ctcccaggagagtgtcacagagcaggacagcaaggacagcacc
tacagcctcagcagcaccctgacgctgagcaaagcagactacg
agaaacacaaagtctacgcctgcgaagtcacccatcagggcct
gagctcgcccgtcacaaagagcttcaacaggggagagtgttga
(SEQ ID NO: 126)

TABLE 27

Antibody z13 Heavy Chain and Light Chain DNA Sequences

Heavy Chain
caggtgcagctggtgcagagcggagccgaagtgaagaagcccg
gcgccagcgtgaaggtgagctgcaaggccagcggctacacctt
caccaactacggcatgaactgggtgagacaggcccctggacag
ggactggagtggatggctggatcaacacctacactggcgagc
ccacctacgccgacgacttcaagggcagggtgaccttcaccct
ggacaccagcaccagcaccgcctacatggagctgaggagcctg
aggagcgacgacatggccgtgtactattgcgccaggaagagca
ccgtggtgagcaggtacttcgacgtgtggggccagggaaccac
cgtcaccgtgagcagcgcgtcgaccaagggcccatccgtcttc
cccctggcaccctcctccaagagcacctctggggcacagcgg
ccctgggctgcctggtcaaggactacttccccgaaccggtgac
ggtgtcctggaactcaggcgctctgaccagcggcgtgcacacc
ttcccggctgtcctacagtcctcaggactctactccctcagca
gcgtggtgaccgtgccctccagcagcttgggcacccagaccta
catctgcaacgtgaatcacaagcccagcaacaccaaggtggac
aagagagttgagcccaaatcttgtgacaaaactcacacatgcc
caccgtgcccagcacctgaactcctggggggaccgtcagtctt
cctcttccccccaaaacccaaggacaccctcatgatctcccgg
accccctgaggtcacatgcgtggtggtggacgtgagccacgaag
accctgaggtcaagttcaactggtacgtggacggcgtggaggt
gcataatgccaagacaaagccgcgggaggagcagtacaacagc
acgtaccgtgtggtcagcgtcctcaccgtcctgcaccaggact
ggctgaatggcaaggagtacaagtgcaaggtctccaacaaagc
cctcccagcccccatcgagaaaaccatctccaaagccaaaggg
cagccccgagaaccacaggtctacaccctgccccatcccggg
aggagatgaccaagaaccaggtcagcctgacctgcctggtcaa
aggcttctatcccagcgacatcgccgtggagtgggagagcaat
gggcagccggagaacaactacaagaccacgcctcccgtgctgg
actccgacggctccttcttcctctatagcaagctcaccgtgga
caagagcaggtggcagcaggggaacgtcttctcatgctccgtg
atgcatgaggctctgcacaaccactacacgcagaagagcttaa
gcctgtctccgggtaaatga
(SEQ ID NO: 128)

Light Chain
gacatccagatgacccagagccccagcttcctgtccgctagcg
tgggcgacagggtgaccatcacctgcaaggccagccaggacgt
gggcgatgccgtgacctggtatcagcagaagcccggcaaggcc
cccaagctgctgatctactgggccagcacaaggcacacaggcg
tgcccgacagattcagcggcagcggaagcggcaccgacttcac
cctgaccatcagcagcctgcagcccgaggacttcgccacctac
tactgccagcagtacaggagctaccccctgaccttcggccagg
gcaccaagctggaaatcaagcgtacggtggctgcaccatctgt

TABLE 27-continued

Antibody z13 Heavy Chain and Light Chain DNA Sequences cttcatcttcccgccatctgatgagcagttgaaatctggaact
gcctctgttgtgtgcctgctgaataacttctatcccagagagg
ccaaagtacagtggaaggtggataacgccctccaatcgggtaa
ctcccaggagagtgtcacagagcaggacagcaaggacagcacc
tacagcctcagcagcaccctgacgctgagcaaagcagactacg
agaaacacaaagtctacgcctgcgaagtcacccatcagggcct
gagctcgcccgtcacaaagagcttcaacaggggagagtgttga
(SEQ ID NO: 126)

TABLE 28

Antibody xAb Heavy Chain and Light Chain DNA Sequences

Heavy Chain
cagatccagttggtgcagtctggacctgagctgaagaagcctg
gagagacagtcaagatctcctgcaaggcttctggatataccttc
cacaaactatggaatgaactgggtgaagcaggctccaggaaag
ggtttaaagtggattgggctggataaacacctacactggagagc
caacatatgctgatgacttcaagggacggtttgtcttctcttt
ggaaacctctgccagcactgcctacttgcagatcaacaacctc
aaaaatgaggacatggccacatatttctgtgcaagaaaagta
cggtagtaagtaggtacttcgatgtctgggggcgcagggaccac
ggtcaccgtctcctcagcgtcgaccaagggcccatccgtcttc
cccctggcaccctcctccaagagcacctctggggcacagcgg
ccctgggctgcctggtcaaggactacttccccgaaccggtgac
ggtgtcctggaactcaggcgctctgaccagcggcgtgcacacc
ttcccggctgtcctacagtcctcaggactctactccctcagca
gcgtggtgaccgtgccctccagcagcttgggcacccagaccta
catctgcaacgtgaatcacaagcccagcaacaccaaggtggac
aagagagttgagcccaaatcttgtgacaaaactcacacatgcc
caccgtgcccagcacctgaactcctggggggaccgtcagtctt
cctcttccccccaaaacccaaggacaccctcatgatctcccgg
accccctgaggtcacatgcgtggtggtggacgtgagccacgaag
accctgaggtcaagttcaactggtacgtggacggcgtggaggt
gcataatgccaagacaaagccgcgggaggagcagtacaacagc
acgtaccgtgtggtcagcgtcctcaccgtcctgcaccaggact
ggctgaatggcaaggagtacaagtgcaaggtctccaacaaagc
cctcccagcccccatcgagaaaaccatctccaaagccaaaggg
cagccccgagaaccacaggtctacaccctgccccatcccggg
aggagatgaccaagaaccaggtcagcctgacctgcctggtcaa
aggcttctatcccagcgacatcgccgtggagtgggagagcaat
gggcagccggagaacaactacaagaccacgcctcccgtgctgg
actccgacggctccttcttcctctatagcaagctcaccgtgga
caagagcaggtggcagcaggggaacgtcttctcatgctccgtg
atgcatgaggctctgcacaaccactacacgcagaagagcttaa
gcctgtctccgggtaaatga
(SEQ ID NO: 129)

Light Chain
gacattgtgctgacccagtctcacaaattcatgtccacatcag
taggagacagggtcagcatcacctgcaaggccagtcaggatgt
gggtgatgctgtaacctggtgtcaacagaaaccaggtcaacct
cctaaactactgatttactgggcatccacccggcacactggag
tccctgatcgcttcacaggcagtgggtctgggacagatttcac
tctcaccattaacaatgtgcagtctgaggacttggcagattat
ttctgtcagcaatatcgcagctatcctctcacgttcggtgctg
ggaccaagctggagctgaaacgtacggtggctgcaccatctgt
cttcatcttcccgccatctgatgagcagttgaaatctggaact
gcctctgttgtgtgcctgctgaataacttctatcccagagagg
ccaaagtacagtggaaggtggataacgccctccaatcgggtaa
ctcccaggagagtgtcacagagcaggacagcaaggacagcacc
tacagcctcagcagcaccctgacgctgagcaaagcagactacg
agaaacacaaagtctacgcctgcgaagtcacccatcagggcct
gagctcgcccgtcacaaagagcttcaacaggggagagtgttga
(SEQ ID NO: 130)

TABLE 29

MERTK Protein Sequences

| | |
|---|---|
| Full-Length Human MERTK (Swiss-Prot ID: Q12866.2) | MGPAPLPLLLGLFLPALWRRAITEAREEAKPYPLFPGPF PGSLQTDHTPLLSLPHASGYQPALMFSPTQPGRPHTGNV AIPQVTSVESKPLPPLAFKHTVGHIILSEHKGVKFNCSI SVPNIYQDTTISWWKDGKELLGAHHAITQFYPDDEVTAI IASFSITSVQRSDNGSYICKMKINNEEIVSDPIYIEVQG LPHFTKQPESMNVTRNTAFNLTCQAVGPPEPVNIFWVQN SSRVNEQPEKSPSVLTVPGLTEMAVFSCEAHNDKGLTVS KGVQINIKAIPSPPTEVSIRNSTAHSILISWVPGFDGYS PFRNCSIQVKEADPLSNGSVMIFNTSALPHLYQIKQLQA LANYSIGVSCMNEIGWSAVSPWILASTTEGAPSVAPLNV TVFLNESSDNVDIRWMKPPTKQQDGELVGYRISHVWQSA GISKELLEEVGQNGSRARISVQVHNATCTVRIAAVTRGG VGPFSDPVKIFIPAHGWVDYAPSSTPAPGNADPVLIIFG CFCGFILIGLILYISLAIRKRVQETKFGNAFTEEDSELV VNYIAKKSFCRRAIELTLHSLGVSEELQNKLEDVVIDRN LLILGKILGEGEFGSVMEGNLKQEDGTSLKVAVKTMKLD NSSQREIEEFLSEAACMKDFSHPNVIRLLGVCIEMSSQG IPKPMVILPFMKYGDLHTYLLYSRLETGPKHIPLQTLLK FMVDIALGMEYLSNRNFLHRDLAARNCMLRDDMTVCVAD FGLSKKIYSGDYYRQGRIAKMPVKWIAIESLADRVYTSK SDVWAFGVTMWEIATRGMTPYPGVQNHEMYDYLLHGHRL KQPEDCLDELYEIMYSCWRTDPLDRPTFSVLRLQLEKLL ESLPDVRNQADVIYVNTQLLESSEGLAQGSTLAPLDLNI DPDSIIASCTPRAAISVVTAEVHDSKPHEGRYILNGGSE EWEDLTSAPSAAVTAEKNSVLPGERLVRNGVSWSHSSML PLGSSLPDELLFADDSSEGSEVLM (SEQ ID NO: 131) |
| Extra-cellular Doman of MERTK Used for Immunization | REEAKPYPLFPGPFPGSLQTDHTPLLSLPHASGYQPALM FSPTQPGRPHTGNVAIPQVTSVESKPLPPLAFKHTVGHI ILSEHKGVKFNCSISVPNIYQDTTISWWKDGKELLGAHH AITQFYPDDEVTAIIASFSITSVQRSDNGSYICKMKINN EEIVSDPIYIEVQGLPHFTKQPESMNVTRNTAFNLTCQA VGPPEPVNIFWVQNSSRVNEQPEKSPSVLTVPGLTEMAV FSCEAHNDKGLTVSKGVQINIKAIPSPPTEVSIRNSTAH SILISWVPGFDGYSPFRNCSIQVKEADPLSNGSVMIFNT SALPHLYQIKQLQALANYSIGVSCMNEIGWSAVSPWILA STTEGAPSVAPLNVTVFLNESSDNVDIRWMKPPTKQQDG ELVGYRISHVWQSAGISKELLEEVGQNGSRARISVQVHN ATCTVRIAAVTRGGVGPFSDPVKIFIPAHGWVDYAPSST PAPGNA (SEQ ID NO: 132) |

In a specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable heavy chain region (VH) CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the Exemplary numbering system, and FR1, FR2, FR3 and FR4 comprise the amino acid sequences of the FR1, FR2, FR3, and FR4 set forth in Table 2, 3, 4 or 5 using the Exemplary numbering system. In another specific embodiment, provided herein is an anti-MERTK or an antigen-binding fragment thereof that specifically binds to MERTK (e.g., human MERTK), wherein the antibody or antigen-binding fragment thereof comprises a framework region (FR) 1, a variable heavy chain region (VH) CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the Kabat numbering system, and FR1, FR2, FR3 and FR4 comprise the amino acid sequences of the FR1, FR2, FR3, and FR4 set forth in Table 2, 3, 4 or 5 using the Kabat numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable heavy chain region (VH) CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the Chothia numbering system, and FR1, FR2, FR3 and FR4 comprise the amino acid sequences of the FR1, FR2, FR3, and FR4 set forth in Table 2, 3, 4 or 5 using the Chothia numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable heavy chain region (VH) CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the AbM numbering system, and FR1, FR2, FR3 and FR4 comprise the amino acid sequences of the FR1, FR2, FR3, and FR4 set forth in Table 2, 3, 4 or 5 using the AbM numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable heavy chain region (VH) CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the Contact numbering system, and FR1, FR2, FR3 and FR4 comprise the amino acid sequences of the FR1, FR2, FR3, and FR4 set forth in Table 2, 3, 4 or 5 using the Contact numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable heavy chain region (VH) CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the IMGT numbering system, and FR1, FR2, FR3 and FR4 comprise the amino acid sequences of the FR1, FR2, FR3, and FR4 set forth in Table 2, 3, 4 or 5 using the IMGT numbering system.

In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable heavy chain region (VH) CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the one numbering system, and FR1, FR2, and FR4 comprise the amino acid sequences of the FR1, FR2, and FR4 set forth in Table 2, 3, or 4 using the same numbering system, and the FR3 comprises the amino acid sequence of the FR3 set forth in Table 5 using the same numbering system.

In a specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH), wherein the VH comprises a framework region (FR) 1, a VH CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the Exemplary numbering system, and FR1, FR2, FR3 and FR4 comprise the amino acid sequences of the FR1, FR2, FR3, and FR4 set forth in Table 2, 3, 4 or 5 using the Exemplary numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH), wherein the VH comprises a framework region (FR) 1, a VH CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the Kabat numbering system, and FR1, FR2, FR3 and FR4 comprise the amino acid sequences of the FR1, FR2, FR3, and FR4 set forth in Table 2, 3, 4 or 5 using the Kabat numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH), wherein the VH comprises a framework region (FR) 1, a VH CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the Chothia numbering system, and FR1, FR2, FR3 and FR4 comprise the amino acid sequences of the FR1, FR2, FR3, and FR4 set forth in Table 2, 3, 4 or 5 using the Chothia numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH), wherein the VH comprises a framework region (FR) 1, a VH CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the AbM numbering system, and FR1, FR2, FR3 and FR4 comprise the amino acid sequences of the FR1, FR2, FR3, and FR4 set forth in Table 2, 3, 4 or 5 using the AbM numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH), wherein the VH comprises a framework region (FR) 1, a VH CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the Contact numbering system, and FR1, FR2, FR3 and FR4 comprise the amino acid sequences of the FR1, FR2, FR3, and FR4 set forth in Table 2, 3, 4 or 5 using the Contact numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH), wherein the VH comprises a framework region (FR) 1, a VH CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using the IMGT numbering system, and FR1, FR2, FR3 and FR4 comprise the amino acid sequences of the FR1, FR2, FR3, and FR4 set forth in Table 2, 3, 4 or 5 using the IMGT numbering system.

In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH), wherein the VH comprises a framework region (FR) 1, a VH CDR1, an FR2, a VH CDR2, an FR3, a VH CDR3 and an FR4, and wherein the VH CDR1, VH CDR2, VH CDR3 comprise the amino acid sequences of the VH CDR1, VH CDR2, and VH CDR3 set forth in Table 1 using one numbering system, and FR1, FR2, and FR4 comprise the amino acid sequences of the FR1, FR2, and FR4 set forth in Table 2, 3, or 4 using the same numbering system, and the FR3 comprises the amino acid sequence of the FR3 set forth in Table 5 using the same numbering system.

In a specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the Exemplary numbering system, and FR1, FR2, FR3 and FR4 comprise the amino acid sequences of the FR1, FR2, FR3, and FR4 set forth in Table 9 using the Exemplary numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the Kabat numbering system, and FR1, FR2, FR3 and FR4 comprise the amino acid sequences of the FR1, FR2, FR3, and FR4 set forth in Table 9 using the Kabat numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the Chothia numbering system, and FR1, FR2, FR3 and FR4 comprise the amino acid sequences of the FR1, FR2, FR3, and FR4 set forth in Table 9 using the Chothia numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the AbM numbering system, and FR1, FR2, FR3 and FR4 comprise the amino acid sequences of the FR1, FR2, FR3, and FR4 set forth in Table 9 using the AbM numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the Contact numbering system, and FR1, FR2, FR3 and FR4 comprise the amino acid sequences of the FR1, FR2, FR3, and FR4 set forth in Table 9 using the Contact numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the IMGT numbering system, and FR1, FR2, FR3 and FR4 comprise the amino acid sequences of the FR1, FR2, FR3, and FR4 set forth in Table 9 using the IMGT numbering system.

In a specific embodiment, provided herein is an anti-MERTK antibody or an antigen-binding fragment thereof that specifically binds to MERTK (e.g., human MERTK), wherein the antibody or antigen-binding fragment thereof comprises a variable light chain region (VL), wherein the VL comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the Exemplary numbering system, and FR1, FR2, FR3 and FR4 comprise the amino acid sequences of the FR1, FR2, FR3, and FR4 set forth in Table 9 using the Exemplary numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable light chain region (VL), wherein the VL comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the Kabat numbering system, and FR1, FR2, FR3 and FR4 comprise the amino acid sequences of the FR1, FR2, FR3, and FR4 set forth in Table 9 using the Kabat numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable light chain region (VL), wherein the VL comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the Chothia numbering system, and FR1, FR2, FR3 and FR4 comprise the amino acid sequences of the FR1, FR2, FR3, and FR4 set forth in Table 9 using the Chothia numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable light chain region (VL), wherein the VL comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the AbM numbering system, and FR1, FR2, FR3 and FR4 comprise the amino acid sequences of the FR1, FR2, FR3, and FR4 set forth in Table 9 using the AbM numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable light chain region (VL), wherein the VL comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the Contact numbering system, and FR1, FR2, FR3 and FR4 comprise the amino acid sequences of the FR1, FR2, FR3, and FR4 set forth in Table 9 using the Contact numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable light chain region (VL), wherein the VL comprises a framework region (FR) 1, a variable light chain region (VL) CDR1, an FR2, a VL CDR2, an FR3, a VL CDR3 and an FR4, and wherein the VL CDR1, VL CDR2, VL CDR3 comprise the amino acid sequences of the VL CDR1, VL CDR2, and VL CDR3 set forth in Table 7 using the IMGT numbering system, and FR1, FR2, FR3 and FR4 comprise the amino acid sequences of the FR1, FR2, FR3, and FR4 set forth in Table 9 using the IGMT numbering system.

In a specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH comprises a VH framework region (FR) 1, a VH CDR1, a VH FR2, a VH CDR2, a VH FR3, a VH CDR3 and a VH FR4, wherein the VL comprises a VL FR1, a VL CDR1, a VL FR2, a VL CDR2, a VL FR3, a VL CDR3, and a VL FR4, wherein the VH CDR1, VH CDR2, VH CDR3 comprise the amino acid sequences of the VH CDR1, VH CDR2, and VH CDR3 set forth in Table 1 using the Exemplary numbering system, wherein the VH FR1, VH FR2, VH FR3 and VH FR4 comprise the amino acid sequences of the VH FR1, VH FR2, VH FR3, and VH FR4 set forth in Table 2, 3, 4 or 5 using the exemplary numbering system, wherein the VL CDR1, VL CDR2, and VL CDR3 comprise the amino acid sequences of the VL CDR1, VL CDR2, and VL CDR3 set forth in Table 7 using the Exemplary numbering system, and wherein the VL FR1, VL FR2, VL FR3, and VL FR4 comprise the amino acid sequences of the VL FR1, VL FR2, VL FR3, and VL FR4 set forth in Table 9 using the exemplary numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH comprises a VH framework region (FR) 1, a VH CDR1, a VH FR2, a VH CDR2, a VH FR3, a VH CDR3 and a VH FR4, wherein the VL comprises a VL FR1, a VL CDR1, a VL FR2, a VL CDR2, a VL FR3, a VL CDR3, and a VL FR4, wherein the VH CDR1, VH CDR2, VH CDR3 comprise the amino acid sequences of the VH CDR1, VH CDR2, and VH CDR3 set forth in Table 1 using the Kabat numbering system, wherein the VH FR1, VH FR2, VH FR3 and VH FR4 comprise the amino acid sequences of the VH FR1, VH FR2, VH FR3, and VH FR4 set forth in Table 2, 3, 4 or 5 using the Kabat numbering system, wherein the VL CDR1, VL CDR2, and VL CDR3 comprise the amino acid sequences of the VL CDR1, VL CDR2, and VL CDR3 set forth in Table 7 using the Kabat numbering system, and wherein the VL FR1, VL FR2, VL FR3, and VL FR4 comprise the amino acid sequences of the VL FR1, VL FR2, VL FR3, and VL FR4 set forth in Table 9 using the Kabat numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH comprises a VH framework region (FR) 1, a VH CDR1, a VH FR2, a VH CDR2, a VH FR3, a VH CDR3 and a VH FR4, wherein the VL comprises a VL FR1, a VL CDR1, a VL FR2, a VL CDR2, a VL FR3, a VL CDR3, and a VL FR4, wherein the VH CDR1, VH CDR2, VH CDR3 comprise the amino acid sequences of the VH CDR1, VH CDR2, and VH CDR3 set forth in Table 1 using the Chothia numbering system, wherein the VH FR1, VH FR2, VH FR3 and VH FR4 comprise the amino acid sequences of the VH FR1, VH FR2, VH FR3, and VH FR4 set forth in Table 2, 3, 4 or 5 using the Chothia numbering system, wherein the VL CDR1, VL CDR2, and VL CDR3 comprise the amino acid sequences of the VL CDR1, VL CDR2, and VL CDR3 set forth in Table 7 using the Chothia numbering system, and wherein the VL FR1, VL FR2, VL FR3, and VL FR4 comprise the amino acid sequences of the VL FR1, VL FR2, VL FR3, and VL FR4 set forth in Table 9 using the Chothia numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH comprises a VH framework region (FR) 1, a VH CDR1, a VH FR2, a VH CDR2, a VH FR3, a VH CDR3 and a VH FR4, wherein the VL comprises a VL FR1, a VL CDR1, a VL FR2, a VL CDR2, a VL FR3, a VL CDR3, and a VL FR4, wherein the VH CDR1, VH CDR2, VH CDR3 comprise the amino acid sequences of the VH CDR1, VH CDR2, and VH CDR3 set forth in Table 1 using the AbM numbering system, wherein the VH FR1, VH FR2, VH FR3 and VH FR4 comprise the amino acid sequences of the VH FR1, VH FR2, VH FR3, and VH FR4 set forth in Table 2, 3, 4 or 5 using the AbM numbering system, wherein the VL CDR1, VL CDR2, and VL CDR3 comprise the amino acid sequences of the VL CDR1, VL CDR2, and VL CDR3 set forth in Table 7 using the AbM numbering system, and wherein the VL FR1, VL FR2, VL FR3, and VL FR4 comprise the amino acid sequences of the VL FR1, VL FR2, VL FR3, and VL FR4 set forth in Table 9 using the AbM numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH comprises a VH framework region (FR) 1, a VH CDR1, a VH FR2, a VH CDR2, a VH FR3, a VH CDR3 and a VH FR4, wherein the VL comprises a VL FR1, a VL CDR1, a VL FR2, a VL CDR2, a VL FR3, a VL CDR3, and a VL FR4, wherein the VH CDR1, VH CDR2, VH CDR3 comprise the amino acid sequences of the VH CDR1, VH CDR2, and VH CDR3 set forth in Table 1 using the Contact numbering system, wherein the VH FR1, VH FR2, VH FR3 and VH FR4 comprise the amino acid sequences of the VH FR1, VH FR2, VH FR3, and VH FR4 set forth in Table 2, 3, 4 or 5 using the Contact numbering system, wherein the VL CDR1, VL CDR2, and VL CDR3 comprise the amino acid sequences of the VL CDR1, VL CDR2, and VL CDR3 set forth in Table 7 using the Contact numbering system, and wherein the VL FR1, VL FR2, VL FR3, and VL FR4 comprise the amino acid sequences of the VL FR1, VL FR2, VL FR3, and VL FR4 set forth in Table 9 using the Contact numbering system. In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH comprises a VH framework region (FR) 1, a VH CDR1, a VH FR2, a VH CDR2, a VH FR3, a VH CDR3 and a VH FR4, wherein the VL comprises a VL FR1, a VL CDR1, a VL FR2, a VL CDR2, a VL FR3, a VL CDR3, and a VL FR4, wherein the VH CDR1, VH CDR2, VH CDR3 comprise the amino acid sequences of the VH CDR1, VH CDR2, and VH CDR3 set forth in Table 1 using the IMGT numbering system, wherein the VH FR1, VH FR2, VH FR3 and VH FR4 comprise the amino acid sequences of the VH FR1, VH FR2, VH FR3, and VH FR4 set forth in Table 2, 3, 4 or 5 using the IMGT numbering system, wherein the VL CDR1, VL CDR2, and VL CDR3 comprise the amino acid sequences of the VL CDR1, VL CDR2, and VL CDR3 set forth in Table 7 using the IMGT numbering system, and wherein the VL FR1, VL FR2, VL FR3, and VL FR4 comprise the amino acid sequences of the VL FR1, VL FR2, VL FR3, and VL FR4 set forth in Table 9 using the IMGT numbering system.

In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH comprises a VH framework region (FR) 1, a VH CDR1, a VH FR2, a VH CDR2, a VH FR3, a VH CDR3 and a VH FR4, wherein the VL comprises a VL FR1, a VL CDR1, a VL FR2, a VL CDR2, a VL FR3, a VL CDR3, and a VL FR4, wherein the VH CDR1, VH CDR2, VH CDR3 comprise the amino acid sequences of the VH CDR1, VH CDR2, and VH CDR3 set forth in Table 1 using one numbering system, wherein the VH FR1, VH FR2, VH FR3 and VH FR4 comprise the amino acid sequences of the VH FR1, VH FR2, and VH FR4 set forth in Table 2, 3, or 4 using the same numbering system, wherein the VH FR3 comprises the amino acid sequence of the VH FR3 set forth in Table 5, wherein the VL CDR1, VL CDR2, and VL CDR3 comprise the amino acid sequences of the VL CDR1, VL CDR2, and VL CDR3 set forth in Table 7 using the same numbering system, and wherein the VL FR1, VL FR2, VL FR3, and VL FR4 comprise the amino acid sequences of the VL FR1, VL FR2, VL FR3, and VL FR4 set forth in Table 9 using the same numbering system.

In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH CDR1 comprises the amino acid sequence of SEQ ID NO: 1, the VH CDR2 comprises the amino acid sequence of SEQ ID NO: 6, the VH CDR3 comprises the amino acid sequence of SEQ ID NO: 11, the VL CDR1 comprises the amino acid sequence of SEQ ID NO: 68, the VL CDR2 comprises the amino acid sequence of SEQ ID NO: 69 and the VL CDR3 comprises the amino acid sequence of SEQ ID NO: 70.

In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH CDR1 comprises the amino acid sequence of SEQ ID NO: 2, the VH CDR2 comprises the amino acid sequence of SEQ ID NO: 7, the VH CDR3 comprises the amino acid sequence of SEQ ID NO: 12, the VL CDR1 comprises the amino acid sequence of SEQ ID NO: 71, the VL CDR2 comprises the amino acid sequence of SEQ ID NO: 72 and the VL CDR3 comprises the amino acid sequence of SEQ ID NO: 73.

In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH CDR1 comprises the amino acid sequence of SEQ ID NO: 3, the VH CDR2 comprises the amino acid sequence of SEQ ID NO: 8, the VH CDR3 comprises the amino acid sequence of SEQ ID NO: 11, the VL CDR1 comprises the amino acid sequence of SEQ ID NO: 68, the VL CDR2 comprises the amino acid sequence of SEQ ID NO: 69 and the VL CDR3 comprises the amino acid sequence of SEQ ID NO: 70.

In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH CDR1 comprises the amino acid sequence of SEQ ID NO: 4, the VH CDR2 comprises the amino acid sequence of SEQ ID NO: 9, the VH CDR3 comprises the amino acid sequence of SEQ ID NO: 13, the VL CDR1 comprises the amino acid sequence of SEQ ID NO: 74, the VL CDR2 comprises the amino acid sequence of SEQ ID NO: 75 and the VL CDR3 comprises the amino acid sequence of SEQ ID NO: 76.

In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH CDR1 comprises the amino acid sequence of SEQ ID NO: 5, the VH CDR2 comprises the amino acid sequence of SEQ ID NO: 10, the VH CDR3 comprises the amino acid sequence of SEQ ID NO: 14, the VL CDR1 comprises the amino acid sequence of SEQ ID NO: 77, the VL CDR2 comprises the amino acid sequence of SEQ ID NO: 72 and the VL CDR3 comprises the amino acid sequence of SEQ ID NO: 70.

In another specific embodiment, provided herein is an anti-MERTK antibody or an antigen-binding fragment thereof that specifically binds to MERTK (e.g., human MERTK), wherein the antibody or antigen-binding fragment thereof comprises a variable heavy chain region (VH) and a variable light chain region (VL), wherein the VH CDR1 comprises the amino acid sequence of SEQ ID NO: 3, the VH CDR2 comprises the amino acid sequence of SEQ ID NO: 6, the VH CDR3 comprises the amino acid sequence of SEQ ID NO: 11, the VL CDR1 comprises the amino acid sequence of SEQ ID NO: 68, the VL CDR2 comprises the amino acid sequence of SEQ ID NO: 69 and the VL CDR3 comprises the amino acid sequence of SEQ ID NO: 70.

In a particular embodiment, an anti-MERTK antibody or an antigen-binding fragment thereof described herein, which specifically binds to MERTK (e.g., human MERTK), comprises a heavy chain variable region (VH) comprising the amino acid sequence of SEQ ID NO: 105. In another particular embodiment, an anti-MERTK antibody or an antigen-binding fragment thereof described herein, which specifically binds to MERTK (e.g., human MERTK), comprises a heavy chain variable region (VH) comprising the amino acid sequence of SEQ ID NO: 107. In another particular embodiment, an anti-MERTK antibody or an antigen-binding fragment thereof described herein, which specifically binds to MERTK (e.g., human MERTK), comprises a heavy chain variable region (VH) comprising the amino acid sequence of SEQ ID: 108. In another particular embodiment, a humanized anti-MERTK or an antigen-binding fragment thereof described herein, which specifically binds to MERTK (e.g., human MERTK), comprises a heavy chain variable region (VH) comprising the amino acid sequence of SEQ ID NO: 109.

In a particular embodiment, an anti-MERTK antibody or an antigen-binding fragment thereof described herein, which specifically binds to MERTK (e.g., human MERTK), comprises a heavy chain variable region (VH) comprising the amino acid sequence of SEQ ID: 110.

In a particular embodiment, an anti-MERTK antibody or an antigen-binding fragment thereof described herein, which specifically binds to MERTK (e.g., human MERTK), comprises a light chain variable region (VL) comprising the amino acid sequence of SEQ ID NO: 106. In another embodiment, an anti-MERTK antibody or an antigen-binding fragment thereof, which specifically binds to MERTK (e.g., human MERTK), comprises a variable light chain region (VL) comprising the amino acid sequence of SEQ ID NO: 111.

In a specific embodiment, an anti-MERTK antibody or antigen-binding fragment thereof, which specifically binds to MERTK (e.g., human MERTK), comprises a heavy chain variable region (VH) and a light chain variable region (VL), wherein the VH comprises the amino acid sequence of SEQ ID NO: 105, and the VL comprises the amino acid sequence of SEQ ID NO: 106. In another specific embodiment, an anti-MERTK antibody or antigen-binding fragment thereof, which specifically binds to MERTK (e.g., human MERTK) comprises a heavy chain variable region (VH) and a light chain variable region (VL), wherein the VH comprises the amino acid sequence of SEQ ID NO: 107, and the VL comprises the amino acid sequence of SEQ ID NO: 106. In another embodiment, an anti-MERTK antibody or antigen-binding fragment thereof, which specifically binds to MERTK (e.g., human MERTK) comprises a heavy chain variable region (VH) and a light chain variable region (VL), wherein the VH comprises the amino acid sequence of SEQ ID NO: 108, and the VL comprises the amino acid sequence of SEQ ID NO: 106. In another embodiment, an anti-MERTK antibody or antigen-binding fragment thereof, which specifically binds to MERTK (e.g., human MERTK) comprises a heavy chain variable region (VH) and a light chain variable region (VL), wherein the VH comprises the amino acid sequence of SEQ ID NO: 110, and the VL comprises the amino acid sequence of SEQ ID NO: 111.

In another specific embodiment, an anti-MERTK antibody or an antigen-binding fragment thereof, which specifically binds to MERTK (e.g., human MERTK), comprises a heavy chain variable region (VH) and a light chain variable region (VL), wherein the VH comprises the amino acid sequence of SEQ ID NO: 109, and the VL comprises the amino acid sequence of SEQ ID NO: 106 or 111.

In another specific embodiment, an anti-MERTK antibody or an antigen-binding fragment thereof, which specifically binds to MERTK (e.g., human MERTK), comprises a heavy chain variable region (VH) and a light chain variable region (VL), wherein the VH comprises the amino acid sequence of the VH set forth in Table 11 and the VL comprises the amino acid sequence of the VL set forth in Table 11. In another specific embodiment, a humanized anti-MERTK antibody or an antigen-binding fragment thereof, which specifically binds to MERTK (e.g., human MERTK), comprises a heavy chain variable region (VH) and a light chain variable region (VL), wherein the VH comprises the amino acid sequence of the VH set forth in Table 12 and the VL comprises the amino acid sequence of the VL set forth in Table 12. In another specific embodiment, an anti-MERTK antibody or an antigen-binding fragment thereof, which specifically binds to MERTK (e.g., human MERTK), comprises a heavy chain variable region (VH) and a light chain variable region (VL), wherein the VH comprises the amino acid sequence of the VH set forth in Table 13 and the VL comprises the amino acid sequence of the VL set forth in Table 13. In another specific embodiment, an anti-MERTK antibody or an antigen-binding fragment thereof, which specifically binds to MERTK (e.g., human MERTK), comprises a heavy chain variable region (VH) and a light chain variable region (VL), wherein the VH comprises the amino acid sequence of the VH set forth in Table 14 and the VL comprises the amino acid sequence of the VL set forth in Table 11, 12 or 13.

In certain aspects, an antibody described herein may be described by its VH domain alone, or its VL domain alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson T et al., (1991) Nature 352: 624-628, which is incorporated herein by reference in its entirety, describing methods of producing antibodies that bind a specific antigen by using a specific VH domain (or VL domain) and screening a library for the complementary variable domains. See also, Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

As used herein, the terms "immunospecifically binds," "immunospecifically recognizes," "specifically binds," and "specifically recognizes" are analogous terms in the context of antibodies and refer to antibodies and antigen-binding fragments thereof that bind to an antigen (e.g., epitope or immune complex) via the antigen-binding sites as understood by one skilled in the art, and does not exclude cross-reactivity of the antibody or antigen-binding fragment with other antigens. Any method known in the art can be used to ascertain whether immunospecific binding to MERTK (e.g., human MERTK) is maintained.

In specific aspects, provided herein is an anti-MERTK antibody or antigen-binding fragment thereof comprising an antibody heavy chain and/or light chain, e.g., a heavy chain alone, a light chain alone, or both a heavy chain and a light chain. With respect to the light chain, in a specific embodiment, the light chain of an anti-MERTK antibody or an antigen-binding fragment thereof described herein is a kappa light chain. In another specific embodiment, the light chain of an anti-MERTK antibody or an antigen-binding fragment thereof described herein is a lambda light chain. In yet another specific embodiment, the light chain of an anti-MERTK antibody or an antigen-binding fragment thereof described herein is a human kappa light chain or a human lambda light chain.

In another particular embodiment, an anti-MERTK antibody or an antigen-binding fragment thereof described herein, which specifically binds to MERTK (e.g., human MERTK), comprises a light chain, wherein the light chain comprises a variable light chain region (VL) and the kappa light chain constant region amino acid sequence, wherein the VL comprises the amino acid sequence of SEQ ID NO: 106 or SEQ ID NO: 111. As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

In a specific embodiment, an anti-MERTK antibody or an antigen-binding fragment thereof described herein, which specifically binds to MERTK (e.g., human MERTK), comprises a light chain, wherein the light chain comprises a variable light chain region (VL) and a human kappa or lambda light chain constant region, wherein the VL comprises the amino acid sequence of SEQ ID NO: 106 or SEQ ID NO: 111. Non-limiting examples of human constant region sequences have been described in the art, e.g., see Kabat E A et al., (1991).

In another particular embodiment, an anti-MERTK antibody or an antigen-binding fragment thereof described herein, which specifically binds to MERTK (e.g., human MERTK), comprises a light chain, wherein the light chain comprises the amino acid sequence of SEQ ID NO: 113 or SEQ ID NO: 118.

With respect to the heavy chain, in a specific embodiment, the heavy chain of an anti-MERTK antibody or an antigen-binding fragment thereof described herein can be a human alpha (α), delta (δ), epsilon (ε), gamma (γ) or mu (μ) heavy chain. In a specific embodiment, an anti-MERTK antibody or an antigen-binding fragment thereof, which specifically binds to MERTK (e.g., human MERTK), comprises a heavy chain, wherein the heavy chain comprises the constant region or a portion thereof (e.g. $C_H1$, $C_H2$ or $C_H3$ or a combination thereof) described herein or known in the art, and a variable heavy chain region (VH) of an anti-MERTK antibody described herein (e.g., SEQ ID NO: 105, SEQ ID NO: 107, SEQ ID NO: 108, 109 or SEQ ID NO: 110).

In a particular embodiment, an anti-MERTK antibody or an antigen-binding fragment thereof, which specifically binds to MERTK (e.g., human MERTK), comprises a heavy chain, wherein the heavy chain comprises a variable heavy chain region (VH) of an anti-MERTK antibody described herein (e.g., SEQ ID NO: 105, 107, 108, 109 or 110), and the constant region or portion thereof (e.g. $C_H1$, $C_H2$ or $C_H3$ or a combination thereof) of the human gamma heavy chain constant region variable region. In a specific embodiment, an anti-MERTK antibody or an antigen-binding fragment thereof, which specifically binds to MERTK (e.g., human MERTK) comprises the amino acid sequence of SEQ ID NO: 112, SEQ ID NO: 114, SEQ ID NO: 115, SEQ ID NO: 116, or SEQ ID NO: 117. Non-limiting examples of human constant region sequences have been described in the art, e.g., see Kabat E A et al., (1991) supra.

In a specific embodiment, an anti-MERTK antibody described herein, which specifically binds to MERTK (e.g., human MERTK), comprises (i) a heavy chain comprising the amino acid sequence of SEQ ID NO: 112 and (ii) a light chain comprising the amino acid of SEQ ID NO: 113. In a specific embodiment, an anti-MERTK antibody described herein, which specifically binds to MERTK (e.g., human MERTK), comprises (i) a heavy chain comprising the amino acid sequence of SEQ ID NO: 114 and (ii) a light chain comprising the amino acid of SEQ ID NO: 113. In a specific embodiment, an anti-MERTK antibody described herein, which specifically binds to MERTK (e.g., human MERTK), comprises (i) a heavy chain comprising the amino acid sequence of SEQ ID NO: 115 and (ii) a light chain comprising the amino acid sequence of SEQ ID NO: 113. In a specific embodiment, an anti-MERTK antibody described herein, which specifically binds to MERTK (e.g., human MERTK), comprises (i) a heavy chain comprising the amino acid sequence of SEQ ID NO: 116 and (ii) a light chain comprising the amino acid of SEQ ID NO: 113. In a specific embodiment, an anti-MERTK antibody described herein, which specifically binds to MERTK (e.g., human MERTK), comprises (i) a heavy chain comprising the amino acid sequence of SEQ ID NO: 117 and (ii) a light chain comprising the amino acid of SEQ ID NO: 118.

In a specific embodiment, an anti-MERTK antibody or antigen-binding fragment thereof described herein, which immunospecifically binds to MERTK (e.g., human MERTK) comprises a heavy chain variable region (VH) and a light chain variable region (VL) comprising any amino acid sequences described herein, and wherein the constant regions comprise the amino acid sequences of the constant regions of a human IgG, IgE, IgM, IgD, IgA or IgY immunoglobulin molecule. In another specific embodiment, an anti-MERTK antibody or antigen-binding fragment thereof described herein, which immunospecifically binds to MERTK (e.g., human MERTK) comprises a VH and a VL comprising any amino acid sequences described herein, and wherein the constant regions comprise the amino acid sequences of the constant regions (e.g., those set forth in Tables 11, 12, 13 or 15) of a human IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_{2a}$ and $IgG_{2b}$) of immunoglobulin molecule.

In certain embodiments, one, two or more mutations (e.g., amino acid substitutions) are introduced into the Fc region of an anti-MERTK antibody or an antigen-binding fragment thereof described herein to alter one or more functional properties of the antibody.

In some embodiments, one, two or more mutations (e.g., amino acid substitutions) are introduced into the Fc region of an anti-MERTK antibody or an antigen-binding fragment thereof described herein (e.g., $C_H2$ domain (residues 231-340 of human $IgG_1$) and/or $C_H3$ domain (residues 341-447 of human $IgG_1$) and/or the hinge region, with numbering according to the Kabat numbering system (e.g., the EU index in Kabat)) to increase or decrease the affinity of the antibody or an antigen-binding fragment thereof for an Fc receptor (e.g., an activated Fc receptor) on the surface of an effector cell. Mutations in the Fc region of an anti-MERTK antibody or antigen-binding fragment thereof that decrease or increase the affinity of an antibody for an Fc receptor, and techniques for introducing such mutations into the Fc receptor or fragment thereof are known to one of skill in the art. Examples of mutations in the Fc receptor of an anti-MERTK antibody or antigen-binding fragment thereof that can be made to alter the affinity of the antibody or an antigen-binding fragment thereof for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, the antibody or antigen-binding fragment thereof described herein comprises a glycosylated constant region. In some embodiments, the antibody or antigen-binding fragment thereof described herein comprises a non-glycosylated constant region. Antibodies with reduced fucose content have been reported to have an increased affinity for Fc receptors, such as, e.g., FcγRIIIa. Accordingly, in certain embodiments, the antibodies or antigen-binding fragments thereof described herein have reduced fucose content or no fucose content. Such antibodies or antigen-binding fragments thereof can be produced using techniques known to one skilled in the art. For example, the antibodies or antigen-binding fragments thereof can be expressed in cells deficient or lacking the ability of fucosylation. In a specific example, cell lines with a knockout of both alleles of α1,6-fucosyltransferase can be used to produce antibodies with reduced fucose content. The Potelligent® system (Lonza) is an example of such a system that can be used to produce antibodies or antigen-binding fragments thereof with reduced fucose content. Alternatively, antibodies or antigen-binding fragments with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies or antigen-binding fragments thereof which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies or antigen-binding fragments thereof with no fucose content or reduced fucose content.

In another particular embodiment, an anti-MERTK antibody or an antigen-binding fragment thereof described herein, which specifically binds to MERTK (e.g., human MERTK), comprises a heavy chain or a light chain, wherein (i) the heavy chain comprises (a) a variable region comprising the amino acid sequence of SEQ ID NO: 105, SEQ ID NO: 107, SEQ ID NO: 108 or SEQ ID NO: 109 and (b) a constant heavy chain domain comprising the amino acid sequence of the constant domain of a human IgG; or (ii) the light chain comprises (a) a variable region comprising the amino acid sequence of SEQ ID NO: 106 and (b) a constant light chain domain comprising the amino acid sequence of the constant domain of a human light chain.

In another particular embodiment, an anti-MERTK antibody or an antigen-binding fragment thereof described herein, which specifically binds to MERTK (e.g., human MERTK), comprises a heavy chain and a light chain, wherein (i) the heavy chain comprises (a) a variable region comprising the amino acid sequence of SEQ ID NO: 105, SEQ ID NO: 107, SEQ ID NO: 108, or SEQ ID NO: 109 and (b) a constant heavy chain domain comprising the amino acid sequence of the constant domain of a human IgG; and (ii) the light chain comprises a variable region comprising the amino acid sequence of SEQ ID NO: 106, and (b) a constant light chain domain comprising the amino acid sequence of the constant domain of a human kappa light chain.

In another particular embodiment, an anti-MERTK antibody or an antigen-binding fragment thereof described herein, which specifically binds to MERTK (e.g., human MERTK), comprises a heavy chain or a light chain, wherein (i) the heavy chain comprises (a) a variable region comprising the amino acid sequence of SEQ ID NO: 110 and (b) a constant heavy chain domain comprising the amino acid sequence of the constant domain of a human IgG; or (ii) the heavy chain comprises (a) a variable region comprising the amino acid sequence of SEQ ID NO: 111 and (b) a constant light chain domain comprising the amino acid sequence of the constant domain of a human kappa light chain. In another particular embodiment, an anti-MERTK antibody or an antigen-binding fragment thereof described herein, which specifically binds to MERTK (e.g., human MERTK), comprises a heavy chain and a light chain, wherein (i) the heavy chain comprises (a) a variable region comprising the amino acid sequence of SEQ ID NO: 110 and (b) a constant heavy chain domain comprising the amino acid sequence of the constant domain of a human IgG; and (ii) the light chain comprises (a) a variable region comprising the amino acid sequence of SEQ ID NO: 111 and (b) a constant light chain domain comprising the amino acid sequence of the constant domain of a human kappa light chain.

The determination of percent identity between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an anti-MERTK antibody or an antigen-binding fragment thereof, which specifically binds to MERTK (e.g., human MERTK), comprises a VH having at least 80%, at least 85%, at least 90%, at least 95%, at least 96%, at least 97%, at least 98%, or at least 99% sequence identity to the amino acid sequence of the VH of SEQ ID NO: 105, SEQ ID NO: 107, or SEQ ID NO: 108 or SEQ ID NO: 109. In some embodiments, an anti-MERTK antibody or an antigen-binding fragment thereof comprises a VH having at least 96%, at least 97%, at least 98%, or at least 99% sequence identity to the amino acid sequence of the VH of SEQ ID NO: 110.

In certain embodiments, an anti-MERTK antibody or an antigen-binding fragment thereof, which immunospecifically binds to MERTK (e.g., human MERTK), comprises a VL having at least 80%, at least 85%, at least 90%, at least 95%, at least 96%, at least 97%, at least 98%, or at least 99% sequence identity to the amino acid sequence of the VL of SEQ ID NO: 106. In certain embodiments, an anti-MERTK antibody or an antigen-binding fragment thereof comprises a VL having at least 99% sequence identity to the VH of SEQ ID NO: 111.

In certain embodiments, an anti-MERTK antibody or antigen-binding fragment thereof, which specifically binds to MERTK (e.g., human MERTK), comprises: (i) a VH domain having at least 80%, at least 85%, at least 90%, at least 95%, at least 96%, at least 97%, at least 98%, or at least 99% sequence identity to the amino acid sequence of the VH domain of SEQ ID NO: 105, SEQ ID NO: 107, or SEQ ID NO: 108 or SEQ ID NO: 109; and (ii) a VL domain having at least 80%, at least 85%, at least 90%, at least 95%, or at least 98% sequence identity to the amino acid sequence of the VL domain of SEQ ID NO: 106.

In certain embodiments, an anti-MERTK antibody or an antigen-binding fragment thereof described herein, which specifically binds to MERTK (e.g., human MERTK), comprises (i) a VH domain having at least 96%, at least 97%, at least 98%, or at least 99% sequence identity to the VH domain of SEQ ID NO: 110, and (ii) a VL domain having at least 99% sequence identity to the VL domain of SEQ ID NO: 111.

In another aspect, provided herein are antibodies that bind the same or an overlapping epitope of MERTK (e.g., human MERTK) as an antibody described herein. As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope of an antibody can be determined by, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) and Cunningham B C & Wells J A (1989) for a description of mutagenesis techniques, including alanine scanning mutagenesis techniques. In addition, antibodies that recognize and bind to the same or overlapping epitopes of MERTK (e.g., human MERTK) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as MERTK. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., MERTK (e.g., human MERTK)) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in a number of different formats, using either labeled antigen or labeled antibody. In a particular embodiment, an antibody can be tested in competition binding assays with an antibody described herein (e.g., antibody z10, z11, or z13).

In another aspect, provided herein are antibodies that compete (e.g., in a dose dependent manner) for binding to MERTK (e.g., human MERTK) with an anti-MERTK antibody described herein (e.g., z10, z11, z13 or xAb) as determined using assays known to one of skill in the art or described herein (e.g., ELISA competitive assays or surface plasmon resonance). In another aspect, provided herein are antibodies that competitively inhibit (e.g., in a dose dependent manner) an anti-MERTK antibody described herein (e.g., z10, z11, z13 or xAb) from binding to MERTK (e.g., human MERTK), as determined using assays known to one of skill in the art or described herein (e.g., ELISA competitive assays, or suspension array or surface plasmon resonance).

In certain embodiments, provided herein is an anti-MERTK antibody that competes with an antibody described herein for binding to MERTK (e.g., human MERTK) to the same extent that the antibody described herein self-competes for binding to MERTK (e.g., human MERTK). In certain embodiments, provided herein is a first antibody that competes with an anti-MERTK antibody described herein for binding to MERTK (e.g., human MERTK), wherein the competition is exhibited as reduced binding of the first antibody to MERTK (e.g., human MERTK) by more than 80% (e.g., 85%, 90%, 95%, or 98%, or between 80% to 85%, 80% to 90%, 85% to 90%, or 85% to 95%).

In specific aspects, provided herein is an anti-MERTK antibody which competes (e.g., in a dose dependent manner) for specific binding to MERTK (e.g., human MERTK), with an antibody comprising a VH domain comprising the amino acid sequence of SEQ ID NO: 105, SEQ ID NO: 107, SEQ ID NO: 108, SEQ ID NO: 109, or SEQ ID NO: 110, and a VL domain comprising the amino acid sequence of SEQ ID NO: 106 or SEQ ID NO: 111

In a specific embodiment, an anti-MERTK antibody (e.g., a humanized antibody or a human antibody) or an antigen-binding fragment thereof that specifically binds to the same or an overlapping epitope of an antibody comprising a VH domain having an amino acid sequence of SEQ ID NO: 105 and a VL domain having an amino acid sequence of SEQ ID NO: 106. In another specific embodiment, an anti-MERTK antibody or an antigen-binding fragment thereof described herein immunospecifically binds to the same or an overlapping epitope of an antibody comprising a VH domain having an amino acid sequence of SEQ ID NO: 107, and a VL domain having an amino acid sequence of SEQ ID NO: 106.

In another specific embodiment, an anti-MERTK antibody or an antigen-binding fragment thereof described herein immunospecifically binds to the same or an overlapping epitope of an antibody comprising a VH domain having an amino acid sequence of SEQ ID NO: 108, and a VL domain having an amino acid sequence of SEQ ID NO: 106. In another specific embodiment, an-MERTK antibody or an antigen-binding fragment thereof described herein immunospecifically binds to the same or an overlapping epitope of an antibody comprising a VH domain having an amino acid sequence of SEQ ID NO: 110, and a VL domain having an amino acid sequence of SEQ ID NO: 111. Assays known to one of skill in the art or described herein (e.g., X-ray crystallography, ELISA assays, etc.) can be used to determine if two antibodies bind to the same epitope. In specific embodiments, an antibody or antigen-binding fragment thereof that competes with an antibody described herein for binding to MERTK (e.g., human MERTK) is not a murine antibody. In specific embodiments, an antibody or antigen-binding fragment thereof that binds to the same or an overlapping epitope of an antibody described herein (e.g., human MERTK) is not a murine antibody.

Affinity can be measured and/or expressed in a number of ways known in the art, including, but not limited to, equilibrium dissociation constant ($K_D$), and equilibrium association constant ($K_A$). The $K_D$ can be determined by techniques known to one of ordinary skill in the art, such as biolayer interferometry or surface plasmon resonance.

In certain embodiments, an anti-MERTK antibody (e.g. a humanized antibody) or an antigen-binding fragment thereof described herein, that competes with an antibody described herein for binding to MERTK (e.g., human MERTK), or an anti-MERTK antibody or antigen-binding fragment thereof that binds to the same or an overlapping epitope of an anti-MERTK antibody described herein, binds to MERTK (e.g. human MERTK) with a $K_D$ of about 8 nM, 7 nM, 6 nM, 5 nM, 4.5 nM, 4 nM, 3.5 nM, 3 nM, 2.5 nM, 2 nM, 1.5 nM, 1 nM, 0.75 nM, 0.5 nM, 0.25 nM, or 0.1 nM. In some embodiments, an anti-MERTK antibody or an antigen-binding fragment thereof described herein, that competes with an antibody described herein for binding to MERTK (e.g., human MERTK), or an anti-MERTK antibody or antigen-binding fragment thereof that binds to the same or an overlapping epitope of an antibody described herein, binds to MERTK (e.g., human MERTK) with a $K_D$ of 0.1 nM to 10 nM, 0.5 nM to 10 nM, 1 nM to 10 nM, 2 nM to 10 nM, 2 nM to 5 nM, 4 nM to 10 nM in an assay such as described herein or known to one of skill in the art. In some embodiments, an anti-MERTK antibody or an antigen-binding fragment thereof described herein that competes with an antibody described herein for binding to MERTK (e.g., human MERTK), or an anti-MERTK antibody or antigen-binding fragment thereof that binds to the same or an overlapping epitope of an antibody described herein, binds to MERTK (e.g., human MERTK) with a $K_D$ avidity of about 2 pM to 8 pM using an assay described herein or known to one of skill in the art.

In a specific embodiment, an anti-MERTK antibody or an antigen-binding fragment thereof described herein binds to MERTK (e.g., human MERTK) with a $K_D$ of about 3 nM in an assay described herein or known to one of skill in the art. In some embodiments, an anti-MERTK antibody or an antigen-binding fragment thereof described herein binds to MERTK (e.g., human MERTK) with a $K_D$ avidity of about 1 pM to 15 pM in an assay described herein or known in the art. In another specific embodiment, an anti-MERTK antibody or an antigen-binding fragment thereof described herein binds to MERTK (e.g., human MERTK) with a $K_D$ avidity of about 1.46 nM in an assay described herein or known to one of skill in the art. In another specific embodiment, an anti-MERTK antibody or an antigen-binding fragment thereof described herein binds to MERTK (e.g., human MERTK) with a $K_D$ avidity of about 5.74 pM in an assay described herein or known to one of skill in the art. In another specific embodiment, an anti-MERTK antibody or an antigen-binding fragment thereof described herein binds to MERTK (e.g., human MERTK) with a $K_D$ avidity of about 3.68 pM in an assay described herein or known to one of skill in the art. In another specific embodiment, an anti-MERTK antibody or an antigen-binding fragment thereof described herein binds to MERTK (e.g., human MERTK) with a $K_D$ avidity of about 2.99 pM in assay described herein or known to one of skill in the art. As used herein, the terms "about" when used to modify a numeric value or numeric range, indicate that deviations of 5% to 10% above and 5% to 10% below the value or range remain within the intended meaning of the recited value or range.

In a specific embodiment, an anti-MERTK antibody or an antigen-binding fragment thereof binds to MERTK (e.g. human MERTK) with an EC50 of 1 nM to 20 nM as assessed by an assay described herein or known in the art. In another specific embodiment, an anti-MERTK antibody or an antigen-binding fragment thereof binds to MERTK (e.g., human MERTK) with an EC50 of 1 nM to 10 nM as assessed by an assay described herein or known in the art. In anther specific embodiment, an anti-MERTK antibody or antigen-binding fragment thereof binds to MERTK (e.g., human MERTK) with an EC50 of about 1 nM, about 2 nM, about 3 nM, about 4 NM, about 5 nM, about 6 nM, about 7 nM, about 8 nM, about 9 nM or about 10 nM as assessed by an assay described herein or known in the art.

In a specific embodiment, an anti-MERTK antibody or an antigen-binding fragment thereof is one described in section 6, infra.

5.1.2. Functional Characteristics

In some aspects, an anti-MERTK antibody or an antigen-binding fragment thereof described herein, which specifically binds to MERTK (e.g., human MERTK), decreases expression levels of human MERTK on cancer cells (e.g. SKMEL5 melanoma cells) by more than 10%, 15%, 20%, 25%, 30%, 35%, 40%, 45%, 50%, 55%, 60%, 65%, 70%, 75%, 80% or 85% as assessed by an assay known to one of skill in the art or described herein. In some aspects, an anti-MERTK antibody or an antigen-binding fragment thereof described herein, which specifically binds to human MERTK, decreases expression levels of human MERTK on human M2 macrophages by more than 10%, 15%, 20%, 25%, 30%, 35%, 40%, 45%, 50%, 55%, 60%, 65%, 70%, 75%, 80% or 85% as assessed by an assay known to one of skill in the art or described herein. In specific embodiment, an anti-MERTK antibody or an antigen-binding fragment thereof binds to MERTK (e.g., human MERTK, but not human Axl, human Tyro3, or murine MERTK, as assessed by methods described herein or known in the art.

In some embodiments, an anti-MERTK antibody or an antigen-binding fragment thereof binds to human MERTK and cynomolgus monkey MERTK.

In some aspects, an anti-MERTK antibody or an antigen-binding fragment thereof described herein, which specifically binds to MERTK (e.g., human MERTK), induces cytokine secretion responses by M2 macrophages, CD14+ monocytes, or both such as set forth in FIG. 10. In certain aspects, an anti-MERTK antibody or an antigen-binding fragment thereof alters the expression of certain cytokines (e.g. the antibody or antigen-binding fragment thereof increases expression of certain cytokines), such as set forth in FIG. 10, by M2 macrophages, CD14+ monocytes, or both by more than 10%, 15%, 20%, 25%, 30%, 35%, 40%, 45%, 50%, 55%, 60%, 65%, 70%, 75%, 80% or 85% as assessed by an assay known to one of skill in the art or described herein.

In some embodiments, an anti-MERTK antibody or an antigen-binding fragment thereof, which specifically binds to MERTK (e.g., human MERTK), blocks (e.g., partially or completely) the level of MERTK phosphorylation induced by Gas-6 in human MERTK expressing cells, such as, e.g., cancer cells (e.g., a melanoma cells), M2 macrophages or both, in an assay known to one of skill in the art. In specific embodiments, an anti-MERTK antibody or an antigen-binding fragment thereof, which specifically binds to MerTK (e.g., human MERTK), reduces the level of human MERTK phosphorylation induced by Gas-6 in human MERTK expressing cells, such as, e.g., cancer cells (e.g., a melanoma cells), M2 macrophages or both, by at least 10%, 15%, 20%, 25%, 30%, 35%, 40%, 45%, 50%, 55%, 60%, 65%, 70%, 75%, 80% or 85% in an assay known to one of skill in the art.

In certain embodiments, an anti-MERTK antibody or an antigen-binding fragment thereof, which specifically binds to MERTK (e.g., human MERTK), induces degradation of human MERTK on human MERTK expressing cells, such as, e.g., cancer cells (e.g., a melanoma cells), M2 macrophages or both. In specific embodiments, an anti-MERTK antibody or an antigen-binding fragment thereof, which specifically binds to MERTK (e.g., human MERTK), reduces the level of human MERTK on the surface of human MERTK expressing cells, such as, e.g., cancer cells (e.g., a melanoma cells), M2 macrophages or both, by at least 10%, 15%, 20%, 25%, 30%, 35%, 40%, 45%, 50%, 55%, 60%, 65%, 70%, 75%, 80% or 85% in an assay described herein or known to one of skill in the art.

In certain embodiments, an anti-MERTK antibody or an antigen-binding fragment thereof, which specifically binds to MERTK (e.g., human MERTK), induces internalization of human MERTK on human MERTK expressing cells, such as, e.g., cancer cells (e.g., a melanoma cells), M2 macrophages or both. In specific embodiments, an anti-MERTK antibody or an antigen-binding fragment thereof, which specifically binds to MERTK (e.g., human MERTK), increases the internalization of human MERTK by human MERTK expressing cells, such as, e.g., cancer cells (e.g., a melanoma cells), M2 macrophages or both, by at least 10%, 15%, 20%, 25%, 30%, 35%, 40%, 45%, 50%, 55%, 60%, 65%, 70%, 75%, 80% or 85% in an assay described herein or known to one of skill in the art.

In some embodiments, an anti-MERTK antibody or an antigen-binding fragment thereof, which specifically binds to MERTK (e.g., human MERTK), inhibits (e.g., partially or completely) colony formation by cancer cells (e.g., a melanoma cells) in an assay described herein or known to one of skill in the art. In specific embodiments, an anti-MERTK antibody or an antigen-binding fragment thereof, which specifically binds to MERTK (e.g., human MERTK), reduces the level of colony formation by cancer cells (e.g., a melanoma cells) by at least 10%, 15%, 20%, 25%, 30%, 35%, 40%, 45%, 50%, 55%, 60%, 65%, 70%, 75%, 80% or 85% in an assay described herein or known to one of skill in the art. In some aspects, an anti-MERTK antibody or an antigen-binding fragment thereof described herein, which immunospecifically binds to MERTK (e.g., human MERTK), reduces the colony forming ability of cancer cells (e.g., SKMEL5 melanoma cells) by more than 10%, 15%, 20%, 25%, 30%, 35%, 40%, 45%, 50%, 55%, 60%, 65%, 70%, 75%, 80% or 85% as assessed by an assay known to one of skill in the art or described herein.

In some aspects, an anti-MERTK antibody or an antigen-binding fragment thereof described herein, which specifically binds to MERTK (e.g., human MERTK), prevents Gas6-induced AKT phosphorylation in an assay described herein or known in the art. In certain embodiments, an anti-MERTK antibody or antigen-binding fragment thereof described herein, which specifically binds to MERTK (e.g., human MERTK), competes with Gas-6 (e.g., human Gas-6) for binding to human MERTK. In some embodiments, an anti-MERTK antibody or antigen-binding fragment thereof described herein inhibits (e.g., completely inhibits or only partially inhibits) Gas-6 from binding to human MERTK. In some embodiments, an anti-MERTK antibody or an antigen-binding fragment thereof described herein, which specifically binds to MERTK (e.g., human MERTK), inhibits the binding of Gas-6 (e.g., human or mouse Gas-6) to human MERTK by more than 10%, 15%, 20%, 25%, 30%, 35%, 40%, 45%, 50%, 55%, 60%, 65%, 70%, 75%, 80% or 85% as assessed by an assay known to one of skill in the art or described herein. In a specific embodiment, the assay that is used to assess inhibition of binding of Gas-6 (e.g., human Gas-6) to human MERTK in the presence of an anti-MERTK antibody or antigen-binding fragment thereof described herein, is antibody the capture ELISA known to one of skill in the art, such as described in International Publication No. WO2016/106221 (e.g., Example 1 of International Publication No. WO2016/106221).

In some embodiments, an anti-MERTK antibody or an antigen-binding fragment thereof, which specifically binds to MERTK (e.g, human MERTK), reduces the level of AKT phosphorylation induced by Gas-6 in human MERTK expressing cancer cells (e.g., a melanoma cells) by at least 10%, 15%, 20%, 25%, 30%, 35%, 40%, 45%, 50%, 55%, 60%, 65%, 70%, 75%, 80% or 85% in an assay described herein or known to one of skill in the art.

In specific embodiments, an anti-MERTK antibody or an antigen-binding fragment thereof described herein, which specifically binds to MERTK (e.g., human MERTK), inhibits angiogenesis within tumors. In some embodiments, the inhibition of angiogenesis is by at least 10%, 15% 20%, 25%, 30%, 35%, 40%, 45%, 50%, 55, 60%, 65%, 70%, 75%, 80% or 85%. In a specific embodiment, the inhibition of angiogenesis is at least 50%, 55%, 60%, 65%, or 70%. Inhibition of angiogenesis can be assessed by methods described herein and/or known to one of skill in the art. The inhibition can be relative to the level of angiogenesis without any antibody or with an unrelated antibody (e.g., an antibody that does not immunospecifically bind to MERTK).

In certain embodiments, an anti-MERTK antibody or an antigen-binding fragment thereof described herein, which specifically binds to MERTK (e.g., human MERTK), inhibits tumor progression. The inhibition of tumor progression by at least 10%, 15% 20%, 25%, 30%, 35%, 40%, 45%, 50%, 55, 60%, 65%, 70%, 75%, 80% or 85%. Tumor progression can be assessed by methods known to one of skill in the art. The tumor progression can be relative to the cancer status without any antibody or with an unrelated antibody (e.g., an antibody that does not specifically bind to human MERTK). In a specific embodiment, an anti-MERTK antibody or an antigen-binding region thereof has one, two, three or more of the characteristics of an antibody described in Section 6, infra.

5.1.3. Bispecific Antibodies

In a specific aspect, provided herein is a bispecific antibody comprising two different antigen binding regions, wherein one of the binding regions specifically binds to human MERTK and the other binding region binds to another antigen of interest, and wherein the binding region that specifically binds to MERTK (e.g., human MERTK) is an anti-MERTK antibody or an antigen-binding fragment thereof described herein. In a specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable heavy chain region of an anti-MERTK antibody or an antigen-binding fragment thereof described herein. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable heavy chain region amino acid sequence of antibody z10 set forth in Table 11. In another specific embodiment, provided herein is a bispecific antibody comprising two different binding regions, wherein one of the binding regions specifically binds to MERTK (e.g., human MERTK) and the other binding region binds to another antigen of interest, and wherein the binding region that specifically binds to MERTK (e.g., human MERTK) comprises the variable heavy chain region amino acid sequence of antibody z11 set forth in Table 12. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable heavy chain region amino acid sequence of antibody z13 set forth in Table 13. In another specific embodiment, provided herein is a bispecific antibody comprising two different binding regions, wherein one of the binding regions specifically binds to MERTK (e.g., human MERTK) and the other binding region binds to another antigen of interest, and wherein the binding region that specifically binds to MERTK (e.g., human MERTK) comprises a variable heavy chain region comprising the amino acid sequence set forth in Table 14.

In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable light chain region of an anti-MERTK antibody or an antigen-binding fragment thereof described herein. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable light chain region amino acid sequence of antibody z10 set forth in Table 11. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable light chain region amino acid sequence of antibody z11 set forth in Table 12. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable light chain region amino acid sequence of antibody z13 set forth in Table 13. In another specific embodiment, provided herein is a bispecific antibody comprising two different binding regions, wherein one of the binding regions specifically binds to MERTK (e.g., human MERTK) and the other binding region binds to another antigen of interest, and wherein the binding region that specifically binds to MERTK (e.g., human MERTK) comprises a variable light chain region, wherein the variable light chain region comprises the amino acid sequence of the VL set forth in Table 11, 12 or 13.

In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable light chain region and the variable heavy chain region of an anti-MERTK antibody or an antigen-binding fragment thereof described herein. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable light chain region and the variable heavy chain region amino acid sequences of antibody z10 set forth in Table 11. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable light chain region and the variable heavy chain region amino acid sequences of antibody z11 set forth in Table 12. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises the variable light chain region and the variable heavy chain region amino acid sequences of antibody z13 set forth in Table 13. In another specific embodiment, provided herein is a bispecific antibody comprising two different antigen binding regions, wherein one of the binding regions specifically binds to MERTK (e.g., human MERTK) and the other binding region binds to another antigen of interest, and wherein the binding region that specifically binds to MERTK (e.g., human MERTK) comprises a variable light chain region and a variable heavy chain region, wherein the variable heavy chain region comprises the amino acid sequence set forth in Table 14 and the variable light chain region comprises the VL amino acid sequence set forth in Table 11, 12 or 13.

In certain embodiments, the antigen of interest to which the other binding region of a bispecific antibody described herein binds is antigen present on an immune cell (e.g., a T cell, an NK cell, or dendritic cell). In some embodiments, the antigen of interest to which the other binding region of a bispecific antibody described herein binds is an immune checkpoint receptor (e.g., PD-1, PD-L1, CTLA-4, LAG3, Tim3, ICOS, CD40, GITR, or OX40). In a specific embodiment, the other binding region of a bispecific antibody described herein comprises an agonistic anti-GITR antibody, an agonistic anti-OX40 antibody or an agonistic anti-CD40 antibody. In specific embodiments, the other binding region of a bispecific antibody comprises a blocking antibody or an antigen-binding fragment thereof that binds to PD-1, PD-L1, CTLA-4 or LAG3. In certain embodiments, the antigen of interest to which the other binding region of a bispecific antibody described herein binds is a T cell receptor. In a specific embodiment, the antigen of interest to which the other binding region of a bispecific antibody described herein binds is CD3, PD-L1, LRP1, LRP8, TGF-β, NKGD2 or TIGIT. In some embodiments, the antigen of interest is a tumor-associated antigen.

In a specific embodiment, the other binding region of a bispecific antibody described herein is nivolumab or an antigen-binding fragment thereof. In another specific embodiment, the other binding region of a bispecific antibody described herein is lambrolizumab or an antigen-binding fragment thereof. In another specific embodiment, the other binding region of a bispecific antibody described herein is MEDI-4736 or an antigen-binding fragment thereof. In another specific embodiment, the other binding region of a bispecific antibody described herein is ipilimumab or an antigen-binding fragment thereof. In another specific embodiment, the other binding region of a bispecific antibody described herein is MPDL-3280A or an antigen-binding fragment thereof. In another specific embodiment, the other binding region of a bispecific antibody described herein is pidilizumab or an antigen-binding fragment thereof. In another specific embodiment, the other binding region of a bispecific antibody described herein is avelumab or an antigen-binding fragment thereof. In another specific embodiment, the other binding region of a bispecific antibody described herein is pembrolizumab or an antigen-binding fragment thereof.

5.2. Antibody-Drug Conjugates.

Provided herein are antibody-drug conjugates comprising: (a) an antibody moiety that is an anti-MERTK antibody or an antigen-binding fragment thereof described herein, which specifically binds to MERTK (e.g., human MERTK); (b) one or more drug moieties, each drug moiety being a cytotoxic agent; and (c) optionally a linker; wherein the cytotoxic agent is conjugated directly to the antibody moiety or is conjugated to the antibody moiety via the linker. The term "conjugated" as used in this disclosure shall mean covalently bound, which can be directly or via an intervening covalently bound structure. The antibody moiety of an antibody-drug conjugate provided herein may be an antibody described in section 5.1 or section 6. An antibody-drug conjugate may be an antibody-drug conjugate described in section 6.

In certain embodiments, the antibody-drug conjugate provided herein has a molar ratio of the antibody moiety to the drug moiety that is between 1:1 and 1:20. In specific embodiments, the antibody-drug conjugate provided herein has a molar ratio of the antibody moiety to the drug moiety that is between 1:1 and 1:15. In specific embodiments, the antibody-drug conjugate provided herein has a molar ratio of the antibody moiety to the drug moiety that is between 1:1 and 1:12. In specific embodiments, the antibody-drug conjugate provided herein has a molar ratio of the antibody moiety to the drug moiety that is between 1:1 and 1:8. In preferred embodiments, the antibody-drug conjugate provided herein has a molar ratio of the antibody moiety to the drug moiety that is between 1:3 and 1:5. In a specific embodiment, the antibody-drug conjugate provided herein has a molar ratio of the antibody moiety to the drug moiety that is 1:3. In another specific embodiment, the antibody-drug conjugate provided herein has a molar ratio of the antibody moiety to the drug moiety that is 1:4. In another specific embodiment, the antibody-drug conjugate provided herein has a molar ratio of the antibody moiety to the drug moiety that is 1:5. In another specific embodiment, the antibody-drug conjugate provided herein has a molar ratio of the antibody moiety to the drug moiety that is 1:9.

The drug moiety is conjugated to one or more chains of the antibody moiety. In some embodiments, the drug moiety is conjugated to one chain of the antibody moiety (for example, when the antibody moiety is a scFv, or when the antibody moiety is a multi-chain antibody, such as an immunoglobulin (which is a tetramer), or antigen-binding fragment thereof). In other embodiments, the drug moiety is conjugated to two or more chains of the antibody moiety (when the antibody moiety is a multi-chain antibody, such as an immunoglobulin, or antigen-binding fragment thereof). In a specific embodiment, the drug moiety is conjugated to two identical chains of an immunoglobulin, e.g., the heavy chains or the light chains. In other embodiments, the drug moiety is conjugated to all chains of the antibody moiety (when the antibody moiety is a multi-chain antibody, such as an immunoglobulin or antigen-binding fragment thereof). In some embodiments, the drug moiety is conjugated to the antibody by a method described in section 6.4 infra.

In a specific embodiment, the drug moiety is conjugated to one or more sites in the constant region of an antibody. In a specific embodiment, the drug moiety is conjugated to one or more sites in the variable region of an antibody. In a specific embodiment, the drug moiety is conjugated to one or more lysine residues in the antibody. In a specific embodiment, the drug moiety is conjugated to one or more cysteine residues in the antibody, e.g., when MMAE or SN-38 is the drug moiety. In a particular embodiment, the drug moiety is conjugated to the Fc region of an antibody that is an immunoglobulin. In specific embodiments, the drug moiety is a peptide or protein fused to the N-terminus or C-terminus of one or more chains of the antibody moiety (directly or via a linker that is a peptide or protein).

For example, when the antibody moiety is an scFv, the drug moiety can be fused at the N- or C-terminus of the scFv (directly or via a linker that is a peptide or protein). In a specific embodiment, when the antibody moiety is a multi-chain antibody or antigen-binding fragment thereof, the drug moiety can be fused to one of the chains of the antibody moiety (directly or via a linker that is a peptide or protein). In the case of an antibody that is an immunoglobulin, in a specific embodiment, both heavy chains can be fused to the drug moiety (directly or via a linker that is a peptide or protein), and/or both light chains can be fused to the drug moiety (directly or via a linker that is a peptide or protein). In such specific embodiments, provided herein are vectors (e.g., expression vectors) comprising polynucleotides comprising a nucleotide sequence encoding a fusion protein composed of the drug moiety and the antibody moiety or a chain thereof, and the linker (if there is one) between the drug moiety and the antibody moiety, for recombinant expression in host cells, preferably in mammalian cells. Also provided herein are ex vivo host cells comprising such vectors for recombinantly expressing the fusion protein composed of the drug moiety and the antibody moiety or a chain thereof, and the linker (if there is one) between the drug moiety and the antibody moiety. Characteristics of and methods for generating such vectors and ex vivo host cells can be the same as described below for anti-MERTK antibodies. Also provided herein are methods of producing the fusion protein composed of the drug moiety and the antibody moiety or a chain thereof, and the linker (if there is one) between the drug moiety and the antibody moiety, comprising culturing such an ex vivo host cell under conditions such that the polynucleotide comprising a nucleotide sequence encoding the fusion protein is expressed by the ex vivo host cell to produce the fusion protein. Antibody-drug conjugates described herein may be produced by a method known in the art or as described in Section 6 infra.

In some embodiments, the antibody-drug conjugate has the structure shown in FIG. 13A or FIG. 13B, and particularly in FIG. 13A. FIG. 13A shows the structure of MMAE linked to an antibody (Ab) via the mc-vc-PABC linker. FIG. 13B shows the structure of SN-38 linked to an antibody (Ab) via the CL2 or CL2A linker. If "AA" in FIG. 13B is phenylalanine-lysine, then FIG. 13B shows an antibody linked to SN-38 via the CL2 linker (which comprises a Cathepsin B cleavable site). If "AA" in FIG. 13B is lysine, then FIG. 13B shows an antibody linked to SN-38 via the CL2A linker (which does not comprise a Cathepsin B cleavable site).

In a specific embodiment, the antibody portion of the antibody-drug conjugate comprises the variable regions of antibody z10. In a specific embodiment, an antibody-drug conjugate provided herein comprises an antibody moiety comprising a heavy chain variable region (VH) and a light chain variable region (VL), wherein the VH comprises the amino acid sequence of sequence of SEQ ID NO: 105 and the VL comprises the amino acid sequence of SEQ ID NO: 106, wherein the antibody moiety is conjugated to MMAE via the mc-vc-PABC linker. In another specific embodiment, an antibody-drug conjugate provided herein comprises an antibody moiety comprising a heavy chain variable region (VH) and a light chain variable region (VL), wherein the VH comprises the amino acid sequence of sequence of SEQ ID NO: 105 and the VL comprises the amino acid sequence of SEQ ID NO: 106, wherein the antibody moiety is conjugated to SN-38 via the CL2A linker.

In an alternative embodiment of the antibody-drug conjugates described throughout this disclosure, the drug moiety is not necessarily a cytotoxic agent. For example, the drug moiety can be any drug known in the art suitable for use, and may include but not be limited to those described in section 5.2.3 infra, or, e.g., for purposes of diagnosis or monitoring of disease, can be an imaging agent.

In a preferred embodiment of the antibody-drug conjugates described throughout this disclosure, the drug moiety is conjugated to the antibody (also referred to herein as the "antibody moiety") via a linker.

5.2.1. Functional Characteristics of the Antibody-Drug Conjugates

In certain embodiments, an antibody-drug conjugate described herein, binds to MERTK (e.g. human MERTK) with a $K_D$ of about 8 nM, 7 nM, 6 nM, 5 nM, 4.5 nM, 4 nM, 3.5 nM, 3 nM, 2.5 nM, 2 nM, 1.5 nM, 1 nM, 0.75 nM, 0.5 nM, 0.25 nM, 0.17 nM, 0.1 nM, 0.081 nM or 0.021 nM. In some aspects, an antibody-drug conjugate provided herein decreases expression levels of human MERTK on cancer cells (e.g. SKMEL5 melanoma cells) by more than 10%, 15%, 20%, 25%, 30%, 35%, 40%, 45%, 50%, 55%, 60%, 65%, 70%, 75%, 80% or 85% as assessed by an assay known to one of skill in the art or described herein, e.g., as described in section 6 infra. In specific embodiments, an antibody-drug conjugate provided herein binds to MERTK (e.g., binds to human MERTK but not human Axl, human Tyro3, or murine MERTK), as assessed by methods described herein or known in the art. In certain embodiments, an antibody-drug conjugate provided herein comprises an antibody moiety wherein the antibody-drug conjugate binds to MERTK with greater affinity than the unconjugated antibody moiety.

In certain embodiments, an antibody-drug conjugate provided herein causes cell death of MERTK (e.g., human MERTK)-expressing cells (e.g., M2 macrophages, cancer cells, or both) in vitro. In some specific embodiments, at least 10%, 15%, 20%, 25%, 30%, 35%, 40%, 45%, 50%, 55%, 60%, 65%, 70%, 75%, 80%, or 85% of MERTK-expressing cells cultured for a period of time in the presence of an antibody-drug conjugate described herein are dead at the end of the period of time, as assessed by methods known to one of skill in the art for measuring cell death in vitro. In other specific embodiments, the percentage of MERTK-expressing cells (e.g., M2 macrophages, cancer cells, or both) that undergo cell death is at least 50%, 100%, 2-fold, 3-fold, 5-fold, 10-fold, 20-fold, 50-fold, 100-fold, 200-fold, 500-fold, or 1000-fold higher when cultured for a period of time in the presence of an antibody-drug conjugate described herein, relative to when cultured without the antibody-drug conjugate (e.g., cultured without any antibody-drug conjugate or cultured with an antibody-drug conjugate comprising an unrelated antibody (e.g., an antibody that does not immunospecifically bind to MERTK (e.g., human MERTK)) or cultured with an unconjugated anti-MERTK antibody or unconjugated anti-MERTK antigen-binding fragment described herein). The period of time can be, for example, about 1 hr, 2 hrs, 4 hrs, 8 hrs, 12 hrs, 16 hrs, 1 day, 2 days, 3 days, 4 days, 5 days, 6 days, or a week.

In some embodiments, an antibody-drug conjugate provided herein does not affect viability of MERTK-expressing macrophages as assessed by methods known to one of skill in the art for measuring cell death in vitro or a method described herein, e.g., in section 6 infra. In some embodiments, an antibody-drug conjugate provided herein does not affect viability of M1 macrophages as assessed by methods known to one of skill in the art for measuring cell death in vitro or a method described herein, e.g., in section 6 infra. In some embodiments, an antibody-drug conjugate provided herein does not affect viability of M2 macrophages as assessed by methods known to one of skill in the art for measuring cell death in vitro or a method described herein, e.g., in section 6 infra.

In certain embodiments, an antibody-drug conjugate provided herein, induces degradation of MERTK on MERTK expressing cells, such as, e.g., cancer cells (e.g., melanoma cells). In specific embodiments, an antibody-drug conjugate provided herein reduces the level of human MERTK on the surface of human MERTK expressing cells, such as, e.g., cancer cells (e.g., melanoma cells) by at least 10%, 15%, 20%, 25%, 30%, 35%, 40%, 45%, 50%, 55%, 60%, 65%, 70%, 75%, 80% or 85% in an assay described herein or known to one of skill in the art. In certain embodiments, an antibody-drug conjugate provided herein induces greater degradation of MERTK on MERTK expressing cells than the unconjugated antibody moiety, as assessed in an assay described herein or known in the art.

In certain embodiments, an antibody-drug conjugate provided herein induces internalization of MERTK on MERTK expressing cells, such as, e.g., cancer cells (e.g., melanoma cells). In specific embodiments, an antibody-drug conjugate provided herein increases the internalization of human MERTK by human MERTK expressing cells, such as, e.g., cancer cells (e.g., melanoma cells), by at least 10%, 15%, 20%, 25%, 30%, 35%, 40%, 45%, 50%, 55%, 60%, 65%, 70%, 75%, 80% or 85% in an assay described herein or known to one of skill in the art. In certain embodiments, an antibody-drug conjugate provided herein comprises an antibody moiety and the antibody-drug induces greater internalization of MERTK expressing cells than the unconjugated antibody moiety as assessed by an assay described herein or known to one of skill in the art.

In certain embodiments, an antibody-drug conjugate provided herein inhibits tumor progression. The inhibition of tumor progression by at least 10%, 15% 20%, 25%, 30%, 35%, 40%, 45%, 50%, 55, 60%, 65%, 70%, 75%, 80% or 85%. Tumor progression can be assessed by methods known to one of skill in the art. The tumor progression can be relative to the cancer status without treatment with any antibody, treated with an unrelated antibody (e.g., an antibody that does not specifically bind to human MERTK), treated with SN-38, treated with MMAE, treated with the unconjugated antibody moiety of the antibody-drug conjugate. In a specific embodiment, an anti-MERTK antibody or an antigen-binding region thereof has one, two, three or more of the characteristics of an antibody described in Section 6, infra.

In specific embodiments, an antibody-drug conjugate described herein inhibits angiogenesis within tumors. In some embodiments, the inhibition of angiogenesis is by at least 10%, 15%, 20%, 25%, 30%, 35%, 40%, 45%, 50%, 55%, 60%, 65%, 70%, 75%, 80%, or 85%. In a specific embodiment, the inhibition of angiogenesis is at least 50%, 55%, 60%, 65%, or 70%. Inhibition of angiogenesis can be assessed by methods described herein and/or known to one of skill in the art. The inhibition can be relative to the level of angiogenesis without the antibody-drug conjugate (e.g., cultured without any antibody-drug conjugate or cultured with an antibody-drug conjugate comprising an unrelated antibody (e.g., an antibody that does not specifically bind to MERTK (e.g., human MERTK)) or cultured with an unconjugated anti-MERTK antibody or unconjugated anti-MERTK antigen-binding fragment described herein).

In certain embodiments, an antibody-drug conjugate described herein inhibits tumor (e.g., human breast cancer tumor) progression. The inhibition of tumor progression by at least 10%, 15%, 20%, 25%, 30%, 35%, 40%, 45%, 50%, 55%, 60%, 65%, 70%, 75%, 80%, or 85%. Tumor progression can be assessed by methods known to one of skill in the art. The tumor progression can be relative to the cancer status without the antibody-drug conjugate (e.g., cultured without any antibody-drug conjugate or cultured with an antibody-drug conjugate comprising an unrelated antibody (e.g., an antibody that does not specifically bind to MERTK (e.g., human MERTK)) or cultured with an unconjugated anti-MERTK antibody or unconjugated anti-MERTK antigen-binding fragment described herein). In a specific embodiment, the assay that is used to assess tumor progression is a murine tumor transplantation model.

5.2.2. The Antibody Moiety

An antibody-drug conjugate provided herein may comprise any anti-MERTK antibody provided herein. See, e.g., Section 5.1.1 for examples of antibody moieties of the antibody-drug conjugates provided herein. In a specific embodiment, the antibody moiety is an immunoglobulin, e.g., an immunoglobulin comprising a human constant domain, or a humanized immunoglobulin. In another specific embodiment, the antibody moiety is a scFv, e.g., comprising the VH and VL domains of an antibody described herein in Section 5.1.1

In some embodiments, the antibody-drug conjugate provided herein comprises a drug moiety conjugated optionally via a linker to an antibody moiety comprising a VH disclosed herein, e.g., a VH described in Section 5.1.1. In some embodiments, the antibody-drug conjugate provided herein comprises a drug moiety conjugated optionally via a linker to an antibody moiety comprising a VL disclosed herein, e.g., a VL described in Section 5.1.1. In some embodiments, the antibody-drug conjugate provided herein comprises a drug moiety conjugated optionally via a linker to an antibody moiety comprising a VH and a VL of an antibody disclosed herein, e.g., as described in Section 5.1.1.

In some embodiments, the antibody-drug conjugate provided herein comprises a drug moiety conjugated optionally via a linker to an antibody moiety comprising a VH comprising the amino acid sequence of SEQ ID NO: 105. In some embodiments, the antibody-drug conjugate provided herein comprises a drug moiety conjugated optionally via a linker to an antibody moiety comprising a VL comprising the amino acid sequence of SEQ ID NO: 106. In some embodiments, the antibody-drug conjugate provided herein comprises a drug moiety conjugated optionally via a linker to an antibody moiety comprising (i) a VH comprising the amino acid sequence of SEQ ID NO: 105 and (ii) a VL comprising the amino acid sequence of SEQ ID NO: 106.

In some embodiments, an antibody-drug conjugate provided herein comprises MMAE conjugated via a linker to an antibody moiety comprising a VH, wherein the VH comprises the amino acid sequence of SEQ ID NO: 105. In some embodiments, an antibody-drug conjugate provided herein comprises MMAE conjugated via a linker to an antibody moiety comprising a VL, wherein the VL comprises the amino acid sequence of SEQ ID NO: 106. In some embodiments, an antibody-drug conjugate provided herein comprises SN-38 conjugated via a linker to an antibody moiety comprising a VH, wherein the VH comprises the amino acid sequence of SEQ ID NO: 105. In some embodiments, an antibody-drug conjugate provided herein comprises SN-38 conjugated via a linker to an antibody moiety comprising a VL, wherein the VL comprises the amino acid sequence of SEQ ID NO: 106.

In a specific embodiment, an antibody-drug conjugate provided herein comprises MMAE conjugated via a linker to an antibody moiety comprising a VH and a VL, wherein the VH comprises the amino acid sequence of SEQ ID NO: 105, and the VL comprises the amino acid sequence of SEQ ID NO: 106. In another specific embodiment, an antibody-drug conjugate provided herein comprises SN-38 conjugated via a linker to an antibody moiety comprising a VH and a VL, wherein the VH comprises the amino acid sequence of SEQ ID NO: 105, and the VL comprises the amino acid sequence of SEQ ID NO: 106.

In some embodiments, the antibody-drug conjugate provided herein comprises a drug moiety conjugated via a linker to an antibody moiety comprising a heavy chain provided herein, e.g., a heavy chain described in Section 5.1.1. In some embodiments, the antibody-drug conjugate provided herein comprises MMAE conjugated via a linker to an antibody moiety comprising a heavy chain provided herein, e.g., a heavy chain described in Section 5.1.1. In some embodiments, the antibody-drug conjugate provided herein comprises SN-38 conjugated via a linker to an antibody moiety comprising a heavy chain provided herein, e.g., a heavy chain described in Section 5.1.1. In some embodiments, the antibody-drug conjugate provided herein comprises a drug moiety conjugated via a linker to an antibody moiety comprising a light chain provided herein, e.g., a light chain described in Section 5.1.1. In some embodiments, the antibody-drug conjugate provided herein comprises MMAE conjugated via a linker to an antibody moiety comprising a light chain provided herein, e.g., a light chain described in Section 5.1.1. In some embodiments, the antibody-drug conjugate provided herein comprises SN-38 conjugated via a linker to an antibody moiety comprising a light chain provided herein, e.g., a light chain described in Section 5.1.1. In some embodiments, the antibody-drug conjugate provided herein comprises a drug moiety conjugated via a linker to an antibody moiety comprising (i) a heavy chain provided herein and (ii) a light chain provided herein, e.g., a heavy chain and a light chain described in Section 5.1.1. In some embodiments, the antibody-drug conjugate provided herein comprises MMAE conjugated via a linker to an antibody moiety comprising (i) a heavy chain provided herein and (ii) a light chain provided herein, e.g., a heavy chain and a light chain described in Section 5.1.1. In some embodiments, the antibody-drug conjugate provided herein comprises SN-38 conjugated via a linker to an antibody moiety comprising (i) a heavy chain provided herein and (ii) a light chain provided herein, e.g., a heavy chain and a light chain described in Section 5.1.1.

In some embodiments, the antibody-drug conjugate provided herein comprises a drug moiety conjugated via a linker to an antibody moiety comprising a heavy chain comprising the amino acid sequence of SEQ ID NO: 112. In some specific embodiments, the antibody-drug conjugate provided herein comprises MMAE conjugated via a linker to an antibody moiety comprising a heavy chain comprising the amino acid sequence of SEQ ID NO: 112. In some specific embodiments, the antibody-drug conjugate provided herein comprises SN-38 conjugated via a linker to an antibody moiety comprising a heavy chain comprising the amino acid sequence of SEQ ID NO: 112. In some embodiments, the antibody-drug conjugate provided herein comprises a drug moiety conjugated via a linker to an antibody moiety comprising a light chain comprising the amino acid of SEQ ID NO: 113. In some specific embodiments, the antibody-drug conjugate provided herein comprises MMAE conjugated via a linker to a light chain comprising the amino acid of SEQ ID NO: 113. In some specific embodiments, the antibody-drug conjugate provided herein comprises SN-38 conjugated via a linker to a light chain comprising the amino acid of SEQ ID NO: 113. In some embodiments, the antibody-drug conjugate provided herein comprises a drug moiety conjugated via a linker to an antibody moiety comprising (i) a heavy chain comprising the amino acid sequence of SEQ ID NO: 112 and (ii) a light chain comprising the amino acid of SEQ ID NO: 113. In a specific embodiment, the antibody-drug conjugate provided herein comprises MMAE conjugated via a linker to an antibody moiety comprising (i) a heavy chain comprising the amino acid sequence of SEQ ID NO: 112 and (ii) a light chain comprising the amino acid of SEQ ID NO: 113. In another specific embodiment, the antibody-drug conjugate provided herein comprises SN-38 conjugated via a linker to an antibody moiety comprising (i) a heavy chain comprising the amino acid sequence of SEQ ID NO: 112 and (ii) a light chain comprising the amino acid of SEQ ID NO: 113.

5.2.3. The Drug Moiety and the Linker

The cytotoxic agent used in antibody-drug conjugates is also often called a payload or warhead. Most of the cytotoxic agents used in antibody-drug conjugates target DNA or microtubules and have high potency of cytotoxicity (with an $IC_{50}$ range of approximately $10^{-10}$-$10^{-12}$ M) (see Beck A et al., (2017) Nat Rev Drug Discov 16: 315-337). However, cytotoxic agents that are not as potent may also be used. The cytotoxic agent can be a small molecule, a nucleotide, a peptide, or a non-antibody protein. In a specific embodiment, the cytotoxic agent is a small molecule. In another specific embodiment, the cytotoxic agent is a non-antibody protein. Non-limiting exemplary cytotoxic agents that can be used in the antibody-drug conjugates according to the invention are described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; and Olivier K J and Hurvitz S A ed., (2016) Antibody-Drug Conjugates: Fundamentals, Drug Development, and Clinical, Wiley.

In certain embodiments, the cytotoxic agent is one of the agents listed in Table 30 or 31. In specific embodiments, the cytotoxic agent used in the antibody-drug conjugate is an auristatin (such as monomethyl auristatin E (MMAE), monomethyl auristatin F (MMAF), Aur0101, PF06380101, Auristatin W, or auristatin F) or derivative thereof, a maytansinoid (such as DM1 or DM4), a pyrrolobenzodiazepine (PBD) (such as SGD1882 or SG3199), an indolinobenzodiazepine (such as DGN462 or DGN549), a calicheamicin (ozogamicin) (such as CM1), a camptothecin analogue (such as SN-38, DX-895 if, or DX-895 if derivative), a duocarmycin (such as seco-duocarmycin-hydroxy-benzamide-azaindole (seco-DUBA), minor groove-binding alkylating agent (MGBA), or MED-2460), a tubulin inhibitor (such as cryptophycin), a tubulysin or tubulysin analogue (such as AZ13599185), amberstatin269, doxorubicin, an antibiotic (such as rifalogue), an anthracycline (such as PNU-159682), a microtubule inhibitor (such as rhizoxin), a spliceostatin, or a thailanstatin. In a specific embodiment, the cytotoxic agent used in the antibody-drug conjugate is MMAE or MMAF. In a specific embodiment, the cytotoxic agent used in the antibody-drug conjugate is MMAE (see, e.g., FIG. 13A). In another specific embodiment, the cytotoxic agent used in the antibody-drug conjugate is DM1 or DM4. In another specific embodiment, the cytotoxic agent used in the antibody-drug conjugate is SN-38. In another specific embodiment, the cytotoxic agent used in the antibody-drug conjugate is SN-38 as shown in FIG. 13B.

TABLE 30

Examples of Drug Moieties

| | | |
|---|---|---|
| Alkylating agents | Busulfan | Chlorambucil |
| | Dacarbazine | Procarbazine |
| | Ifosfamide | Altretamine |

TABLE 30-continued

Examples of Drug Moieties

| | | |
|---|---|---|
| | hexamethylmelamine | estramustine phosphate |
| | Thiotepa | Mechlorethamine |
| | Dacarbazine | Streptozocin |
| | Lomustine | Temozolomide |
| | cyclophosphamide | Semustine |
| Platinum agents | Spiroplatin | lobaplatin (Aeterna) |
| | Tetraplatin | satraplatin (Johnson Matthey) |
| | Ormaplatin | BBR-3464 (Hoffmann-La Roche) |
| | Iproplatin | SM-11355 (Sumitomo) |
| | ZD-0473 (AnorMED) | AP-5280 (Access) |
| | Oxaliplatin | Cisplatin |
| | Carboplatin | |
| Antimetabolites | Azacytidine | Trimetrexate |
| | Floxuridine | Deoxycoformycin |
| | 2-chlorodeoxyadenosine | Pentostatin |
| | 6-mercaptopurine | Hydroxyurea |
| | 6-thioguanine | decitabine (SuperGen) |
| | Cytarabine | clofarabine (Bioenvision) |
| | 2-fluorodeoxy cytidine | irofulven (MGI Pharma) |
| | Methotrexate | DMDC (Hoffmann-La Roche) |
| | tomudex | ethynylcytidine (Taiho) |
| | Fludarabine | Gemcitabine |
| | Raltitrexed | Capecitabine |
| Topoisomerase Inhibitors | Amsacrine | exatecan mesylate (Daiichi) |
| | Epirubicin | quinamed (ChemGenex) |
| | Etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | Topotecan | |
| Antitumor antibiotics | Valrubicin | Azonafide |
| | Therarubicin | Anthrapyrazole |
| | Idarubicin | Oxantrazole |
| | Rubidazone | Losoxantrone |
| | Plicamycin | MEN-10755 (Menarini) |
| | Porfiromycin | GPX-100 (Gem Pharmaceuticals) |
| | mitoxantrone (novantrone) | Epirubicin |
| | Amonafide | Mitoxantrone |
| | | Doxorubicin |
| Antimitotic Agents | Colchicine | E7010 (Abbott) |
| | Vinblastine | PG-TXL (Cell Therapeutics) |
| | Vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ 10992 (Asahi) |
| | cryptophycin 52 (Eli Lilly) | IDN-5109 (Indena) |
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | Docetaxel |
| | Vinorelbine | Vincristine |
| | Trichostatin A | Paclitaxel |
| Aromatase inhibitors | aminoglutethimide | YM-511 (Yamanouchi) |
| | atamestane (BioMedicines) | Formestane |
| | Letrozole | Exemestane |
| | Anastrazole | |

TABLE 30-continued

Examples of Drug Moieties

| | | |
|---|---|---|
| Thymidylate synthase inhibitors | pemetrexed (Eli Lilly) ZD-9331 (BTG) | nolatrexed (Eximias) CoFactor ™ (BioKeys) |
| DNA antagonists | trabectedin (PharmaMar) glufosfamide (Baxter International) albumin + 32P (Isotope Solutions) thymectacin (NewBiotics) | edotreotide (Novartis) mafosfamide (Baxter International) apaziquone (Spectrum Pharmaceuticals) O6 benzyl guanine (Paligent) |
| Farnesyltransferase Inhibitors | arglabin (NuOncology Labs) lonafarnib (Schering-Plough) BAY-43-9006 (Bayer) | tipifarnib (Johnson & Johnson) perillyl alcohol (DOR BioPharma) |
| Pump inhibitors | CBT-1 (CBA Pharma) tariquidar (Xenova) MS-209 (Schering AG) | zosuquidar trihydrochloride (Eli Lilly) biricodar dicitrate (Vertex) |
| Histone acetyltransferase Inhibitors | tacedinaline (Pfizer) SAHA (Aton Pharma) MS-275 (Schering AG) | pivaloyloxymethyl butyrate (Titan) depsipeptide (Fujisawa) |
| Metalloproteinase Inhibitors | Neovastat (Aeterna Laboratories) marimastat (British Biotech) | CMT-3 (CollaGenex) BMS-275291 (Celltech) |
| Ribonucleoside reductase inhibitors | gallium maltolate (Titan) triapine (Vion) | tezacitabine (Aventis) didox (Molecules for Health) |
| TNF alpha agonists/antagonists | virulizin (Lorus Therapeutics) CDC-394 (Celgene) | revimid (Celgene) YM-598 (Yamanouchi) |
| Endothelin A receptor antagonist | atrasentan (Abbott) ZD-4054 (AstraZeneca) | alitretinoin (Ligand) ISF-154 (Tragen) |
| Retinoic acid receptor agonists | fenretinide (Johnson & Johnson) LGD-1550 (Ligand) | β-alethine (Dovetail) CLL therapy (Vasogen) |
| Immunomodulators | Interferon IRX-2 (Immuno-Rx) PEP-005 (Peplin Biotech) abatacept (BMS) Lag-3 TGF-beta RGX-104 | MAGE-A3 (GSK) CM-10 (cCam Biotherapeutics) AMP-224 (GSK) MPDL3280A (Genentech) GITR OX40 RGX-202 |
| Hormonal and antihormonal agents | Estrogens conjugated estrogens ethinyl estradiol Chlortrianisen Idenestrol hydroxyprogesterone caproate medroxyprogesterone Testosterone testosterone propionate; fluoxymesterone methyltestosterone diethylstilbestrol Megestrol Bicalutamide Flutamide Nilutamide | dexamethasone Prednisone methylprednisolone prednisolone aminoglutethimide Leuprolide Octreotide Mitotane P-04 (Novogen) 2-methoxyestradiol (EntreMed) arzoxifene (Eli Lilly) Tamoxifen Toremofine Goserelin Leuporelin bicalutamide |
| Photodynamic Agents | talaporfin (Light Sciences) Theralux (Theratechnologies) motexafin gadolinium (Pharmacyclics) | Pd-bacteriopheophorbide (Yeda) lutetium texaphyrin (Pharmacyclics) Hypericin |
| Kinase Inhibitors | imatinib (Novartis) leflunomide (Sugen/Pharmacia) ZD1839 (AstraZeneca) erlotinib (Oncogene Science) canertinib (Pfizer) squalamine (Genaera) SU5416 (Pharmacia) SU6668 (Pharmacia) ZD4190 (AstraZeneca) ZD6474 (AstraZeneca) vatalanib (Novartis) PKI166 (Novartis) GW2016 (GlaxoSmithKline) EKB-509 (Wyeth) trastuzumab (Genentech) OSI-774 (Tarceva ™) CI-1033 (Pfizer) | EKB-569 (Wyeth) kahalide F (PharmaMar) CEP-701 (Cephalon) CEP-751 (Cephalon) MLN518 (Millenium) PKC412 (Novartis) Phenoxodiol (Novogen) C225 (ImClone) rhu-Mab (Genentech) MDX-H210 (Medarex) 2C4 (Genentech) MDX-447 (Medarex) ABX-EGF (Abgenix) IMC-1C11 (ImClone) Tyrphostins Gefitinib (Iressa) PTK787 (Novartis) |

TABLE 30-continued

Examples of Drug Moieties

| | |
|---|---|
| SU11248 (Pharmacia) | EMD 72000 (Merck) |
| RH3 (York Medical) | Emodin |
| Genistein | Radicinol |
| Radicinol | Vemurafenib (B-Raf enzyme inhibitor, Daiichi Sankyo) |
| Met-MAb (Roche) | |
| trametinib (GSK) | |

TABLE 31

Additional examples of drug moieties.

| | | |
|---|---|---|
| SR-27897 (CCK A inhibitor, Sanofi-Synthelabo) | CDA-II (apoptosis promotor, Everlife) | triacetyluridine (uridine prodrug, Wellstat) |
| tocladesine (cyclic AMP agonist, Ribapharm) | SDX-101 (apoptosis promotor, Salmedix) | SN-4071 (sarcoma agent, Signature BioScience) |
| alvocidib (CDK inhibitor, Aventis) | Carmustine | TransMID-107 ™ (immunotoxin, KS Biomedix) |
| CV-247 (COX-2 inhibitor, Ivy Medical) | Mitoxantrone | PCK-3145 (apoptosis promotor, Procyon) |
| P54 (COX-2 inhibitor, Phytopharm) | Bleomycin | doranidazole (apoptosis promotor, Pola) |
| CapCell ™ (CYP450 stimulant, Bavarian Nordic) | Absinthin | CHS-828 (cytotoxic agent, Leo) |
| GCS-100 (gal3 antagonist, GlycoGenesys) | Chrysophanic acid | trans-retinoic acid (differentiator, NIH) |
| G17DT immunogen (gastrin inhibitor, Aphton) | Cesium oxides | MX6 (apoptosis promotor, MAXIA) |
| efaproxiral (oxygenator, Allos Therapeutics) | BRAF inhibitors, | apomine (apoptosis promotor, ILEX Oncology) |
| PI-88 (heparanase inhibitor, Progen) | PDL1 inhibitors | urocidin (apoptosis promotor, Bioniche) |
| tesmilifene (histamine antagonist, YM BioSciences) | MEK inhibitors | Ro-31-7453 (apoptosis promotor, La Roche) |
| histamine (histamine H2 receptor agonist, Maxim) | angiogenesis inhibitors | brostallicin (apoptosis promotor, Pharmacia) |
| tiazofurin (IMPDH inhibitor, Ribapharm) | dabrafenib | β-lapachone |
| cilengitide (integrin antagonist, Merck KGaA) | ceflatonin (apoptosis promotor, ChemGenex) | Gelonin |
| SR-31747 (IL-1 antagonist, Sanofi-Synthelabo) | BCX-1777 (PNP inhibitor, BioCryst) | Cafestol |
| CCI-779 (mTOR kinase inhibitor, Wyeth) | ranpirnase (ribonuclease stimulant, Alfacell) | Kahweol |
| exisulind (PDE V inhibitor, Cell Pathways) | galarubicin (RNA synthesis inhibitor, Dong-A) | caffeic acid |
| CP-461 (PDE V inhibitor, Cell Pathways) | tirapazamine (reducing agent, SRI International) | Tyrphostin AG |
| AG-2037 (GART inhibitor, Pfizer) | N-acetylcysteine (reducing agent, Zambon) | PD-1 inhibitors |
| WX-UK1 (plasminogen activator inhibitor, Wilex) | R-flurbiprofen (NF-kappaB inhibitor, Encore) | CTLA-4 inhibitors |
| PBI-1402 (PMN stimulant, ProMetic LifeSciences) | 3CPA (NF-kappaB inhibitor, Active Biotech) | Sorafenib |
| bortezomib (proteasome inhibitor, Millennium) | seocalcitol (vitamin D receptor agonist, Leo) | BRAF inhibitors |
| SRL-172 (T cell stimulant, SR Pharma) | 131-I-TM-601 (DNA antagonist, TransMolecular) | indisulam (p53 stimulant, Eisai) |
| TLK-286 (glutathione S transferase inhibitor, Telik) | eflornithine (ODC inhibitor, ILEX Oncology) | aplidine (PPT inhibitor, PharmaMar) |
| PT-100 (growth factor agonist, Point Therapeutics) | minodronic acid (osteoclast inhibitor, Yamanouchi) | gemtuzumab (CD33 antibody, Wyeth Ayerst) |
| midostaurin (PKC inhibitor, Novartis) | PG2 (hematopoiesis enhancer, Pharmagenesis) | |
| bryostatin-1 (PKC stimulant, GPC Biotech) | Immunol ™ (triclosan oral rinse, Endo) | |

As used herein, the term "small molecule" refers to an organic or inorganic compound (which can be, for example, a heteroorganic or organometallic compound) having a molecular weight of less than about 10,000 grams per mole. In specific embodiments, the small molecule has a molecular weight of less than about 5,000 grams per mole, or less than about 2,000 grams per mole, or less than about 1,000 grams per mole, or less than about 500 grams per mole, or less than about 100 grams per mole.

In some embodiments, the cytotoxic agent is conjugated directly to the antibody moiety. In other embodiments, the cytotoxic agent is conjugated to the antibody moiety via a linker. Appropriate linkers to be used according to the invention preferably are stable in the blood stream to limit off-target toxicity and labile at the cancer site to allow for release of the cytotoxic agent (see Peters C and Brown S, (2015) Biosci Rep 35: art:e00225). Non-limiting exemplary linkers that can be used according to the invention are described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; and Olivier K J and Hurvitz S A ed., (2016) Antibody-Drug Conjugates: Fundamentals, Drug Development, and Clinical, Wiley. In some embodiments, the linker is a cleavable linker, for example, having a motif sensitive to a lysosomal protease (for example, cathepsin B), a motif sensitive to an acidic pH (for example, hydrazone), or a motif containing a disulfide bridge that can be reduced by glutathione. In other embodiments, the linker is a non-cleavable linker. By way of example but not limitation, the linker can be a small molecule, a nucleotide, a peptide, or a non-antibody protein. In a specific embodiment, the linker is a small molecule. In a specific embodiment, the linker used in the antibody-drug conjugate is cathepsin B, hydrazone, succinimidyl-4-(N-maleimidomethyl)cyclohexane-1-carboxylate (SMCC), maleimidocaproic acid (mc), valine-citrulline (vc), N-hydroxysuccinimidyl 4-(2-pyridyldithio)-2-sulfobutanoate (sulfo-SPDB), N-hydroxysuccinimidyl 4-(2-pyridydithio)butanoate (SPDB), N-succinimidyl 4-(2-pyridyldithio)pentanoate (SPP), valine-alanine (va), polyethylene glycol 8-valine-citrulline (PEG8-va), mb-vc, CL2A, cleavable vc-based linker, or fleximer polymer linker. In a specific embodiment, a linker selected for use in an antibody drug conjugate described herein does not interfere with the antibody moiety binding to its antigen, the cytotoxic agent, or both. In specific embodiments, a linker selected for use in an antibody-drug conjugate described herein is maleimidocaproyl-valine-citrulline-p-aminobenzyloxycarbonyl (mc-vc-PABC). In other specific embodiments, a linker selected for use in an antibody-drug conjugate described herein is CL2. In other specific embodiments, a linker selected for use in an antibody-drug conjugate described herein is CL2A. In some specific embodiments, a linker selected for use in an antibody drug conjugate described herein is the linker shown in FIG. 13A. In other specific embodiments, a linker selected for use in an antibody-drug conjugate described herein is the linker shown in FIG. 13B where AA is lysine. In other specific embodiments, a linker selected for use in an antibody-drug conjugate described herein is the linker shown in FIG. 13B where AA is phenylalanine-lysine. In a specific embodiment, the antibody-drug conjugate comprises a linker and the linker is maleimidocaproyl-valine-citrulline-p-aminobenzyloxycarbonyl (also known as "mc-vc-PABC") (for the structure of mc-vc-PABC; see FIG. 13A). In another specific embodiment, the antibody-drug conjugate comprises a linker and the linker is CL2 (for the structure of CL2, see FIG. 13B and Cardillo et al. 2011, Clin Cancer Res; 17(10); 3157-69). In another specific embodiment, the antibody-drug conjugate comprises the linker and the linker is CL2A (for the structure of CL2A, see FIG. 13B and Goldberg et al. 2018, Oncotarget; 9(48); 28989-29006, and Cardillo et al. 2011, Clin Cancer Res; 17(10); 3157-69).

In some embodiments, a linker selected for use in an antibody-drug conjugate described herein comprises one or more cleavage sites. In specific embodiments, a linker selected for use in an antibody-drug conjugate described herein contains a Cathepsin B protease site. In other specific embodiments, a linker selected for use in an antibody-drug conjugate described herein contains a Cathepsin B protease site and a pH-dependent cleavage site.

Non-limiting exemplary linker-drug moiety pairs that can be used in antibody-drug conjugates described herein are described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; and Olivier K J and Hurvitz S A ed., (2016) Antibody-Drug Conjugates: Fundamentals, Drug Development, and Clinical, Wiley. In specific embodiments, the linker-drug moiety pair in the antibody-drug conjugate is vc-MMAE, mc-MMAF, SMCC-DM1, sulfo-SPDB-DM4, SPDB-DM4, SPP-DM1, va-SGD1882, polyethylene glycol 8 (PEG8)-va-SG3199, sulfo-SPDB-DGN462, hydrazone-CM1, vc-seco-DUBA, mb-vc-MGBA, CL2A-SN-38, peptide linker with DX-8951 derivative, hydrazone-doxorubicin, cleavable vc-based linker with Aur0101, vc-PF06380101, fleximer polymer linker with auristatin F, cleavable linker-tubulin inhibitor, or vc-rifalogue. In specific embodiments, the linker-drug moiety pair in the antibody-drug conjugate is mc-vc-PABC-MMAE (as shown in FIG. 13A). In other specific embodiments, the linker-drug moiety pair in the antibody-drug conjugate is CL2-SN-38 (as shown in FIG. 13B where AA is phenylalanine-lysine). In other specific embodiments, the linker-drug moiety pair in the antibody-drug conjugate is CL2A-SN-38 (as shown in FIG. 13B where AA is lysine).

In a specific embodiment, the drug moiety of an antibody-drug conjugate described herein does not interfere with the antibody moiety binding to its antigen (e.g., MERTK (e.g., human MERTK)).

5.3. Antibody Production 5.3.1. Producing and Screening Antibodies

In another aspect, provided herein are methods of producing anti-MERTK antibodies or antigen-binding fragments thereof described herein, that specifically bind to MERTK (e.g., human MERTK).

The antibodies or antigen-binding fragments thereof described herein can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences that are encoded by DNA sequences that do not naturally exist within the antibody germline repertoire of an animal or mammal (e.g., human) in vivo. In a specific embodiment, an antibody described herein is made by a method comprising using human MERTK (SEQ ID NO: 131 or the extracellular domain thereof (SEQ ID NO: 132) as an immunogen.

In a certain aspect, provided herein is a method of making an anti-MERTK antibody or antigen-binding fragment thereof, which specifically binds to MERTK (e.g., human MERTK), comprising culturing a cell or host cell described herein. In a certain aspect, provided herein is a method of making an anti-MERTK antibody or antigen-binding fragment thereof, which specifically binds to MERTK (e.g., human MERTK), comprising expressing (e.g., recombinantly expressing) the antibody or antigen-binding fragment thereof using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment thereof obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

The term "monoclonal antibody" as used herein is not limited to antibodies produced through hybridoma technology. Monoclonal antibodies can be prepared using a wide variety of techniques known in the art including the use of hybridoma, recombinant, and phage display technologies, or a combination thereof. For example, monoclonal antibodies can be produced recombinantly from host cells exogenously expressing an antibody described herein or a fragment thereof, for example, a light chain and/or heavy chain of such antibody. Methods for the preparation of clonal cell lines and of monoclonal antibodies expressed thereby are well known in the art (see, for example, Chapter 11 in Short Protocols in Molecular Biology, (2002) 5th Ed., Ausubel F M et al., supra). For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981); and Kohler G & Milstein C (1975) Nature 256: 495. Methods for producing and screening for specific antibodies using hybridoma technology are routine and well known in the art. In some embodiments, mice (or other animals, such as rats, monkeys, donkeys, pigs, sheep, hamster, or dogs) can be immunized with an antigen (e.g., human) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP2/0 available from the American Type Culture Collection (ATCC®) (Manassas, Va.), to form hybridomas. Hybridomas are selected and cloned by limited dilution.

The hybridoma cells thus prepared are seeded and grown in a suitable culture medium that preferably contains one or more substances that inhibit the growth or survival of the unfused, parental myeloma cells. Culture medium in which hybridoma cells are growing is assayed for production of monoclonal antibodies directed against MERTK (e.g., human MERTK). After hybridoma cells that produce antibodies of the desired specificity, affinity, and/or activity are identified, the clones may be subcloned, grown, and separated from the culture medium by standard methods (Goding J W (Ed), Monoclonal Antibodies: Principles and Practice, supra). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

In specific embodiments, disclosed herein are monoclonal antibodies that are produced by a single cell (e.g., hybridoma or host cell producing a recombinant antibody), wherein the antibody immunospecifically binds to MERTK (e.g., human MERTK) as determined, e.g., by ELISA or other antigen-binding or competitive binding assay known in the art or as described in Section 6 herein. In certain embodiments, a monoclonal antibody is a monovalent antibody or multivalent (e.g., bivalent) antibody. In particular embodiments, a monoclonal antibody is a monospecific or multispecific antibody (e.g., bispecific antibody).

Antibody fragments which recognize MERTK (e.g., human MERTK) can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, an anti-MERTK antibody or antigen-binding fragment thereof described herein, can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated into E. coli cells and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including humanized antibodies, chimeric antibodies, or any other desired antigen-binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415. In a specific embodiment, a chimeric antibody comprises a variable heavy chain region (VH) and a variable light chain region (VL), wherein the VH and VL each comprise the amino acid sequences of VH and VL, respectively, set forth in Table 13.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_2$, IgG$_3$ and IgG$_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

In a specific embodiment, a humanized antibody or an antigen-binding fragment thereof, which specifically binds to MERTK (e.g., human MERTK), comprises the VH and VL of antibody z10 (see Table 11), the VH and VL of antibody z11 (see Table 12), or the VH and VL of antibody z13 (see Table 13). Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301.

Further, antibodies that immunospecifically bind to a MERTK (e.g., human MERTK) antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, an anti-MERTK antibody or antigen-binding fragment thereof described herein binds to the same or an overlapping epitope of MERTK (e.g., human MERTK) as an anti-MERTK antibody or antigen-binding fragment thereof described herein. In particular embodiments, an antibody described herein, which competitively blocks (e.g., in a dose-dependent manner) any one of the antibodies described herein, (e.g., z10, z11, or z13, or xAb) from binding to MERTK (e.g., human MERTK), is a human anti-MERTK antibody or antigen-binding fragment thereof. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., MERTK). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661, 016, 5,545,806, 5,814,318 and 5,939,598. Examples of mice capable of producing human antibodies include the Xeno-mouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which specifically bind to MERTK (e.g., human MERTK) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., human MERTK). Such methods are known and are described in the art, see, e.g., Shinmoto H et al., (2004) Cytotechnology 46: 19-23; Naganawa Y et al., (2005) Human Antibodies 14: 27-31.

In specific embodiments, the methods of screening and selecting antibodies or antigen-binding fragments thereof described herein, which specifically bind to MERTK (e.g., human MERTK) are as described in Example 1, infra.

Once an anti-MERTK antibody or an antigen-binding fragment thereof described herein, has been produced, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an anti-MERTK antibody or an antigen-binding fragment thereof described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.3.2. Polynucleotides

In certain aspects, provided herein are polynucleotides comprising a nucleotide sequence encoding an anti-MERTK antibody or an antigen-binding fragment thereof described herein that specifically binds to a MERTK (e.g., human MERTK) antigen, and vectors, e.g., vectors comprising such polynucleotides for their efficient expression in host cells (e.g., *E. coli* and mammalian cells). In some embodiments, a polynucleotide is isolated or purified.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% of other material, e.g., cellular material, culture medium, other nucleic acid molecules, chemical precursors and/or other chemicals.

In particular aspects, provided herein are polynucleotides comprising nucleotide sequences encoding an anti-MERTK antibody or antigen-binding fragment thereof described herein, which specifically binds to a MERTK (e.g., human MERTK) polypeptide and comprises an amino acid sequence as described herein, as well as antibodies which compete with such antibodies for binding to a MERTK (e.g., human MERTK) polypeptide (e.g., in a dose-dependent manner), or which binds to the same or an overlapping epitope as that of such antibodies.

In certain aspects, provided herein are polynucleotides comprising a nucleotide sequence encoding the light chain or heavy chain of an antibody described herein.

In certain embodiments, a polynucleotide described herein comprises a nucleotide sequence encoding an anti-MERTK antibody or an antigen-binding fragment thereof, which specifically binds to MERTK (e.g., human MERTK), wherein the antibody or antigen-binding fragment thereof comprises a heavy chain variable region that comprises an amino acid sequence described herein (SEQ ID NO: 105, SEQ ID NO: 107, SEQ ID NO: 108 or SEQ ID NO: 109). In certain embodiments, a polynucleotide described herein comprises a nucleotide sequence encoding an anti-MERTK antibody or antigen-binding fragment thereof described herein, which specifically binds to MERTK (e.g., human MERTK), wherein the anti-MERTK antibody or antigen-binding fragment thereof comprises a light chain variable region that comprises an amino acid sequence described herein (SEQ ID NO: 106 or SEQ ID NO: 111). In certain embodiments, a polynucleotide described herein comprises a nucleotide sequence encoding an anti-MERTK antibody or antigen-binding fragment thereof described herein, which specifically binds to MERTK (e.g., human MERTK), wherein the antibody or antigen-binding fragment thereof comprises a heavy chain variable region that comprises the amino acid sequence of SEQ ID NO: 105, and a light chain variable region that comprises the amino acid sequence of SEQ ID NO: 106. In certain embodiments, a polynucleotide described herein comprises a nucleotide sequence encoding an anti-MERTK antibody or an antigen-binding fragment thereof described herein, which specifically binds to MERTK (e.g., human MERTK), wherein the antibody or antigen-binding fragment thereof comprises a heavy chain variable region that comprises the amino acid sequence of SEQ ID NO: 107 and a light chain variable region that comprises the amino acid sequence of SEQ ID NO: 106. In certain embodiments, a polynucleotide described herein comprises a nucleotide sequence encoding an anti-MERTK antibody or antigen-binding fragment thereof described herein, which specifically binds to MERTK (e.g., human MERTK), wherein the antibody or antigen-binding fragment thereof comprises a heavy chain variable region that comprises the amino acid sequence of SEQ ID NO: 108 and a light chain variable region that comprises the amino acid sequence of SEQ ID NO: 106. In certain embodiments, a polynucleotide described herein comprises a nucleotide sequence encoding an anti-MERTK antibody or antigen-binding fragment thereof, which specifically binds to MERTK (e.g., human MERTK), wherein the antibody or antigen-binding fragment thereof comprises a heavy chain variable region that comprises the amino acid of SEQ ID No: 110 and a light chain variable region that comprises the amino acid sequence of SEQ ID NO: 111. In certain embodiments, a polynucleotide described herein comprises a nucleotide sequence encoding an anti-MERTK antibody or antigen-binding fragment thereof, which specifically binds to MERTK (e.g., human MERTK), wherein the antibody or antigen-binding fragment thereof comprises a heavy chain variable region that comprises the amino acid of SEQ ID NO: 109 and a light chain variable region that comprises the amino acid sequence of SEQ ID NO: 106.

In certain embodiments, a polynucleotide described herein encodes a VH, wherein the polynucleotide comprises a nucleic acid sequence of SEQ ID NO: 119, SEQ ID NO: 121, SEQ ID NO: 122, or SEQ ID NO: 123. In certain embodiments, a polynucleotide described herein encodes a VL, wherein the polynucleotide comprises a nucleic acid sequence of SEQ ID NO: 120 or SEQ ID NO: 124. In a specific embodiment, a polynucleotide described herein encodes a VH and a VL, wherein the polynucleotide comprises a nucleic acid sequence of SEQ ID NO: 119, and wherein the polynucleotide comprises the nucleic acid sequence of SEQ ID NO: 120. In another specific embodiment, a polynucleotide described herein encodes a VH and a VL, wherein the polynucleotide comprises a nucleic acid sequence of SEQ ID NO: 121, and wherein the polynucleotide comprises the nucleic acid sequence of SEQ ID NO: 120. In another specific embodiment, a polynucleotide described herein encodes a VH and a VL, wherein the polynucleotide comprises a nucleic acid sequence of SEQ ID NO: 122, and wherein the polynucleotide comprises the nucleic acid sequence of SEQ ID NO: 120. In another embodiment, a polynucleotide described herein encodes a VH and a VL, wherein the polynucleotide comprises a nucleic acid SEQ ID NO: 123 and wherein the polynucleotide comprises the nucleic acid sequence of SEQ ID NO: 124.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding an antibody described herein comprising a human kappa light chain or a human lambda light chain.

In specific aspects, a polynucleotide provided herein comprises a nucleotide sequence encoding a light chain of an antibody, wherein the nucleotide sequence comprises a variable light chain region of SEQ ID NO: 106, and a human light chain constant region nucleotide sequence of the human kappa or lambda light chain. In another aspect, a polynucleotide provided herein comprises a nucleotide sequence encoding a light chain of an antibody, wherein the light chain comprises a variable light chain region of SEQ ID NO: 111, and a human light chain constant region of the human kappa or lambda light chain.

In a particular embodiment, a polynucleotide provided herein comprises a nucleotide sequence encoding an antibody described herein, which specifically binds to MERTK (e.g., human MERTK), wherein the antibody comprises a light chain, and wherein the amino acid sequence of the variable region of the light chain can comprise any amino acid sequence of SEQ ID NO: 106 or SEQ ID NO: 111, and wherein the constant region of the light chain comprises the amino acid sequence of a human kappa light chain constant region. In another particular embodiment, a polynucleotide provided herein comprises a nucleotide sequence encoding an antibody described herein, which specifically binds to MERTK (e.g., human MERTK) and comprises a light chain, wherein the amino acid sequence of the variable region of the light chain can comprise any amino acid sequence of SEQ ID NO: 106 or SEQ ID NO: 111, and wherein the constant region of the light chain comprises the amino acid sequence of a human lambda light chain constant region. In another aspect, a polynucleotide provided herein comprises a nucleotide sequence encoding a light chain of an antibody, wherein the light chain comprises the amino acid sequence of SEQ ID NO: 113 or 118. In another aspect, a polynucleotide provided herein comprises a nucleotide sequence encoding a light chain of an antibody which specifically binds to MERTK (e.g., human MERTK), wherein the nucleotide sequence comprises SEQ ID NO: 126 or 130.

In a particular embodiment, a polynucleotide provided herein comprises a nucleotide sequence encoding an antibody described herein, which specifically binds to MERTK (e.g., human MERTK), wherein the antibody comprises a heavy chain, wherein the heavy chain comprises amino acid sequence of SEQ ID NO: 105, and a heavy constant region. In another particular embodiment, a polynucleotide provided herein comprises a nucleotide sequence encoding an antibody described herein, which specifically binds to MERTK (e.g., human MERTK) and comprises a heavy chain, wherein the heavy chain comprises amino acid sequence of SEQ ID NO: 107, and a heavy constant region. In another particular embodiment, a polynucleotide provided herein comprises a nucleotide sequence encoding an antibody described herein, which specifically binds to MERTK (e.g., human MERTK) and comprises a heavy chain, wherein the heavy chain comprises amino acid sequence of SEQ ID NO: 108, and a heavy constant region. In another particular embodiment, a polynucleotide provided herein comprises a nucleotide sequence encoding an antibody described herein, which specifically binds to MERTK (e.g., human MERTK) and comprises a heavy chain, wherein the heavy chain comprises amino acid sequence of SEQ ID NO: 109, and a heavy constant region. In another particular embodiment, a polynucleotide provided herein comprises a nucleotide sequence encoding an antibody described herein, which specifically binds to MERTK (e.g., human MERTK) and comprises a heavy chain, wherein the heavy chain comprises amino acid sequence of SEQ ID NO: 110, and a heavy constant region.

In a particular embodiment, a polynucleotide provided herein comprises a nucleotide sequence encoding an antibody described herein, which specifically binds to MERTK (e.g., human MERTK), wherein the antibody comprises a heavy chain, wherein the heavy chain comprises amino acid sequence of SEQ ID NO: 112. In a particular embodiment, a polynucleotide provided herein comprises a nucleotide sequence encoding an antibody described herein, which specifically binds to MERTK (e.g., human MERTK), wherein the antibody comprises a heavy chain, wherein the heavy chain comprises amino acid sequence of SEQ ID NO: 114. In a particular embodiment, a polynucleotide provided herein comprises a nucleotide sequence encoding an antibody described herein, which specifically binds to MERTK (e.g., human MERTK), wherein the antibody comprises a heavy chain, wherein the heavy chain comprises amino acid sequence of SEQ ID NO: 115. In a particular embodiment, a polynucleotide provided herein comprises a nucleotide sequence encoding an antibody described herein, which specifically binds to MERTK (e.g., human MERTK), wherein the antibody comprises a heavy chain, wherein the heavy chain comprises amino acid sequence of SEQ ID NO: 116. In a particular embodiment, a polynucleotide provided herein comprises a nucleotide sequence encoding an antibody described herein, which specifically binds to MERTK (e.g., human MERTK), wherein the antibody comprises a heavy chain, wherein the heavy chain comprises amino acid sequence of SEQ ID NO: 117.

In a specific aspect, polynucleotide provided herein comprises a nucleotide sequence encoding a heavy chain of an antibody, which specifically binds to MERTK (e.g., human MERTK), wherein the nucleotide sequence comprises SEQ ID NO: 119 and a human heavy chain constant region nucleotide sequence. In another aspect, a polynucleotide provided herein comprises a nucleotide sequence encoding a heavy chain of an antibody which specifically binds MERTK, wherein the nucleotide sequence comprises SEQ ID NO: 125.

In a specific aspect, polynucleotide provided herein comprises a nucleotide sequence encoding a heavy chain of an antibody, which specifically binds to MERTK (e.g., human MERTK), wherein the nucleotide sequence comprises SEQ ID NO: 121 and a human heavy chain constant region nucleotide sequence. In another aspect, a polynucleotide provided herein comprises a nucleotide sequence encoding a heavy chain of an antibody which specifically binds MERTK, wherein the nucleotide comprises SEQ ID NO: 127.

In a specific aspect, polynucleotide provided herein comprises a nucleotide sequence encoding a heavy chain of an antibody, which specifically binds to MERTK (e.g., human MERTK), wherein the nucleotide sequence comprises SEQ ID NO: 122 and a human heavy chain constant region nucleotide sequence. In another aspect, a polynucleotide provided herein comprises a nucleotide sequence encoding a heavy chain of an antibody which specifically binds MERTK (e.g., human MERTK), wherein the nucleotide sequence comprises SEQ ID NO: 128.

In a specific aspect, polynucleotide provided herein comprises a nucleotide sequence encoding a heavy chain of an antibody, which specifically binds to MERTK (e.g. human MERTK), wherein the nucleotide sequence comprises SEQ ID NO: 123 and a human heavy chain constant region nucleotide sequence. In another aspect, a polynucleotide provided herein comprises a nucleotide sequence encoding a heavy chain of an antibody which specifically binds MERTK (e.g. human MERTK), wherein the nucleotide comprises SEQ ID NO: 129.

In a specific aspect, a polynucleotide provided herein comprises a nucleotide sequence encoding light chain of an antibody described herein that specifically binds to MERTK (e.g., human MERTK) and a nucleotide sequence encoding a heavy of chain of the antibody, wherein the nucleotide sequence encoding the heavy chain comprises SEQ ID NO: 119 and a human heavy chain constant region nucleotide sequence, and wherein the nucleotide sequence encoding the light chain comprises SEQ ID NO: 120, and a human heavy chain constant region nucleotide sequence. In another specific aspects, a polynucleotide provided herein comprises a nucleotide sequence encoding light chain of an antibody described herein that specifically binds to MERTK (e.g., human MERTK) and a nucleotide sequence encoding a heavy of chain of the antibody, wherein the nucleotide sequence encoding the light chain comprises SEQ ID NO: 120, and a human light chain constant region nucleotide sequence, and wherein the nucleotide sequence encoding the heavy chain comprises SEQ ID NO: 121 and a human heavy chain constant region nucleotide sequence. In another specific aspects, a polynucleotide provided herein comprises a nucleotide sequence encoding light chain of an antibody described herein that specifically binds to MERTK (e.g., human MERTK) and a nucleotide sequence encoding a heavy of chain of the antibody, wherein the nucleotide sequence encoding the light chain comprises SEQ ID NO: 120 and a human light chain constant region nucleotide sequence, and wherein the nucleotide sequence encoding tge heavy chain comprises SEQ ID NO: 122 and a human heavy chain constant region nucleotide sequence. In another specific aspects, a polynucleotide provided herein comprises a nucleotide sequence encoding light chain of an antibody described herein that specifically binds to MERTK (e.g., human MERTK) and a nucleotide sequence encoding a heavy of chain of the antibody, wherein the nucleotide sequence encoding the light chain comprises SEQ ID NO: 124 and a human light chain constant region nucleotide sequence, and wherein the nucleotide sequence encoding the heavy chain comprises SEQ ID NO: 123 and a human heavy chain constant region nucleotide sequence.

In a specific aspect, a polynucleotide provided herein comprises a nucleotide sequence encoding an antibody, which specifically binds to MERTK (e.g., human MERTK), wherein the antibody comprises: (1) a variable heavy chain region comprising the amino acid sequence of SEQ ID NO: 105 and a human heavy chain constant region; and (2) a variable light chain region comprising the amino acid sequence of SEQ ID NO: 106, and a human light chain constant region. In another specific aspect, a polynucleotide provided herein comprises a nucleotide sequence encoding an antibody, which specifically binds to MERTK (e.g., human MERTK), wherein the antibody comprises: (1) a variable heavy chain region comprising the amino acid sequence of SEQ ID NO: 107 and a human heavy chain constant region; and (2) a variable light chain region comprising the amino acid sequence of SEQ ID NO: 106, and a human light chain constant region. In another specific aspect, a polynucleotide provided herein comprises a nucleotide sequence encoding an antibody, which specifically binds to MERTK (e.g., human MERTK), wherein the antibody comprises: (1) a variable heavy chain region comprising the amino acid sequence of SEQ ID NO: 108 and a human heavy chain constant region; and (2) a variable light chain region comprising the amino acid sequence of SEQ ID NO: 106, and a human light chain constant region. In another specific aspect, a polynucleotide provided herein comprises a nucleotide sequence encoding an antibody, which specifically binds to MERTK (e.g., human MERTK), wherein the antibody comprises: (1) a variable heavy chain region comprising the amino acid sequence of SEQ ID NO: 110, and a human heavy chain constant region; and (2) a variable light chain region comprising the amino acid sequence of SEQ ID NO: 111 and a human light chain constant region.

In another specific aspect, a polynucleotide provided herein comprises a nucleotide sequence encoding an antibody, which specifically binds to MERTK (e.g., human MERTK), wherein the antibody comprises: (1) a variable heavy chain region comprising the amino acid sequence of SEQ ID NO: 109, and a human heavy chain constant region; and (2) a variable light chain region comprising the amino acid sequence of SEQ ID NO: 106 and a human light chain constant region.

In another specific embodiment, a polynucleotide provided herein comprises nucleotide sequences encoding an anti-MERTK antibody, or an antigen-binding fragment thereof, which specifically binds to MERTK (e.g., human MERTK), wherein one nucleotide sequence encodes a heavy chain of the antibody and the other nucleotide sequence encodes a light chain of the antibody, and wherein the nucleotide sequence encoding the heavy chain comprises SEQ ID NO: 125 and the nucleotide sequence encoding the light chain comprises SEQ ID NO: 126. In another specific embodiment, a polynucleotide provided herein comprises nucleotide sequences encoding an anti-MERTK antibody, or an antigen-binding fragment thereof, which specifically binds to MERTK (e.g., human MERTK), wherein one nucleotide sequence encodes a heavy chain of the antibody and the other nucleotide sequence encodes a light chain of the antibody, and wherein the nucleotide sequence encoding the heavy chain comprises SEQ ID NO: 127 and the nucleotide sequence encoding the light chain comprises SEQ ID NO: 126. In another specific embodiment, a polynucleotide provided herein comprises nucleotide sequences encoding an anti-MERTK antibody, or an antigen-binding fragment thereof, which specifically binds to MERTK (e.g., human MERTK), wherein one nucleotide sequence encodes a heavy chain of the antibody and the other nucleotide sequence encodes a light chain of the antibody, and wherein the nucleotide sequence encoding the heavy chain comprises SEQ ID NO: 128 and the nucleotide sequence encoding the light chain comprises SEQ ID NO: 126. In another specific embodiment, a polynucleotide provided herein comprises nucleotide sequences encoding an anti-MERTK antibody, or an antigen-binding fragment thereof, which specifically binds to MERTK (e.g., human MERTK), wherein one nucleotide sequence encodes a heavy chain of the antibody and the other nucleotide sequence encodes a light chain of the antibody, and wherein the nucleotide sequence encoding the heavy chain comprises SEQ ID NO: 129 and the nucleotide sequence encoding the light chain comprises SEQ ID NO: 130.

In another specific embodiment, a polynucleotide provided herein comprises nucleotide sequences encoding an anti-MERTK antibody or antigen-binding fragment thereof, which specifically binds to MERTK (e.g., human MERTK), wherein one nucleotide sequence encodes a heavy chain of the antibody and the other encodes the light chain of the antibody, wherein the heavy chain comprises the amino acid sequence of SEQ ID NO: 112 and the light chain comprises the amino acid sequence of SEQ ID NO: 113. In another specific embodiment, a polynucleotide provided herein comprises nucleotide sequences encoding an anti-MERTK antibody or antigen-binding fragment thereof, which specifically binds to MERTK (e.g., human MERTK), wherein one nucleotide sequence encodes a heavy chain of the antibody and the other encodes the light chain of the antibody, wherein the heavy chain comprises the amino acid sequence of SEQ ID NO: 114 and the light chain comprises the amino acid sequence of SEQ ID NO: 113. In another specific embodiment, a polynucleotide provided herein comprises nucleotide sequences encoding an anti-MERTK antibody or antigen-binding fragment thereof, which specifically binds to MERTK (e.g., human MERTK), wherein one nucleotide sequence encodes a heavy chain of the antibody and the other encodes the light chain of the antibody, wherein the heavy chain comprises the amino acid sequence of SEQ ID NO: 115 and the light chain comprises the amino acid sequence of SEQ ID NO: 113. In another specific embodiment, a polynucleotide provided herein comprises nucleotide sequences encoding an anti-MERTK antibody or antigen-binding fragment thereof, which specifically binds to MERTK (e.g., human MERTK), wherein one nucleotide sequence encodes a heavy chain of the antibody and the other encodes the light chain of the antibody, wherein the heavy chain comprises the amino acid sequence of SEQ ID NO: 116 and the light chain comprises the amino acid sequence of SEQ ID NO: 113. In another specific embodiment, a polynucleotide provided herein comprises nucleotide sequences encoding an anti-MERTK antibody or antigen-binding fragment thereof, which specifically binds to MERTK (e.g., human MERTK), wherein one nucleotide sequence encodes a heavy chain of the antibody and the other encodes the light chain of the antibody, wherein the heavy chain comprises the amino acid sequence of SEQ ID NO: 117 and the light chain comprises the amino acid sequence of SEQ ID NO: 118.

In certain embodiments, a polynucleotide(s), nucleic acid(s) or nucleotide(s) includes deoxyribonucleic acids, ribonucleic acids, ribonucleotides, and polymeric forms thereof. In some embodiments, the polynucleotides(s), nucleic acid(s) or nucleotide(s) is single or double stranded. In a specific embodiment, a polynucleotide, nucleic acid, or nucleotide sequence is a cDNA sequence.

In some embodiments, a polynucleotide sequence described herein (e.g., a nucleic acid sequence) encoding an anti-MERTK antibody or an antigen-binding fragment thereof is codon optimized using methodology known to one of skill in the art. In certain embodiments, an optimized polynucleotide sequence encoding an anti-MERTK antibody or antigen-binding fragment thereof described herein or an antigen-binding fragment thereof (e.g., VH domain and/or VL domain) can hybridize to an antisense (e.g., complementary) polynucleotide of an unoptimized polynucleotide sequence encoding an anti-MERTK antibody described herein or an antigen-binding fragment thereof (e.g., VH domain and/or VL domain). In specific embodiments, an optimized nucleotide sequence encoding an anti-MERTK antibody or an antigen-binding fragment thereof described herein, hybridizes under high stringency conditions to antisense polynucleotide of an unoptimized polynucleotide sequence encoding an anti-MERTK antibody described herein or an antigen-binding fragment thereof. In a specific embodiment, an optimized nucleotide sequence encoding an anti-MERTK antibody or an antigen-binding fragment thereof hybridizes under high stringency, intermediate or lower stringency hybridization conditions to an antisense polynucleotide of an unoptimized nucleotide sequence encoding an anti-MERTK antibody or an antigen-binding fragment thereof described herein. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, and modified versions of these antibodies can be determined using methods well known in the art, i.e., nucleotide codons known to encode particular amino acids are assembled in such a way to generate a nucleic acid sequence that encodes the antibody. Such a polynucleotide encoding the antibody can be assembled from chemically synthesized oligonucleotides (e.g., as described in Kutmeier G et al., (1994), BioTechniques 17: 242-6), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate humanized antibodies.

If a clone containing a nucleic acid sequence encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-MERTK antibodies described herein can be readily isolated and sequenced using conventional procedures (e.g., by using oligonucleotide probes that are capable of binding specifically to genes encoding the heavy and light chains of the anti-MERTK antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), 293F cells, HEK293 cells, or myeloma cells that do not otherwise produce immunoglobulin protein, to obtain the synthesis of MERTK agonistic antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise a promoter, a secretion signal, a cloning site for the variable domain, constant domains, and a selection marker. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein or an antigen-binding fragment thereof. In specific embodiments, polynucleotides described herein hybridize under high stringency, intermediate or lower stringency hybridization conditions to polynucleotides encoding a VH (SEQ ID NO: 119, 121, 122 or 123) and/or VL (SEQ ID NO: 120 or 124) provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

5.3.3. Cells and Vectors

In certain aspects, provided herein are vectors (e.g., expression vectors) comprising polynucleotides comprising nucleotide sequences encoding an anti-MERTK antibody or an antigen-binding fragment thereof described herein for recombinant expression in host cells, preferably in mammalian cells. Expression vectors may be, e.g., plasmids or viral vectors (such as Newcastle disease virus, adenovirus, adeno-associated virus, vaccinia, etc.). Also provided herein are host cells comprising such vectors for recombinantly expressing anti-MERTK antibodies or antigen-binding fragments thereof described herein.

Recombinant expression of an antibody described herein (e.g., a full-length antibody, heavy and/or light chain of an antibody, or a single chain antibody described herein) that specifically binds to MERTK (e.g., human MERTK) involves construction of an expression vector containing a polynucleotide that encodes the antibody. Once a polynucleotide encoding an antibody molecule, heavy and/or light chain of an antibody, or an antigen-binding fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain, or both) encoding nucleotide sequence are described herein. Methods which are well known to those skilled in the art can be used to construct expression vectors containing antibody or antibody fragment (e.g., light chain or heavy chain, or both) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, or a heavy or light chain variable domain of an anti-MERTK antibody or antigen-binding fragment thereof, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an anti-MERTK antibody described herein or an antigen-binding fragment thereof. Thus, provided herein are host cells containing a polynucleotide encoding an antibody described herein or an antigen-binding fragment thereof, or a heavy or light chain thereof, or a fragment thereof, or a single chain antibody described herein, operably linked to a promoter for expression of such sequences in the host cell. As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

A variety of host-expression vector systems can be utilized to express antibody molecules described herein. Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, 293F, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7). In certain embodiments, antibodies described herein are produced by CHO cells or NS0 cells. In a specific embodiment, the expression of nucleotide sequences encoding antibodies described herein which immunospecifically bind MERTK (e.g., human MERTK) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544).

In addition, a host cell strain which modulates the expression of the inserted sequences, or modifies and processes the gene product in the specific fashion desired can be chosen. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, 293F, BT483, Hs578T, HTB2, BT20 and T47D, NS0 (a murine myeloma cell line that does not endogenously produce any immunoglobulin chains), CRL7030, COS (e.g., COS1 or COS), PER.C6, VERO, HsS78Bst, HEK-293T, HEK293, HepG2, SP210, R1.1, B-W, L-M, BSC1, BSC40, YB/20, BMT10 and HsS78Bst cells. In certain embodiments, anti-MERTK antibodies described herein are produced in mammalian cells, such as CHO cells.

In a specific embodiment, the antibodies described herein or antigen-binding fragments thereof have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies or antigen-binding fragments thereof with reduced fucose content. The Potelligent® system (Lonza) is an example of such a system that can be used to produce antibodies or antigen-binding fragments thereof with reduced fucose content.

For long-term, high-yield production of recombinant proteins, stable expression cells can be generated. For example, cell lines which stably express an anti-MERTK antibody described herein or an antigen-binding fragment thereof or a chimeric anti-MERTK antibody or antigen-binding fragment thereof described herein, can be engineered. In specific embodiments, a cell provided herein stably expresses a light chain/light chain variable domain and a heavy chain/heavy chain variable domain which associate to form an antibody described herein or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express a humanized anti-MERTK antibody described herein or an antigen-binding fragment thereof or a chimeric anti-MERTK antibody or antigen-binding fragment thereof described herein. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) Cell 11(1): 223-32), hypoxanthineguanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes can be employed in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

In a specific aspect, a host cell provided herein comprises a vector, wherein the vector comprises a nucleotide sequence encoding a variable light chain region (VL) of an antibody described herein that specifically binds to MERTK (e.g., human MERTK) and a nucleotide sequence encoding a variable heavy chain region (VH) of the antibody, wherein the VL comprises the amino acid sequence of SEQ ID NO: 106, and wherein the VH comprises the amino acid sequence of SEQ ID NO: 105. In another specific aspect, a host cell provided herein comprises a vector, wherein the vector comprises a nucleotide sequence encoding light chain of an antibody described herein that specifically binds to MERTK (e.g., human MERTK) and a nucleotide sequence encoding a heavy chain of the antibody, wherein the light chain comprises a variable light chain region comprising the amino acid of SEQ ID NO: 106, and a human light chain constant region, and wherein the heavy chain comprises a variable heavy chain region comprising the amino acid sequence of SEQ ID NO: 105, and a human heavy chain constant region.

In a specific aspect, a host cell provided herein comprises a vector, wherein the vector comprises a nucleotide sequence encoding a variable light chain region (VL) of an antibody described herein that specifically binds to MERTK (e.g., human MERTK) and a nucleotide sequence encoding a variable heavy chain region (VH) of the antibody, wherein the VL comprises the amino acid sequence of SEQ ID NO: 106, and wherein the VH comprises the amino acid sequence of SEQ ID NO: 109 In another specific aspect, a host cell provided herein comprises a vector, wherein the vector comprises a nucleotide sequence encoding light chain of an antibody described herein that specifically binds to MERTK (e.g., human MERTK) and a nucleotide sequence encoding a heavy chain of the antibody, wherein the light chain comprises a variable light chain region comprising the amino acid of SEQ ID NO: 106, and a human light chain constant region, and wherein the heavy chain comprises a variable heavy chain region comprising the amino acid sequence of SEQ ID NO: 109, and a human heavy chain constant region.

In a specific aspect, a host cell provided herein comprises a vector, wherein the vector comprises a nucleotide sequence encoding VL of an antibody described herein that specifically binds to MERTK (e.g., human MERTK) and a nucleotide sequence encoding a VH of the antibody, wherein the VL comprises the amino acid sequence of SEQ ID NO: 106, and wherein the VH comprises the amino acid sequence of SEQ ID NO: 107. In another specific aspect, a host cell provided herein comprises a vector, wherein the vector comprises a nucleotide sequence encoding the light chain of an antibody described herein that specifically binds to MERTK (e.g., human MERTK) and a nucleotide sequence encoding a heavy chain of the antibody, wherein the light chain comprises a VL comprising the amino acid sequence of SEQ ID NO: 106 and a human light constant region, and wherein the heavy chain comprises a VH comprising the amino acid sequence of SEQ ID NO: 107 and a human heavy constant region.

In a specific aspect, a host cell provided herein comprises a vector, wherein the vector comprises a nucleotide sequence encoding a VL of an antibody described herein that specifically binds to MERTK (e.g., human MERTK) and a nucleotide sequence encoding a VH of the antibody, wherein the VL comprises the amino acid sequence of SEQ ID NO: 106, and wherein the VH comprises the amino acid sequence of SEQ ID NO: 108. In another specific aspect, a host cell provided herein comprises a vector, wherein the vector comprises a nucleotide sequence encoding light chain of an antibody described herein that specifically binds to MERTK (e.g., human MERTK) and a nucleotide sequence encoding a heavy chain of the antibody, wherein the light chain comprises a variable light chain region of SEQ ID NO: 108, and a human light chain constant region, and wherein the heavy chain comprises a variable heavy chain region nucleotide sequence of SEQ ID NO: 105, and a human heavy chain constant region.

In a specific aspect, a host cell provided herein comprises a vector, wherein the vector comprises a nucleotide sequence encoding a VL of an antibody described herein that specifically binds to MERTK (e.g., human MERTK) and a nucleotide sequence encoding a VH of the antibody, wherein the VL comprises the amino acid sequence of SEQ ID NO: 111, and wherein the VH comprises the amino acid sequence of SEQ ID NO: 110.

In another specific aspect, a host cell provided herein comprises a vector, wherein the vector comprises a nucleotide sequence encoding light chain of an antibody described herein that specifically binds to MERTK (e.g., human MERTK) and a nucleotide sequence encoding a heavy chain of the antibody, wherein the nucleotide sequence encoding the light chain comprises SEQ ID NO: 120, and a human light chain constant region nucleotide sequence, and wherein the nucleotide sequence encoding the heavy chain comprises of SEQ ID NO: 119, and a human heavy chain constant region nucleotide sequence.

In another specific aspect, a host cell provided herein comprises a vector, wherein the vector comprises a nucleotide sequence encoding light chain of an antibody described herein that specifically binds to MERTK (e.g., human MERTK) and a nucleotide sequence encoding a heavy chain of the antibody, wherein the nucleotide sequence encoding the light chain comprises SEQ ID NO: 120, and a human light chain constant region nucleotide sequence, and wherein the nucleotide sequence encoding the heavy chain comprises of SEQ ID NO: 121, and a human heavy chain constant region nucleotide sequence. In another specific aspect, a host cell provided herein comprises a vector, wherein the vector comprises a nucleotide sequence encoding light chain of an antibody described herein that specifically binds to MERTK (e.g., human MERTK) and a nucleotide sequence encoding a heavy chain of the antibody, wherein the nucleotide sequence encoding the light chain comprises SEQ ID NO: 120, and a human light chain constant region nucleotide sequence, and wherein the nucleotide sequence encoding the heavy chain comprises of SEQ ID NO: 122, and a human heavy chain constant region nucleotide sequence. In another specific aspect, a host cell provided herein comprises a vector, wherein the vector comprises a nucleotide sequence encoding light chain of an antibody described herein that specifically binds to MERTK (e.g., human MERTK) and a nucleotide sequence encoding a heavy chain of the antibody, wherein the nucleotide sequence encoding the light chain comprises SEQ ID NO: 124, and a human light chain constant region nucleotide sequence, and wherein the nucleotide sequence encoding the heavy chain comprises of SEQ ID NO: 123, and a human heavy chain constant region nucleotide sequence.

In a specific aspect, a host cell provided herein comprises a first vector and a second vector, wherein the first vector comprises a nucleotide sequence encoding a variable heavy chain region of an antibody described herein, which specifically binds to MERTK (e.g., human MERTK), wherein the second vector comprises a variable light chain region of the antibody, wherein the variable heavy chain region comprises the amino acid sequence of SEQ ID NO: 105, and wherein the variable light chain region comprises the amino acid sequence of SEQ ID NO: 106. In another specific aspect, a host cell provided herein comprises a first vector and a second vector, wherein the first vector comprises a nucleotide sequence encoding a variable heavy chain region of an antibody described herein, which specifically binds to MERTK (e.g., human MERTK), wherein the second vector comprises a variable light chain region of the antibody, wherein the variable heavy chain region comprises the amino acid sequence of SEQ ID NO: 107, and wherein the variable light chain region comprises the amino acid sequence of SEQ ID NO: 106. In another specific aspect, a host cell provided herein comprises a first vector and a second vector, wherein the first vector comprises a nucleotide sequence encoding a variable heavy chain region of an antibody described herein, which specifically binds to MERTK (e.g., human MERTK), wherein the second vector comprises a variable light chain region of the antibody, wherein the variable heavy chain region comprises the amino acid sequence of SEQ ID NO: 108, and wherein the variable light chain region comprises the amino acid sequence of SEQ ID NO: 106. In another specific aspect, a host cell provided herein comprises a first vector and a second vector, wherein the first vector comprises a nucleotide sequence encoding a variable heavy chain region of an antibody described herein, which specifically binds to MERTK (e.g., human MERTK), wherein the second vector comprises a variable light chain region of the antibody, wherein the variable heavy chain region comprises the amino acid sequence of SEQ ID NO: 109, and wherein the variable light chain region comprises the amino acid sequence of SEQ ID NO: 106. In another specific aspect, a host cell provided herein comprises a first vector and a second vector, wherein the first vector comprises a nucleotide sequence encoding a variable heavy chain region of an antibody described herein, which specifically binds to MERTK (e.g., human MERTK), wherein the second vector comprises a variable light chain region of the antibody, wherein the variable heavy chain region comprises the amino acid sequence of SEQ ID NO: 110 and wherein the variable light chain region comprises the amino acid sequence of SEQ ID NO: 111. In some embodiments, the first vector comprises a heavy chain constant region and/or the second vector comprises a light chain constant region.

Alternatively, a single vector can be used which encodes, and is capable of expressing, both heavy and light chain polypeptides. In such an expression vector, the transcription of both genes can be driven by a common promoter, whereas the translation of the mRNA from the first gene can be by a cap-dependent scanning mechanism and the translation of the mRNA from the second gene can be by a cap-independent mechanism, e.g., by an IRES.

In a specific aspect, a host cell provided herein comprises a vector, wherein the vector comprises a nucleotide sequence encoding a variable heavy chain region of an antibody described herein, which specifically binds to MERTK (e.g., human MERTK), and a nucleotide encoding a variable light chain region of the antibody, wherein the variable heavy chain region comprises the amino acid sequence of SEQ ID NO: 105, and wherein the variable light chain region comprises the amino acid sequence of SEQ ID NO: 106. In another specific aspect, a host cell provided herein comprises a vector, wherein the vector comprises a nucleotide sequence encoding a variable heavy chain region of an antibody described herein, which specifically binds to MERTK (e.g., human MERTK), and a nucleotide encoding a variable light chain region of the antibody, wherein the variable heavy chain region comprises the amino acid sequence of SEQ ID NO: 107, and wherein the variable light chain region comprises the amino acid sequence of SEQ ID NO: 106. In another specific aspect, a host cell provided herein comprises a vector, wherein the vector comprises a nucleotide sequence encoding a variable heavy chain region of an antibody described herein, which specifically binds to MERTK (e.g., human MERTK), and a nucleotide encoding a variable light chain region of the antibody, wherein the variable heavy chain region comprises the amino acid sequence of SEQ ID NO: 108, and wherein the variable light chain region comprises the amino acid sequence of SEQ ID NO: 106. In another specific aspect, a host cell provided herein comprises a vector, wherein the vector comprises a nucleotide sequence encoding a variable heavy chain region of an antibody described herein, which specifically binds to MERTK (e.g., human MERTK), and a nucleotide encoding a variable light chain region of the antibody, wherein the variable heavy chain region comprises the amino acid sequence of SEQ ID NO: 109, and wherein the variable light chain region comprises the amino acid sequence of SEQ ID NO: 106. In another specific aspect, a host cell provided herein comprises a vector, wherein the vector comprises a nucleotide sequence encoding a variable heavy chain region of an antibody described herein, which specifically binds to MERTK (e.g., human MERTK), and a nucleotide encoding a variable light chain region of the antibody, wherein the variable heavy chain region comprises the amino acid sequence of SEQ ID NO: 110, and wherein the variable light chain region comprises the amino acid sequence of SEQ ID NO: 111. In some embodiments, the vector comprises a heavy chain constant region and/or a light chain constant region.

In a specific embodiment, a host cell (e.g., an ex vivo host cell) described herein is cultured under conditions to produce the antibody or antigen-binding fragment thereof encoded by the polynucleotide sequence contained in the host cell using a technique known in the art. In certain embodiments, the antibody or antigen-binding fragment thereof is isolated or purified from the host cell using a technique known in the art.

5.4. Production of the Antibody-Drug Conjugates

In another aspect, provided herein are methods of producing an antibody-drug conjugate described herein wherein a linker is not present, the method comprising: (a) conjugating the cytotoxic agent directly to the antibody moiety to produce the antibody-drug conjugate; and (b) purifying the antibody-drug conjugate. Examples of methods of producing antibody-drug conjugates are described in section 6 (e.g., in Example 4).

In another aspect, provided herein are methods of producing an antibody-drug conjugate described herein wherein the antibody-drug conjugate comprises a linker, the method comprising the following steps in the order stated: (a) conjugating the linker directly to the antibody moiety to produce a linker-antibody moiety; (b) conjugating the linker of the linker-antibody moiety directly to the cytotoxic agent to produce the antibody-drug conjugate; and (c) purifying the antibody-drug conjugate.

In another aspect, provided herein are methods of producing an antibody-drug conjugate described herein wherein the antibody-drug conjugate comprises a linker, the method comprising the following steps in the order stated: (a) conjugating the linker directly to the cytotoxic agent to produce a linker-cytotoxic agent moiety; (b) conjugating the linker of the linker-cytotoxic agent moiety directly to the antibody moiety to produce the antibody-drug conjugate; and (c) purifying the antibody-drug conjugate.

The conjugating and purifying steps can be performed by methods known in the art used for producing antibody-drug conjugates, such as the methods described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; or Olivier K J and Hurvitz S A ed., (2016) Antibody-Drug Conjugates: Fundamentals, Drug Development, and Clinical, Wiley. In some embodiments, the drug moiety is conjugated to one chain of the antibody moiety (for example, when the antibody moiety is a scFv, or when the antibody moiety is a multi-chain antibody, such as an immunoglobulin (which is a tetramer), or antigen-binding fragment thereof). In other embodiments, the drug moiety is conjugated to two or more chains of the antibody moiety (when the antibody moiety is a multi-chain antibody, such as an immunoglobulin, or antigen-binding fragment thereof). In a specific embodiment, the drug moiety is conjugated to two identical chains of an immunoglobulin, e.g., the heavy chains or the light chains. In other embodiments, the drug moiety is conjugated to all chains of the antibody moiety (when the antibody moiety is a multi-chain antibody, such as an immunoglobulin or antigen-binding fragment thereof). In a specific embodiment, the antibody-drug conjugate described herein is purified by chromatograph. In another specific embodiment, the antibody-drug conjugate described herein is purified by centrifugation. By way of example but not limitation, the conjugation chemistry that can be used for generating the antibody-drug conjugate can be thiol plus maleimide, thiol plus self-hydrolyzing maleimide, thiol plus phenyloxadiazole sulfone, oxime ligation, alkoxyamine-to-keto-group reaction, strain-promoted azide-alkyne cycloaddition (SPAAC), copper-free click chemistry, cysteine oxidized to formylglycine, hydrazino-iso-Pictet-Spengler (HIPS) ligation, ligation of γ-carboxyamide group from glutamine residues plus primary amines, ligation LPETG plus primary amine of polyglycine motif, maleimide plus 6-thiofucose, fucose-specific conjugation of hydrazide, periodate oxidation (aldehyde) plus amino-oxy-payload, strain-promoted alkyn-azide cycloaddition, C2-keto-gal oximation, site selective aldehyde oxidation plus oxime ligation, oxime ligation NH2 plus indole-based 5-difluoro-2,4-dinitrobenzene derivatives, thiol plus bis-sulfone, thiol plus dibromomaleimide, thiol plus maleimide followed by pH 9.2 treatment (45° C., 48 hours), or thiol plus arylpropionitrile (see Beck A et al., (2017) Nat Rev Drug Discov 16: 315-337).

The anti-MERTK antibody or an antigen-binding fragment thereof described herein can be generated as described in 5.3 infra. In specific embodiments, the anti-MERTK antibody or an antigen-binding fragment thereof described herein is engineered or modified by a method known in the art to facilitate conjugation with the drug moiety(ies), in particular to facilitate site-specific conjugation with the drug moiety(ies), for example, by a method described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; or Olivier K J and Hurvitz S A ed., (2016) Antibody-Drug Conjugates: Fundamentals, Drug Development, and Clinical, Wiley. Non-limiting exemplary methods that can be used (see Beck A et al., (2017) Nat Rev Drug Discov 16: 315-337) to engineer or modify an anti-MERTK antibody or an antigen-binding fragment thereof to facilitate conjugation with the drug moiety(ies) include adding one or more additional cysteines or selenocysteines, unnatural amino acid engineering, adding one or more amino acid tags recognizable by certain enzymes that can assist with the conjugation, glycan remodeling, adding an amino-terminal serine, and native cysteine bridging.

The linker and the cytotoxic agent can be generated by any method known in the art for producing the linker and the cytotoxic agent, respectively.

5.5. Pharmaceutical Compositions

Provided herein are pharmaceutical compositions comprising (a) an anti-MERTK antibody (e.g., a humanized antibody) or an antigen-binding fragment thereof described herein and (b) a pharmaceutically acceptable carrier. In a specific embodiment, the antibody or antigen-binding fragment thereof is purified. In a specific embodiment, the antibody or antigen-binding fragment thereof is present in the pharmaceutical composition in a therapeutically effective amount. In a specific embodiment, the pharmaceutical composition comprises an anti-MERTK antibody or an antigen-binding fragment thereof comprising a VH comprising the amino acid sequence of SEQ ID NO: 105 and a VL comprising the amino acid sequence of SEQ ID NO: 106 (e.g., antibody z10). In another specific embodiment, the pharmaceutical composition comprises an anti-MERTK antibody or an antigen-binding fragment thereof comprising a VH comprising the amino acid sequence of SEQ ID NO: 107 and a VL comprising the amino acid sequence of SEQ ID NO: 106 (e.g. antibody z11). In another specific embodiment, the pharmaceutical composition comprises an anti-MERTK antibody or an antigen-binding fragment thereof comprising a VH comprising the amino acid sequence of SEQ ID NO: 108 and a VL comprising the amino acid sequence of SEQ ID NO: 106 (e.g., antibody z13). In another specific embodiment, the pharmaceutical composition comprises an anti-MERTK antbody or antigen-binding fragment thereof comprising the amino acid sequence of SEQ ID NO: 109 and a VL comprising the amino acid sequence of SEQ ID NO: 106.

Also provided herein are pharmaceutical compositions comprising (a) a chimeric anti-MERTK antibody or an antigen-binding fragment thereof described herein and (b) a pharmaceutically acceptable carrier. In a specific embodiment, the antibody or antigen-binding fragment thereof is purified. In a specific embodiment, the antibody or antigen-binding fragment thereof is present in the pharmaceutical composition in a therapeutically effective amount. In a specific embodiment, the pharmaceutical composition comprises a chimeric antibody or an antigen-binding fragment thereof comprising a VH comprising the amino acid sequence of SEQ ID NO: 110 and a VL comprising the amino acid sequence of SEQ ID NO: 111 (e.g., antibody xAb). Also provided herein are pharmaceutical compositions comprising a polynucleotide or vector(s) described herein and a pharmaceutically acceptable carrier.

Also provided herein are pharmaceutical compositions comprising (a) an antibody-drug conjugate described herein and (b) a pharmaceutically acceptable carrier. In a specific embodiment, the antibody-drug conjugate is present in the pharmaceutical composition in a therapeutically effective amount.

Also provided herein are pharmaceutical compositions comprising (a) a bispecific antibody that binds MERTK (e.g., human MERTK) and another antigen of interest (e.g., as described herein) and (b) a pharmaceutically acceptable carrier. In a specific embodiment, the bispecific antibody is purified. In a specific embodiment, the bispecific antibody is present in the pharmaceutical composition in a therapeutically effective amount.

In a specific embodiment, a population of antibody-drug conjugates contained in the pharmaceutical composition have a drug-to-antibody ratio (DAR) between 1 to 20. DAR is the average number of cytotoxic agents conjugated to the antibodies. In another specific embodiment, a population of antibody-drug conjugates contained in the pharmaceutical composition have a DAR between 1 to 15. In another specific embodiment, a population of antibody-drug conjugates contained in the pharmaceutical composition have a DAR between 1 to 12. In another specific embodiment, a population of antibody-drug conjugates contained in the pharmaceutical composition have a DAR between 1 to 8. In another specific embodiment, a population of antibody-drug conjugates contained in the pharmaceutical composition have a DAR between 3 to 5. In another specific embodiment, a population of antibody-drug conjugates contained in the pharmaceutical composition have a DAR between 3.5 to 4.

Acceptable carriers, which can be excipients or stabilizers, are nontoxic to recipients at the dosages and concentrations employed, and include but are not limited to buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-MERTK antibody or an antigen-binding fragment thereof described herein, and optionally one or more additional prophylactic or therapeutic agents, in a pharmaceutically acceptable carrier. In a specific embodiment, pharmaceutical compositions comprise an effective amount of an anti-MERTK antibody or an antigen-binding fragment thereof described herein, and optionally one or more additional prophylactic or therapeutic agents, in a pharmaceutically acceptable carrier. In a specific embodiment, the pharmaceutical compositions and/or antibodies or antigen-binding fragments thereof described herein, can be combined with a therapeutically effective amount of any of the additional therapeutic agents described herein (See Section 5.4.2, infra).

In a specific embodiment, pharmaceutical compositions comprise an antibody-drug conjugate described herein, and optionally one or more additional prophylactic or therapeutic agents, in a pharmaceutically acceptable carrier. In a specific embodiment, pharmaceutical compositions comprise an effective amount of an antibody-drug conjugate described herein, and optionally one or more additional prophylactic or therapeutic agents, in a pharmaceutically acceptable carrier. In a specific embodiment, the pharmaceutical compositions and/or antibody-drug conjugate described herein, can be combined with a therapeutically effective amount of any of the additional therapeutic agents described herein (See Section 5.4.2, infra).

In some embodiments, the antibody-drug conjugate is the only active ingredient included in the pharmaceutical composition.

In some embodiments, an anti-MERTK antibody is the only active ingredient included in the pharmaceutical composition. In a specific embodiment, a humanized antibody described herein or an antigen-binding fragment thereof is the only active ingredient included in the pharmaceutical composition. In another embodiment, a polynucleotide(s) or a vector(s) encoding an antibody or an antigen-binding fragment thereof is the only active ingredient in the pharmaceutical composition.

Pharmaceutical compositions described herein can be used to treat cancer. Pharmaceutical compositions may be formulated for any route of administration (e.g., parenteral, topical, intratumoral, etc.).

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-MERTK antibody or an antigen-binding fragment thereof, or an antibody-drug conjugate described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-MERTK antibody or an antigen-binding fragment thereof, or an antibody-drug-conjugate described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an anti-MERTK antibody or an antigen-binding fragment thereof, or an antibody-drug conjugate described herein is a lyophilized powder, which can be reconstituted for administration as solutions, emulsions and other mixtures. It may also be reconstituted and formulated as solids or gels. The lyophilized powder is prepared by dissolving an anti-MERTK antibody or an antigen-binding fragment thereof, or an antibody-drug conjugate described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

In some embodiments, pharmaceutical compositions comprising an anti-MERTK antibody or an antigen-binding fragment thereof described herein, or an antibody-drug conjugate described herein, are supplied in liquid form without the need to reconstitute.

The antibodies or antigen-binding fragments thereof described herein, or antibody-drug conjugates described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In a specific embodiment, an anti-MERTK antibody or an antigen-binding fragment thereof described herein, or an antibody-drug conjugate described herein is targeted to a tumor.

The compositions to be used for in vivo administration can be sterile. This is readily accomplished by filtration through, e.g., sterile filtration membranes.

5.6 Uses and Methods 5.6.1 Therapeutic Uses and Methods 5.6.1.1 Cancer

In one aspect, presented herein are methods for treating cancer in a subject, comprising administering to a subject in need thereof an anti-MERTK antibody or antigen-binding fragment thereof described herein, or a pharmaceutical composition comprising an anti-MERTK antibody or an antigen-binding fragment thereof described herein. In a specific embodiment, the method for treating cancer comprises administering to a subject in need thereof an anti-MERTK antibody comprising a VH comprising an amino acid sequence of SEQ ID NO: 105 and a VL comprising an amino acid sequence of SEQ ID NO: 106 (e.g., antibody z10). In another specific embodiment, the method for treating cancer comprises administering to a subject in need thereof an anti-MERTK antibody comprising a VH comprising an amino acid sequence of SEQ ID NO: 107 and a VL comprising an amino acid sequence of SEQ ID NO: 106 (e.g., antibody z11). In a specific embodiment, the method for treating cancer comprises administering to a subject in need thereof an anti-MERTK antibody comprising a VH comprising an amino acid sequence of SEQ ID NO: 108 and a VL comprising an amino acid sequence of SEQ ID NO: 106 (e.g., antibody z13). In a specific embodiment, the method for treating cancer comprises administering to a subject in need thereof an anti-MERTK antibody comprising a VH comprising an amino acid sequence of SEQ ID NO: 109 and a VL comprising an amino acid sequence of SEQ ID NO: 106 (e.g., antibody z13).

In another aspect, presented herein are methods for treating cancer in a subject, comprising administering to a subject in need thereof a chimeric anti-MERTK antibody or antigen-binding fragment thereof described herein, or a pharmaceutical composition comprising a chimeric anti-MERTK antibody or an antigen-binding fragment thereof described herein. In a specific embodiment, the method for treating cancer comprises administering to a subject in need thereof a chimeric antibody comprising a VH comprising an amino acid sequence of SEQ ID NO: 110 and a VL comprising an amino acid sequence of SEQ ID NO: 111 (e.g., antibody xAb).

In another aspect, presented herein are methods for treating cancer in a subject, comprising administering to a subject in need thereof an antibody-drug conjugate described herein, or a pharmaceutical composition comprising an antibody-drug conjugate described herein. In another aspect, presented herein are methods for treating cancer in a subject, comprising administering to a subject in need thereof a bispecific antibody described herein, or a pharmaceutical composition comprising a bispecific antibody described herein. In another aspect, presented herein are methods for treating cancer in a subject, comprising administering to a subject in need thereof a polynucleotide or vector encoding an anti-MERTK antibody or antigen-binding fragment thereof described herein, or a pharmaceutical composition comprising a polynucleotide(s) or vector(s) encoding an anti-MERTK antibody or antigen-binding fragment thereof described herein.

In a specific embodiment, presented herein are methods for treating cancer in a subject, comprising administering to a subject in need thereof a pharmaceutical composition comprising an anti-MERTK antibody or an antigen-binding fragment thereof described herein that specifically binds to MERTK (e.g., human MERTK), or an antibody-drug conjugate described herein.

In certain embodiments, the methods for treating cancer described herein include obtaining a tumor biopsy, tumor sample, or cancer cell sample from a subject and assessing the level of expression of MERTK (e.g., human MERTK) using an assay described herein or known to one of skill in the art. In some embodiments, the level of phosphorylation of MERTK (e.g., human MERTK) by cancer cells, a tumor sample or a tumor biopsy obtained from a subject is assessed using an assay described herein or known to one of skill in the art. In some embodiments, the methods for treating cancer described herein include obtaining a tumor biopsy, tumor sample, or cancer cell sample from a subject and assessing the level of mutated MERTK (e.g., mutant human MERTK) using an assay described herein or known in the art. Techniques known to one of skill in the art may be used to obtain a tumor biopsy or cancer cell sample. In some embodiments, a Western blot, an ELISA or flow cytometry is used to assess MERTK (e.g., human MERTK) expression levels. In certain embodiments, a Western blot or an ELISA is used to assess the level of phosphorylation of MERTK (e.g., human MERTK). In some embodiments, an anti-MERTK antibody or antigen-binding fragment thereof described herein, or an anti-MERTK known to one of skill in the art (e.g., an anti-MERTK antibody described in International Patent Application Publication No. WO 2016106221) is used to measure MERTK (e.g., human MERTK) levels. In some embodiments, a subject treated in accordance with the methods described herein has cancer cells overexpressing MERTK, cancer cells expressing constitutively activated MERTK, or both.

In certain embodiments, the methods for treating cancer described herein include obtaining PMBCs from a subject, isolating macrophages and assessing the level of expression of MERTK (e.g., human MERTK) using an assay described herein or known to one of skill in the art. In some embodiments, PMBCs from a subject are obtained, macrophages are isolated, and the level of phosphorylation of expression of MERTK (e.g., human MERTK), or level of mutated MERTK (e.g., mutated human MERTK), or both by the macrophages is assessed using an assay described herein or known to one of skill in the art. Techniques known to one of skill in the art may be used to obtain PMBCs and isolate macrophages. In some embodiments, a Western blot, an ELISA or flow cytometry is used to assess MERTK (e.g., human MERTK) expression levels. In certain embodiments, a Western blot or an ELISA is used to assess the level of phosphorylation of MERTK (e.g., human MERTK). In some embodiments, an anti-MERTK antibody or antigen-binding fragment thereof described herein, or an anti-MERTK known to one of skill in the art (e.g., an anti-MERTK antibody described in International Patent Application Publication No. WO 2016106221) is used to measure MERTK (e.g., human MERTK) levels. In some embodiments, a subject treated in accordance with the methods described herein has cancer cells overexpressing MERTK, cancer cells expressing constitutively activated MERTK, or both.

In certain embodiments, the level of expression of MERTK (e.g., human MERTK) on cancer cells, macrophages, or both is assessed prior to treating a subject in accordance with the methods described herein. In certain embodiments, the level of mutated MERTK (e.g. mutated human MERTK) on cancer cells is assessed prior to treating a subject in accordance with the methods described herein. In some embodiments, the level of phosphorylated MERTK (e.g., human MERTK) as well as the level of mutated MERTK (e.g., mutated human MERTK) expressed by cancer cells, macrophages or both is assessed prior to treating a subject in accordance with the methods described herein. In certain embodiments, the level of expression and phosphorylation of MERTK (e.g., human MERTK) on cancer cells, macrophages, or both is assessed prior to treating a subject in accordance with the methods described herein.

In certain embodiments, the level of expression of MERTK (e.g., human MERTK) on cancer cells, macrophages, or both is assessed while treating a subject in accordance with the methods described herein in order to assess the effectiveness of the treatment. In some embodiments, the level of phosphorylated MERTK (e.g., human MERTK) expressed by cancer cells, macrophages or both is assessed while treating a subject in accordance with the methods described herein in order to assess the effectiveness of the treatment. In some embodiments, the level of mutated MERTK (e.g., mutated human MERTK) is assessed while treating a subject in accordance with the methods described herein in order to assess the effectiveness of the treatment. In certain embodiments, the level of expression and phosphorylation of MERTK (e.g., human MERTK) as well as the level of mutated MERTK (e.g., mutated human MERTK) on cancer cells, macrophages, or both is assessed while treating a subject in accordance with the methods described herein in order to assess the effectiveness of the treatment.

In specific embodiments, the administration of an antibody or antigen-binding fragment, or the antibody-drug conjugate described herein, or a pharmaceutical composition described herein to a subject with cancer achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) the inhibition of the development or onset of one or more symptoms associated with cancer; (ix) the reduction in the number of symptoms associated with cancer; (x) improvement in quality of life as assessed by methods well known in the art; (x) inhibition of the recurrence of a tumor; (xi) the regression of tumors and/or one or more symptoms associated therewith; (xii) the inhibition of the progression of tumors and/or one or more symptoms associated therewith; (xiii) a reduction in the growth of a tumor; (xiv) a decrease in tumor size (e.g., volume or diameter); (xv) a reduction in the formation of a newly formed tumor; (xvi) prevention, eradication, removal, or control of primary, regional and/or metastatic tumors; (xvii) a decrease in the number or size of metastases; (xviii) a reduction in mortality; (xix) an increase in relapse free survival; (xx) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; and/or (xxi) an increase in the length of remission in patients.

In some embodiments, a method of treating cancer as described herein results in one, two, three or more of the following effects: complete response, partial response, objective response, increase in overall survival, increase in disease free survival, increase in objective response rate, increase in time to progression, stable disease, increase in progression-free survival, increase in time-to-treatment failure, and improvement or elimination of one or more symptoms of cancer. In a specific embodiment, a method of treating cancer as described herein results in an increase in overall survival. In another specific embodiment, a method of treating cancer as described herein results in an increase in progression-free survival. In another specific embodiment, a method of treating cancer as described herein results in an increase in overall survival and an increase in progression-free survival.

In a specific embodiment, complete response has the meaning understood by one of skill in the art. In a specific embodiment, complete response refers to the disappearance of all signs of cancer in response to treatment. A complete response may not mean that the cancer is cured but that patient is in remission. In a specific embodiment, colorectal cancer is in complete remission if clinically detectable disease is not detected by known techniques such as radiographic studies, bone marrow, and biopsy or protein measurements.

In a specific embodiment, partial response has the meaning understood by one of skill in the art. For example, a partial response may refer to a decrease in the size of colorectal cancer in the human body in response to the treatment. In a specific embodiment, a partial response refers to at least about a 10%, 20%, 30%, 40%, 50%, 60%, 70%, 80%, or 90% decrease in all measurable tumor burden (e.g., the number of malignant cells present in the subject, or the measured bulk of tumor masses or the quantity of abnormal monoclonal protein) in the absence of new lesions.

In a specific embodiment, overall survival has the meaning understood by one of skill in the art. In a specific embodiment, overall survival refers to the length of time from either the date of the diagnosis or the start of treatment for colorectal cancer, that the human subject diagnosed with colorectal cancer is still alive. Demonstration of a statistically significant improvement in overall survival can be considered to be clinically significant if the toxicity profile is acceptable, and has often supported new drug approval.

Several endpoints are typically based on tumor assessments. These endpoints include disease free survival (DFS), objective response rate (ORR), time to progression (TTP), progression-free survival (PFS), and time-to-treatment failure (TTF). The collection and analysis of data on these time-dependent endpoints are often based on indirect assessments, calculations, and estimates (e.g., tumor measurements).

In a specific embodiment, disease free survival (DFS) has the meaning understood by one of skill in the art. In a specific embodiment, disease-free survival may refer to the length of time after primary treatment for colorectal cancer ends that the human subject survives without any signs or symptoms of cancer. DFS can be an important endpoint in situations where survival may be prolonged, making a survival endpoint impractical. DFS can be a surrogate for clinical benefit or it can provide direct evidence of clinical benefit. This determination is typically based on the magnitude of the effect, its risk-benefit relationship, and the disease setting. The definition of DFS can be complicated, particularly when deaths are noted without prior tumor progression documentation. These events may be scored either as disease recurrences or as censored events. Although all methods for statistical analysis of deaths have some limitations, considering all deaths (deaths from all causes) as recurrences can minimize bias. DFS can be overestimated using this definition, especially in patients who die after a long period without observation. Bias can be introduced if the frequency of long-term follow-up visits is dissimilar between the study arms or if dropouts are not random because of toxicity.

In a specific embodiment, objective response rate has the meaning understood by one of skill in the art. In one embodiment, an objective response rate is defined as the proportion of patients with tumor size reduction of a predefined amount and for a minimum time period. Response duration maybe measured from the time of initial response until documented tumor progression. Generally, the FDA has defined ORR as the sum of partial responses plus complete responses. When defined in this manner, ORR is a direct measure of drug antitumor activity, which can be evaluated in a single-arm study. If available, standardized criteria should be used to ascertain response. A variety of response criteria have been considered appropriate (e.g., RECIST1.1 criteria) (See e.g., Eisenhower et al., 2009, European J. of Cancer, 45: 228-247)). The significance of ORR is assessed by its magnitude and duration, and the percentage of complete responses (no detectable evidence of tumor).

In a specific embodiment, time to progression (TTP) has the meaning understood by one of skill in the art. In a specific embodiment, time to progression refers to the length of time from the date of diagnosis or start of treatment for colorectal cancer until the cancer gets worse or spreads to other parts of the human body.

In a specific embodiment, TTP is the time from randomization until objective tumor progression; TTP does not include deaths.

In a specific embodiment, progression free survival (PFS) has the meaning understood by one of skill in the art. In a specific embodiment, PFS refers to the length of time during and after treatment of colorectal cancer that the human patient lives with the cancer but it does not get worse. In a specific embodiment, PFS is defined as the time from randomization until objective tumor progression or death. PFS may include deaths and thus can be a better correlate to overall survival.

In a specific embodiment, time-to-treatment failure (TTF) has the meaning understood by one of skill in the art. In a specific embodiment, TTF is composite endpoint measuring time from randomization to discontinuation of treatment for any reason, including disease progression, treatment toxicity, and death.

In a specific embodiment, stable disease refers to colorectal cancer that is neither decreasing or increasing in extent or severity.

In a specific embodiment, the RECIST 1.1 criteria is used to measure how well a human subject responds to the treatment methods described herein.

In some embodiments, the cancer treated in accordance with the methods described herein is a cancer of the head and neck, lung, breast, bone, ovary, stomach, pancreas, larynx, esophagus, testes, liver, gastric, parotid, biliary tract, colon, rectum, cervix, uterus, endometrium, kidney, bladder, prostate or thyroid. In some embodiments, the cancer is a sarcoma, squamous cell carcinoma, melanoma, glioma, glioblastoma, neuroblastoma, non-small cell lung carcinoma (NSCLC), head and neck cancer, colorectal cancer, or Kaposi's sarcomas. In some embodiments, the cancer is a leukemia or lymphoma. In some embodiments, the cancer is multiple myeloma. In some embodiments, the cancer treated in accordance with the methods is metastatic.

In a specific embodiment, the cancer treated in accordance with the methods described herein is breast cancer. In a particular embodiment, the cancer treated in accordance with the methods described herein is triple-negative breast cancer. Triple-negative breast cancer refers to any tumor or cell derived from or growing in breast tissue that does not express the genes Her2 (also known as Neu), Estrogen Receptor (also known as ER) or Progesterone Receptor (also known as PR).

In another specific embodiment, the cancer treated in accordance with the methods described herein is acute myelogenous leukemia. In yet another specific embodiment, the cancer treated in accordance with the methods described herein is acute lymphocytic leukemia.

In certain embodiments, the cancerous cells of the cancer treated in accordance with the methods described herein overexpress MERTK. In a specific embodiment, MERTK is constitutively active in the cancerous cells of the cancer treated in accordance with the methods described herein.

In certain embodiments, the cancer treated in accordance with the methods described herein is associated with constitutively active MERTK. In another specific embodiment, the cancer treated in accordance with the methods described herein is associated with overexpression of MERTK. In another specific embodiment, the cancer treated in accordance with the methods described herein is associated with overexpression of MERTK which is constitutively active.

As used herein, the terms "subject" and "patient" are used interchangeably. In some embodiments, the subject is a mammal such as a primate (e.g., monkey or human), most preferably a human.

In a specific embodiment, an anti-MERTK antibody or antigen-binding fragment thereof that specifically binds to MERTK (e.g., human MERTK), (e.g., z10, z11, z13 or xAb antibodies), or an antibody-drug conjugate described herein are administered to a subject. In certain embodiments, two or more different antibodies or antigen-binding fragments thereof that specifically binds MERTK (e.g., human MERTK), described herein are administered to a subject. In certain embodiments, an anti-MERTK antibody or antigen-binding fragments thereof described herein that specifically binds MERTK (e.g., human MERTK), described herein are administered to a subject in combination with one or more other therapies (See Section 5.4.2, Infra.).

In certain embodiments, two or more different antibody-drug conjugates described herein are administered to a subject. In some embodiments, an antibody-drug conjugate described herein is administered to a subject in combination with one or more other therapies. In some embodiments, an anti-MERTK antibody (e.g., a humanized antibody) or an antigen-binding fragment thereof, or an antibody-drug conjugate described herein is administered to a subject in combination with one or more other therapies (See Section 5.4.2, Infra.). In specific embodiments, the one or more other therapies are anti-cancer therapies.

5.6.1.2 Routes of Administration and Dosage

An anti-MERTK antibody or antigen-binding fragment thereof, a chimeric anti-MERTK antibody or antigen-binding fragment thereof, or an antibody-drug conjugate described herein, or a pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intratumoral and subcutaneous routes. Pulmonary administration can also be employed, e.g., by use of an inhaler or nebulizer, and formulation with an aerosolizing agent for use as a spray. In one embodiment, an anti-MERTK antibody or antigen-binding fragment thereof or an antibody-drug conjugate described herein, or a pharmaceutical composition described herein is administered parenterally to a subject. In a specific embodiment, said parenteral administration is intravenous, intramuscular, or subcutaneous.

The amount of an anti-MERTK antibody or antigen-binding fragment thereof, or an antibody-drug conjugate, or pharmaceutical composition which will be effective in the treatment and/or prevention of a condition will depend on the nature of the disease, and can be determined by standard clinical techniques.

The precise dose of an anti-MERTK antibody or antigen-binding fragment thereof, or the antibody-drug conjugate to be employed in a pharmaceutical composition will also depend on the route of administration, and the type of cancer, and should be decided according to the judgment of the practitioner and each subject's circumstances. For example, effective doses may also vary depending upon means of administration, target site, physiological state of the patient (including age, body weight and health), whether the patient is human or animal, other medications administered, or whether treatment is prophylactic or therapeutic. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For an antibody (or an antigen-binding fragment thereof) or an antibody drug conjugates, the dosage ranges from about 0.0001 to 100 mg/kg, and more usually 0.01 to 15 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. In some embodiments, the dosage administered to the patient is about 1 mg/kg to about 20 mg/kg of the patient's body weight.

An exemplary treatment regime entails administration once per every two weeks or once a month or once every 3 to 6 months for a period of one year or over several years, or over several year-intervals. In some methods, two or more antibodies or antigen-binding fragments thereof with different binding specificities are administered simultaneously to a subject. An anti-MERTK antibody or antigen-binding fragment thereof, or an antibody-drug conjugate is usually administered on multiple occasions. Intervals between single dosages can be weekly, monthly, every 3 months, every 6 months or yearly.

5.6.1.3 Combination Therapies

In a specific aspect, the methods for treating cancer described herein further comprise administering one or more other therapies, such as anti-cancer therapies (e.g., surgery, radiation, chemotherapy, or an additional therapeutic agent). In a specific embodiment, the methods provided herein for treating cancer in a subject, comprising administering to a subject in need thereof a pharmaceutical composition comprising an anti-MERTK antibody or an antigen-binding fragment thereof, or an antibody-drug conjugate described herein, further comprise administering to the subject one or more additional therapeutic agents. In a specific embodiment, the additional therapeutic agent is for treating the cancer. In a specific embodiment, the additional therapeutic agent is for treating any side effects of treatment with an anti-MERTK antibody or antigen binding fragment thereof, or an antibody-drug conjugate described herein.

In specific embodiments, the additional agent is an agent used to treat breast cancer, an agent used to treat melanoma, an immunotherapy, or an angiogenesis inhibitor.

In a specific embodiment, the additional therapeutic agent is an agent used to treat breast cancer that is selected from the group consisting of Tamoxifen, Raloxifene, Paclitaxel (TAXOL®), Cyclophosphamide, Docetaxel, Vinblastine, Fluorouracil, Everolimus, Trastuzumab, Trastuzumab-Emtansine, Pertuzumab, and Lapatinib Ditosylate.

In a specific embodiment, the additional therapeutic agent is an agent used to treat melanoma that is selected from the group consisting of a BRAF inhibitor, a MEK inhibitor, and Dacarbazine.

In a specific embodiment, the additional therapeutic agent is an agent that blocks immune checkpoint signaling. In specific embodiments, the additional therapeutic agent is an anti-CTLA-4 blocking antibody, an anti-PD-1 blocking antibody, or an anti-PD-L1 blocking antibody.

In a specific embodiment, the additional therapeutic agent is an angiogenesis inhibitor that is selected from the group consisting of a VEGF inhibitor, a VEGFR2 inhibitor, Sunitinib, and Sorafenib.

In other embodiments, the additional therapeutic agent is an agent listed in Table 32.

TABLE 32

Additional Therapeutic Agents for Use in Combination Therapy with MERTK Antibodies or Antigen-Binding Fragments Thereof

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |

TABLE 32-continued

Additional Therapeutic Agents for Use in Combination Therapy
with MERTK Antibodies or Antigen-Binding Fragments Thereof

| Category | | |
|---|---|---|
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | SM-11355 (Sumitomo) |
| | ZD-0473 (AnorMED) | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | Epirubicin |
| | amonafide | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ10992 (Asahi) |
| | cryptophycin 52 (Eli Lilly) | IDN-5109 (Indena) |
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | docetaxel |
| | Vinorelbine | vincristine |
| | Trichostatin A | paclitaxel |
| Aromatase inhibitors | aminoglutethimide | YM-511 (Yamanouchi) |
| | atamestane (BioMedicines) | formestane |
| | letrozole | exemestane |
| | anastrazole | |

TABLE 32-continued

Additional Therapeutic Agents for Use in Combination Therapy
with MERTK Antibodies or Antigen-Binding Fragments Thereof

| Category | Agent | Agent |
|---|---|---|
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | edotreotide (Novartis) |
| | glufosfamide (Baxter International) | mafosfamide (Baxter International) |
| | albumin + 32P (Isotope Solutions) | apaziquone (Spectrum Pharmaceuticals) |
| | thymectacin (NewBiotics) | O6 benzyl guanine (Paligent) |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immunomodulators | interferon | dexosome therapy (Anosys) |
| | oncophage (Antigenics) | pentrix (Australian Cancer Technology) |
| | GMK (Progenics) | ISF-154 (Tragen) |
| | adenocarcinoma vaccine (Biomira) | cancer vaccine (Intercell) |
| | CTP-37 (AVI BioPharma) | norelin (Biostar) |
| | IRX-2 (Immuno-Rx) | BLP-25 (Biomira) |
| | PEP-005 (Peplin Biotech) | MGV (Progenics) |
| | synchrovax vaccines (CTL Immuno) | β-alethine (Dovetail) |
| | melanoma vaccine (CTL Immuno) | CLL therapy (Vasogen) |
| | p21 RAS vaccine (GemVax) | Ipilimumab (BMS), |
| | MAGE-A3 (GSK) | CM-10 (cCam Biotherapeutics) |
| | nivolumab (BMS) | MPDL3280A (Genentech) |
| | abatacept (BMS) | pidilizumab (CureTech) |
| | lambrolizumab (Merck) | AMP-224 (GSK) |
| | MEDI-4736 (AstraZeneca) | Pembrolizumab |
| | Avelumab | Anti-Lag-3 therapies |
| | Anti-GITR therapies | Anti-TFG-beta therapies |
| | OX40 agonists | CAR-T Cell Therapies |
| | Kymriah | JCar017 |
| | Yescarta | RGX-014 |
| | RGX-202 | M7824 (bintrafusp alfa) |
| Hormonal and anti hormonal agents | estrogens | dexamethasone |
| | conjugated estrogens | Prednisone |
| | ethinyl estradiol | Methylprednisolone |
| | chlortrianisen | Prednisolone |
| | idenestrol | Aminoglutethimide |
| | hydroxyprogesterone caproate | Leuprolide |
| | medroxyprogesterone | Octreotide |
| | testosterone | Mitotane |
| | testosterone propionate; fluoxymesterone | P-04 (Novogen) |
| | methyltestosterone | 2-methoxyestradiol (EntreMed) |
| | diethylstilbestrol | arzoxifene (Eli Lilly) |
| | megestrol | Tamoxifen |
| | bicalutamide | Toremofine |
| | flutamide | Goserelin |
| | nilutamide | Leuporelin |
| | | Bicalutamide |
| Photodynamic agents | talaporfin (Light Sciences) | Pd-bacteriopheophorbide (Yeda) |
| | Theralux (Theratechnologies) | lutetium texaphyrin (Pharmacyclics) |
| | motexafin gadolinium (Pharmacyclics) | hypericin |

TABLE 32-continued

Additional Therapeutic Agents for Use in Combination Therapy
with MERTK Antibodies or Antigen-Binding Fragments Thereof

| | | |
|---|---|---|
| Kinase Inhibitors | imatinib (Novartis) | EKB-569 (Wyeth) |
| | leflunomide (Sugen/Pharmacia) | kahalide F (PharmaMar) |
| | ZD1839 (AstraZeneca) | CEP-701 (Cephalon) |
| | erlotinib (Oncogene Science) | CEP-751 (Cephalon) |
| | canertinib (Pfizer) | MLN518 (Millenium) |
| | squalamine (Genaera) | PKC412 (Novartis) |
| | SU5416 (Pharmacia) | Phenoxodiol (Novogen) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | trastuzumab (Genentech) | Tyrphostins |
| | OSI-774 (Tarceva ™) | Gefitinib (Iressa) |
| | CI-1033 (Pfizer) | PTK787 (Novartis) |
| | SU11248 (Pharmacia) | EMD 72000 (Merck) |
| | RH3 (York Medical) | Emodin |
| | Genistein | Radicinol |
| | Radicinol | Vemurafenib (B-Raf enzyme inhibitor, Daiichi Sankyo) |
| | Met-MAb (Roche) | |
| | trametinib (GSK) | |
| Additional Agents | SR-27897 (CCK A inhibitor, Sanofi-Synthelabo) | ceflatonin (apoptosis promotor, ChemGenex) |
| | tocladesine (cyclic AMP agonist, Ribapharm) | BCX-1777 (PNP inhibitor, BioCryst) |
| | alvocidib (CDK inhibitor, Aventis) | ranpirnase (ribonuclease stimulant, Alfacell) |
| | CV-247 (COX-2 inhibitor, Ivy Medical) | galarubicin (RNA synthesis inhibitor, Dong-A) |
| | P54 (COX-2 inhibitor, Phytopharm) | tirapazamine (reducing agent, SRI International) |
| | CapCell ™ (CYP450 stimulant, Bavarian Nordic) | N-acetylcysteine (reducing agent, Zambon) |
| | GCS-100 (gal3 antagonist, GlycoGenesys) | R-flurbiprofen (NF-kappaB inhibitor, Encore) |
| | G17DT immunogen (gastrin inhibitor, Aphton) | 3CPA (NF-kappaB inhibitor, Active Biotech) |
| | efaproxiral (oxygenator, Allos Therapeutics) | seocalcitol (vitamin D receptor agonist, Leo) |
| | PI-88 (heparanase inhibitor, Progen) | 131-I-TM-601 (DNA antagonist, TransMolecular) |
| | tesmilifene (histamine antagonist, YM BioSciences) | eflornithine (ODC inhibitor, ILEX Oncology) |
| | histamine (histamine H2 receptor agonist, Maxim) | minodronic acid (osteoclast inhibitor, Yamanouchi) |
| | tiazofurin (IMPDH inhibitor, Ribapharm) | indisulam (p53 stimulant, Eisai) |
| | cilengitide (integrin antagonist, Merck KGaA) | aplidine (PPT inhibitor, PharmaMar) |
| | SR-31747 (IL-1 antagonist, Sanofi-Synthelabo) | gemtuzumab (CD33 antibody, Wyeth Ayerst) |
| | CCI-779 (mTOR kinase inhibitor, Wyeth) | PG2 (hematopoiesis enhancer, Pharmagenesis) |
| | exisulind (PDE V inhibitor, Cell Pathways) | Immunol ™ (triclosan oral rinse, Endo) |
| | CP-461 (PDE V inhibitor, Cell Pathways) | triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promotor, Procyon) |
| | bortezomib (proteasome inhibitor, Millennium) | doranidazole (apoptosis promotor, Pola) |
| | SRL-172 (T cell stimulant, SR Pharma) | CHS-828 (cytotoxic agent, Leo) |
| | TLK-286 (glutathione S transferase inhibitor, Telik) | trans-retinoic acid (differentiator, NIH) |
| | PT-100 (growth factor agonist, Point Therapeutics) | MX6 (apoptosis promotor, MAXIA) |
| | midostaurin (PKC inhibitor, Novartis) | apomine (apoptosis promotor, ILEX Oncology) |

TABLE 32-continued

Additional Therapeutic Agents for Use in Combination Therapy
with MERTK Antibodies or Antigen-Binding Fragments Thereof

| | |
|---|---|
| bryostatin-1 (PKC stimulant, GPC Biotech) | urocidin (apoptosis promotor, Bioniche) |
| CDA-II (apoptosis promotor, Everlife) | Ro-31-7453 (apoptosis promotor, La Roche) |
| SDX-101 (apoptosis promotor, Salmedix) | brostallicin (apoptosis promotor, Pharmacia) |
| rituximab (CD20 antibody, Genentech | β-lapachone |
| carmustine | gelonin |
| Mitoxantrone | cafestol |
| Bleomycin | kahweol |
| Absinthin | caffeic acid |
| Chrysophanic acid | Tyrphostin AG |
| Cesium oxides | PD-1 inhibitors |
| BRAF inhibitors, | CTLA-4 inhibitors |
| PDL1 inhibitors | sorafenib |
| MEK inhibitors | BRAF inhibitors |
| bevacizumab | |
| angiogenesis inhibitors | |
| dabrafenib | |

In a specific embodiment, a method for treating cancer described herein comprising administering an anti-MERTK antibody or antigen-binding fragment thereof to a subject, may further comprise administering an anti-PD1 antibody (e.g., pembrolizumab, cemiplimab, pidilizumab, or nivolumab), an anti-PD-L1 antibody (e.g., atezolizumab avelumab, durvaniab, BMS-936552, or CK-301), an anti-LAG3 antibody, agonistic anti-GITR antibody, an anti-TGF-beta antibody, an agonistic anti-OX 40 antibody, a CAR-T therapy (e.g., Kymriah, JCar017, or Yescarta), RGX-104, or RGX-202.

An anti-MERTK antibody or antigen-binding fragment thereof or an antibody-drug conjugate described herein can be administered with an additional therapeutic agent concurrently or sequentially (before and/or after). The antibody or antigen binding fragment thereof and the additional therapeutic agent, or the antibody-drug conjugate and the additional therapeutic agent can be administered in the same or different compositions, and by the same or different routes of administration. A first therapy (which is an anti-MERTK antibody or antigen-binding fragment thereof or an antibody-drug conjugate described herein, or the additional therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapy (the anti-MERTK antibody or antigen-binding fragment thereof or the antibody-drug conjugate described herein, or the additional therapeutic agent) to a subject with cancer. In certain embodiments, an additional therapeutic agent administered to a subject in combination with an anti-MERTK antibody or antigen-binding fragment thereof or an antibody-drug conjugate is administered in the same composition (pharmaceutical composition). In other embodiments, an additional therapeutic agent administered in combination with an anti-MERTK antibody or antigen-binding fragment thereof or an antibody-drug conjugate is administered to a subject in a different composition than the anti-MERTK antibody or antigen-binding fragment thereof or the antibody-drug conjugate (e.g., two or more pharmaceutical compositions are used).

5.7 Kits

Also provided herein are kits comprising one or more antibodies or antibody-drug conjugates described herein, or antigen-binding fragments thereof. In a specific embodiment, provided herein is a pharmaceutical pack or kit comprising one or more containers filled with one or more of the ingredients of the pharmaceutical compositions described herein, such as one or more antibodies or an antigen-binding fragment thereof or one or more antibody-drug conjugates described herein. In some embodiments, the kits contain a pharmaceutical composition described herein and a prophylactic or therapeutic agent.

Optionally associated with such container(s) can be a notice in the form prescribed by a governmental agency regulating the manufacture, use or sale of pharmaceuticals or biological products, a dosage form, and/or instructions for use thereof. In certain embodiments, the instructions included with the kit provide guidance with respect to the dosage amounts and/or dosing regimens for administration of the pharmaceutical composition(s).

Examples of pharmaceutical packaging materials include, but are not limited to, blister packs, bottles, packets, sachets, tubes, inhalers, pumps, bags, vials, containers, syringes and any packaging material suitable for a selected pharmaceutical composition and intended mode of administration and treatment.

Kits provided herein can further include devices that are used to administer the active ingredients. Examples of such devices include, but are not limited to, syringes, needle-less injectors, drip bags, patches and inhalers.

Kits provided herein can further include pharmaceutically acceptable vehicles that can be used to administer the ingredients. For example, if an ingredient is provided in a solid form that must be reconstituted for parenteral administration, the kit can comprise a sealed container of a suitable vehicle in which the ingredient can be dissolved to form a particulate-free sterile solution that is suitable for parenteral administration or can be reconstituted as a suspension for oral administration. Examples of pharmaceutically acceptable vehicles include, but are not limited to: aqueous vehicles including, but not limited to, Water for Injection USP, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol, and polypropylene glycol; and non-aqueous vehicles including, but not limited to, corn oil, cottonseed oil, peanut oil, sesame oil, ethyl oleate, isopropyl myristate, and benzyl benzoate.

In some embodiments, a kit described herein includes a reagent (e.g., an anti-MERTK antibody or antigen-binding fragment thereof described herein, or an anti-MERTK antibody known to one of skill in the art (e.g., an anti-MERTK antibody described in International Patent Application Publication No. WO 2016106221)) to measure MERTK (e.g., human MERTK) levels on cells (e.g., cancer cells, macrophages or both) from a subject prior to and/or while treating the subject in accordance with the methods described herein. In certain embodiments, a kit described herein includes a reagent(s) to measure the level of phosphorylated MERTK (e.g., human MERTK) by cells (e.g., cancer cells, macrophages or both) from a subject to be treated in accordance with the methods described herein. In certain embodiments, a kit described herein includes a reagent(s) to measure the level of mutated MERTK (e.g., human MERTK) by cells (e.g., cancer cells, macrophages or both) from a subject to be treated in accordance with the methods described herein. In some embodiments, a kit includes information that guides a clinician/physician regarding the readout of one, two, or all of the following: MERTK (e.g., human MERTK) expression level, level of phosphorylated MERTK (e.g., human MERTK), levels of mutated MERTK (e.g., human MERTK).

The following examples are offered by way of illustration and not by way of limitation.

6. EXAMPLES

6.1. Example 1: Generation of a Humanized, High-Affinity, Specific Antibody Specific to Human MERTK This example describes a monoclonal antibody that leads to degradation of MERTK from the cell surface by internalization.

6.1.1. Humanization, Expression and Purification of Candidate Antibodies

To generate humanized anti-MERTK, the heavy chain and light chain framework regions of a subclone of the M6 antibody, a murine anti-MERTK antibody disclosed in U.S. Pat. No. 10,221,248 were replaced by human heavy chain and light chain framework regions, respectively, optionally with one or more back mutations. Combinations of heavy chains (S24, S25, S26, S27, S28, S29, S30, S31) and light chains (S32, S33) produced 16 humanized antibodies in total. The humanized antibody candidates were expressed in HEK-293 cells or 293 F cells and expression was confirmed by gel electrophoresis (data not shown). A band was present at the expected size of approximately 150 kD for humanized antibodies z1 though z16, as well as xAb (a chimeric antibody, Lane 17) and two hybridoma lines (HyAb 1 and HyAb2, Lanes 18 and 19). Binding affinity of the candidate antibodies to human MERTK was measured by SPR. SPR results are summarized in FIG. 1. Off-rate ($K_d$) values of less than $1\times10^{-6}$ in FIG. 1 indicate that the Kd is below the detection limit of the instrument. With respect to the variable light chain region, the back mutation of the fourth residue (serine, S) in framework region 3 (under the Exemplary definition) of the variable light chain region to aspartic acid (D) was found to be associated with an increase in binding affinity of the humanized antibodies to human MERTK. With respect to the variable heavy chain region, the back mutation of the $27^{th}$ residue (Tyrosine, T, second to last residue) was found to be associated with a lower binding affinity of the humanized antibodies to human MERTK. As shown in FIG. 2, the combination of the variable region of the heavy chain with the framework regions for z10, z11 and z13 and the variable region of the light chain with the framework region for z10, z11 and z13, which are identical, resulted in humanized antibodies with a higher affinity than when the variable region heavy chain with the framework region for z10, z11 and z13 were combined with a variable region light chain with the framework regions in Table 33 infra.

Table 34, infra, provides the avidity of the z10, z11 and z13 antibodies using SPR. Table 34, infra, provides the affinity of the z10 antibody using SPR and the ELISA cell-based assays. With respect to avidity and affinity measurements using SPR, the protocols below were used. The z10 antibody used in this study comprises the heavy and light chains set forth in Tables 16. The z11 antibody used in this study comprises the heavy and light chains set forth in Tables 17. The z13 antibody used in this study comprises the heavy and light chains set forth in Tables 18.

Affinity Measurement of z10 to Human MERTK Using SPR

A CM5 sensor chip was activated for 420 s with a mixture of 400 mM EDC and 100 mM NHS. 30 µg/mL of Anti-human Fc IgG antibody (Jackson, 109-005-098) in 10 mM NaAc (pH 4.5) was then injected for 420 s at a flow rate of 10 µL/min. The chip was deactivated by 1 M ethanolamine-HCl. 5 µg/mL z10 antibody in running buffer (1×HBS-EP+) was injected at a flow rate of 10 µL/min for 15 s. 6 concentrations (2.78, 5.56, 11.11, 22.22, 44.44 and 88.88 nM) of the extracellular MERTK domain (W3725-hPro1, Sino Biological, 10298-HCCH) and running buffer were injected at a flow rate of 30 µL/min for an association phase of 180 s, followed by 600 s dissociation. 10 mM glycine pH 1.5 as regeneration buffer was injected following every dissociation phase. The chip was regenerated with 10 mM glycine pH 1.5. One surface channel (without captured ligand) was used as control surface for reference subtraction. Final data of each interaction was deducted from reference channel and buffer channel data. The experimental data of z10 antibody binding to W3725-hPro1 was fitted by 1:1 binding mode. A molecular weight of 54 kDa was used to calculate the molar concentration of the analyte.

Avidity Measurement of z10, z11 and z13 to Human MERTK Using SPR

The activator was prepared with a mixture of 400 mM EDC and 100 mM NHS immediately prior to injection. The CM5 sensor chip was activated for 420 s with the mixture. 5 µg/mL rhMer/Fc Chimera (R&D Systems, 8910MR) in 10 mM NaAc (pH 4.5) was then injected for 30 s at a flow rate of 10 µL/min. The chip was deactivated by 1 M ethanolamine-HCl. Z10, z11 and z13 antibodies were diluted with running buffer (1×HBS-EP+). 8 concentrations (0.3125, 0.625, 1.25, 2.5, 5, 10, 20 and 40 nM) of the antibodies and running buffer were injected at a flow rate of 30 µL/min for an association phase of 240 s, followed by 4800 s dissociation. 10 mM glycine pH 1.5 as regeneration buffer was injected following every dissociation phase. The chip was regenerated with 10 mM glycine pH 1.5. One surface channel without capturing ligand was used as control surface for reference subtraction. Final data of each interaction was deducted from reference channel and buffer channel data. The experimental data of the antibodies binding to rhMer/Fc Chimera was fitted by 1:1 binding mode. The curves of 40 nM and 0.3125 nM antibodies were removed to allow a better fit. A molecular weight of 150 kDa was used to calculate the molar concentration of the antibodies.

TABLE 33

S32 heavy chain framework regions

| | FR1 | FR2 | FR3 | FR4 |
|---|---|---|---|---|
| z32 | DIQMTQTPSFLSA SVGDRVTITC | WYQQKPGK APKLLIY | GVPSRFSGSGSGTDFTL TISSLQPEDFATYYC | FGQGTK LEIK |

TABLE 34

Avidity and affinity of the z10, z11 and z13 antibodies using SPR

| Antibody | Binding type | Method | Value | Comment |
|---|---|---|---|---|
| Z10 | Avidity | SPR | KD = 5.74 $10^{-12}$ M | KD |
| | | ELISA | 1.46 nM | KD |
| | Affinity | SPR | 3 nM | KD |
| Z11 | Avidity | SPR | KD = 2.99 $10^{-12}$ M | KD |
| Z13 | | SPR | KD = 3.68 $10^{-12}$ M | KD |

Based on their high affinity for MERTK, z10, z11 and z13 were selected for further studies. Antibodies were purified using protein A and analyzed by size-exclusion high performance liquid chromatography (SEC HPLC). FIG. 2 shows a summary of the purity analysis for the four antibodies. SDS-PAGE was used to characterize the four antibodies. As expected, 150 kDa, 50 kDa and 25 kDa bands were visible on the gel, suggesting the antibodies are normal.

6.2. Example 2: Activity of a Humanized Anti-MERTK Antibody

This example demonstrates that a particular humanized antibody specifically binds to human MERTK and does not bind to the extracellular domain of human Axl, human Tyro3, or murine MERTK. This example also demonstrates that a humanized antibody that specifically binds to human MERTK blocks Gas6-induced activation and inhibits colony formation of cancer cells in vitro. Further, the example demonstrates that a humanized antibody that specifically binds to human MERTK, reduces the expression of human MERTK on the surface of cancer cells and macrophages by inducing internalization and degradation of human MERTK.

6.2.1. Materials and Methods

Cell Lines, Antibodies and Reagents

SKMEL5 cells were obtained from ATCC (atcc, HTB-70) and cultured in Eagle's Minimum Essential Medium (EMEM) supplemented with 10% FBS, penicillin and streptomycin at 37° C. with 5% $CO_2$. Antibodies for flow cytometry were obtained from the following sources: anti-MERTK (Biolegend, 367603), anti-CD86 (ThermoFisher, 12-0869-41), and anti-CD163 (ThermoFisher, 17-1639-41). Fixable Viability Dye (eFluor 780) was obtained from Thermofisher. Antibodies for Western blots were obtained from following sources: anti-MERTK (abcam, ab52968), anti-AKT (abcam, ab32505), anti-AKT1 phospho S473 (abcam, ab81283), anti-β-Actin (Sigma, A5316), and anti-α-Tubulin (Sigma, T5168).

Cell Surface Binding Assay

Z10 and human IgG control (R&D Systems, 1-001-A) were labeled with Zenon Allophycocyanin (APC) Human IgG Labeling Kit (ThermoFisher, Z25451) according to the manufacturer's instructions. SKMEL5 cells were harvested with trypsin, washed twice with PBS and strained through a 70 μm filter. 50,000 cells were resuspended in 60 μL FACS buffer (2% BSA, 10 mM EDTA, 25 mM HEPES, 0.1% sodium azide in Ca/Mg-free PBS) containing 10% human AB serum (Sigma, H4522). The cells were stained with DAPI (500 ng/mL) and APC-labeled Z10 or IgG control at concentrations ranging from 0.002 to 13.5 μg/mL (0.13 to 90 nM) for 20 min on ice, then washed twice with FACS buffer, and subjected to flow cytometer analysis (BD LSR Fortessa). The APC signals from live single cells were analyzed in FlowJo and the MFIs were plotted with GraphPad Prism. Single color control samples were used to create a compensation matrix.

Internalization Assay

Z10 and human IgG control (R&D Systems) were labeled with pHrodo Red, a pH-sensitive dye, using pHrodo Red Microscale Labeling Kit (ThermoFisher, Cat #) according to the manufacturer's instructions. Internalization of antibody was determined by flow cytometry detecting pHrodo fluorescence, which is minimal at neutral pH and maximal in acidic environments, such as the lysosomes. One million SKMEL5 were plated on 6-well plates and incubated with 1 μg/mL pHrodo-labeled Z10 or IgG control antibody for 1, 3, 6 or 24 hrs. The cells were harvested with Cell Dissociation Buffer (ThermoFisher), washed twice, strained through a 70 μm filter, and resuspended in 200 μL FACS buffer (2% BSA, 10 mM EDTA, 25 mM HEPES, 0.1% sodium azide in Ca/Mg-free PBS) containing 10% human AB serum. Cells were sequentially stained with BV421-conjugated antibodies against MERTK for 20 min on ice, and then stained with Fixable Viability Dye (eFluor 780) for 20 min on ice. 5,000 event multispectral images were acquired for each sample by ImageStream Imaging Flow Cytometer (Aminis). Single color control samples were used to create a compensation matrix, and resulting compensated data were analyzed by IDEA software (Amnis) and GraphPad Prism.

PBMC-Derived Cell Culture and Macrophage Differentiation

Peripheral blood mononuclear cells (PBMCs) were prepared from buffy coats of healthy donors by Histopaque-1077 (Sigma, 10771) density gradient centrifugation at 250×g at room temperature for 30 min. The intermediate layer containing PBMCs was collected and cells washed with PBS with 2 mM EDTA three times. Human monocytes were isolated from PBMCs by magnetic separation using human Classical Monocyte Isolation Kit (Miltenyi, 130-117-337) according to the manufacturer's instructions. 2.5× $10^5$ monocytes were cultured in 24-well plates in RPMI 1640 medium (Gibco, 11875093) containing 10% human AB serum, 10% FBS, L-glutamine, penicillin, and streptomycin at 37° C. with 5% $CO_2$. Monocytes were treated for 24 hr with 1 μg/mL Z10 or IgG control and supernatant was harvested for cytokine analysis. To differentiate M1 or M2 macrophages, monocytes were incubated with GM-CSF (100 ng/mL; Miltenyi, 130-093-864) or M-CSF (50 ng/mL; Miltenyi, 130-096-485) for 7 days, respectively, and the effect of Z10 on differentiation was assessed by culturing in the presence of 0.3 to 1 μg/mL Z10 or IgG throughout the whole time of differentiation. To determine the effect on cytokine production of M2 macrophages, the culture medium was replaced by serum-free X-Vivo15 medium (Lonza, 04-418Q) with M-CSF (50 ng/mL) on Day 5 of differentiation and treated with 1 μg/mL Z10 or IgG for 48 hrs, as indicated. To measure cytokines, cell culture supernatants were collected and sent to Eve Technologies, Canada for Human Cytokine/Chemokine Array (HD42) analysis.

Analysis of Surface Molecules on Macrophages

Polarized macrophages were harvested with Cell Dissociation Buffer (ThermoFisher), washed twice, strained through a 70 µm filter, and resuspended in FACS buffer (2% BSA, 10 mM EDTA, 25 mM HEPES, 0.1% sodium azide in Ca/Mg-free PBS) containing 10% human AB serum. The cells were stained with fluorophore-conjugated antibodies against MERTK (BV421), CD86 (PE), and CD163 (APC) for 20 min on ice, and then with Fixable Viability Dye (eFluor 780) for 20 min on ice. Fluorescence signals were acquired with a flow cytometer (BD LSR Fortessa), and analyzed with FlowJo and GraphPad Prism. Single color control samples were used to create a compensation matrix.

Proliferation Assay

SKMEL5 cells were seeded at 2,000 cells/well in a 96 well assay plate with Z10 or IgG control at concentrations of 0.1, 0.3, 0.9, 2.7, 8.1, and 24.3 µg/mL. After 72 hr of culture, cell proliferation was determined by WST-8 Cell Proliferation Assay Kit (Cayman Chemical, 10010199). The cells were incubated with WST-8 mixture for 1 hr and the optical density was read at 450 nm using GloMax Multi Detection Plate Reader (Promega). Background values from no cell control wells were subtracted, and the means of triplicate wells were plotted using GraphPad Prism.

Colony Formation Assay

SKMEL5 cells were plated at 500 cells/well in 6-well plates. The cells were treated with 0.3 or 1 µg/mL of IgG control or Z10 in triplicates. After 7 days of culture, the media was exchanged with fresh media containing the articles at the same concentration. The cells were stained on day 12. The wells were first washed once with PBS and then stained with 2 mL of 6% glutaraldehyde (v/v), 0.5% crystal violet (w/v) in PBS for 30 minutes at room temperature. The plates were then rinsed twice by immersing in a container filled with tap water. They then were allowed to dry at room temperature. Once the plates were completely dry, the number of colonies of more than 50 cells were counted by microscopic observation. The results were plotted as a bar graph using GraphPad Prism.

Western Blots

SKMEL5 cells were cultured at $3 \times 10^5$ cells/well in 6-well plates overnight, and treated with Z10 at 0.01, 0.03, 0.1, 0.3, 1, 3, and 10 µg/mL for 24 hr, or at 0.3 µg/mL for 10 min, 30 min, 2 hr, 4 hr, 8 hr, 24 hr, 48 hr, and 72 hr. For GAS6 stimulation studies, SKMEL5 cells were cultured at $1 \times 10^5$ cells/well in 24-well plate overnight, treated with 0.3 µg/mL Z10 or IgG control for 2 hr, then stimulated with 200 nM GAS6 (R&D Systems, 885-GSB-050) for 10 min.

Whole-cell lysates were prepared in RIPA buffer (Sigma, 20-188) containing protease inhibitor (Sigma, 4693159001) and phosphatase inhibitor (Sigma, P2850 and P5726). Protein concentrations were measured using BCA Protein Assay Kit (ThermoFisher, 23225). Equal protein amounts were loaded on 4-20% Tris-Glycine gel (Bio-Rad, 4561094), then transferred to PVDF membranes (Bio-Rad, 1620177). After blocking with 5% BSA, membranes were probed with primary antibodies for 1 hr at room temperature. Bound antibodies were detected with HRP-conjugated secondary antibodies (Sigma, AP187P and AP181P) and visualized by ECL Western Blotting Substrate (ThermoFisher, 32106), using ChemiDoc Imaging Systems (Bio-Rad).

Affinity Measurements by Competition ELISA of hMER, mMER, hAxl and hTyro3

Ninety-six well Nunc MaxiSorp flat-bottom plates (ThermoFisher, 44-2404-21) were coated with 0.01 ug/mL hMER recombinant protein (RnD Systems, 891-MR-100) overnight at 4° C. Plates were washed three times with PBS 0.1% Tween and blocked with 3% non-fat dry skim milk in PBS for 2 h.

During the saturation step, dilutions of the antigen hAxl (RnD Systems, 154-AL-100), hTyro3 (RnD Systems, 859-DK-100) or mMER (RnD Systems, 591-MR-100)] were prepared at 50 nM as the highest concentration, and serially diluted 1:1 to 0.098 nM in PBS. Each dilution of the antigen was incubated with 150 uL of 6 nM of the MERTK (z10) antibody at room temperature for 1 h. Then, the saturated plate was washed three times with PBS 0.1% Tween and the antigen-antibody mixture was added to the wells in duplicate and incubated for 1 h at room temperature. The plate was then washed three times with PBS 0.1% Tween and incubated with anti-human Alkaline Phosphatase antibody (Sigma, SAB 3701248) at a dilution of 1:3000 in PBS for 1 h at room temperature. After washing three times with PBS 0.1% Tween, 100 uL of Alkaline Phosphatase Yellow (pNPP) liquid substrate system (Sigma, P7998) was added in each well and incubated for 70 min at room temperature. Plates were read at 405 nm and at 570 nm, to correct plate inconsistencies, using Glomax Discover System from Promega The absorbance was plotted as a function of antigen concentration and the Kd was calculated using GraphPad Prism 7.0c.

6.2.2. Results

MERTK expressing melanoma cells (SKMEL5) were incubated with increasing concentrations (0.002-13.5 µg/mL, (0.013-90 nM)) of APC-labeled z10 antibody and then assessed by flow cytometry for APC MFI. As shown in FIG. 3A, the z10 antibody binds to human MERTK expressing melanoma cells with high affinity ($EC_{50}$=6.7 nM). SPR measurements also demonstrate that the z10 antibody has high affinity for human MERTK ($K_D$=3 nM).

The z10 antibody specifically binds to human MERTK and does not bind to the extracellular domain of human Axl, human Tyro3 or murine MERTK, as shown in FIGS. 4A-4D. An equilibrium between the z10 antibody (0.6 nM) and human MERTK, human Axl, human Tyro3 and murine MERTK extracellular domains (50 nM-0.1 nM) was established before binding to solid-phase antigen (human MERTK). Bound z10 antibody was labeled with alkaline phosphatase (AP) secondary antibody and developed for ELISA.

The z10 antibody was shown to induce human MERTK degradation of cancer cells (see FIGS. 5A-5B). In particular, substantial degradation of human MERTK was observed in SKMEL5 cells after 24 hours using concentrations of 0, 0.03, 0.1, 0.3 and 1 µg/mL of the z10 antibody. Further, substantial degradation of human MERTK on SKMEL5 cells was observed after 4 hours using 0.3 µg/mL of the z10 antibody.

In addition, the z10 antibody was demonstrated to induce degradation of human MERTK of in vitro differentiated M2 macrophages (see FIGS. 6A-6B). Approximately 4 hours after in vitro differentiated M2 macrophages were treated with 0.3 µg/mL of the z10 antibody, a decrease in more than 50% of the human MERTK was detected by Western Blot analysis (see FIGS. 6A-6B). Even greater decreases in human MERTK on in vitro differentiated M2 macrophages were detected after 8 hours of treatment with 0.3 µg/mL of the z10 antibody (see FIGS. 6A-6B).

The z10 antibody seems to degrade human MERTK on SKMEL5 human cancer cells via internalization of the human MERTK and subsequent trafficking to the lysosome. As shown in FIGS. 7A-7B, after 24 h of incubation of SKMEL5 cells with z10 antibody, the majority of the MERTK signal is found in the lysosome and only minimal signal (<20%) is detected on the cell surface.

The z10 antibody prevents Gas6-induced AKT phosphorylation in human MERTK-expressing SKMEL5 cells (see FIGS. 8A-8C). In particular, the AKT phosphorylation induced by Gas6 is blocked by treating cells with the z10 antibody. SKMEL5 cells were incubated with 0.3 µg/mL of the z10 antibody or IgG control for 2 hours, followed by Gas6 treatment at 200 nM for 10 minutes or buffer. As shown in FIG. 8A-8C, the incubation of SKMEL5 cells with the z10 antibody prior to incubation with Gas6 reduces the level of AKT phosphorylation induced by Gas6. FIG. 8B shows that human MERTK levels in the total lysate decreased after treatment with the z10 antibody.

As shown in FIGS. 9A-9D, the z10 antibody inhibits colony formation of cancer cells. 500 SKMEL5 cells were cultured on 6 well plates for 12 days in the presence of control IgG or the z10 antibody (0.3 and 1 µg/mL). Colonies of greater than 50 cells were counted. The number of colonies counted when the SKMEL5 cells were incubated with the z10 antibody was significantly reduced relative to the colonies counted when the cells were incubated with control IgG.

The z10 antibody induced cytokine responses in M2 macrophages and CD14+ monocytes (see FIG. 10). In particular, M2 macrophages were incubated with 1 µg/mL of the z10 antibody or control IgG for 48 hours and the expression of certain cytokines was assessed. CD14+ monocytes were incubated with 1 µg/mL of the z10 antibody or control IgG for 24 hours and the expression of certain cytokines was assessed. Relative to control IgG, the z10 antibody incudes increases in the expression of certain cytokines by M2 macrophages and CD14+ monocytes (see FIG. 10). M2 macrophages have been shown to suppress anti-tumor responses (see J. Immunol. Cancer 5(1):53 (2017) and human MERTK expression is mostly restricted to M2 macrophages (Crittenden et al. Oncotarget. 2016; 7:78653-78666). Thus, the z10 antibody may have an anti-cancer effect indirectly in cancer cells and makes the z10 antibody useful for delivery of toxic agents to cancer cells. In addition, human MERTK as been found to be expressed by various cancer cell lines (see entry for MERTK in The Human Protein Atlas, available from www.proteinatlas.org [accessed Feb. 26, 2019]). Thus, the z10 antibody, which has high affinity and specificity for human MERTK induces cytokine responses by immune cells and inhibits colony formation by cancer cells, has therapeutic potential to treat a variety of cancers.

In addition, the $EC_{50}$s of antibodies z11 and z13 were determined using a cell-based assay similar to that described in Section 6.2 above for z10. The z11 antibody has an $EC_{50}$ of 7.9 nM for human MERTK, while the z13 antibody has an $EC_{50}$ of 7.6 nM for human MERTK.

6.3. Example 3: Effect of z10 on Cancer Cell Viability and Survival 6.3.1. Materials and Methods
Viability Assay
One thousand SKMEL5 cells and RPMI8226 cells were plated in 96-well plate wells and cultured in 100 µL RPMI-1640 medium (ATCC) supplemented with 10% FBS and Penicillin/Streptomycin containing either IgG control (BioXCell, BE0092) or z10 at 3 and 30 µg/mL. On day 4 (SKMEL5) or day 6 (RPMI8226), 100 µL of CellTiter-Glo 2.0 Cell Viability Assay reagent (Promega, G9241) was added to each well, incubated for 10 mins and the luminescence signal was detected with a GloMax Discover Microplate Reader (Promega). The mean relative luminometer units (RLU) from duplicate wells were plotted with GraphPad Prism.

Metastasis Assays
MDA-MB-231 LM2 TR triple negative breast cancer cells (received from Prof. Sohail Tavazoie, Rockefeller University, NYC) harboring a luciferase reporter gene (Minn et al., Nature. 2005 Jul. 28; 436(7050): 518-524) were cultured in D10F culture medium (DMEM Life Technologies, 11965-092), 10% FBS (Sigma, F4135-500 ml), 1% NEAA (Fisher, 11140-050), 1% sodium pyruvate (Fisher, 11360-070), 1% Hepes (Fisher, 15630-080) and 1% Pen/Strep (Fisher, 15140-122). On the day of injection, cells were washed with DPBS (Fisher, 14190-144) and detached using 3 mL of 0.25% Trypsin-EDTA (Fisher, 25200-056) per 15 cm cell culture dish for 5 min in a 37° C. cell culture incubator. Detached cells were resuspended in 5 mL of D10F, counted using a hemocytometer and centrifuged at 220×g for 5 min at room temperature. The pellet was resuspended in DPBS at a concentration of 500,000 cells/mL. 8-week-old NSG female mice (Jackson, 005557) were exposed to a small animal heat lamp (Morganville Scientific, HL0100) for 2-3 minutes. 100 µl of the cell suspension (50'000 cells) was injected into the dilated lateral tail vein of female 8-week old NSG mice. IgG isotype control (BioXCell, BE0092) or z10 was prepared in sterile 0.9% NaCl solution and administered i.p. every 3.5 days, starting on the day of MDA-MB-231 LM2 cell injection. IgG isotype control was dosed at 10 mg/kg and z10 was dosed at 1, 3, 10, and 30 mg/kg. Lung colonization was monitored using IVIS imaging upon i.p. administration of 150 mg/kg D-luciferin (Thermofisher Scientific, Waltham, Mass.). The luminescent data for each time point was normalized to day 0, or the day of tumor injection, and plotted using Prism (Graphpad Software, La Jolla, Calif.). Mann-Whitney U-test, one tailed was used to assess significance of the metastasis as measured by bioluminescence imaging.

6.3.2. Results:
RPMI8226 multiple myeloma or SKMEL5 melanoma cells were cultured in the presence of either IgG control or z10, respectively. On day 6 (RPMI8226) or day 4 (SKMel5), viability was assessed using CellTiter-Glo 2.0 Cell Viability Assay. FIGS. 11A and 11B show that z10 inhibits cell survival in RPMi8226 and SKMEL5 cells, respectively.

50,000 MDA-MB-231-LM2 TNBC cells were injected into the tail vein of NSG mice. Treatment started on the day of tumor cell inoculation, twice/week i.p. for the duration of the study. FIG. 12A shows tumor reduction in mice treated with z10. Data are quantified in FIG. 12B.

6.4. Example 4: Activity of Antibody-Drug Conjugates Comprising a Humanized Anti-MERTK Antibody This example demonstrates that antibody-drug conjugates comprising a humanized anti-MERTK antibody lead to MERTK internalization and degradation, and inhibit the growth of cancer cells in vitro and in vivo.

6.4.1. Materials and Methods
Synthesis of IgG1-Mc-Vc-PABC-MMAE (Also Termed Herein "IgG-MMAE")
mc-vc-PABC-MMAE: 6317.7 µL of IgG1 isotype control (11.08 mg/mL, WuXi, 562) was incubated with 432.6 µL of Tris (2-carboxyethyl) phosphine (TCEP) (2.5 mM, Sigma, 1002068588) in 40 mM PB pH 7.0 solution (Sigma, 101943380 and 101900512) at a final volume of 12.6 mL for 3 h at 37° C. with gentle rotation. Then, 830.5 µL Dimethylacetamide (DMA) (Sigma, ARK2190) and 569.5 µL of mc-vc-PABC-MMAE (10 mg/mL, Levena Biopharma, LN101-006) in DMA were added for a final DMA content of 10% v/v and maleimidocaproyl-valine-citrulline-p-aminobenzyloxycarbonyl-monomethyl auristatin E (mc-vc-PABC-MMAE)/mAb ratio of 9. The reaction mixture was incubated at 22° C. for 1 h with gentle rotation.

During the reaction, a 40 KD spin desalting column was equilibrated with PBS pH 7.2. This desalting column was used for the buffer exchange and purification of the final product. The product was stored in 20 mM Histidine, pH 5.5. Protein concentration of this product was determined by absorbance at 280 nm with EC280 as 1.61. Purity and aggregation level of the product where determined by size-exclusion high performance liquid chromatography (SEC-HPLC) with the conditions shown in Table 35 below. Aggregation level of this product was 0.57% and monomeric purity of the product was 99.43%. Drug to antibody ratio (DAR) of the product was measured with HIC-HPLC as 4.06.

Synthesis of z10-mc-vc-PABC-MMAE (also Termed Herein "z10-MMAE")

9002.8 µL of z10 (7.22 mg/mL) was incubated with 410.535 µL TCEP (2.5 mM) in 40 mM PB pH 7.0 solution at a final volume of 11.7 mL for 3 h at 37° C. with gentle rotation. Then, 771.2 µL DMA and 528.76 µL mc-vc-PABC-MMAE (10 mg/mL) in DMA were added for a final DMA content of 10% v/v and mc-vc-PABC-MMAE/mAb ratio of 9. The reaction mixture was incubated at 4° C. for 22 h with gentle rotation. During the reaction, a 40 KD spin desalting column was equilibrated with PBS pH 7.2. This desalting column was used for the buffer exchange and purification. The product was stored in 20 mM Histidine, pH 5.5. Protein concentration of this product was determined by absorbance at 280 nm with EC280 as 1.53. Purity and aggregation level of the product were determined by size-exclusion high performance liquid chromatography (SEC-HPLC) with the conditions shown in Table 35 below. Monomeric purity of the product was 100%. DAR of the product was determined with HIC-HPLC as 3.88.

Synthesis of IgG1-CL2A-SN-38 (Also Termed Herein "IgG-SN-38")

6272 µL of IgG1 isotype control (11.16 mg/mL, WuXi, 562) was incubated with 8 eq TCEP (769 µL, 5 mM) in PB pH 7.0 solution in a total volume of 12.6 mL. The reaction was incubated at 37° C. for 3 h with gentle rotation. After that, the reaction mixture was cooled to 4° C. over an ice bath followed by the addition of 327 µL of DMA and 1073 µL of CL2A-SN-38 (10 mg/mL, Levena Biopharma, LN291-60) in DMA. The mixture was kept at 4° C. for 1 h. During the reaction, a 40 KD spin desalting column was equilibrated with acetic acid pH 6.0. This desalting column was used for the buffer exchange and purification of the final product. The product was stored in 20 mM acetic acid pH 6.0. Protein concentration of this product was determined by the absorbance at 280 nm with EC280 as 1.88 and reference wavelength at 700 nm. Aggregation and purity of the product was determined with SEC-HPLC with the conditions shown in Table 36 below. Aggregation level of this product was 1.14% and purity 99.14%. DAR of the product was determined with LC-MS as 7.78.

Synthesis of z10-CL2A-SN-38 (Also Termed Herein "z10-SN-38")

9002 µL of z10 (7.22 mg/mL) was incubated with 8 eq TCEP (714 µL, 5 mM) in PB pH 7.0 solution in a total volume of 11.7 mL. The reaction mixture was incubated at 37° C. for 3 h with gentle rotation. After that, the reaction mixture was cooled to 4° C. over an ice bath followed by the addition of 90 µL DMA and 1210 µL of CL2A-SN-38 (10 mg/ml, Levena Biopharma, LN291-60) in DMA. The mixture was kept at 4° C. for 1 h. During the reaction, a 40 KD spin desalting column was equilibrated with acetic acid pH 6.0. This desalting column was used for the buffer exchange and purification of the final product. The product was stored in 20 mM acetic acid pH 6.0. Protein concentration of this product was determined by the absorbance at 280 nm with EC280 as 1.82. Monomeric purity of the product was determined with SEC-HPLC with the conditions shown in Table 36 below. Thus aggregation level of this product is 1.14% and the monomeric purity of the product is 98.86%. DAR of the product was determined with LC-MS as 7.49.

Determination of Purity and Aggregation Levels

Tables 35 and 36 present the SEC-HPLC parameters by which purification and aggregation of the antibody-drug conjugates were determined.

TABLE 35

SEC-HPLC for purity and aggregation level of Ab-mc-vc-PABC-MMAE product
HPLC parameters

| | |
|---|---|
| Equipment | Agilent 1260 series HPLC |
| Column | TSKgel G3000SWXL 7.8 mm*300 mm, 5 µm particle size |
| Column Temp. | 25° C. |
| Mobile phase | A: 200 mM KPO$_4$, 250 mM KCl, 15% IPA, PH 7.0 |
| Flow rate | 0.75 mL/min |
| Sampler Temp. | 4° C. |
| Injection volume | 11 µL |
| Detection wavelength | 280 nm |

| | Time (min) | A % | B % |
|---|---|---|---|
| Gradient | 0 | 100 | 25 |
| | 18 | 100 | 40 |

TABLE 36

SEC-HPLC for purity and aggregation level of Ab-CL2A-SN-38
HPLC parameters

| | |
|---|---|
| Equipment | Agilent 1260 series HPLC |
| Column | TSKgel G3000SWXL 7.8 mm*300 mm, 5 µm particle size |
| Column Temp. | 25° C. |
| Mobile phase | A: 200 mM KPO$_4$, 250 mM KCl, 15% IPA, PH 7.0 |
| Flow rate | 0.75 mL/min |
| Sampler Temp. | 4° C. |
| Injection volume | 11 µL |
| Detection wavelength | 280 nm |

| | Time (min) | A % | B % |
|---|---|---|---|
| Gradient | 0 | 100 | 25 |
| | 18 | 100 | 40 |

Internalization Assay

IgG control (R&D 1-001-A), z10, z10-MMAE, and z10-SN-38 were labeled with pHrodo iFL Red, a pH-sensitive dye, using pHrodo iFL Red Microscale Protein Labeling Kit (ThermoFisher, P36014) according to the manufacturer's instructions. Internalization of the antibody was determined by flow cytometry detecting pHrodo fluorescence, which is minimal at neutral pH and maximal in acidic environments, such as the lysosome.

A hundred thousand SKMEL5 cells per well were plated on 24-well plates in 1 mL RPMI-1640 medium (ATCC) supplemented with 10% FBS and Penicillin/Streptomycin and incubated with 10 nM pHrodo-labeled IgG, z10, z10-MMAE, or z10-SN-38, respectively, for 3 or 6 hrs. The cells were trypsinized, strained through a 70 µm filter, and resuspended in FACS buffer (2% BSA, 10 mM EDTA, 25 mM HEPES, 0.1% sodium azide in Ca/Mg-free PBS) containing Human TruStain FcX blocking reagent (Biolegend, 422301). Cells were sequentially stained with BV421-conjugated antibodies against MERTK to detect surface MERTK levels (Biolegend, 367603) for 20 min on ice, and then stained with Fixable Viability Dye (eFluor 780) (Thermofisher, 65-0865-14) for 20 min on ice.

The Mean Fluorescence Intensities (MFI) of pHrodo and BV-421 were analyzed with LSRFortessa flow cytometer (BD Biosciences) and compensated data were plotted with GraphPad Prism. The MFI of pHrodo was normalized with Degree of Labeling (DOL) of pHrodo-labeled IgG, z10, z10-MMAE and z10-SN-38. DOL was calculated from A280 and A560 absorbance of the protein after labeling, according to the formula provided by the manufacturer.

Cancer Cell Line Viability Assay

Two hundred SKMEL5 cells or one thousand RPMI8226 cells per well were plated in 96-well plate wells and cultured in 100 µL RPMI-1640 medium (ATCC) supplemented with 10% FBS and Penicillin/Streptomycin containing either IgG control (BioXCell, BE0092), IgG1-MMAE, z10-MMAE, IgG1-SN-38 or z10-SN-38, respectively, at 0.015, 0.046, 0.137, 0.412, 1.24, 3.70, 11.1, 33.3, and 100 nM. On day 7, 100 µL of CellTiter-Glo 2.0 Cell Viability Assay reagent (Promega, G9241) was added to each well, incubated for 10 mins and the luminescence signal was detected with a GloMax Discover Microplate Reader (Promega). The mean relative luminometer units (RLU) from duplicate wells were plotted with GraphPad Prism.

Macrophage Viability Assay

Peripheral blood mononuclear cells (PBMCs) were prepared from buffy coats of healthy donors by Histopaque-1077 (Sigma, 10771) density gradient centrifugation at 250×g at room temperature for 30 min. The intermediate layer containing PBMCs was collected and cells were washed with PBS/2 mM EDTA three times. Human monocytes were isolated from PBMCs by magnetic separation using human Classical Monocyte Isolation Kit (Miltenyi, 130-117-337) according to the manufacturer's instructions. Eighty thousand monocytes per well were cultured on 96-well plates in 150 µL PBMC medium (RPMI 1640 medium (Gibco, 11875093) containing 10% human AB serum, 10% FBS, L-glutamine, penicillin, and streptomycin) at 37° C. with 5% $CO_2$. Monocytes were treated with GM-CSF (20 ng/mL; Biolegend, 766102) or M-CSF (50 ng/mL; Biolegend, 574804) for 8 days to differentiate to M1 or M2 macrophages, respectively. Differentiated macrophages were then treated with IgG control (2 or 20 nM; BioXCell, BE0092), z10 (2 or 20 nM), IgG1-MMAF (1 or 10 nM), z10-MMAE (1 or 10 nM), IgG1-SN-38 (0.03 or 0.3 nM), z10-SN-38 (0.03 or 0.3 nM) or 1 µM of the small molecule MERTK inhibitor UNC-1062 (Aobious, AOB4488), in 100 µL GM-CSF or M-CSF containing differentiation medium. On day 4, 100 µL of CellTiter-Glo 2.0 Cell Viability Assay reagent (Promega, G9241) was added to each well, incubated for 10 mins and the luminescence signal was detected with a GloMax Discover Microplate Reader (Promega). The mean relative luminometer units (RLU) from duplicate wells were plotted with GraphPad Prism.

Western Blot

SKMEL5 cells and RPMI8226 cells were cultured and maintained in RPMI-1640 medium (ATCC) supplemented with 10% FBS and Penicillin/Streptomycin. Whole-cell lysates were prepared in RIPA buffer (Sigma, 20-188) containing protease inhibitor (Sigma, 4693159001) and phosphatase inhibitor (Sigma, P2850 and P5726). Protein concentrations were measured using BCA Protein Assay Kit (ThermoFisher, 23225). Equal protein amounts (30 µg) were loaded on 4-20% Tris-Glycine gel (Bio-Rad, 4561094), then transferred to PVDF membranes (Bio-Rad, 1620177). After blocking with 5% BSA, membranes were probed with primary antibodies for 1 hr at room temperature in PBST (0.1% Tween-20 in PBS) with 1% BSA. After 3 wash steps in PBST with 1% BSA, HRP-conjugated secondary antibodies were added in PBST with 1% BSA and incubated for 1 h (Sigma, AP187P and AP181P). The blot was washed with PBST and developed using ECL Western Blotting Substrate (ThermoFisher, 32106), using ChemiDoc Imaging Systems (Bio-Rad). The signal was normalized to tubulin, used as internal control. The Following primary antibodies were used in Western blot assays; MERTK (abcam, ab52968), phospho MERTK (abcam, ab14921), AXL (CST, 8661), Tyro3 (CST, 5585), AKT (abcam, ab32505), phospho AKT (abcam, ab81283), Tubulin (Sigma, T5168).

Metastasis Assays

MDA-MB-231 LM2 TR triple negative breast cancer cells (received from Prof. Sohail Tavazoie, Rockefeller University, NYC) harboring a luciferase reporter gene (Minn et al., Nature. 2005 Jul. 28; 436(7050): 518-524) were cultured in D10F culture medium (DMEM Life Technologies, 11965-092, 10% FBS Sigma, F4135-500 ml, 1% NEAA Fisher, 11140-050, 1% sodium pyruvate Fisher, 11360-070, 1% Hepes Fisher, 15630-080 and 1% Pen/Strep Fisher, 15140-122. On the day of injection, cells were washed with DPBS (Fisher, 14190-144) and detached using 3 mL of 0.25% Trypsin-EDTA (Fisher, 25200-056) per 15 cm cell culture dish for 5 min in a 37° C. cell culture incubator. Detached cells were resuspended in 5 mL of D1F, counted using a hemocytometer and centrifuged at 220×g for 5 min at RT. The pellet was resuspended in DPBS at a concentration of 500,000 cells/mL. 8-week-old NSG female mice (Jackson, 005557) were exposed to a small animal heat lamp (Morganville Scientific, HL0100) for 2-3 minutes. 100 µL of the cell suspension (50'000 cells) was injected into the dilated lateral tail vein of female 8-week old NSG mice. IgG-MMAE isotype control and z10-MMAE were prepared in sterile PBS and administered i.p. on Day 0, 3, 10, 18, 33, and 41 after MDA-MB-231 LM2 cell injection. IgG-MMAE and z10-MMAE were initially dosed at 3 mg/kg, and reduced to 2 mg/kg on Day 18, and to 1 mg/kg on Day 33.

Lung colonization was monitored using IVIS imaging upon i.p. administration of 150 mg/kg D-luciferin (Thermofisher Scientific, Waltham, Mass.). The luminescent data for each time point was normalized to day 0, or the day of tumor injection, and plotted using Prism (Graphpad Software, La Jolla, Calif.). Mann-Whitney U-test, one tailed was used to assess significance of the metastasis as measured by bioluminescence imaging.

Affinity Measurements by Competitive ELISA

Ninety-six well Nunc MaxiSorp flat-bottom plates (ThermoFisher, 44-2404-21) were coated with 0.01 μg/mL hMER recombinant protein (R&D Systems, 891-MR-100) overnight at 4° C. Plates were washed three times with PBS 0.1% Tween and blocked with 3% non-fat dry skim milk in PBS for 2 h. During the pre-incubation of the plate, hMER recombinant protein in PBS at various concentrations (50, 25, 12.5, 6.25, 3.13, 1.56, 0.78, 0.39, 0.20, 0.10, 0.05 and 0 nM) were equilibrated with 0.3 nM z10, z10-MMAE, or z10-SN-38, respectively at room temperature for 1 h. Then, the hMER-coated plate was washed three times with PBST (0.1% Tween-20 in PBS) and the antigen-antibody mixture was added to the wells in duplicates and incubated for 1 h at room temperature. The plate was washed three times with PBST and incubated with Alkaline Phosphatase-conjugated anti-human IgG antibody (Sigma, SAB3701248) at a dilution of 1:3000 in PBS for 1 h at room temperature. After washing three times with PBST, 100 μL of Alkaline Phosphatase Yellow (pNPP) liquid substrate (Sigma, P7998) was added to each well and incubated for 70 min at room temperature. Plates were measured for absorbance at 405 nm and 560 nm using GloMax® Discover Microplate Reader (Promega). The 405 nm absorbance was normalized with 560 nm absorbance. The mean values from duplicate wells were plotted as a function of antigen concentration and the Kd was determined by nonlinear regression analysis with GraphPad Prism 7.0c.

6.4.2. Results z10-mc-vc-PABC-MMAE (z10-MMAE) and IgG1-mc-vc-PABC-MMAE (IgG-MMAE) were synthesized, with their structures shown in FIG. 13A where the Ab (antibody portion) was z10 and control IgG, respectively. z10-CL2A-SN-38 (z10-SN-38) and IgG$_1$-CL2A-SN-38 (IgG-SN-38) were synthesized, with their structures shown in FIG. 13B where the Ab (antibody portion) was z10 and control IgG, respectively.

Purity of the antibody-drug conjugates was assessed by SEC-HPLC. FIGS. 14A and 14B show SEC-HPLC results for z10-MMAE and z10-SN-38, respectively. For both conjugates, no or minimal aggregation was measured, indicating high purity of the conjugates.

To assess the binding affinity of the antibody-drug conjugates and z10, hMER recombinant protein (50 nM-0.05 nM) was equilibrated with 0.3 nM z10, z10-MMAE, or z10-SN-38, respectively before addition to ELISA plates pre-coated with hMER recombinant protein. Antibody binding was detected using AP-conjugated anti-human IgG secondary antibody and developed using a GloMax microplate reader. FIG. 15 shows that z10, z10-MMAE and z10-SN-38 bind to human MER with Kd values of 0.17 nM, 0.081 nM and 0.021 nM, respectively.

SKMel5 cells were incubated with 6.7 nM of pHrodo-labeled z10, z10-MMAE, z10-SN-38, or IgG control. Surface MERTK was stained with a BV421-conjugated MERTK antibody. Binding was measured by flow cytometry. The data shown in FIG. 16A demonstrate that z10 as well as the z10-MMAE and z10-SN-38 conjugates induce MERTK internalization. The data shown in FIG. 16B demonstrate that z10 as well as the z10-MMAE and z10-SN-38 conjugates induce MERTK degradation.

SKMel5 or RPMI8226 cells were incubated with IgG control, IgG-MMAE, z10-MMAE, IgG-SN-38 or z10-SN-38 for 7 days. Cell viability was measured using CellTiter-Glo. The data shown in FIGS. 17A and 17B demonstrate that z10-MMAE decreased viability of SKMel5 melanoma and RPMI8226 multiple myeloma cells, respectively, compared to the viability of these cells following incubation with IgG-MMAE or IgG control. The data shown in FIGS. 17C and 17D demonstrate that z10-SN-38 decreased viability of SKMel5 melanoma and RPMI8226 multiple myeloma cells, respectively, compared to the viability of those cells incubated with IgG-SN-38 or IgG control. FIG. 17E shows the expression of MERTK, phospho MERTK, AXL, Tyro3, AKT, phospho AKT, and tubulin in whole cell lysates prepared from SKMel5 and RPMI8226 cells.

50,000 MDA-MB-231-LM2 TNBC cells were injected into the tail vein of NSG mice. Treatment started on the day of tumor cell inoculation and lung metastatic colonization was monitored by bioluminescence imaging. FIG. 18A shows that z10-MMAE inhibits lung colonization of MDA-MB-231 triple-negative breast cancer cells compared to IgG-MMAE in vivo. Data are quantified in FIG. 18B.

M2 macrophages were differentiated by culturing $8\times10^4$ monocytes in PBMC medium with M-CSF (50 ng/mL) for 8 days. M1 macrophages were differentiated by culturing $8\times10^4$ monocytes in PBMC medium with GM-CSF (20 ng/mL) for 5 days, then cultured with GM-CSF (20 ng/mL), IFNg (20 ng/mL), IL-6 (20 ng/mL), and LPS (10 pg/mL) for additional 3 days. M2 and M1 macrophages were treated with indicated antibodies or ADCs for 4 days in differentiating medium and viability was assessed using CellTiter-Glo 2.0 Cell Viability Assay. The data shown in FIG. 19A demonstrate that neither z10 nor z10-MMAE nor z10-SN-38 nor the MERTK inhibitor UNC1062 affect the viability of MERTK-expressing M1 macrophages. The data shown in FIG. 19B demonstrate that neither z10 nor z10-MMAE nor z10-SN-38 nor the MERTK inhibitor UNC1062 affect the viability of MERTK-expressing M2 macrophages.

The foregoing is not to be limited in scope by the specific embodiments described herein. Indeed, various modifications of the antibodies and methods provided herein and their equivalents, in addition to those described herein will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. An antibody or an antigen-binding fragment thereof that specifically binds to human Mer Tyrosine Kinase (MERTK), wherein the antibody or antigen-binding fragment comprises a heavy chain variable region (VH) and a light chain variable region (VL), wherein
   - (i) the VH comprises the amino acid sequence of sequence of SEQ ID NO: 105 and the VL comprises the amino acid sequence of SEQ ID NO: 106;
   - (ii) the VH comprises the amino acid sequence of sequence of SEQ ID NO: 107 or 108 and the VL comprises the amino acid sequence of SEQ ID NO: 106;
   - (iii) the VH comprises the amino acid sequence of sequence of SEQ ID NO: 108 or 109 and the VL comprises the amino acid sequence of SEQ ID NO: 106; or
   - (iv) the VH comprises the amino acid sequence of sequence of SEQ ID NO: 110 and the VL comprises the amino acid sequence of SEQ ID NO: 111.

2. The antibody or antigen-binding fragment thereof of claim 1, wherein said antibody is a monoclonal antibody.

3. The antibody or antigen-binding fragment thereof of claim 1, wherein the antibody is an immunoglobulin comprising two identical heavy chains and two identical light chains.

4. The antibody or antigen-binding fragment thereof of claim 1, wherein the antibody comprises human-derived heavy and light chain constant regions.

5. The antibody or antigen-binding fragment thereof of claim 1, wherein the antibody is an IgG.

6. The antibody or antigen-binding fragment thereof of claim 1, wherein the antibody comprises a portion of human-derived heavy and light chain constant regions.

7. The antibody or antigen-binding fragment thereof of claim 1, wherein the antigen-binding fragment is an Fab or F(ab')2 fragment.

8. A bispecific antibody comprising two different antigen-binding regions, wherein one antigen-binding region comprises the antibody or antigen-binding fragment of claim 1, and wherein the other antigen-binding region binds to an antigen of interest.

9. The bispecific antibody of claim 8, wherein the antigen of interest is an immune cell receptor or tumor-associated antigen.

10. The bispecific antibody of claim 8, wherein the antigen of interest is CD3, PD-L1, LRP1, LPR8, TGF-β, ICOS, CD40, NKGD2, or TIGIT.

11. An antibody-drug conjugate comprising: (a) an antibody moiety that is the antibody or an antigen-binding fragment thereof of claim 1; (b) one or more drug moieties, each drug moiety being a cytotoxic agent, and (c) optionally a linker, wherein the cytotoxic agent is conjugated directly to the antibody moiety or is conjugated to the antibody moiety via the linker.

12. The antibody-drug conjugate of claim 11, which has a molar ratio of the antibody moiety to the drug moiety that is between 1:3 and 1:12.

13. The antibody-drug conjugate of claim 11, which has a molar ratio of the antibody moiety to the drug moiety of 1:9.

14. The antibody-drug conjugate of claim 11, wherein the cytotoxic agent is an auristatin, a maytansinoid, a pyrrolobenzodiazepine, an indolinobenzodiazepine, a calicheamicin, a camptothecin analogue, a duocarmycin, a tubulin inhibitor, a tubulysin or tubulysin analogue, amberstatin269, doxorubicin, SN-38, an antibiotic, an anthracycline, a microtubule inhibitor, a spliceostatin, or a thailanstain.

15. The antibody-drug conjugate of claim 11, wherein the cytotoxic agent is monomethyl auristatin E (MMAE) or monomethyl auristatin F (MMAF).

16. The antibody-drug conjugate of claim 11, wherein the cytotoxic agent is DM1 or DM4.

17. The antibody-drug conjugate of claim 11, wherein the cytotoxic agent is monomethyl auristatin E.

18. The antibody-drug conjugate of claim 11, wherein the cytotoxic agent is SN-38.

19. The antibody-drug conjugate of claim 11, wherein the antibody-drug conjugate comprises the linker, and the linker is a cleavable linker.

20. The antibody-drug conjugate of claim 11, wherein the antibody-drug conjugate comprises the linker, and the linker is a non-cleavable linker.

21. The antibody-drug conjugate of claim 11, wherein the antibody-drug conjugate comprises the linker, and the linker is maleimidocaproyl-valine-citrulline-p-aminobenzyloxycarbonyl.

22. The antibody-drug conjugate of claim 11, wherein the antibody-drug conjugate comprises the linker, and the linker is CL2.

23. The antibody-drug conjugate of claim 11, wherein the antibody-drug conjugate comprises the linker, and the linker is CL2A.

24. An isolated nucleic acid sequence comprising a polynucleotide encoding the antibody or antigen-binding fragment thereof of claim 1.

25. An isolated nucleic acid sequence comprising a polynucleotide encoding the VH of claim 1.

26. An isolated nucleic acid sequence comprising a polynucleotide encoding the VL of claim 1.

27. An ex vivo cell containing one or more polynucleotides encoding the antibody or antigen-binding fragment of claim 1.

28. A method of producing an antibody or antigen-binding fragment comprising culturing the cell of claim 27 under conditions such that said one or more polynucleotides are expressed by the cell to produce the antibody or antigen-binding fragment encoded by the polynucleotides.

29. A method of producing the antibody-drug conjugate of claim 11, wherein said linker is not present, said method comprising: (a) conjugating the cytotoxic agent directly to the antibody moiety to produce the antibody-drug conjugate; and (b) purifying the antibody-drug conjugate.

30. A method of producing the antibody-drug conjugate of claim 11, wherein said antibody-drug conjugate comprises said linker, said method comprising the following steps in the order stated: (a) conjugating the linker directly to the antibody moiety to produce a linker-antibody moiety; (b) conjugating the linker of the linker-antibody moiety directly to the cytotoxic agent to produce the antibody-drug conjugate; and (c) purifying the antibody-drug conjugate.

31. A method of producing the antibody-drug conjugate of claim 11, wherein said antibody-drug conjugate comprises said linker, said method comprising the following steps in the order stated: (a) conjugating the linker directly to the cytotoxic agent to produce a linker-cytotoxic agent moiety; (b) conjugating the linker of the linker-cytotoxic agent moiety directly to the antibody moiety to produce the antibody-drug conjugate; and (c) purifying the antibody-drug conjugate.

32. A pharmaceutical composition comprising a therapeutically effective amount of the antibody or antigen-binding fragment of claim 1, and a pharmaceutically acceptable carrier.

33. A method of treating a MERTK-expressing cancer in a subject in need thereof, comprising administering to said subject the pharmaceutical composition of claim 32.

34. An antibody-drug conjugate comprising an antibody moiety comprising a heavy chain variable region (VH) and a light chain variable region (VL), wherein the VH comprises the amino acid sequence of sequence of SEQ ID NO: 105 and the VL comprises the amino acid sequence of SEQ ID NO: 106, wherein the antibody moiety is conjugated to MMAE via an mc-vc-PABC linker.

35. An antibody-drug conjugate comprising an antibody moiety comprising a heavy chain variable region (VH) and a light chain variable region (VL), wherein the VH comprises the amino acid sequence of sequence of SEQ ID NO: 105 and the VL comprises the amino acid sequence of SEQ ID NO: 106, wherein the antibody moiety is conjugated to SN-38 via the CL2A linker.

36. A pharmaceutical composition comprising a therapeutically effective amount of the antibody-drug conjugate of claim 11, and a pharmaceutically acceptable carrier.

37. A method of treating a MERTK-expressing cancer in a subject in need thereof, comprising administering to said subject the pharmaceutical composition of claim 36.

\* \* \* \* \*